(12) United States Patent
Weinberg et al.

(10) Patent No.: US 12,121,524 B2
(45) Date of Patent: Oct. 22, 2024

(54) DNA-PK INHIBITORS

(71) Applicant: VERTEX PHARMACEUTICALS INCORPORATED, Boston, MA (US)

(72) Inventors: Marc Saul Weinberg, Encinitas, CA (US); Diego Sebastian D'Astolfo, San Diego, CA (US); Sudipta Mahajan, Framingham, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 1132 days.

(21) Appl. No.: 16/962,441

(22) PCT Filed: Jan. 16, 2019

(86) PCT No.: PCT/US2019/013783
§ 371 (c)(1),
(2) Date: Jul. 15, 2020

(87) PCT Pub. No.: WO2019/143675
PCT Pub. Date: Jul. 25, 2019

(65) Prior Publication Data
US 2021/0060028 A1    Mar. 4, 2021

Related U.S. Application Data

(60) Provisional application No. 62/618,598, filed on Jan. 17, 2018.

(51) Int. Cl.
| | | |
|---|---|---|
| *A61K 31/5377* | (2006.01) | |
| *A61K 9/00* | (2006.01) | |
| *A61K 31/498* | (2006.01) | |
| *A61K 31/501* | (2006.01) | |
| *A61K 31/506* | (2006.01) | |
| *A61K 31/5375* | (2006.01) | |
| *A61K 31/7088* | (2006.01) | |
| *A61K 38/46* | (2006.01) | |
| *A61P 43/00* | (2006.01) | |
| *C07D 413/12* | (2006.01) | |
| *C12N 9/22* | (2006.01) | |
| *C12N 15/11* | (2006.01) | |

(52) U.S. Cl.
CPC ........ *A61K 31/5377* (2013.01); *A61K 9/0019* (2013.01); *A61K 9/0053* (2013.01); *A61K 31/498* (2013.01); *A61K 31/501* (2013.01); *A61K 31/506* (2013.01); *A61K 31/5375* (2013.01); *A61K 31/7088* (2013.01); *A61K 38/465* (2013.01); *A61P 43/00* (2018.01); *C07D 413/12* (2013.01); *C12N 9/22* (2013.01); *C12N 15/11* (2013.01); *C12N 2310/20* (2017.05); *C12N 2320/31* (2013.01); *C12N 2320/32* (2013.01); *C12N 2320/35* (2013.01); *C12N 2800/80* (2013.01)

(58) Field of Classification Search
CPC .......................... C12N 9/12; C12Y 207/11011
See application file for complete search history.

(56) References Cited

U.S. PATENT DOCUMENTS

| | | |
|---|---|---|
| 3,773,919 A | 11/1973 | Boswell et al. |
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,797,368 A | 1/1989 | Carter et al. |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 5,356,802 A | 10/1994 | Chandrasegaran |
| 5,436,150 A | 7/1995 | Chandrasegaran |
| 5,487,994 A | 1/1996 | Chandrasegaran |
| 5,789,538 A | 8/1998 | Rebar et al. |
| 5,925,523 A | 7/1999 | Dove et al. |
| 6,007,988 A | 12/1999 | Choo et al. |
| 6,008,336 A | 12/1999 | Hanson et al. |
| 6,013,453 A | 1/2000 | Choo et al. |
| 6,140,081 A | 10/2000 | Barbas |
| 6,140,466 A | 10/2000 | Barbas, III et al. |
| 6,200,759 B1 | 3/2001 | Dove et al. |
| 6,242,568 B1 | 6/2001 | Barbas, III et al. |

(Continued)

FOREIGN PATENT DOCUMENTS

| | | |
|---|---|---|
| AU | 2019209293 | 1/2019 |
| CN | 105246883 | 1/2016 |

(Continued)

OTHER PUBLICATIONS

Pawelczak "Modulating DNA Repair Pathways to Improve Precision Genome Engineering" ACS Chem. Biol. 2018, 13, 389-396, published online Dec. 6, 2017 (Year: 2017).*

Ran et al. "Genome engineering using the CRISPR-Cas9 system" Nature Protocols | vol. 8 No. 11 | 2013, 2281-2308 (Year: 2013).*

Ahmad, I., and Allen, T.M., "Antibody-Mediated Specific Binding and Cytotoxicity of Liposome-Entrapped Doxorubicin to Lung Cancer Cells in Vitro," Cancer Research, pp. 4817-4820, Sep. 1, 1992, vol. 52, No. 17, American Society for Cancer Research, Philadelphia, PA, US.

(Continued)

*Primary Examiner* — Thane Underdahl
(74) *Attorney, Agent, or Firm* — Barnes & Thornburg LLP

(57) ABSTRACT

The present invention relates to compounds useful as inhibitors of DNA-PK. The invention also provides pharmaceutically acceptable compositions comprising said compounds and methods of using the compositions in the treatment of various diseases, conditions, or disorders.

36 Claims, 8 Drawing Sheets
Specification includes a Sequence Listing.

(56) References Cited

U.S. PATENT DOCUMENTS

| | | |
|---|---|---|
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,503,717 B2 | 1/2003 | Case et al. |
| 6,534,261 B1 | 3/2003 | Cox, III et al. |
| 6,599,692 B1 | 7/2003 | Case et al. |
| 6,689,558 B2 | 2/2004 | Case |
| 6,794,136 B1 | 9/2004 | Eisenberg et al. |
| 6,903,185 B2 | 6/2005 | Kim et al. |
| 7,030,215 B2 | 4/2006 | Liu et al. |
| 7,067,317 B2 | 6/2006 | Rebar et al. |
| 7,070,934 B2 | 7/2006 | Cox, III et al. |
| 7,074,596 B2 | 7/2006 | Darzynkiewicz et al. |
| 7,153,949 B2 | 12/2006 | Kim et al. |
| 7,253,273 B2 | 8/2007 | Collingwood |
| 7,262,054 B2 | 8/2007 | Jamieson et al. |
| 7,361,635 B2 | 4/2008 | Miller et al. |
| 8,153,773 B2 | 4/2012 | Jemielity et al. |
| 8,404,681 B2 | 3/2013 | Halbrook et al. |
| 8,697,359 B1 | 4/2014 | Zhang |
| 8,771,945 B1 | 7/2014 | Zhang |
| 8,795,965 B2 | 8/2014 | Zhang |
| 8,865,406 B2 | 10/2014 | Zhang et al. |
| 8,871,445 B2 | 10/2014 | Cong et al. |
| 8,889,356 B2 | 11/2014 | Zhang |
| 8,889,418 B2 | 11/2014 | Zhang et al. |
| 8,895,308 B1 | 11/2014 | Zhang et al. |
| 8,906,616 B2 | 12/2014 | Zhang et al. |
| 8,932,814 B2 | 1/2015 | Cong et al. |
| 8,945,839 B2 | 2/2015 | Zhang |
| 8,993,233 B2 | 3/2015 | Zhang et al. |
| 8,999,641 B2 | 4/2015 | Zhang et al. |
| 9,145,565 B2 | 9/2015 | Carroll et al. |
| 9,181,535 B2 | 11/2015 | Liu et al. |
| 9,365,964 B2 | 6/2016 | Kim |
| 9,771,333 B2 | 9/2017 | Zhang |
| 2005/0064474 A1 | 3/2005 | Urnov et al. |
| 2005/0267061 A1 | 12/2005 | Martin |
| 2006/0188987 A1 | 8/2006 | Guschin et al. |
| 2007/0218528 A1 | 9/2007 | Miller |
| 2008/0131962 A1 | 6/2008 | Miller |
| 2011/0201055 A1 | 8/2011 | Doyon et al. |
| 2013/0281431 A1 | 10/2013 | Charifson et al. |
| 2014/0068797 A1 * | 3/2014 | Doudna ............ H01L 21/02312 |
| | | 435/375 |
| 2014/0170753 A1 | 6/2014 | Zhang |
| 2014/0179006 A1 | 6/2014 | Zhang |
| 2014/0179770 A1 | 6/2014 | Zhang et al. |
| 2014/0186843 A1 | 7/2014 | Zhang et al. |
| 2014/0186919 A1 | 7/2014 | Zhang et al. |
| 2014/0186958 A1 | 7/2014 | Zhang et al. |
| 2014/0189896 A1 | 7/2014 | Zhang et al. |
| 2014/0227787 A1 | 8/2014 | Zhang |
| 2014/0234972 A1 | 8/2014 | Zhang |
| 2014/0242664 A1 | 8/2014 | Zhang et al. |
| 2014/0242699 A1 | 8/2014 | Zhang |
| 2014/0242700 A1 | 8/2014 | Zhang et al. |
| 2014/0248702 A1 | 9/2014 | Zhang et al. |
| 2014/0256046 A1 | 9/2014 | Zhang et al. |
| 2014/0273231 A1 | 9/2014 | Zhang et al. |
| 2014/0273232 A1 | 9/2014 | Zhang et al. |
| 2014/0273234 A1 | 9/2014 | Zhang et al. |
| 2014/0275059 A1 | 9/2014 | Maxwell et al. |
| 2014/0287938 A1 | 9/2014 | Zhang et al. |
| 2014/0310830 A1 | 10/2014 | Zhang et al. |
| 2020/0353101 A1 | 11/2020 | Maxwell et al. |
| 2021/0060028 A1 | 3/2021 | Weinberg et al. |

FOREIGN PATENT DOCUMENTS

| | | | |
|---|---|---|---|
| EP | 1381857 | 1/2004 | |
| EP | 1417038 | 5/2004 | |
| EP | 2764103 B1 | 8/2014 | |
| EP | 2771468 | 9/2014 | |
| EP | 2784162 A1 | 10/2014 | |
| EP | 2771468 B1 | 2/2015 | |
| EP | 2784162 B1 | 4/2015 | |
| EP | 3057959 B1 | 2/2018 | |
| EP | 3388517 A1 * | 10/2018 | ........... A61K 31/165 |
| EP | 3740480 A1 | 11/2020 | |
| EP | 3740483 B1 | 1/2023 | |
| GB | 2338237 | 12/1999 | |
| JP | 2006-523681 A | 10/2006 | |
| JP | 2016-509063 | 3/2016 | |
| JP | 2016-516706 | 6/2016 | |
| JP | 2016-522190 A | 7/2016 | |
| JP | 2017-535271 | 11/2017 | |
| JP | 2021-511038 A | 5/2021 | |
| JP | 2021-511312 A | 5/2021 | |
| JP | 2021-511314 A | 5/2021 | |
| JP | 2021-611314 A | 5/2021 | |
| KR | 2015-0126051 | 11/2015 | |
| WO | WO 1991/016024 | 10/1991 | |
| WO | WO 1991/017424 | 11/1991 | |
| WO | WO 1993/024641 | 12/1993 | |
| WO | WO 1995/019431 | 7/1995 | |
| WO | WO 1996/006166 | 2/1996 | |
| WO | WO 1998/037186 | 8/1998 | |
| WO | WO 1998/053057 | 11/1998 | |
| WO | WO 1998/053058 | 11/1998 | |
| WO | WO 1998/053059 | 11/1998 | |
| WO | WO 1998/053060 | 11/1998 | |
| WO | WO 1998/054311 | 12/1998 | |
| WO | WO 2000/027878 | 5/2000 | |
| WO | WO 2001/060970 | 8/2001 | |
| WO | WO 2001/088197 | 11/2001 | |
| WO | WO 2002/016536 | 2/2002 | |
| WO | WO 2002/020500 | 3/2002 | |
| WO | WO 2002/077227 | 10/2002 | |
| WO | WO 2002/099084 | 12/2002 | |
| WO | WO 2003/016496 | 2/2003 | |
| WO | WO 2007/014275 | 2/2007 | |
| WO | WO 2010/017562 | 2/2010 | |
| WO | WO 2013/072015 | 5/2013 | |
| WO | WO 2013/130824 | 9/2013 | |
| WO | WO 2014/018423 | 1/2014 | |
| WO | WO 2014/093595 | 6/2014 | |
| WO | WO 2014/093622 | 6/2014 | |
| WO | WO 2014/093635 | 6/2014 | |
| WO | WO 2014/093655 | 6/2014 | |
| WO | WO 2014/093661 | 6/2014 | |
| WO | WO 2014/093694 | 6/2014 | |
| WO | WO 2014/093701 | 6/2014 | |
| WO | WO 2014/093709 | 6/2014 | |
| WO | WO 2014/093712 | 6/2014 | |
| WO | WO 2014/093718 | 6/2014 | |
| WO | WO 2014/130955 | 8/2014 | |
| WO | WO 2014/172458 | 10/2014 | |
| WO | WO-2014159690 A1 * | 10/2014 | ........... A61K 31/506 |
| WO | WO 2014/183850 | 11/2014 | |
| WO | WO 2014/204723 | 12/2014 | |
| WO | WO 2014/204724 | 12/2014 | |
| WO | WO 2014/204725 | 12/2014 | |
| WO | WO 2014/204726 | 12/2014 | |
| WO | WO 2014/204727 | 12/2014 | |
| WO | WO 2014/204728 | 12/2014 | |
| WO | WO 2014/204729 | 12/2014 | |
| WO | WO 2015/048557 | 4/2015 | |
| WO | WO 2015/048577 | 4/2015 | |
| WO | WO 2015/058067 | 4/2015 | |
| WO | WO 2016/028682 | 4/2015 | |
| WO | WO 2015/077375 | 5/2015 | |
| WO | WO 2015/168079 | 11/2015 | |
| WO | WO 2016/081923 | 5/2016 | |
| WO | WO 2017/165655 | 9/2017 | |
| WO | 2018/013840 A1 | 1/2018 | |
| WO | WO-2018189186 A1 * | 10/2018 | ........... A61K 31/165 |
| WO | WO 2019/143675 | 7/2019 | |

(56) References Cited

FOREIGN PATENT DOCUMENTS

| WO | WO 2019/143677 | 7/2019 |
|----|----------------|--------|
| WO | WO 2019/143678 | 7/2019 |

OTHER PUBLICATIONS

Beerli, R.R., and Barbas, C.F. III., "Engineering Polydactyl Zinc-Finger Transcription Factors," Nature Biotechnology, Feb. 2002, pp. 135-141, vol. 20, Nature Portfolio, London, UK.

Behr, J.-P., "Gene Transfer with Synthetic Cationic Amphiphiles: Prospects for Gene Therapy," Bioconjugate Chemistry, Sep. 1, 1994, pp. 382-389, vol. 5, No. 5, American Chemical Society, Washington, DC.

Bell, C.C., et al., "A High-Throughput Screening Strategy for Detecting CRISPR-Cas9 Induced Mutations Using Next-Generation Sequencing," BMC Genomics, 7 pages, Nov. 20, 2014, 15, No. 1, Article No. 1002, Springer Nature, London, UK.

Bennardo, N., et al., "Alternative-NHEJ Is a Mechanistically Distinct Pathway of Mammalian Chromosome Break Repair," PLoS Genetics, 10 pages, Jun. 27, 2008, vol. 4, Issue 6, e1000110, Public Library of Science, San Francisco, CA, US.

Berge, S.M., et al., "Pharmaceutical Salts", Journal of Pharmaceutical Sciences, Jan. 1977, pp. 1-19, vol. 66, No. 1, vol. 66, Elsevier, Amsterdam, NL.

Bitinaite, J., et al., "FokI Dimerization is Required for DNA Cleavage," Proceedings of the National Academy of Sciences of the United States of America, pp. 10570-10575, Sep. 1998, vol. 95, United States National Academy of Sciences, Washington, DC, US.

Blaese, M., et al., "Vectors in Cancer Therapy: How Will They Deliver?" Cancer Gene Therapy, pp. 291-297, 1995, vol. 2, No. 4, Nature Portfolio, London, UK.

Brinkman, E.K. et al., "Easy Quantitative Assessment of Genome Editing by Sequence Trace Decomposition," Nucleic Acids Research, 8 pages, Dec. 16, 2014, vol. 42, No. 22, p. e168, Oxford University Press, Oxford, UK.

Choo, Y., and Isalan, M., "Advances in Zinc Finger Engineering," Current Opinion in Structural Biology, pp. 411-416, Aug. 1, 2000, vol. 10, Issue 4, Elsevier, Amsterdam, NL.

Crystal, R.G., "Transfer of Genes to Humans: Early Lessons and Obstacles to Success," Science, Oct. 20, 1995, pp. 404-410, vol. 270, American Association for the Advancement of Science, Washington, DC, US.

Dexheimer T. S., "Chapter 2—DNA repair pathways and mechanisms,", Springer, (2013), pp. 19-32.

Fonfara, Ines et al., "The CRISPR-associated DNA-cleaving enzyme Cpf1 also processes precursor CRISPR RNA", Nature, vol. 532, pp. 517-521.

Gao, X., and Huang, L., "Cationic Liposome-Mediated Gene Transfer," Gene Therapy, 1995, pp. 710-722, vol. 2, Nature Portfolio, London, UK.

Heigwer, F., et al., "E-CRISP: Fast CRISPR Target Site Identification," Nature Methods, Feb. 2014, pp. 122-123, vol. 11, No., 2, Nature Portfolio, London, UK.

Hermonat, P.L., and Muzyczka, N., "Use of Adeno-Associated Virus as a Mammalian DNA Cloning Vector: Transduction of Neomycin Resistance into Mammalian Tissue Culture Cells," Proceedings of the National Academy of Sciences of the United States of America, pp. 6466-6470, Oct. 1984, vol. 81, United States National Academy of Sciences, Washington, DC, US.

Heyer, W.-D., et al., "Regulation of Homologous Recombination in Eukaryotes," Annual Review of Genetics, 2010, pp. 113-139, vol. 44, Annual Reviews, San Mateo, CA.

Hsu, P.D., et al., "DNA Targeting Specificity of RNA-Guided Cas9 Nucleases," Nature Biotechnology, pp. 827-832, Sep. 2013, vol. 31, No. 9, Nature Portfolio, London, UK.

Isalan, M., et al., "A Rapid, Generally Applicable Method to Engineer Zinc Fingers Illustrated by Targeting the HIV-1 Promoter," Nature Biotechnology, pp. 656-660, Jul. 2001, vol. 19, Nature Portfolio, London, UK.

Kim, Y.-G., et al., "Chimeric Restriction Endonuclease," Proceedings of the National Academy of Sciences of the United States of America, pp. 883-887, Feb. 1994, vol. 91, United States National Academy of Sciences, Washington, DC, US.

Kim, Y.-G., et al., "Insertion and Deletion Mutants of FokI Restriction Endonuclease," The Journal of Biological Chemistry, pp. 31978-31982, Dec. 16, 1994, vol. 269, No. 50, The American Society for Biochemistry and Molecular Biology, Rockville, MD, US.

Kotin, R.M., "Prospects for the Use of Adeno-Associated Virus as a Vector for Human Gene Therapy," Human Gene Therapy, pp. 793-801, 1994, vol. 5, Mary Ann Liebert, Inc., Larchmont, NY, US.

Li, L., and Chandrasegaran, S., "Alteration of the Cleavage Distance of FokI Restriction Endonuclease by Insertion Mutagenesis," Proceedings of the National Academy of Sciences of the United States of America, pp. 2764-2768, 1993-04, vol. 90, United States National Academy of Sciences, Washington, DC, US.

Li, L., et al., "Functional Domains in FokI Restriction Endonuclease," Proceedings of the National Academy of Sciences of the United States of America, pp. 4275-4279, May 1992, vol. 89, United States National Academy of Sciences, Washington, DC, US.

Lin, S., et al., "Enhanced Homology-Directed Human Genome Engineering by Controlled Timing of CRISPR/Cas9 Delivery," eLife, 13 pages, Dec. 15, 2014, e04766, eLife Sciences Publications Ltd., Cambridge, UK.

MacDiarmid, J.A., et al., "Sequential Treatment of Drug-Resistant Tumors with Targeted Minicells Containing siRNA or a Cytotoxic Drug," Nature Biotechnology, pp. 643-651, Jul. 2009, vol. 27, No. 7, Nature Portfolio, London, UK.

Mali, P., et al., "RNA-Guided Human Genome Engineering via Cas9," Science, pp. 823-826, Feb. 15, 2013, vol. 339, American Association for the Advancement of Science, Washington, DC, US.

Muzyczka, N., "Adeno-Associated Virus (AAV) Vectors: Will They Work?" Journal of Clinical Investigation, p. 1351, Oct. 1994, vol. 94, The American Society for Clinical Investigation, Inc., Ann Arbor, MI, US.

Pabo, C.O, et al., "Design and Selection of Novel Cys2His2 Zinc Finger Proteins," Annual Review of Biochemistry, pp. 313-340, 2001, vol. 70, Annual Reviews, San Mateo, CA, US.

Remy, J.-S., et al., "Gene Transfer with a Series of Lipophilic DNA-Binding Molecules," Bioconjugate Chemistry, pp. 647-654, Nov. 1, 1994, vol. 5, Issue 6, American Chemical Society, Washington, DC, US.

Roberts, R.J., et al., "REBASE: Restriction Enzymes and Methyltransferases," Nucleic Acids Research, Jan. 1, 2003, pp. 418-420, vol. 31, No. 1, Oxford University Press, Oxford, UK.

Samulski, R.J., et al., "Helper-Free Stocks of Recombinant Adeno-Associated Viruses: Normal Integration Does Not Require Viral Gene Expression," Journal of Virology, pp. 3822-3828, Sep. 1989, vol. 63, No. 9, American Society for Microbiology, Washington, DC, US.

Segal, D.J., and Barbas, C.F. III, "Custom DNA-Binding Proteins Come of Age: Polydactyl Zinc-Finger Proteins," Current Opinion in Biotechnology, pp. 632-637, 2001, vol. 12, Elsevier, Amsterdam, NL.

Swiech, L. et al., "In vivo Interrogation of Gene Function in the Mammalian Brain Using CRISPR-Cas9", Nature Biotechnology, pp. 102-106, (2015), vol. 33, No. 1, Nature Portfolio, London, UK.

Tratschin, J. D., et al., "A Human Parvovirus, Adeno-Associated Virus, as a Eucaryotic Vector: Transient Expression and Encapsidation of the Procaryotic Gene for Chloramphenicol Acetyltransferase," Molecular and Cellular Biology, pp. 2072-2081, Oct. 1984, vol. 4, No. 10, American Society for Microbiology, Washington, DC, US.

Tratschin, J. D., et al., "Adeno-Associated Virus Vector for High-Frequency Integration, Expression, and Rescue of Genes in Mammalian Cells," Molecular and Cellular Biology, pp. 3251-3260, Nov. 1985, vol. 5, No. 11, American Society for Microbiology, Washington, DC, US.

West, M.H.P., et al., "Gene Expression in Adeno-Associated Virus Vectors: The Effects of Chimeric mRNA Structure, Helper Virus, and Adenovirus VAI RNA," Virology, pp. 38-47, 1987, vol. 160, Elsevier, Amsterdam, NL.

(56) References Cited

OTHER PUBLICATIONS

Zetsche, B., et al., "Cpf1 Is a Single RNA-Guided Endonuclease of a Class 2 CRISPR-Cas System," Cell, pp. 759-771, Oct. 22, 2015, vol. 163, No. 3, Elsevier, Amsterdam, NL.

Robert, F., et al. "Pharmacological inhibition of DNA-PK stimulates Cas9-mediated genome editing", Genome Medicine, Aug. 27, 2015, pp. 1-11, vol. 7, No. 1.

Peng, R. et al. "Potential pitfalls of CRISPR/Cas9-mediated genome editing", FEBS Journal, Nov. 27, 2015, pp. 1218-1231, vol. 283, No. 7.

International Search Report dated Mar. 19, 2019, prepared in International Application No. PCT/US2019/013783.

Bae, S., et al., "Cas-OFFinder: A Fast and Versatile Algorithm That Searches for Potential Off-Target Sites of Cas9 RNA-Guided Endonucleases," Bioinformatics, pp. 1473-1475, Jan. 24, 2014, vol. 30, No. 10, Oxford University Press, Oxford, UK.

Certo, M.T. et al., "Tracking Genome Engineering Outcome at Individual DNA Breakpoints", Nature Methods, Aug. 2011, pp. 671-676, vol. 8, No. 8, Nature Portfolio, London, UK.

Fu, Y. et al., "Improving CRISPR-Cas Nuclease Specificity Using Truncated Guide RNAs," Nature Biotechnology, pp. 279-284, Mar. 2014, vol. 32, No. 3, Nature Portfolio, London, UK.

Gao, F., et al., "DNA-guided Genome Editing Using the Natronobacterium gregoryi Argonaute," Nature Biotechnology, pp. 768-773, May 2016, vol. 34, No. 7, Nature Portfolio, London, UK, with Aug. 1, 2017 Retraction.

Heppell, Jacob T., and Jasim Al-Rawi, "Synthesis, structures elucidation, DNA-PK, P13K and antiplatelet activity of a series of novel 7- or 8-(N-substituted)-2-morpholino-quinazolines." Medicinal Chemistry Research, 2016, 25(8): pp. 1695-1704.

International Search Report dated Mar. 21, 2019, prepared in International Application No. PCT/US2019/013785.

International Search Report dated Mar. 19, 2019, prepared in International Application No. PCT/US2019/013788.

Miyaoka, Y., et al., "Systematic Quantification of HDR and NHEJ Reveals Effects of Locus, Nuclease, and Cell Type on Genome-Editing," Scientific Reports, 12 pages, Mar. 21, 2016, 6, Article No. 23549, Scientific Reports, London, UK.

Wiedenheft, B., et al., "RNA-guided genetic silencing systems in bacteria and archaea," Nature, Feb. 15, 2012, 482, (7385, pp. 331-338.

Xiao, A., et al., "CasOT: A Genome-Wide Cas9/gRNA Off-Target Searching Tool," Bioinformatics, pp. 1180-1182, (2014), vol. 30, No. 8, Oxford University Press, Oxford, UK.

Zhu, F. et al, "Nickel-Catalyzed Cross-Coupling of Aryl Fluorides and Organozinc Reagents," Journal of Organic Chemistry, 2014, 79, pp. 4285-4292.

* cited by examiner

```
                      SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: AAVS1 target site

<400> SEQUENCE: 1
accccacagt ggggccacta                                              20

<210> SEQ ID NO 2
<211> LENGTH: 20
<212> TYPE: DNA
<213> ORGANISM: Artificial Sequence
<220> FEATURE:
<223> OTHER INFORMATION: NAV1.7 target

<400> SEQUENCE: 2
ggctgagcgt ccatcaacca                                              20

<210> SEQ ID NO 3
<211> LENGTH: 100
<212> TYPE: RNA
<213> ORGANISM: Artificial Sequence
<220> FEATURE:
<223> OTHER INFORMATION: AAVS1 sgRNA
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (97)..(99)
<223> OTHER INFORMATION: 2'-O-methyl 3'-phosphorothioate

<400> SEQUENCE: 3
accccacagu ggggccacua guuuuagagc uagaaauagc aaguuaaaau aaggcuaguc    60
cguuaucaac uugaaaaagu ggcaccgagu cggugcuuuu                        100

<210> SEQ ID NO 4
<211> LENGTH: 100
<212> TYPE: RNA
<213> ORGANISM: Artificial Sequence
<220> FEATURE:
<223> OTHER INFORMATION: NAV1.7 sgRNA
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
```

```
<221> NAME/KEY: misc_feature
<222> LOCATION: (97)..(99)
<223> OTHER INFORMATION: 2'-O-methyl 3'-phosphorothioate

<400> SEQUENCE: 4
ggcugagcgu ccaucaacca guuuuagagc uagaaauagc aaguuaaaau aaggcuaguc    60
cguuaucaac uugaaaaagu ggcaccgagu cggugcuuuu                         100

<210> SEQ ID NO 5
<211> LENGTH: 90
<212> TYPE: DNA
<213> ORGANISM: Artificial Sequence
<220> FEATURE:
<223> OTHER INFORMATION: AAVS1 PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 5
gggtactttt atctgtcccc tccacccac agtggggcca gaattctcag ctagggacag    60
gattggtgac agaaaagccc catccttagg                                    90

<210> SEQ ID NO 6
<211> LENGTH: 90
<212> TYPE: DNA
<213> ORGANISM: Artificial Sequence
<220> FEATURE:
<223> OTHER INFORMATION: AAVS1 Non-PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 6
cctaaggatg gggcttttct gtcaccaatc ctgtccctag ctgagaattc tggccccact    60
gtggggtgga ggggacagat aaaagtaccc                                    90

<210> SEQ ID NO 7
<211> LENGTH: 90
<212> TYPE: DNA
<213> ORGANISM: Artificial Sequence
<220> FEATURE:
<223> OTHER INFORMATION: NAV1.7 PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 7
agctgtccat tggggagcat gagggctgag cgtccatcaa ctgagaattc ccagggagac    60
cacaccgttg cagtccacag cactgtgcat                                    90

<210> SEQ ID NO 8
<211> LENGTH: 90
```

```
<212> TYPE: DNA
<213> ORGANISM: Artificial Sequence
<220> FEATURE:
<223> OTHER INFORMATION: NAV1.7 Non-PAM
<220> FEATURE:
<221> NAME/KEY: misc_feature
<222> LOCATION: (1)..(3)
<223> OTHER INFORMATION: 2'-O-methyl 3'-phosphorothioate
<220> FEATURE:
<221> NAME/KEY: misc_feature
<222> LOCATION: (87)..(89)
<223> OTHER INFORMATION: 2'-O-methyl 3'-phosphorothioate

<400> SEQUENCE: 8
atgcacagtg ctgtggactg caacggtgtg gtctccctgg gaattctcag ttgatggacg    60
ctcagccctc atgctcccca atggacagct                                    90

<210> SEQ ID NO 9
<211> LENGTH: 20
<212> TYPE: DNA
<213> ORGANISM: Artificial Sequence
<220> FEATURE:
<223> OTHER INFORMATION: AAVS1 FW

<400> SEQUENCE: 9
ggacaacccc aaagtacccc                                               20

<210> SEQ ID NO 10
<211> LENGTH: 20
<212> TYPE: DNA
<213> ORGANISM: Artificial Sequence
<220> FEATURE:
<223> OTHER INFORMATION: AAVS1 RV

<400> SEQUENCE: 10
aggatcagtg aaacgcacca                                               20

<210> SEQ ID NO 11
<211> LENGTH: 20
<212> TYPE: DNA
<213> ORGANISM: Artificial Sequence
<220> FEATURE:
<223> OTHER INFORMATION: NAV1.7 FW

<400> SEQUENCE: 11
gccagtgggt tcagtggtat                                               20

<210> SEQ ID NO 12
<211> LENGTH: 25
<212> TYPE: DNA
<213> ORGANISM: Artificial Sequence
<220> FEATURE:
<223> OTHER INFORMATION: NAV1.7 RV

<400> SEQUENCE: 12
tcagcattat ccttgcattt tctgt                                         25

<210> SEQ ID NO 13
<211> LENGTH: 100
<212> TYPE: RNA
<213> ORGANISM: Artificial Sequence
<220> FEATURE:
<223> OTHER INFORMATION: VEGFA

<400> SEQUENCE: 13
auucccucuu uagccagagc guuuuaguac ucuggaaaca gaaucuacua aacaaggca    60
```
aaaugccgug uuuaucucgu caacuuguug gcgagauuuu        100

<210> SEQ ID NO 14
<211> LENGTH: 100
<212> TYPE: RNA
<213> ORGANISM: Artificial Sequence
<220> FEATURE:
<223> OTHER INFORMATION: EMX1

<400> SEQUENCE: 14
caaccacaaa cccacgaggg guuuuaguac ucuggaaaca gaaucuacua aaacaaggca        60
aaaugccgug uuuaucucgu caacuuguug gcgagauuuu        100

<210> SEQ ID NO 15
<211> LENGTH: 100
<212> TYPE: RNA
<213> ORGANISM: Artificial Sequence
<220> FEATURE:
<223> OTHER INFORMATION: FANCF

<400> SEQUENCE: 15
caaggcccgg cgcacggugg guuuuaguac ucuggaaaca gaaucuacua aaacaaggca        60
aaaugccgug uuuaucucgu caacuuguug gcgagauuuu        100

<210> SEQ ID NO 16
<211> LENGTH: 100
<212> TYPE: RNA
<213> ORGANISM: Artificial Sequence
<220> FEATURE:
<223> OTHER INFORMATION: RUNX

<400> SEQUENCE: 16
aaagagagau guagggcuag guuuuaguac ucuggaaaca gaaucuacua aaacaaggca        60
aaaugccgug uuuaucucgu caacuuguug gcgagauuuu        100

<210> SEQ ID NO 17
<211> LENGTH: 20
<212> TYPE: DNA
<213> ORGANISM: Artificial Sequence
<220> FEATURE:
<223> OTHER INFORMATION: VEGFA FW

<400> SEQUENCE: 17
agacgttcct tagtgctggc        20

<210> SEQ ID NO 18
<211> LENGTH: 20
<212> TYPE: DNA
<213> ORGANISM: Artificial Sequence
<220> FEATURE:
<223> OTHER INFORMATION: VEGFA RV

<400> SEQUENCE: 18
aggagggagc aggaaagtga        20

<210> SEQ ID NO 19
<211> LENGTH: 20
<212> TYPE: DNA
<213> ORGANISM: Artificial Sequence
<220> FEATURE:
<223> OTHER INFORMATION: VEGFA SEQ

<400> SEQUENCE: 19
attccctctt tagccagagc        20

<210> SEQ ID NO 20
<211> LENGTH: 20
<212> TYPE: DNA
<213> ORGANISM: Artificial Sequence
<220> FEATURE:
<223> OTHER INFORMATION: EMX1 FW

<400> SEQUENCE: 20
tggctgtcca ggcactgctc                                               20

<210> SEQ ID NO 21
<211> LENGTH: 18
<212> TYPE: DNA
<213> ORGANISM: Artificial Sequence
<220> FEATURE:
<223> OTHER INFORMATION: EMX1 RV

<400> SEQUENCE: 21
ggcctgtcct ccctcaag                                                 18

<210> SEQ ID NO 22
<211> LENGTH: 20
<212> TYPE: DNA
<213> ORGANISM: Artificial Sequence
<220> FEATURE:
<223> OTHER INFORMATION: EMX1 SEQ

<400> SEQUENCE: 22
caaccacaaa cccacgaggg                                               20

<210> SEQ ID NO 23
<211> LENGTH: 20
<212> TYPE: DNA
<213> ORGANISM: Artificial Sequence
<220> FEATURE:
<223> OTHER INFORMATION: FANCF FW

<400> SEQUENCE: 23
acacggataa agacgctggg                                               20

<210> SEQ ID NO 24
<211> LENGTH: 20
<212> TYPE: DNA
<213> ORGANISM: Artificial Sequence
<220> FEATURE:
<223> OTHER INFORMATION: FANCF RV

<400> SEQUENCE: 24
acacggataa agacgctggg                                               20

<210> SEQ ID NO 25
<211> LENGTH: 20
<212> TYPE: DNA
<213> ORGANISM: Artificial Sequence
<220> FEATURE:
<223> OTHER INFORMATION: FANCF SEQ

<400> SEQUENCE: 25
caaggcccgg cgcacggtgg                                               20

<210> SEQ ID NO 26
<211> LENGTH: 20
<212> TYPE: DNA
<213> ORGANISM: Artificial Sequence
<220> FEATURE:

```
<223> OTHER INFORMATION: RUNX1 FW

<400> SEQUENCE: 26
aacccagcat agtggtcagc                                              20

<210> SEQ ID NO 27
<211> LENGTH: 20
<212> TYPE: DNA
<213> ORGANISM: Artificial Sequence
<220> FEATURE:
<223> OTHER INFORMATION: RUNX1 RV

<400> SEQUENCE: 27
tctgtgcatg tgcctgctaa                                              20

<210> SEQ ID NO 28
<211> LENGTH: 20
<212> TYPE: DNA
<213> ORGANISM: Artificial Sequence
<220> FEATURE:
<223> OTHER INFORMATION: RUNX1 SEQ

<400> SEQUENCE: 28
aaagagagat gtagggctag                                              20
```

DNA-PK INHIBITORS

RELATED APPLICATIONS

This application claims the benefit of U.S. Provisional Application No. U.S. 62/618,598, filed Jan. 17, 2018, which is incorporated by reference herein in its entirety.

SEQUENCE LISTING

The instant application contains a Sequence Listing which has been submitted electronically in ASCII format and is hereby incorporated by reference in its entirety. The ASCII copy, created on Jan. 15, 2019, is named 14390-686 Sequence listing_ST25.txt and is 8 KB in size.

TECHNICAL FIELD OF THE INVENTION

The present invention relates to compounds useful as inhibitors of DNA-dependent protein kinase (DNA-PK). The invention also provides pharmaceutically acceptable compositions comprising the compounds of the invention and methods of using the compositions in the treatment of cancer, and for increasing genome editing efficiency by administering a DNA-PK inhibitor and a genome editing system to a cell(s).

BACKGROUND OF THE INVENTION

Ionizing radiation (IR) induces a variety of DNA damage of which double strand breaks (DSBs) are the most cytotoxic. These DSBs can lead to cell death via apoptosis and/or mitotic catastrophe if not rapidly and completely repaired. In addition to IR, certain chemotherapeutic agents including topoisomerase II inhibitors, bleomycin, and doxorubicin also cause DSBs. These DNA lesions trigger a complex set of signals through the DNA damage response network that function to repair the damaged DNA and maintain cell viability and genomic stability. In mammalian cells, the predominant repair pathway for DSBs is the Non-Homologous End Joining Pathway (NHEJ). This pathway functions regardless of the phase of the cell cycle and does not require a template to re-ligate the broken DNA ends. NHEJ requires coordination of many proteins and signaling pathways. The core NHEJ machinery consists of the Ku70/80 heterodimer and the catalytic subunit of DNA-dependent protein kinase (DNA-PKcs or DNA-PK), which together comprise the active DNA-PK enzyme complex. DNA-PKcs is a member of the phosphatidylinositol 3-kinase-related kinase (PIKK) family of serine/threonine protein kinases that also includes ataxia telangiectasia mutated (ATM), ataxia telangiectasia and Rad3-related (ATR), mTOR, and four PI3K isoforms. However, while DNA-PKcs is in the same protein kinase family as ATM and ATR, these latter kinases function to repair DNA damage through the Homologous Recombination (HR) pathway and are restricted to the S and G2 phases of the cell cycle. While ATM is also recruited to sites of DSBs, ATR is recruited to sites of single stranded DNA breaks.

NHEJ is thought to proceed through three key steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-PKcs to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. In some cases DNA polymerase may be required to synthesize new ends prior to the ligation step. The auto-phosphorylation of DNA-PKcs is believed to induce a conformational change that opens the central DNA binding cavity, releases DNA-PKcs from DNA, and facilitates the ultimate religation of the DNA ends.

It has been known for some time that DNA-PK$^{-/-}$ mice are hypersensitive to the effects of IR and that some non-selective small molecule inhibitors of DNA-PKcs can radio-sensitize a variety of tumor cell types across a broad set of genetic backgrounds. While it is expected that inhibition of DNA-PK will radiosensitize normal cells to some extent, this has been observed to a lesser degree than with tumor cells likely due to the fact that tumor cells possess higher basal levels of endogenous replication stress and DNA damage (oncogene-induced replication stress) and DNA repair mechanisms are less efficient in tumor cells. Most importantly, an improved therapeutic window with greater sparing of normal tissue will be imparted from the combination of a DNA-PK inhibitor with recent advances in precision delivery of focused IR, including image-guide RT (IGRT) and intensity-modulated RT (IMRT).

Inhibition of DNA-PK activity induces effects in both cycling and non-cycling cells. This is highly significant since the majority of cells in a solid tumor are not actively replicating at any given moment, which limits the efficacy of many agents targeting the cell cycle. Equally intriguing are recent reports that suggest a strong connection between inhibition of the NHEJ pathway and the ability to kill traditionally radioresistant cancer stem cells (CSCs). It has been shown in some tumor cells that DSBs in dormant CSCs predominantly activate DNA repair through the NHEJ pathway; it is believed that CSCs are usually in the quiescent phase of the cell cycle. This may explain why half of cancer patients may experience local or distant tumor relapse despite treatment as current strategies are not able to effectively target CSCs. A DNA-PK inhibitor may have the ability to sensitize these potential metastatic progenitor cells to the effects of IR and select DSB-inducing chemotherapeutic agents.

Given the involvement of DNA-PK in DNA repair processes, an application of specific DNA-PK inhibitory drugs would be to act as agents that will enhance the efficacy of both cancer chemotherapy and radiotherapy. Accordingly, it would be desirable to develop compounds useful as inhibitors of DNA-PK.

In addition, precise genome targeting technologies are needed to enable systematic engineering of genetic variations. The use of genome editing systems, specifically Clustered Regularly Interspaced Short Palindromic Repeats (CRISPR)-endonuclease based genome editing technology has grown exponentially in the past few years. The type II CRISPR-Cas9 bacterial innate immune system has emerged as an effective genome editing tool for targeted modification of the human genome (Wiedenheft, B. 2012; Hsu, P. D. eta. 2014). Recently, CRISPR-Cpf genome editing systems have been described. CRISPR-endonuclease based genome editing is dependent, in part, upon non-homologous end joining (NHEJ) and homology directed repair (HDR) pathways to repair DNA double strand breaks. Cellular repair mechanism favors NHEJ over HDR.

While the achievement of insertion or deletions (indels) from NHEJ is up to 70% effective in some reports, the efficiency of HDR remains challenging, with rates at less than 1%.

Accordingly, a need exists for increasing genome editing efficiency, in particular, HDR efficiency. Another application of specific DNA-PK inhibitory drugs would be to act as agents that will enhance the efficacy of genome editing systems.

SUMMARY OF THE INVENTION

It has been found that compounds of this invention, and pharmaceutically acceptable compositions thereof, are effective as inhibitors of DNA-PK. Accordingly, the invention features compounds having the general formula:

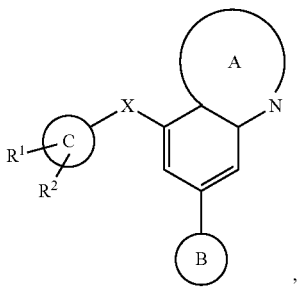

I or a pharmaceutically acceptable salt thereof, where each of $R^1$, $R^2$, X, Ring A, Ring B and Ring C is as defined elsewhere herein.

The invention also provides pharmaceutical compositions that include a compound of formula I and a pharmaceutically acceptable carrier, adjuvant, or vehicle. These compounds and pharmaceutical compositions are useful for treating or lessening the severity of cancer.

The compounds and compositions provided by this invention are also useful for the study of DNA-PK in biological and pathological phenomena; the study of intracellular signal transduction pathways mediated by such kinases; and the comparative evaluation of new kinase inhibitors.

The present invention can also improve HDR efficiency by suppressing NHEJ enzymes such as DNA-PK using DNA-PK inhibitors.

In some embodiments, the disclosure provides a method of editing one or more target genomic regions, the method includes administering to one or more cells that have one or more target genomic regions, a genome editing system and a compound represented by Formula I:

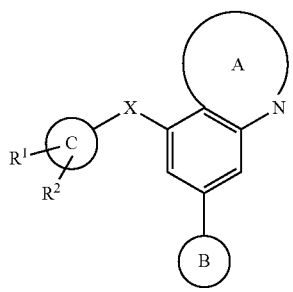

I or pharmaceutically acceptable salts thereof, where each of $R^1$, $R^2$, X, Ring A, Ring B and Ring C independently is as defined elsewhere herein.

In some embodiments, the disclosure also provides a method of repairing a DNA break in one or more target genomic regions via a homology directed repair (HDR) pathway, the method includes administering to one or more cells that have one or more target genomic regions, a genome editing system and a compound represented by Formula I or pharmaceutically acceptable salts thereof.

The genome editing system interacts with a nucleic acid(s) of the target genomic regions, resulting in a DNA break, and wherein the DNA break is repaired at least in part via a HDR pathway.

In some embodiments, the disclosure also provides a method of inhibiting or suppressing repair of a DNA break in one or more target genomic regions via a NHEJ pathway, the method includes administering to one or more cells that have one or more target genomic regions, a genome editing system and a compound represented by Formula I or pharmaceutically acceptable salts thereof.

The genome editing system interacts with a nucleic acid(s) of the one or more target genomic regions, resulting in a DNA break, and wherein repair of the DNA break via a NHEJ pathway is inhibited or suppressed.

In some embodiments, the disclosure also provides a method of modifying expression of one or more genes or proteins, the method includes administering to one or more cells that comprise one or more target genomic regions, a genome editing system and a compound represented by Formula I or pharmaceutically acceptable salts thereof.

The genome editing system interacts with a nucleic acid(s) of the one or more target genomic regions of a target gene(s), resulting in editing the one or more target genomic regions and wherein the edit modifies expression of a downstream gene (s) and/or protein(s) associated with the target gene(s).

In some embodiments, a kit or composition is provided for editing one or more target genomic regions. In some embodiments, the kit or composition includes a genome editing system; and a compound represented by Formula I or pharmaceutically acceptable salts thereof.

Other features, objects, and advantages of the invention are apparent in the detailed description that follows. It should be understood, however, that the detailed description, while indicating embodiments and aspects of the invention, is given by way of illustration only, not limitation. Various changes and modification within the scope of the invention will become apparent to those skilled in the art from the detailed description.

DETAILED DESCRIPTION OF THE INVENTION

Definitions and General Terminology

Figure 1:
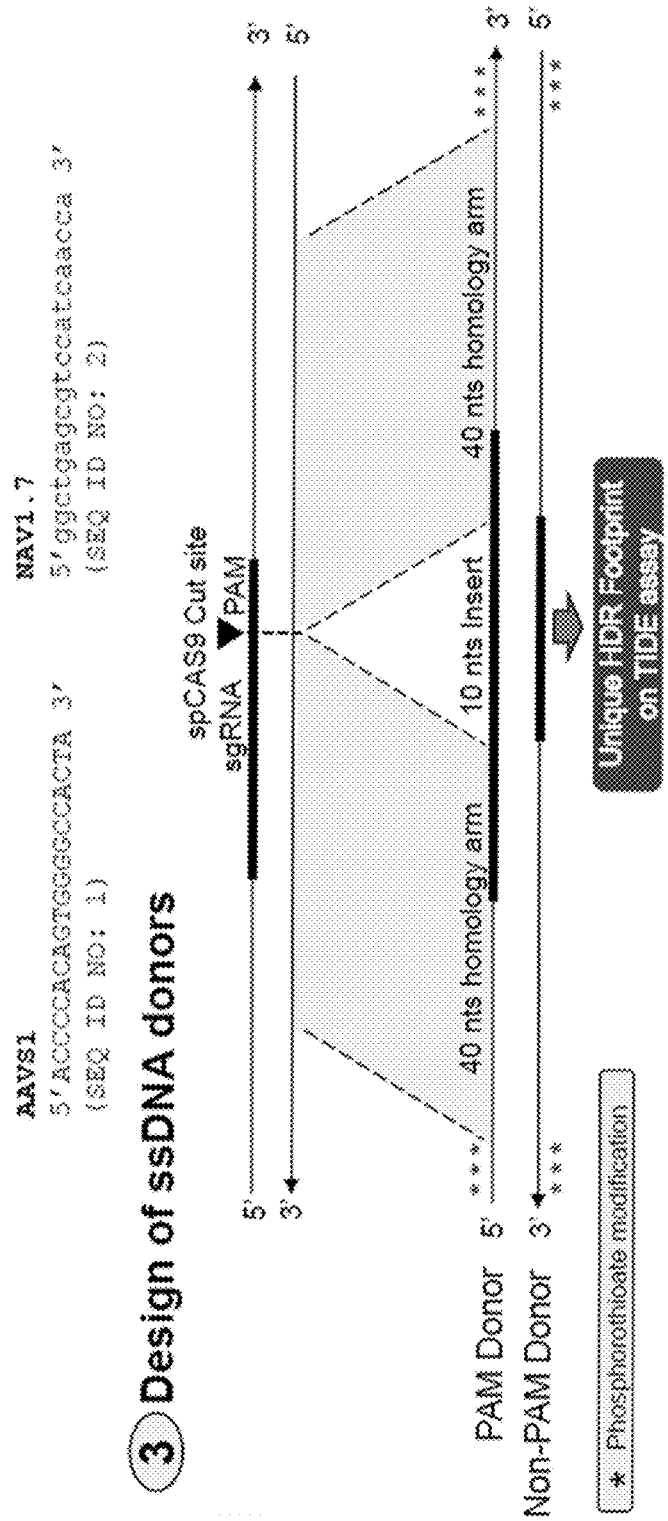
FIG. 1 depicts the design of the gene editing assays.

As used herein, the following definitions shall apply unless otherwise indicated. For purposes of this invention, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry," Thomas Sorrell, University Science Books, Sausalito: 1999, and "March's Advanced Organic Chemistry," 5$^{th}$ Ed., Smith, M. B. and March, J., eds. John Wiley & Sons, New York: 2001, the entire contents of which are hereby incorporated by reference. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout this disclosure. See e.g., Sambrook et al. Molecular Cloning: A Laboratory Manual (2d ed., Cold Spring Harbor Laboratory Press, Cold Spring Harbor, N.Y. (1989)).

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted," whether preceded by the term "optionally" or not, refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position.

As described herein, when the term "optionally substituted" precedes a list, said term refers to all of the subsequent substitutable groups in that list. For example, if X is halogen; optionally substituted $C_{1-3}$ alkyl or phenyl; X may be either optionally substituted alkyl or optionally substituted phenyl. Likewise, if the term "optionally substituted" follows a list, said term also refers to all of the substitutable groups in the prior list unless otherwise indicated. For example: if X is halogen, $C_{1-3}$ alkyl, or phenyl, wherein X is optionally substituted by $J^X$, then both $C_{1-3}$ alkyl and phenyl may be optionally substituted by $J^X$. As is apparent to one having ordinary skill in the art, groups such as H, halogen, $NO_2$, CN, $NH_2$, OH, or $OCF_3$ would not be included because they are not substitutable groups. As is also apparent to a skilled person, a heteroaryl or heterocyclic ring containing an NH group can be optionally substituted by replacing the hydrogen atom with the substituent. If a substituent radical or structure is not identified or defined as "optionally substituted," the substituent radical or structure is unsubstituted.

Combinations of substituents envisioned by this invention are preferably those that result in the formation of stable or chemically feasible compounds. The term "stable," as used herein, refers to compounds that are not substantially altered when subjected to conditions to allow for their production, detection, and, preferably, their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" or "alkyl group," as used herein, means a straight-chain (i.e., unbranched) or branched, substituted or unsubstituted hydrocarbon chain that is completely saturated. Unless otherwise specified, alkyl groups contain 1-8 carbon atoms. In some embodiments, alkyl groups contain 1-6 carbon atoms, and in yet other embodiments, alkyl groups contain 1-4 carbon atoms (represented as "$C_{1-4}$ alkyl"). In other embodiments, alkyl groups are characterized as "$C_{0-4}$ alkyl" representing either a covalent bond or a $C_{1-4}$ alkyl chain. Examples of alkyl groups include methyl, ethyl, propyl, butyl, isopropyl, isobutyl, sec-butyl, and tert-butyl. The term "alkylene," as used herein, represents a saturated divalent straight or branched chain hydrocarbon group and is exemplified by methylene, ethylene, isopropylene and the like. The term "alkylidene," as used herein, represents a divalent straight chain alkyl linking group. The term "alkenyl," as used herein, represents monovalent straight or branched chain hydrocarbon group containing one or more carbon-carbon double bonds. The term "alkynyl," as used herein, represents a monovalent straight or branched chain hydrocarbon group containing one or more carbon-carbon triple bonds.

The term "cycloalkyl" (or "carbocycle") refers to a monocyclic $C_3$-$C_8$ hydrocarbon or bicyclic $C_8$-$C_{12}$ hydrocarbon that is completely saturated and has a single point of attachment to the rest of the molecule, and wherein any individual ring in said bicyclic ring system has 3-7 members. Suitable cycloalkyl groups include, but are not limited to, cyclopropyl, cyclobutyl, cyclopentyl, cyclohexyl, and cycloheptyl.

The term "heterocycle," "heterocyclyl," "heterocycloalkyl," or "heterocyclic" as used herein refers to a monocyclic, bicyclic, or tricyclic ring system in which at least one ring in the system contains one or more heteroatoms, which is the same or different, and that is completely saturated or that contains one or more units of unsaturation, but which is not aromatic, and that has a single point of attachment to the rest of the molecule. In some embodiments, the "heterocycle,"

"heterocyclyl," "heterocycloalkyl," or "heterocyclic" group has three to fourteen ring members in which one or more ring members is a heteroatom independently selected from oxygen, sulfur, nitrogen, or phosphorus, and each ring in the system contains 3 to 8 ring members.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

The term "heteroatom" means one or more of oxygen, sulfur, nitrogen, or phosphorus, including any oxidized form of nitrogen, sulfur, or phosphorus; the quaternized form of any basic nitrogen; or a substitutable nitrogen of a heterocyclic ring, for example N (as in 3,4-dihydro-2H-pyrrolyl), NH (as in pyrrolidinyl) or NR$^+$ (as in N-substituted pyrrolidinyl).

The term "unsaturated," as used herein, means that a moiety has one or more units of unsaturation.

The term "alkoxy," or "thioalkyl," as used herein, refers to an alkyl group, as previously defined, attached to the principal carbon chain through an oxygen ("alkoxy") or sulfur ("thioalkyl") atom.

The terms "haloalkyl," "haloalkenyl," and "haloalkoxy" mean alkyl, alkenyl, or alkoxy, as the case may be, substituted with one or more halogen atoms. The term "halogen" means F, Cl, Br, or I.

The term "aryl" used alone or as part of a larger moiety as in "aralkyl," "aralkoxy," or "aryloxyalkyl," refers to a monocyclic, bicyclic, or tricyclic carbocyclic ring system having a total of six to fourteen ring members, wherein said ring system has a single point of attachment to the rest of the molecule, at least one ring in the system is aromatic and wherein each ring in the system contains 4 to 7 ring members. The term "aryl" may be used interchangeably with the term "aryl ring." Examples of aryl rings include phenyl, naphthyl, and anthracene.

The term "heteroaryl," used alone or as part of a larger moiety as in "heteroaralkyl," or "heteroarylalkoxy," refers to a monocyclic, bicyclic, and tricyclic ring system having a total of five to fourteen ring members, wherein said ring system has a single point of attachment to the rest of the molecule, at least one ring in the system is aromatic, at least one ring in the system contains one or more heteroatoms independently selected from nitrogen, oxygen, sulfur or phosphorus, and wherein each ring in the system contains 4 to 7 ring members. The term "heteroaryl" may be used interchangeably with the term "heteroaryl ring" or the term "heteroaromatic."

Further examples of heteroaryl rings include the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As described herein, a bond drawn from a substituent to the center of one ring within a multiple-ring system (as shown below) represents substitution of the substituent at any substitutable position in any of the rings within the multiple ring system. For example, Structure a represents possible substitution in any of the positions shown in Structure b.

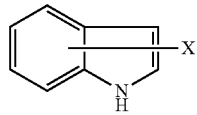

Structure a

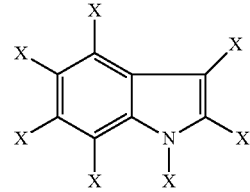

Structure b

This also applies to multiple ring systems fused to optional ring systems (which would be represented by dotted lines). For example, in Structure c, X is an optional substituent both for ring A and ring B.

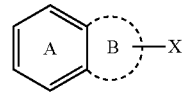

Structure c

If, however, two rings in a multiple ring system each have different substituents drawn from the center of each ring, then, unless otherwise specified, each substituent only represents substitution on the ring to which it is attached. For example, in Structure d, Y is an optionally substituent for ring A only, and X is an optional substituent for ring B only.

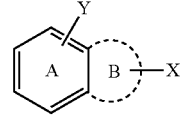

Structure d

The term "protecting group," as used herein, represent those groups intended to protect a functional group, such as, for example, an alcohol, amine, carboxyl, carbonyl, etc., against undesirable reactions during synthetic procedures. Commonly used protecting groups are disclosed in Greene and Wuts, *Protective Groups In Organic Synthesis*, 3$^{rd}$ Edition (John Wiley & Sons, New York, 1999), which is incorporated herein by reference. Examples of nitrogen protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl and chiral auxiliaries such as protected or unprotected D, L or D, L-amino acids such as alanine, leucine, phenylalanine and the like; sulfonyl groups such as benzenesulfonyl, p-toluenesulfonyl and the like; carbamate groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxycarbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl and the like, arylalkyl groups such as benzyl, triphenylmethyl, benzyloxymethyl and the like and silyl groups such as trimethylsilyl and the like. Preferred N-protecting groups are formyl, acetyl, benzoyl, pivaloyl, t-butylacetyl, alanyl, phenylsulfonyl, benzyl, t-butyloxycarbonyl (Boc) and benzyloxycarbonyl (Cbz). Examples of hydroxyl protecting groups include ethers, such as tetrahydropyranyl, tert butyl, benzyl, allyl, and the like; silyl ethers such as trimethyl silyl, triethyl silyl, triisopropylsilyl, tert-butyl diphenyl silyl, and the like; esters such as acetyl, trifluoroacetyl, and the like; and carbonates. Hydroxyl protecting groups also include those appropriate for the protection of phenols.

Unless otherwise depicted or stated, structures recited herein are meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Compounds that have been drawn with stereochemical centers defined, usually through the use of a hatched ( ⋯⋯⋯ ) or bolded ( ▬ ) bond, are stereochemically pure, but with the absolute stereochemistry still undefined. Such compounds can have either the R or S configuration. In those cases where the absolute configuration has been determined, the chiral center(s) are labeled (R) or (S) in the drawing.

Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools, probes in biological assays, or as DNA-PK inhibitors with an improved therapeutic profile.

Description of Compounds

In one aspect, the invention features compounds having the formula (III-E-1) or (III-E-2), or a pharmaceutically acceptable salt thereof,

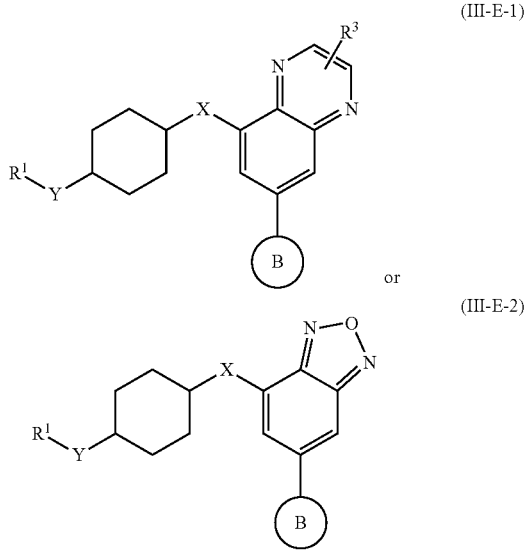

X is O or NR; wherein R is H or $C_1$-$C_4$ alkyl.
Y is O, or NR; wherein R is H or $C_1$-$C_4$ alkyl.
$R^3$ is hydrogen, $C_{1-4}$ alkyl, or $OC_{1-2}$ alkyl.
$R^1$ is a 6-membered heteroaromatic ring containing one or two nitrogen atoms wherein the heteroaromatic ring may be substituted by 0, 1, 2 or 3 substituents $R^2$ independently selected from the group consisting of halo, CN, $C_1$-$C_4$-alkyl, $C_1$-$C_4$-haloalkyl, $C_3$-$C_4$-cycloalkyl, $OR^6$, $C(=O)OR^6$, $C(=O)NR^7R^6$, and $NR^4R^5$.

Each $C_1$-$C_4$-alkyl and $C_1$-$C_4$-haloalkyl is substituted by 0, 1, or 2 $OR^6$ groups.

Each $R^6$ and $R^7$ is independently H, $C_1$-$C_4$ alkyl or $C_1$-$C_4$-haloalkyl.

Each $R^4$ and $R^5$ is independently H, $C_1$-$C_4$ alkyl, or $C(=O)C_1$-$C_4$ alkyl.

$R^4$ and $R^5$ together with the N atom to which they are attached form a heterocyclic ring comprising 0 or 1 additional O or N atom wherein said heterocyclic ring may be substituted by $C_1$-$C_4$ alkyl or $OR^6$.

Ring B is selected from the group consisting of:

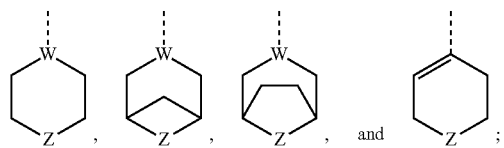

wherein W is N or $CR^7$; and Z is O or S; wherein $R^7$ is H or $C_1$-$C_4$ alkyl.

In another aspect, $R^1$ is a 6-membered heteroaromatic ring containing one or two nitrogen atoms wherein the heteroaromatic ring may be substituted by 0, 1, or 2 substituents $R^2$ independently selected from the group consisting of $C_1$-$C_4$-alkyl, $C_1$-$C_4$-haloalkyl, $C(=O)NHR^6$, and $NR^4R^5$.

$R^6$ is $C_1$-$C_4$-alkyl.

each $R^4$ and $R^5$ is independently H, $C_1$-$C_4$-alkyl, or $C(=O)C1$-$C4$ alkyl.

$R^4$ and $R^5$ together with the N atom to which they are attached form a heterocyclic ring comprising 0 or 1 additional N atom wherein said heterocyclic ring may be substituted by $C_1$-$C_4$-alkyl.

Ring B is selected from the group consisting of:

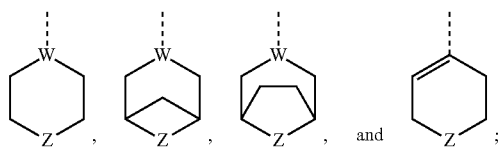

W is N or $CR^7$; and Z is O or S; wherein $R^7$ is H or $C_1$-$C_4$-alkyl.

In one embodiment, the compounds have the formula

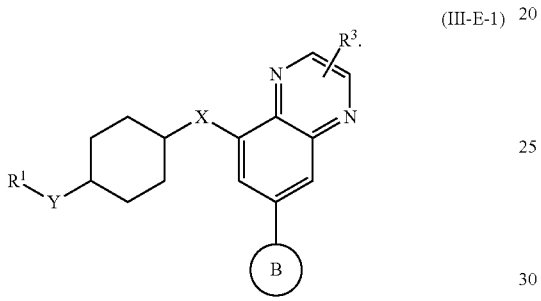

(III-E-1)

In one embodiment, X is O.

In another embodiment, X is NH.

In one embodiment, Y is O.

In another embodiment, Y is NH.

In a further embodiment, X is O or NH, Y is O or NH, and $R^3$ is hydrogen.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, $C(=O)NHR^{2'}$, and $NR^4R^5$.

In another embodiment, X is O or NH, Y is O or NH, $R^3$ is hydrogen and $R^1$ is a pyrimidine ring which is substituted by one substituents $R^2$ selected from the group consisting of $C_1$-$C_4$-alkyl, $C_1$-$C_4$-haloalkyl, $C(=O)NHR^{2'}$, and $NR^4R^5$.

In another embodiment, X is O or NH, Y is O or NH, $R^3$ is hydrogen and $R^1$ is a pyrimidine ring which is substituted by one substituent $R^2$ selected from the group consisting of $C_1$-$C_4$-alkyl and $C(=O)NHR^{2'}$.

In another embodiment, X is O or NH, Y is O or NH, $R^3$ is hydrogen and $R^1$ is a pyrimidine ring which is substituted by one substituent $R^2$ selected from the group consisting of $C_1$-$C_2$-alkyl and $C(=O)NHC_1$-$C_2$-alkyl.

In another embodiment, X is O, Y is NH, $R^3$ is hydrogen and $R^1$ is a pyrimidine ring which is substituted by one substituent $R^2$ selected from the group consisting of $C_1$-$C_2$-alkyl and $C(=O)NHC_1$-$C_2$-alkyl.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, $C(=O)NHR^6$, and $NR^4R^5$; Ring B is selected from the group consisting of:

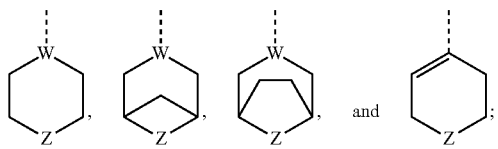

W is N or $CR^3$; and Z is O or S; wherein $R^3$ is H or $C_1$-$C_4$ alkyl.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, $C(=O)NHR^6$, and $NR^4R^5$; Ring B is

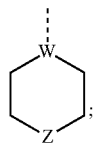

W is N or $CR^3$; and Z is O or S; wherein $R^3$ is H or $C_1$-$C_4$ alkyl.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, $C(=O)NHR^6$, and $NR^4R^5$; Ring B is

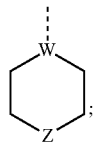

W is N; and Z is O or S.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl and $C(=O)NHR^6$; Ring B is

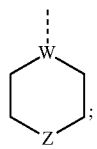

W is N; and Z is O or S.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_2$-alkyl and $C(=O)NH$ $C_1$-$C_2$-alkyl; Ring B is

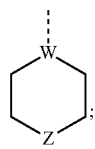

W is N; and Z is O or S.

In another embodiment, the compounds have the formula

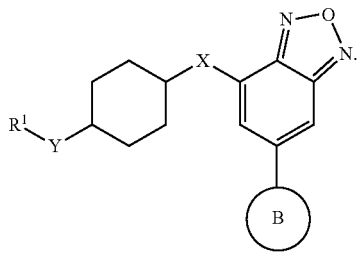

(III-E-2)

In another embodiment, X is NH.

In one embodiment, Y is O.

In another embodiment, Y is NH.

In a further embodiment, X is O or NH, Y is O or NH, and $R^3$ is hydrogen.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, C(=O)$NHR^6$, and $NR^4R^5$.

In another embodiment, X is O or NH, Y is O or NH, $R^3$ is hydrogen and $R^1$ is a pyrimidine ring which is substituted by one substituents $R^2$ selected from the group consisting of $C_1$-$C_4$-alkyl, $C_1$-$C_4$-haloalkyl, C(=O)$NHR^6$, and $NR^4R^5$.

In another embodiment, X is O or NH, Y is O or NH, $R^3$ is hydrogen and $R^1$ is a pyrimidine ring which is substituted by one substituent $R^2$ selected from the group consisting of $C_1$-$C_4$-alkyl and C(=O)$NHR^6$.

In another embodiment, X is O or NH, Y is O or NH, $R^3$ is hydrogen and $R^1$ is a pyrimidine ring which is substituted by one substituent $R^2$ selected from the group consisting of $C_1$-$C_2$-alkyl and C(=O)NH$C_1$-$C_2$-alkyl.

In another embodiment, X is O, Y is NH, $R^3$ is hydrogen and $R^1$ is a pyrimidine ring which is substituted by one substituent $R^2$ selected from the group consisting of $C_1$-$C_2$-alkyl and C(=O)NH$C_1$-$C_2$-alkyl.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, C(=O)$NHR^{2'}$, and $NR^4R^5$; Ring B is selected from the group consisting of:

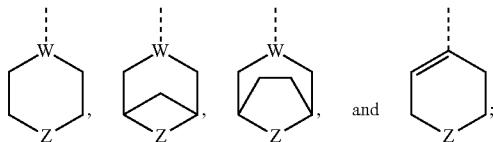

W is N or $CR^3$; and Z is O or S; wherein $R^3$ is H or $C_1$-$C_4$ alkyl.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, C(=O)$NHR^6$, and $NR^4R^5$; Ring B is

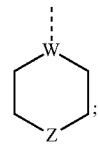

W is N or $CR^3$; and Z is O or S; wherein $R^3$ is H or $C_1$-$C_4$ alkyl.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl, $C_1$-$C_4$-haloalkyl, C(=O)$NHR^{2'}$, and $NR^4R^5$; Ring B is

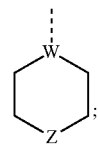

W is N; and Z is O or S.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_4$-alkyl and C(=O)$NHR^6$; Ring B is

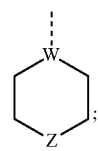

W is N; and Z is O or S.

In another embodiment, X is O or NH, Y is O or NH, $R^3$ is hydrogen and $R^1$ is a pyrimidine ring which is substituted by 0, 1, or 2 substituents $R^2$ independently selected from the group consisting of $C_1$-$C_2$-alkyl and C(=O)NH $C_1$-$C_2$-alkyl; Ring B is

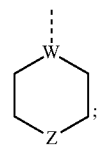

W is N; and Z is O or S.

In one embodiment of compounds having formula (III-E-1) or (III-E-2),

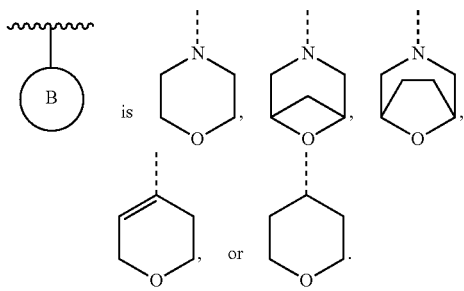

In another embodiment,

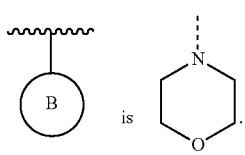

In another embodiment, the invention features a compound selected from the group of compounds listed in Table 1.

In another embodiment, the invention features a compound selected from the group of compounds listed in Table 2.

Compositions, Formulations, and Administration of Compounds

In another embodiment, the invention provides a pharmaceutical composition comprising a compound of any of the formulae described herein and a pharmaceutically acceptable excipient. In a further embodiment, the invention provides a pharmaceutical composition comprising a compound of Table 1. In a further embodiment, the composition additionally comprises an additional therapeutic agent.

According to another embodiment, the invention provides a composition comprising a compound of this invention or a pharmaceutically acceptable derivative thereof and a pharmaceutically acceptable carrier, adjuvant, or vehicle. In one embodiment, the amount of compound in a composition of this invention is such that is effective to measurably inhibit a DNA-PK in a biological sample or in a patient. In another embodiment, the amount of compound in the compositions of this invention is such that is effective to measurably inhibit DNA-PK. In one embodiment, the composition of this invention is formulated for administration to a patient in need of such composition. In a further embodiment, the composition of this invention is formulated for oral administration to a patient.

The term "patient," as used herein, means an animal, preferably a mammal, and most preferably a human.

The term "agent" is used herein to denote a chemical compound, a small molecule, a mixture of chemical compounds, a biological macromolecule, or an extract made from biological materials.

As used herein, "treatment" or "treating," or "palliating" or "ameliorating" are used interchangeably. These terms refer to an approach for obtaining beneficial or desired results including but not limited to a therapeutic benefit and/or a prophylactic benefit. By therapeutic benefit is meant any therapeutically relevant improvement in or effect on one or more diseases, conditions, or symptoms under treatment. For prophylactic benefit, the compositions may be administered to a subject at risk of developing a particular disease, condition, or symptom, or to a subject reporting one or more of the physiological symptoms of a disease, even though the disease, condition, or symptom may not have yet been manifested. These terms also mean the treatment of a disease in a mammal, e.g., in a human, including (a) inhibiting the disease, i.e., arresting or preventing its development; (b) relieving the disease, i.e., causing regression of the disease state; or (c) curing the disease.

The term "effective amount" or "therapeutically effective amount" refers to the amount of an agent that is sufficient to effect beneficial or desired results. The therapeutically effective amount may vary depending upon one or more of: the subject and disease condition being treated, the weight and age of the subject, the severity of the disease condition, the manner of administration and the like, which can readily be determined by one of ordinary skill in the art. The term also applies to a dose that will provide an image for detection by any one of the imaging methods described herein. The specific dose may vary depending on one or more of: the particular agent chosen, the dosing regimen to be followed, whether it is administered in combination with other compounds, timing of administration, the tissue to be imaged, and the physical delivery system in which it is carried.

As used herein, "administer" refers to contacting, injecting, dispensing, delivering, or applying a DNA-PK inhibitor to a subject, a genomic editing system and/or a DNA-PK inhibitor to a cell or a subject. In some embodiments, the administration is contacting a genomic editing system and/or a DNA-PK inhibitor with a cell(s). In some embodiments, the administration is delivering a genomic editing system and/or a DNA-PK inhibitor to a cell(s). In some embodiments, the administration is applying a genomic editing system and/or a DNA-PK inhibitor to a cell(s). In some embodiments, the administration is injecting a genomic editing system and/or a DNA-PK inhibitor to a cell(s). Administering can occur in vivo, ex vivo, or in vitro. Administering a genomic editing system and a DNA-PK inhibitor to a cell(s) can be done simultaneously or sequentially.

The term "acquired" in reference to a condition or disease as used herein means a disorder or medical condition which develops post-fetally; in contrast with a congenital disorder, which is present at birth. A congenital disorder may be antecedent to an acquired disorder.

The terms "congenital" or "inherited" condition or disease is a genetic disorder found in the genome of a subject that is present in a subject at birth. The "genome" as used herein includes all of the genetic material in the nucleus and the cytoplasm, and further includes the mitochondrial genome and ribosomal genome. The congenital or inherited may be expressed at any time during the subject's life, for example at birth or at adulthood.

The term "genetic disorder" or "genetic disease" includes inherited or acquired mutations in the genome of a subject that causes or may cause disease.

The terms "polymorphisms" or "genetic variations" means different forms of a gene at a genetic locus.

It will also be appreciated that certain of the compounds of the present invention can exist in free form for treatment, or where appropriate, as a pharmaceutically acceptable derivative thereof. According to the present invention, a pharmaceutically acceptable derivative includes, but is not limited to, pharmaceutically acceptable prodrugs, salts, esters, salts of such esters, or any other adduct or derivative which upon administration to a patient in need is capable of providing, directly or indirectly, a compound as otherwise described herein, or a metabolite or residue thereof. As used herein, the term "inhibitory active metabolite or residue thereof" means that a metabolite or residue thereof is also an inhibitor of DNA-PK.

As used herein, the term "pharmaceutically acceptable salt" refers to those salts which are, within the scope of sound medical judgment, suitable for use in contact with the tissues of humans and lower animals without undue toxicity, irritation, allergic response and the like.

Pharmaceutically acceptable salts are well known in the art. For example, S. M. Berge et al., describe pharmaceutically acceptable salts in detail in *J. Pharmaceutical Sciences*, 66:1-19, 1977, which is incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, $C_{1-8}$ sulfonate and aryl sulfonate.

As described above, the pharmaceutically acceptable compositions of the present invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. In Remington: *The Science and Practice of Pharmacy*, 21st edition, 2005, ed. D. B. Troy, Lippincott Williams & Wilkins, Philadelphia, and *Encyclopedia of Pharmaceutical Technology*, eds. J. Swarbrick and J. C. Boylan, 1988-1999, Marcel Dekker, New York, the contents of each of which is incorporated by reference herein, are disclosed various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraocular, intrahepatic, intralesional, epidural, intraspinal, and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

The pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutically acceptable compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutically acceptable compositions may be formulated, e.g., as micronized suspensions in isotonic, pH adjusted sterile saline or other aqueous solution, or, preferably, as solutions in isotonic, pH adjusted sterile saline or other aqueous solution, either with or without a preservative such as benzylalkonium chloride. Alternatively, for ophthalmic uses, the pharmaceutically acceptable compositions may be formulated in an ointment such as petrolatum. The pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, the pharmaceutically acceptable compositions of this invention are formulated for oral administration.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, dissolving or suspending the compound in an oil vehicle accomplishes delayed absorption of a parenterally administered compound form. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

The amount of the compounds of the present invention that may be combined with the carrier materials to produce a composition in a single dosage form will vary depending upon the host treated, the particular mode of administration. Preferably, the compositions should be formulated so that a dosage of between 0.01-100 mg/kg body weight/day of the inhibitor can be administered to a patient receiving these compositions.

Depending upon the particular proliferative condition or cancer to be treated, additional therapeutic agents, which are normally administered to treat or prevent that condition, may also be present in the compositions of this invention. As used herein, additional therapeutic agents which are normally administered to treat or prevent a particular proliferative condition or cancer are known as "appropriate for the disease, or condition, being treated." Examples of additional therapeutic agents are provided infra.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

Uses of the Compounds and Compositions

In some embodiments, provided herein are methods for sensitizing a cell to a therapeutic agent or a disease state that induces a DNA lesion comprising the step of contacting the cell with one or more DNA-PK inhibitors disclosed herein, such as those of formula (III-E-1) or (III-E-2), or pharmaceutically acceptable salts thereof.

In some embodiments, provided herein are methods for methods of potentiating a therapeutic regimen for treatment of cancer comprising the step of administering to an individual in need thereof an effective amount of a DNA-PK inhibitors disclosed herein, such as those of formula (III-E-1) or (III-E-2) or pharmaceutically acceptable salts thereof. In one aspect, the therapeutic regimen for treatment of cancer includes radiation therapy.

The DNA-PK inhibitors disclosed herein are useful in instances where radiation therapy is indicated to enhance the therapeutic benefit of such treatment. In addition, radiation therapy frequently is indicated as an adjuvant to surgery in the treatment of cancer. The goal of radiation therapy in the adjuvant setting is to reduce the risk of recurrence and enhance disease-free survival when the primary tumor has been controlled. Adjuvant radiation therapy is indicated in several diseases including colon, rectal, lung, gastroesophageal, and breast cancers as described below.

In some embodiments, another anti-cancer chemotherapeutic agent with a DNA-PK inhibitor disclosed herein are used in a therapeutic regimen for the treatment of cancer, with or without radiation therapy. The combination of a DNA-PK inhibitor disclosed herein with such other agents can potentiate the chemotherapeutic protocol. For example, the DNA-PK inhibitor disclosed herein can be administered with etoposide or bleomycin, agents known to cause DNA strand breakage.

In some embodiments, further disclosed are methods for radiosensitizing tumor cells utilizing a compound of a DNA-PK inhibitor disclosed herein A DNA-PK inhibitor that can "radiosensitize" a cell, as used herein, is defined as a molecule, preferably a low molecular weight molecule, administered to animals in therapeutically effective amount to increase the sensitivity of cells to electromagnetic radiation and/or to promote the treatment of diseases that are treatable with electromagnetic radiation (e.g., X-rays). Diseases that are treatable with electromagnetic radiation include neoplastic diseases, benign and malignant tumors, and cancerous cells.

In some embodiments, also provided herein are methods for treating cancer in an animal that includes administering to the animal an effective amount of a DNA-PK disclosed herein. In some embodiments, further provided herein are methods of inhibiting cancer cell growth, including processes of cellular proliferation, invasiveness, and metastasis in biological systems. Such methods include use of a DNA-PK inhibitor disclosed herein as an inhibitor of cancer cell growth. In some specific embodiments, the methods are employed to inhibit or reduce cancer cell growth, invasiveness, metastasis, or tumor incidence in living animals, such as mammals. The DNA-PK inhibitors disclosed herein can be used, either alone or in combination with the use of IR or one or more chemotherapeutic agents, in treating cancer or inhibiting cancer cell growth. In some embodiments, such methods are adaptable for use in assay systems, e.g., assaying cancer cell growth and properties thereof, as well as identifying compounds that affect cancer cell growth.

Tumors or neoplasms include growths of tissue cells in which the multiplication of the cells is uncontrolled and progressive. Some such growths are benign, but others are termed "malignant" and can lead to death of the organism. Malignant neoplasms or "cancers" are distinguished from benign growths in that, in addition to exhibiting aggressive cellular proliferation, they can invade surrounding tissues and metastasize. Moreover, malignant neoplasms are characterized in that they show a greater loss of differentiation (greater "dedifferentiation") and their organization relative to one another and their surrounding tissues. This property is also called "anaplasia."

Neoplasms treatable by the present invention also include solid tumors, i.e., carcinomas and sarcomas. Carcinomas include those malignant neoplasms derived from epithelial cells which infiltrate (invade) the surrounding tissues and give rise to metastases. Adenocarcinomas are carcinomas derived from glandular tissue, or from tissues which form recognizable glandular structures. Another broad category of cancers includes sarcomas, which are tumors whose cells are embedded in a fibrillar or homogeneous substance like embryonic connective tissue. The DNA-PK hibitors disclosed herein can also enables treatment of cancers of the myeloid or lymphoid systems, including leukemias, lymphomas, and other cancers that typically do not present as a tumor mass, but are distributed in the vascular or lymphoreticular systems.

DNA-PK activity can be associated with various forms of cancer in, for example, adult and pediatric oncology, growth of solid tumors/malignancies, myxoid and round cell carcinoma, locally advanced tumors, metastatic cancer, human soft tissue sarcomas, including Ewing's sarcoma, cancer metastases, including lymphatic metastases, squamous cell carcinoma, particularly of the head and neck, esophageal squamous cell carcinoma, oral carcinoma, blood cell malignancies, including multiple myeloma, leukemias, including acute lymphocytic leukemia, acute nonlymphocytic leukemia, chronic lymphocytic leukemia, chronic myelocytic leukemia, and hairy cell leukemia, effusion lymphomas (body cavity based lymphomas), thymic lymphoma lung cancer, including small cell lung carcinoma, cutaneous T cell lymphoma, Hodgkin's lymphoma, non-Hodgkin's lymphoma, cancer of the adrenal cortex, ACTH-producing tumors, nonsmall cell cancers, breast cancer, including small cell carcinoma and ductal carcinoma, gastrointestinal cancers, including stomach cancer, colon cancer, colorectal cancer, polyps associated with colorectal neoplasia, pancreatic cancer, liver cancer, urological cancers, including bladder cancer, including primary superficial bladder tumors, invasive transitional cell carcinoma of the bladder, and muscle-invasive bladder cancer, prostate cancer, malignancies of the female genital tract, including ovarian carcinoma, primary peritoneal epithelial neoplasms, cervical carcinoma, uterine endometrial cancers, vaginal cancer, cancer of the vulva, uterine cancer and solid tumors in the ovarian follicle, malignancies of the male genital tract, including testicular cancer and penile cancer, kidney cancer, including renal cell carcinoma, brain cancer, including intrinsic brain tumors, neuroblastoma, astrocytic brain tumors, gliomas, metastatic tumor cell invasion in the central nervous system, bone cancers, including osteomas and osteosarcomas, skin cancers, including malignant melanoma, tumor progression of human skin keratinocytes, squamous cell cancer, thyroid cancer, retinoblastoma, neuroblastoma, peritoneal effusion, malignant pleural effusion, mesothelioma, Wilms's tumors, gall bladder cancer, trophoblastic neoplasms, hemangiopericytoma, and Kaposi's sarcoma. Methods to potentiate treatment of these and other forms of cancer are also disclosed herein.

Also provided herein are methods for inhibiting DNA-PK activity in a biological sample that includes contacting the biological sample with a compound or composition of the invention. The term "biological sample," as used herein, means a sample outside a living organism and includes, without limitation, cell cultures or extracts thereof; biopsied material obtained from a mammal or extracts thereof; and blood, saliva, urine, feces, semen, tears, or other body fluids or extracts thereof. Inhibition of kinase activity, particularly DNA-PK activity, in a biological sample is useful for a variety of purposes known to one of skill in the art. Examples of such purposes include, but are not limited to, biological specimen storage and biological assays. In one embodiment, the method of inhibiting DNA-PK activity in a biological sample is limited to non-therapeutic methods.

In some embodiments, this disclosure provides methods, compositions and kits for editing a target genome, e.g., by correcting a mutation. Such methods, compositions and kits can increase genome editing efficiency by the use of a DNA-PK inhibitor.

A genomic editing system can stimulate or induce a DNA break(s), such as DSB(s) at the desired locus in the genome (or target genomic region). The creation of DNA cleavage prompts cellular enzymes to repair the site of break through either the error prone NHEJ pathway or through the error-free HDR pathway. In NHEJ, the DNA lesion is repaired by fusing the two ends of the DNA break in a series of enzymatic processes involving Ku70/80 heterodimer and DNA dependent protein kinase (DNA-PK) enzymes. The repair mechanism involves tethering and alignment of two DNA ends, resection, elongation and ligation (Rouet et al.; Dexheimer T. DNA repair pathways and mechanisms. In: Mathews L, Cabarcas S, Hurt E, editors. DNA repair of cancer stem cells. Dordrecht: Springer; 2013. p. 19-32.) resulting in the formation of small insertion or deletion mutations (indels) at the break site. Indels introduced into the coding sequence of a gene can cause either premature stop codon or frame-shift mutations that lead to the production of nonfunctional, truncated proteins. The mechanism of HDR pathway is less understood and involves a different set of repair proteins such as Rad51 that stimulate strand invasion by a donor repair template for base insertion or gene replacement. Hence, HDR allows introduction of exogenous DNA template to obtain a desired outcome of DNA editing within a genome and can be a powerful strategy for translational disease modeling and therapeutic genome editing to restore gene function.

Of the two DNA repair pathways, NHEJ occurs at a much higher frequency and reports of more than 70% efficiency can be achieved even in neurons (Swiech et al., "In vivo interrogation of gene function in the mammalian brain using CRISPR-Cas9," *Nat Biotechnol.* 2015 January; 33(1):102-62014). The HDR gene correction however, occurs at very low frequency and during S and G2 phase when DNA replication is completed and sister chromatids are available to serve as repair templates (Heyer et al., Regulation of homologous recombination in eukaryotes. Annual Review of Genetics 44:113-139, 2010). Since NHEJ occurs throughout the cell cycle, in competition and is favored over HDR during the S and G2 phase, targeted insertion through the HDR pathway remains a challenge and a focus of continued studies.

DNA protein-kinase (DNA-PK) plays a role in various DNA repair processes. DNA-PK participates in DNA double-stranded break repair through activation of the non-homologous end-joining (NHEJ) pathway. NHEJ is thought to proceed through three steps: recognition of the DSBs, DNA processing to remove non-ligatable ends or other forms of damage at the termini, and finally ligation of the DNA ends. Recognition of the DSB is carried out by binding of the Ku heterodimer to the ragged DNA ends followed by recruitment of two molecules of DNA-dependent protein kinase catalytic subunit (DNA-PKcs) to adjacent sides of the DSB; this serves to protect the broken termini until additional processing enzymes are recruited. Recent data supports the hypothesis that DNA-PKcs phosphorylates the processing enzyme, Artemis, as well as itself to prepare the DNA ends for additional processing. In some cases DNA polymerase may be required to synthesize new ends prior to the ligation step. The auto-phosphorylation of DNA-PKcs is believed to induce a conformational change that opens the central DNA binding cavity, releases DNA-PKcs from DNA, and facilitates the ultimate re-ligation of the DNA ends.

In some embodiments, this disclosure provides methods, compositions, and kits to enhance gene editing, in particular increasing the efficiency of repair of DNA break(s) via a HDR pathway, or the efficiency of inhibiting or suppressing repair of DNA break(s) via a NHEJ pathway, in genome editing systems, including CRISPR-based HDR repair in cells. While not being bound by a particular theory, it is believed that a genome editing system administered to a cell(s) interacts with a nucleic acid(s) of the target gene, resulting in or causing a DNA break; such DNA break is repaired by several repair pathways, e.g., HDR, and a DNA-PK inhibitor administered to a cell(s) inhibits, blocks, or suppresses a NHEJ repair pathway, and the frequency or efficiency of HDR DNA repair pathway can be increased or promoted.

The interaction between a genome editing system with a nucleic acid(s) of the target gene can be hybridization of at least part of the genome editing system with the nucleic acid(s) of the target gene, or any other recognition of the nucleic acid(s) of the target gene by the genone editing system. In some embodiments, such interaction is a protein-DNA interactions or hybridization between base pairs.

In some embodiments, this disclosure provides methods of editing one or more target genomic regions in a cell(s) by administering to the cell(s) a genome editing system and a DNA-PK inhibitor. The editing can occur simultaneously or sequentially. Editing of the one or more target genomic regions includes any kind of genetic manipulations or engineering of a cell's genome. In some embodiments, the editing of the one or more target genomic regions can include insertions, deletions, or replacements of genomic regions in a cell(s). Genomic regions comprise the genetic material in a cell(s), such as DNA, RNA, polynucleotides, and oligonucleotides. Genomic regions in a cell(s) also comprise the genomes of the mitochondria or chloroplasts contained in a cell(s).

In some embodiments, the insertions, deletions or replacements can be either in a coding or a non-coding genomic region, in intronic or exonic regions, or any combinations thereof including overlapping or non-overlapping segments thereof. As used herein, a "non-coding region" refers to genomic regions that do not encode an amino acid sequence. For example, non-coding regions include introns. Coding regions refer to genomic regions that code for an amino acid sequence. For example, coding regions include exons.

In some embodiments, the editing of one or more target genomic regions can occur in any one or more target regions in a genome of a cell(s). In some embodiments, the editing of one or more target genomic regions can occur, for example, in an exon, an intron, a transcription start site, in a promoter region, an enhancer region, a silencer region, an insulator region, an antirepressor, a post translational regulatory element, a polyadenylation signal (e.g. minimal poly A), a conserved region, a transcription factor binding site, or any combinations thereof.

In some embodiments, administration to a cell(s) with a DNA-PK inhibitor and a genomic editing system results in increased targeted genome editing efficiency as compared to conditions in which a DNA-PK inhibitor and a genomic editing system is not administered to a cell(s). In some embodiments, the increased editing efficiency is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s). The efficiency of genomic editing can be measured by any method known in the art, for example, by any method that ascertains the frequency of targeted polynucleotide integration or by measuring the frequency of targeted mutagenesis. Targeted polynucleotide integrations can also result in alteration or replacement of a sequence in a genome, chromosome or a region of interest in cellular chromatin. Targeted polynucleotide integrations can result in targeted mutations including, but not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

In some embodiments, the methods of editing one or more target genomic regions in a cell(s) involve administering to the cell(s) a genome editing system and a DNA-PK inhibitor. In some embodiments, the cell(s) is synchronized at the S or the G2 cell cycle phase. Synchronization of the cell(s) at the S or G2 cell cycle phase can be achieved by any method known in the art. As a non-limiting example, agents that can be used to synchronize a cell(s) at the S or G2 cell cycle phase include aphidicolin, dyroxyurea, lovastatin, mimosine, nocodazole, thymidine, or any combinations thereof. (See, Lin et al. "Enhanced homology-directed human genome engineering by controlled timing of CRISPR/Cas9 delivery," *Elife*. 2014 Dec. 15; 3). In some embodiments, the agents for cell synchronization can be administered at any time during the gene-editing process. In some embodiments, a cell(s) can be synchronized at the S or the G2 phase of the cell cycle before, during, or after administering to a cell(s) a genome editing system and/or a DNA-PK inhibitor.

In some embodiments, the methods of editing one or more target genomic regions in a cell(s) by administering to the cell(s) a genome editing system and a DNA-PK inhibitor results in increased cell survival in comparison to conditions in which a genome editing system and a DNA-PK inhibitor were not administered to a cell(s), or in comparison to conditions in which only a gene editing system is contacted or administered into a cell(s) and not a DNA-PK inhibitor.

In some embodiments, provided herein are methods of repairing a DNA break in one or more target genomic regions via an HDR pathway. The administering to a cell(s) a genome editing system and a DNA-PK inhibitor results in a DNA break of a targeted region of the genome, and the DNA break is subsequently repaired, at least in part, by a HDR pathway. These methods result in increased amounts of HDR-mediated repair (e.g. HDR pathway) in the one or more target genomic regions resulting in greater efficiency of HDR-mediated repair as compared to conditions in which a DNA-PK inhibitor and a genomic editing system is not administered to a cell(s). In some embodiments, the efficiency of HDR pathway mediated repair of the DNA break is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s). The efficiency of HDR pathway mediated repair can be measured by any method known in the art, for example, by ascertaining the frequency of targeted polynucleotide integration or by measuring the frequency of targeted mutagenesis.

In some embodiments, the methods herein provide for repairing the DNA break by increasing the efficiency of the HDR pathway.

The HDR pathway can be "canonical" or "alternative." "HDR" (homology directed repair) refers to a specialized form of DNA repair that takes place, for example, during repair of double-strand breaks or a DNA nick in a cell(s). HDR of double stranded breaks is generally based on nucleotide sequence homology, uses a "donor" molecule to template repair of a "target" molecule (e.g., the one that experienced the double-strand break), and can lead to the transfer of genetic information from the donor to the target. Canonical HDR of double stranded breaks is generally based on BRCA2 and RAD51 and typically employs a dsDNA donor molecule. Non-canonical, or "alternative," HDR is an HDR mechanism that is suppressed by BRCA2, RAD51, and/or functionally-related genes. Alternative HDR may use a ssDNA or nicked dsDNA donor molecule. See, for example, WO 2014172458.

In some embodiments, the methods of repairing a DNA break in one or more target genomic regions via an HDR pathway by administering to the cell(s) a genome editing system and a DNA-PK inhibitor result in increased cell survival in comparison to conditions in which a genome editing system and a DNA-PK inhibitor are not administered to a cell(s), or in comparison to conditions in which only a gene editing system is administered to a cell(s) and not a DNA-PK inhibitor.

In some embodiments, provided herein are methods of inhibiting or suppressing NHEJ-mediated repair of a DNA break in one or more target genomic regions in a cell(s). In some embodiments, the inhibiting or suppressing of NHEJ-mediated repair of a DNA break is performed by inhibiting or suppressing the NHEJ pathway. The NHEJ pathway can be either classical ("canonical") or an alternative NHEJ pathway (alt-NHEJ, or microhomology-mediated end joining (MMEJ)). The NHEJ pathway or alt-NHEJ pathway is suppressed in a cell(s) by administering to a cell(s) a genome editing system and a DNA-PK inhibitor.

The classical NHEJ repair pathway is a DNA double stranded break repair pathway in which the ends of the double stranded break are ligated without extensive homology. Classical NHEJ repair uses several factors, including KU70/80 heterodimer (KU), XRCC4, Ligase IV, and DNA protein kinases catalytic subunit (DNA-PKcs). Alt-NHEJ is another pathway for repairing double strand breaks. Alt-NHEJ uses a 5-25 base pair microhomologous sequence during alignment of broken ends before joining the broken ends. Alt-NHEJ is largely independent of KU70/80 heterodimer (KU), XRCC4, Ligase IV, DNA protein kinases catalytic subunit (DNA-PKcs), RAD52, and ERCC1. See, Bennardo et al., "Alternative-NHEJ is a Mechanistically Distinct Pathway of Mammalian Chromosome Break Repair," *PLOS Genetics*, Jun. 27, 2008.

In some embodiments, the methods of inhibiting or suppressing NHEJ-mediated repair of a DNA break via the NHEJ pathway in one or more target genomic regions in a cell(s) by inhibiting or suppressing the NHEJ pathway though the administering to a cell(s) a genomic editing system and a DNA-PK inhibitor result in increased efficiency of inhibiting or suppressing the NHEJ-mediated repair of the DNA break in comparison to a cell(s) that have not received a genomic editing system and a DNA-PK inhibitor, or in comparison to a condition in which a cell(s)

receives a genomic editing system and not a DNA-PK inhibitor. In some embodiments, the increased efficiency of inhibiting or suppressing repair of a DNA break via the NHEJ pathway by contacting a cell(s) with a DNA-PK inhibitor and a genome editing system is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s). The efficiency inhibiting or suppressing repair of a DNA break via the NHEJ pathway can be measured by any method known in the art, for example, by ascertaining the frequency of targeted polynucleotide integration or by measuring the frequency of targeted mutagenesis.

In some embodiments, the methods of inhibiting or suppressing NHEJ-mediated repair of a DNA break in one or more target genomic regions in a cell(s) by inhibiting or suppressing the NHEJ pathway though the administering to a cell(s) a genomic editing system and a DNA-PK inhibitor result in increased cell survival in comparison to conditions in which a genome editing system and a DNA-PK inhibitor were not contacted or administered to a cell(s), or in comparison to conditions in which only a gene editing system is contacted or administered into a cell(s) and not a DNA-PK inhibitor.

The DNA break can be a double stranded break (DSB) or two single stranded breaks (e.g. two DNA nicks). The DSB can be blunt ended or have either a 5' or 3' overhang, if the strands are each cleaved too far apart, the overhangs will continue to anneal to each other and exist as two nicks, not one DSB.

In some embodiments, provided herein are methods of modifying expression of one or more genes (a target gene(s)), and/or corresponding or downstream proteins, by administering to a cell(s) a genome editing system and a DNA-PK inhibitor. In some embodiments, the genome editing system can create, for example, insertions, deletions, replacements, modification or disruption in a target genomic region(s) of a target gene(s) of the cell(s), resulting in modified expression of the target gene(s). In some embodiments, the insertion, deletions, replacement, modification or disruption can result in targeted expression of a specific protein, or group of proteins, or of downstream proteins. In some embodiments, the genome editing system can create insertions, deletions or replacements in non-coding regions or coding regions. In some embodiments, the genome editing system can create insertions, deletions, replacements, modification or disruption in a promoter region, enhancer region, and/or any other gene regulatory element, including an exon, an intron, a transcription start site, a silencer region, an insulator region, an antirepressor, a post translational regulatory element, a polyadenylation signal (e.g. minimal poly A), a conserved region, a transcription factor binding site, or any combinations thereof. In some embodiments, the genome editing system can create the insertions, deletions, replacements, modification or disruption in more than one target region, simultaneously or sequentially. In some embodiments, administering to a cell(s) with a genome editing system and a DNA-PK inhibitor can allow for targeted modified gene expression in the cell(s). Such targeted modified gene expression can lead to expression of specific proteins and downstream proteins thereof.

In some embodiments, the expression of a downstream gene and/or protein is increased by at least 10%, 20%, 30%, 40%, 50%, 60%, 70%, 80%, 90%, 1, 1.5-fold, 2-fold, 2.5-fold, 3-fold, 3.5-fold, 4-fold, 4.5-fold, 5-fold, or 10-fold in comparison to a condition in which a DNA-PK inhibitor and a genome editing system is not administered to a cell(s), or compared to a condition in which only a genome editing system and not a DNA-PK inhibitor is administered to a cell(s).

In some embodiments, the gene expression of a downstream gene and/or protein is decreased by at least 10%, 20%, 30%, 40%, 50%, 60%, 70%, 80%, 90%, 95%, 96%, 97%, 98%, or 99% in comparison to a condition in which a DNA-PK inhibitor and a genome editing system is not administered to a cell(s), or compared to a condition in which only a genome editing system and not a DNA-PK inhibitor is administered to a cell(s).

The cell of the methods herein can be any cell. In some embodiments, the cell is a vertebrate cell. In some embodiments, the vertebrate cell is a mammalian cell. In some embodiment, the vertebrate cell is a human cell.

The cell can be any kind of cell at any developmental stage. In some embodiments, the cell can be a differentiated cell, a totipotent stem cell, a pluripotent stem cell, an embryonic stem cell, an embryonic germ cell, an adult stem cell, a precursor cell, an induced pluripotent stem cell, or any combinations thereof. A differentiated cell is a specialized cell that performs a specific function in a tissue. A totipotent stem cell is an undifferentiated cell from an embryo, fetus or adult that can divide for extended periods and has the capability of differentiating into any cell type of any of the three germ layers of an organism. A pluripotent stem cell is an undifferentiated cell from an embryo, fetus or adult that can divide for extended periods and has the capability of differentiating into any cell type of an organism except extra-embryonic tissue or the placenta. An embryonic stem cell is an undifferentiated stem cell that is found in the inner cell mass of an embryo and has the capability to differentiate into any type of cell of any of the three germ layers. An embryonic germ cell is an embryonic cell that can give rise to reproductive cells, such as sperm cells or egg cells. An adult stem cell is an undifferentiated cell that is found in differentiated tissue, is capable of self-renewal and can differentiate into any of the cells of the tissue in which it resides. A precursor or progenitor cell is a partially differentiated cell which typically can only differentiate into one kind of cell (e.g. a unipotent cell). An induced pluripotent stem cell is a kind of pluripotent stem cell that is generated from an adult differentiated or partially differentiated cell. See, for example, WO/2010/017562.

As used herein, the singular form "a", "an" and "the" include plural references unless the context clearly dictates otherwise. For example, the term "a cell" includes a plurality of cells, including mixtures thereof. For example "one or more cells" and "a cell(s)" are interchangeably used herein. Similarly, "one or more target genomic regions" and "a target genomic region(s)" are interchangeably used herein.

The terms, "approximately" and "about" are used interchangeably herein. The term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

The terms "polynucleotide", "nucleotide", "nucleotide sequence", "nucleic acid" and "oligonucleotide" are used interchangeably. They refer to a polymeric form of nucleotides of any length, either deoxyribonucleotides (DNA) or ribonucleotides (RNA), or analogs thereof. Polynucleotides may have any three dimensional structure, and may perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers. A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term "ssDNA" means a single stranded DNA molecule. The term "ssODN" means single stranded oligodeoxynucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselerloate, phosphorodiselenoate, phosphoroanilothioate, phoshoraniladate, phosphoronmidate, and the like. An oligonucleotide can include a label for detection, if desired.

The term "synthetic RNA" refers to RNA that is engineered or non-naturally occurring.

As used herein the term "wild type" is a term of the art understood by skilled persons and means the typical form of an organism, strain, gene or characteristic as it occurs in nature as distinguished from mutant or variant forms.

The terms "non-naturally occurring" or "engineered" are used interchangeably and indicate the involvement of the hand of man. The terms, when referring to nucleic acid molecules or polypeptides mean that the nucleic acid molecule or the polypeptide is at least substantially free from at least one other component with which they are naturally associated in nature and as found in nature.

"Complementarity" refers to the ability of a nucleic acid to form hydrogen bond(s) with another nucleic acid by either traditional Watson-Crick or other non-traditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%. 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "expression" refers to the process by which a polynucleotide is transcribed from a DNA template (such as into mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

The terms "polypeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified; for example, disulfide bond formation, glycosylation, lipidation, acetylation, phosphorylation, or any other manipulation, such as conjugation with a labeling component. As used herein the term "amino acid" includes natural and/or unnatural or synthetic amino acids, including glycine and both the D or L optical isomers, and amino acid analogs and peptidomimetics.

A "viral vector" is defined as a recombinantly produced virus or viral particle that comprises a polynucleotide to be delivered into a host cell, either in vivo, ex vivo or in vitro. Examples of viral vectors include retroviral vectors, adeno-viral vectors, adeno-associated virus vectors, adenoviral vectors, lentiviral vectors, herpes simplex viral vectors, and chimeric viral vectors and the like. In some embodiments where gene transfer is mediated by a retroviral vector, a vector construct refers to the polynucleotide comprising the retroviral genome or part thereof.

Some embodiments of the disclosure relate to vector systems comprising one or more vectors, or vectors as such. Vectors can be designed for expression of CRISPR transcripts (e.g. nucleic acid transcripts, proteins, or enzymes) in prokaryotic or eukaryotic cells. For example, CRISPR transcripts can be expressed in bacterial cells such as *Escherichia coli*, insect cells (using baculovirus expression vectors), yeast cells, or mammalian cells.

The cells can be primary cells, induced pluripotent stem cells (iPSCs), embryonic stem cells (hESCs), adult stem cells, progenitor cells or cell lines. "Primary cells" are cells taken directly from living tissue and placed in vitro for growth. Primary cells have few population doublings, and have a finite lifespan for population doublings in vitro. "Stem cells," "embryonic stem cells," and "induced pluripotent stem cells," are unspecialized and undifferentiated cells capable of self-renewal and having the potential to differentiate into cells of different types with specialized function. "Cell lines" include cell cultures that are derived from one cell type or a set of cells of the same type which can proliferate indefinitely. Non-limiting examples of mammalian cell lines can include CD34 cells, 293 cells, HEK cells, CHO cells, BHK cells, CV-1 cells, Jurkat cells, HeLa cells, or any variants thereof.

In some embodiments, a vector is capable of driving expression of one or more sequences in mammalian cells using a mammalian expression vector. Examples of mammalian expression vectors include pCDM8 and pMT2PC. When used in mammalian cells, the expression vector's control functions are typically provided by one or more regulatory elements. For example, commonly used promoters are derived from polyoma, adenovirus 2, cytomegalovirus, simian virus 40, and others disclosed herein and known in the art. Other promoters can include, for example, EF1 promoter, or EF1 alpha promoter. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I) fluorescent labels (e.g., FITC, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, "substantially pure" means an object species is the predominant species present (i.e., on a molar basis it is more abundant than any other individual species in the composition). In some embodiments, a substantially purified fraction is a composition wherein the object species comprises at least about 50 percent (on a molar basis) of all macromolecular species present.

Generally, a substantially pure composition will comprise more than about 80 percent of all macromolecular species present in the composition. In some embodiments, a substantially pure composition will comprise more than about 85%, 90%, 95%, and 99% of all macromolecular species present in the composition. In some embodiments, the object species is purified to essential homogeneity (contaminant species are not detected in the composition by conventional detection methods) wherein the composition consists essentially of a single macromolecular species.

Genome Editing System

Various types of genome engineering systems can be used. The terms "genome editing system," "gene editing system," and the like, are used interchangeably herein, and refer to a system or technology which edits a target gene or the function or expression thereof. A genome editing system comprises: at least one endonuclease component enabling cleavage of a target genomic region(s) (or target sequence(s)); and at least one genome-targeting element which brings or targets the endonuclease component to a target genomic region(s). Examples of genome-targeting element include a DNA-binding domain (e.g., zinc finger DNA-binding protein or a TALE DNA-binding domain), guide RNA elements (e.g., CRISPR guide RNA), and guide DNA elements (e.g., NgAgo guide DNA). Programmable genome-targeting and endonuclease elements enable precise genome editing by introducing DNA breaks, such as double strand breaks (DSBs) at specific genomic loci. DSBs subsequently recruit endogenous repair machinery for either non-homologous end-joining (NHEJ) or homology directed repair (HDR) to the DSB site to mediate genome editing. The "endonuclease component" comprises an endonuclease or a nucleic acid comprising a nucleotide sequence(s) encoding such endonuclease.

The term "endonuclease" refers to any wild-type, mutant, variant, or engineered enzyme capable of catalyzing the hydrolysis (cleavage) of a bond between nucleic acids within a DNA or RNA molecule. Endonucleases can recognize and cleave a DNA or RNA molecule at its target genomic regions. Examples of endonucleases include a homing endonuclease; restriction enzyme such as FokI; a chimeric Zinc-Finger nuclease (ZFN) resulting from the fusion of engineered zinc-finger domains with the catalytic domain of a restriction enzyme such as FokI; Cas enzymes, and Cpf enzymes. Chemical endonucleases in which a chemical or peptidic cleaver is conjugated either to a polymer of nucleic acids or to another DNA recognizing a specific target sequence, thereby targeting the cleavage activity to a specific sequence, are comprised in the term "endonuclease". Examples of chemical enonucleases include synthetic nucleases like conjugates of ortho-phenanthroline, a DNA cleaving molecule, and triplex-forming oligonucleotides (TFOs).

By "variant" it is intended a recombinant protein obtained by replacement of at least one residue in the amino acid sequence of the parent protein with a different amino acid.

In some embodiments, endonucleases such as ZFNs, TALENs and/or meganucleases comprise a cleavage domain and/or cleavage half-domain. The cleavage domain may be homologous or heterologous to the DNA-binding domain. For example, a zinc finger DNA-binding domain and a cleavage domain from a nuclease or a meganuclease DNA-binding domain and cleavage domain from a different nuclease can be used. Heterologous cleavage domains can be obtained from any endonuclease or exonuclease. Exemplary endonucleases from which a cleavage domain can be derived include, but are not limited to, restriction endonucleases and homing endonucleases. See, for example, WO2013/130824. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

A cleavage half-domain can be derived from any nuclease or portion thereof, as set forth above, that requires dimerization for cleavage activity. In some embodiments, two fusion proteins are required for cleavage if the fusion proteins comprise cleavage half-domains. In some embodiments, a single protein comprising two cleavage half-domains can be used. In some embodiments, the two cleavage half-domains can be derived from the same endonuclease (or functional fragments thereof). In some embodiments, each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-50 nucleotides, 5-8 nucleotides or by 15-18 nucleotides. It is noted that any integral number of nucleotides or nucleotide pairs can intervene between two target sites (e.g., from 2 to 50 nucleotide pairs or more). In some embodiments, the site of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA. See, for example, U.S. Pat. Nos. 5,356,802; 5,436,150 and 5,487,994; as well as Li et al. (1992) Proc. Natl. Acad. Sci. USA 89:4275-4279; Li et al. (1993) Proc. Natl. Acad. Sci. USA 90:2764-2768; Kim et al. (1994a) Proc. Natl. Acad. Sci. USA 91:883-887; Kim et al. (1994b) J. Biol. Chem. 269:31,978-31,982.

In some embodiments, the endonuclease component comprises a fusion protein(s) that include a cleavage domain (or cleavage half-domain) from at least one Type IIS restriction enzyme and one or more zinc finger binding domains, which may or may not be engineered. An exemplary Type IIS restriction enzyme, whose cleavage domain is separable from the binding domain, is Fok I. This particular enzyme is active as a dimer. Bitinaite et al. (1998) Proc. Natl. Acad. Sci. USA 95: 10,570-10,575. The portion of the Fok I enzyme used in such fusion proteins is considered a cleavage half-domain. Thus, for targeted double-stranded cleavage and/or targeted replacement of cellular sequences using zinc finger- or TALE-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used.

Exemplary Type IIS restriction enzymes are described in International Publication WO 07/014275, incorporated herein in its entirety. Additional restriction enzymes also contain separable binding and cleavage domains, and these are contemplated by the disclosure. See, for example, Roberts et al. (2003) Nucleic Acids Res. 31:418-420.

In certain embodiments, the cleavage domain comprises one or more engineered cleavage half-domain (also referred to as dimerization domain mutants) that minimize or prevent homodimerization, as described, for example, in U.S. Patent Publication Nos. 20050064474 and 20060188987 and WO 2013/130824. Exemplary engineered cleavage half-domains of Fok I that form obligate heterodimers include a pair in which a first cleavage half-domain includes mutations at amino acid residues at positions 490 and 538 of Fok I and a second cleavage half-domain includes mutations at amino acid residues 486 and 499. See, e.g., U.S. Patent Publication No. 2008/0131962 and 2011/0201055. Engineered cleavage half-domains described herein can be prepared using any suitable method, for example, by site-directed mutagenesis of wild-type cleavage half-domains (Fok I) as described in U.S. Patent Publication Nos. 20050064474 and 20080131962.

The term "edit", "edits," "editing," and the like refer to any kind of engineering, altering, modifying or modulating (in each case which includes, but not limited to, by means of gene knockout, gene tagging, gene disruption, gene mutation, gene insertion, gene deletion, gene activation, gene silencing or gene knock-in).

As used herein, "genetic modification," "genome editing," "genome modification," "gene modification," and "gene editing," refer to any gene addition, deletion, knockout, knock-in, tagging, mutation, activation, silencing, modification, and/or disruption to a cell's nucleotides. The cell in this context can be in vitro, in vivo, or ex vivo.

By "target genomic region," "target gene," "DNA target", "DNA target sequence", "target sequence", "target nucleotide sequence", "target-site", "target", "site of interest", "recognition site", "polynucleotide recognition site", "recognition sequence", "cleavage site" is intended a polynucleotide sequence that is recognized and cleaved by a genome editing system. These terms refer to a distinct DNA location, preferably a genomic location, at which a DNA break (cleavage) is to be induced by the genome editing system.

The aforesaid editing, including engineering, altering, modifying and modulating, can occur simultaneously or sequentially. Any genome editing system known in the art can be used. In some embodiments, the genome editing system is a meganuclease based system, a zinc finger nuclease (ZFN) based system, a Transcription Activator-Like Effector-based Nuclease (TALEN) based system, a CRISPR-based system, or NgAgo-based system.

Meganuclease-based, ZFN-based and TALEN-based each comprise at least one DNA-binding domain or a nucleic acid comprising a nucleic acid sequence(s) encoding the DNA-binding domain, and achieve specific targeting or recognition of a target genomic region(s) via protein-DNA interactions. A CRISPR-based system comprises at least one guide RNA element or a nucleic acid comprising a nucleic acid sequence(s) encoding the guide RNA element, and achieves specific targeting or recognition of a target genomic region(s) via base-pairs directly with the DNA of the target genomic region(s). A NgAgo-based system comprises at least one guide DNA element or a nucleic acid comprising a nucleic acid sequence(s) encoding the guide DNA element, and achieves specific targeting or recognition of a target genomic region(s) via base-pairs directly with the DNA of the target genomic region(s).

In some embodiments, the genome editing system is a meganuclease-based system. A meganuclease-based system employs meganucleases which are endonucleases with large (>14 bp) recognition sites, and its DNA binding domains are also responsible for cleavage of target sequences. The DNA-binding domain of meganucleases may have a double-stranded DNA target sequence of 12 to 45 bp. In some embodiments, the meganuclease is either a dimeric enzyme, wherein each meganuclease domain is on a monomer, or a monomeric enzyme comprising the two domains on a single polypeptide. Not only wild-type meganucleases but also various meganuclease variants have been generated by protein engineering to cover a myriad of unique sequence combinations. In some embodiments, chimeric meganucleases with a recognition site composed of a half-site of meganuclease A and a half-site of protein B can also be used. Specific examples of such chimeric meganucleases compriaing the protein domains of I-DmoI and I-CreI. Examples of meganucleases include homing endonucleases from the LAGLIDADG family.

The LAGLIDADG meganuclease can be I-SceI, I-ChuI, I-CreI, I-CsmI, PI-SceI, PI-TliI, PI-MtuI, I-CeuI, I-SceII, I-SceIII, HO, PI-CivI, PI-CtrI, PI-AaeI, PI-BsuI, PI-DhaI, PI-DraI, PI-MavI, PI-MchI, PI-MfuI, PI-MflI, PI-MgaI, PI-MgoI, PI-MinI, PI-MleI, PI-MuraI, PI-MshI, PI-MsmI, PI-MthI, PI-MtuI, PI-MxeI, PI-NpuI, PI-PfuI, PI-RmaI, PI-SpbI, PI-SspI, PI-FacI, PI-MjaI, PI-PhoI, PI-TagI, PI-ThyI, PI-TkoI, PI-TspI, or I-MsoI; or can be a functional mutant or variant thereof, whether homodimeric, heterodimeric or monomeric. In some embodiments, the LAGLIDADG meganuclease is a I-CreI derivative. In some embodiments, the LAGLIDADG meganuclease shares at least 80% similarity with the natural I-CreI LAGLIDADG meganuclease. In some embodiments, the LAGLIDADG meganuclease shares at least 80% similarity with residues 1-152 of the natural I-CreI LAGLIDADG meganuclease. In some embodiments, the LAGLIDADG meganuclease may consists of two monomers sharing at least 80% similarity with residues 1-152 of the natural I-CreI LAGLIDADG meganuclease linked together, with or without a linker peptide.

The "LAGLIDADG meganuclease" refers to a homing endonuclease from the LAGLIDADG family, as defined in Stoddard et al (Stoddard, 2005), or an engineered variant comprising a polypeptide sharing at least 80%, 85%, 90%, 95%, 97.5%, 99% or more identity or similarity with said natural homing endonuclease. Such engineered LAGLIDADG meganucleases can be derived from monomeric or dimeric meganucleases. When derived from dimeric meganucleases, such engineered LAGLIDADG meganucleases can be single-chain or dimeric endonucleases.

By "I-CreI" is intended the natural wild-type I-CreI meganuclease having the sequence of pdb accession code 1g9y.

The DNA recognition and cleavage functions of meganucleases are generally intertwined in a single domain. Unlike meganulceases, the DNA binding domains of ZFN-based and TALEN-based systems are distinct from the endonuclease for cleavage function. The ZFN-based system comprises: at least one zinc finger protein or a variant thereof, or a nucleic acid comprising a nucleotide sequence(s) encoding the zinc finer protein or variant thereof as its DNA-binding domain; and an endonuclease element, such as zinc finger nuclease (ZFN) or FokI cleavage domain. The zinc finder protein (ZFP) is non-naturally occurring in that it is engineered to bind to a target site of choice. See, for example, Beerli et al. (2002) Nature Biotechnol. 20: 135-141; Pabo et al. (2001) Ann. Rev. Biochem. 70:313-340; Isalan ei al. (2001) Nature Biotechnol. 19:656-660; Segal et al. (2001) Curr. Opin. Biotechnol. 12:632-637; Choo et al. (2000) Curr. Opin. Struct Biol. 10:411-416; U.S. Pat. Nos. 6,453,242; 6,534,261; 6,599,692; 6,503,717; 6,689,558; 7,030,215; 6,794,136; 7,067,317; 7,262,054; 7,070,934; 7,361,635; 7,253,273; and U.S. Patent Publication Nos. 2005/0064474; 2007/0218528; 2005/0267061.

An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, U.S. Pat. Nos. 6,453,242 and 6,534,261, incorporated by reference herein in their entireties.

Various kinds of selection methods can be used with the methods herein. Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237. In addition, enhancement of binding specificity for zinc finger binding domains has been described, for example, in WO 02/077227. In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein. Selection of target sites; ZFPs and methods for design and construction of fusion proteins (and polynucleotides encoding same) are known to those of skill in the art and described in detail in U.S. Pat. Nos. 6,140,815; 789,538; 6,453,242; 6,534,261; 5,925,523; 6,007,988; 6,013,453; 6,200,759; WO 95/19431; WO 96/06166; WO 98/53057; WO 98/54311; WO 00/27878; WO 01/60970 WO 01/88197; WO 02/099084; WO 98/53058; WO 98/53059; WO 98/53060; WO 02/016536 and WO 03/016496.

In addition, as disclosed in these and other references, zinc finger domains and/or multi-fingered zinc finger proteins may be linked together using any suitable linker sequences, including for example, linkers of 5 or more amino acids in length. See, also, U.S. Pat. Nos. 6,479,626; 6,903,185; and 7,153,949 for exemplary linker sequences 6 or more amino acids in length. The proteins described herein may include any combination of suitable linkers between the individual zinc fingers of the protein.

A Transcription Activator-Like Effector-based Nuclease (TALEN) system refers to a genome editing system that employs one or more Transcription Activator-Like Effector (TALE)-DNA binding domain and an endonuclease element, such as FokI cleavage domain. The TALE-DNA binding domain comprises one or more TALE repeat units, each having 30-38 (such as, 31, 32, 33, 34, 35, or 36) amino acids in length. The TALE-DNA binding domain may employ a full length TALE protein or fragment thereof, or a variant thereof. The TALE-DNA binding domain can be fused or linked to the endonuclease domain by a linker.

The terms "CRISPR-based system," "CRISPR-based gene editing system," "CRISPR-genome editing," "CRISPR-gene editing," "CRISPR-endonuclease based genome editing," and the like are used interchangeably herein, and collectively refer to a genome editing system that comprises one or more guide RNA elements; and one or more RNA-guided endonuclease elements. The guide RNA element comprises a targeter RNA comprising a nucleotide sequence substantially complementary to a nucleotide sequence at the one or more target genomic regions or a nucleic acid comprising a nucleotide sequence(s) encoding the targeter RNA. The RNA-guided endonuclease element comprises an endonuclease that is guided or brought to a target genomic region(s) by a guide RNA element; or a nucleic acid comprising a nucleotide sequence(s) encoding such endonuclease. Examples of such CRISPR-based gene editing system includes CRISPR-based system is a CRISPR-Cas system or a CRISPR-Cpf system.

As used herein, the terms "guide RNA element," "guide RNA", "gRNA," "gRNA molecule," and "synthetic guide RNA" are used interchangeably and refer to the polynucleotide sequence comprising a targeter RNA that hybridizes with a target nucleic sequence or a nucleic acid comprising a nucleotide sequence(s) encoding the targeter RNA. A targeter RNA of gRNA comprises a targeting domain that includes a nucleotide sequence substantially complementary to the nucleotide sequence at a target genomic region. The phrase "substantially complementary" means a degree of complementarity that is at least 60%, 65%, 70%, 75%, 80%, 85%, 90%. 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

A guide RNA element can further comprise an activator RNA that is capable of hybridizing with the targeter RNA, or a nucleic acid comprising a nucleotide sequence(s) encoding the activator RNA. The activator RNA and targeter RNA can be separate or fused as a single nucleic acid via a linker loop sequence to form a single gRNA molecule. A gRNA molecule may comprise a number of domains. For example, such gRNA comprises, for example from 5' to 3': a targeting domain (which is complementary to a target nucleic acid); a first complementarity domain; a linking domain; a second complementarity domain (which is complementary to the first complementarity domain); a proximal domain; and a optionally, a tail domain. See WO2015048557.

A "first complementarity domain" has substantial complementarity with the second complementarity domain, and may form a duplexed region under at least some physiological conditions.

A "linking domain" serves to link the first complementarity domain with the second complementarity domain of a unimolecular gRNA. The linking domain can link the first and the second complementarity domains covalently or non-covalently.

A "proximal domain" can be 3-25 nucleotides in length, or 5-20 nucleotides in length. The proximal domain can share homology with or be derived from a naturally occurring proximal domain.

A "tail domain" can be absent, or be 1, 2, 3, 4, 5, 6, 7, 8, 9, or 10 nucleotides in length. The tail domain may include sequences that are complemtary to each other and which, under at least some physiological conditions, form a duplexed region.

The guide RNA element may form a complex with an endonuclease of the RNA-guided endonuclease element, such as Cas endonuclease ("gRNA/nuclease complex"). An example of gRNA/nuclease complex is a CRISPR complex as described below with respect to a CRISR-based system. In some embodiments, the CRISPR complex comprises an endonuclease of RNA-guided endonuclease system that is complexed with the targeter RNA. In some embodiments, the CRISPR complex comprises an endonuclease of RNA-guided endonuclease system that is complexed with the targeter RNA and the activator RNA.

The targeting domain of targeter RNA promotes specific targeting or homing of a gRNA/nuclease complex to a target nucleotide sequence. In some embodiments, the targeting domain can be 10-30 bp, such as 15-25 bp, 18-22 bp, or 20 bp.

Methods for designing gRNAs are known in the art, including methods for selecting, designing, and validating target domain. See, for example, WO2015048577, Mali et al., 2013 SCIENCE 339(6121): 823-826; Hsu et al., 2013 NATBIOTECHNOL, 31(9): 827-32; Fu et al., 2014 NATBTOTECHNOL, doi: 10.1038/nbt.2808. PubMed PMID: 24463574; Heigwer et al., 2014 NAT METHODS 11 (2): 122-3. doi: 10.1038/nmeth.2812. PubMed PMID: 24481216; Bae et al., 2014 BIOTNFORMATICS PubMed PMID: 24463181; Xiao A et al., 2014 BIOINFORMATICS Pub Med PMID: 24389662.

In some embodiments, RNA-guided endonucleases, such as a Cas enzyme or protein (e.g., Type-II Cas9 protein) or Cpf enzyme or protein (e.g., Cpf1 protein) can be used. In some embodiments, a modified version of such Cas or Cpf enzyme or protein can also be used.

In some embodiments, the CRISPR-based system is a CRISPR-Cas system. The CRISPR-Cas system comprises: (a) at least one guide RNA element or a nucleic acid comprising a nucleotide sequence(s) encoding the guide RNA element, the guide RNA element comprising a targeter RNA that includes a nucleotide sequence substantially complementary to a nucleotide sequence at the one or more target genomic regions, and an activator RNA that includes a nucleotide sequence that is capable of hybridizing with the targeter RNA; and (b) a Cas protein element comprising a Cas protein or a nucleic acid comprising a nucleotide sequence encoding the Cas protein. The targeter RNA and activator RNAs can be separate or fused together into a single RNA.

In some embodiments, the CRISPR-based system includes Class 1 CRISPR and/or Class 2 CRISPR systems. Class 1 systems employ several Cas proteins together with a CRISPR RNAs (crRNA) as the targeter RNA to build a functional endonuclease. Class 2 CRISPR systems employ a single Cas protein and a crRNA as the targeter RNA. Class 2 CRISPR systems, including the type II Cas9-based system, comprise a single Cas protein to mediate cleavage rather than the multi-subunit complex employed by Class I systems. The CRISPR-based system also includes Class II, Type V CRISPR system employing a Cpf1 protein and a crRNA as the targeter RNA.

The Cas protein is a CRISPR-associated (Cas) double stranded nuclease. In some embodiments, CRISPR-Cas system comprises a Cas9 protein. In some embodiments, the Cas9 protein is SaCas9, SpCas9, SpCas9n, Cas9-HF, Cas9-H840A, FokI-dCas9, or D10A nickase. The term "Cas protein," such as Cas9 protein, include wild-type Cas protein or functional derivatives thereof (such as truncated versions or variants of the wild-type Cas protein with a nuclease activity).

In some embodiments, Cas9 proteins from species other than *S. pyogenes* and *S. thermophiles* can be used. Additional Cas9 protein species may be obtained and used herein include: *Acidovorax avenae, Actinobacillus pleuropneumonias, Actinobacillus succinogenes, Actinobacillus suis, Actinomyces* sp., *cycliphilus denitrificans, Aminomonas paucivorans, Bacillus cereus; Bacillus smithii, Bacillus thuringiensis, Bacteroides* sp., *Blastopirellula marina, Bradyrhizobium* sp., *Brevibacillus laterosporus, Campylobacter coli, Campylobacter jejuni, Campylobacter lari, Candidatus Puniceispirillum, Clostridium cellulolyticum, Clostridium perfingens, Corynebacterium accolens, Corynebacterium dolichum, Corynebacterium matruchotii, Dinoroseobacter shibae, Eubacterium dolichum, gamma proteobacterium, Gluconacetobacter diazotrophicus, Haemoplzilus parainfluenzae, Haemophilus sputorum, Helicobacter canadensis, Helicohacter cinaedi, Helicobacter mustelae, llyobacter polytropus, Kingella kingae, Lactobacillus crispatus, Listeria ivanovii, Listeria monocytogenes, Listeriaceae bacterium, Methylocystis* sp., *Methylosinus trichosporium, Mobiluncus mulieris, Neisseria bacilliformis, Neisseria cinerea, Neisseria flavescens, Neisseria lactamica, Neisseria* sp., *Neisseria wadsworthii, Nitrosomonas* sp., *Parvibaculum lavamentivorans, Pasteurella multocida, Phascolarctobacterium succinatutells, Ralstonia syzygii, Rhodopseudomonas palustris, Rhodovulum* sp., *Simonsiella muelleri, Sphingomonas* sp., *Sporolactobacillus vineae, Staphylococcus lugdunensis, Streptococcus* sp., *Subdoligranulum* sp., *Tistrella mobilis, Treponema* sp., or *Verminephrobacter eiseniae*.

In some embodiments, one or more elements of a CRISPR-based system is derived from a type I, type II, or type III CRISPR system In some embodiments, one or more elements of a CRISPR-based system is derived from a particular organism comprising an endogenous CRISPR system, such as *Streptococcus pyogenes, Staphylococcus aureus, Francisella tularensis, Prevotella* sp., *Acidaminococcus* sp., and *Lachnospiraceae* sp. In general, a CRISPR-based system is characterized by elements that promote the formation of a CRISPR complex at the target genomic regions or the site of a target sequence (also referred to as a protospacer in the context of an endogenous CRISPR system). In the context of formation of a CRISPR complex, "target sequence" refers to a sequence to which a guide sequence is designed to have substantial complementarity, where hybridization between a target sequence and a guide sequence promotes the formation of a CRISPR complex. Full complementarity is not necessarily required, provided there is sufficient complementarity to cause hybridization and promote formation of a CRISPR complex. A target sequence may comprise any polynucleotide, such as DNA or RNA polynucleotides. In some embodiments, a target sequence is located in the nucleus or cytoplasm of a cell(s). In some embodiments, the target sequence may be within an organelle of a eukaryotic cell(s), for example, mitochondrion or chloroplast.

A sequence or template that may be used for recombination into the targeted locus comprising the target sequences is referred to as an "editing template" or "editing polynucleotide" or "editing sequence". An exogenous template polynucleotide may be referred to as an editing template or donor template. In some embodiments, single stranded DNA and double stranded DNA from either synthetic or biologic origin may be used. By way of non-limiting example, suitable editing templates include ssODN, dsODN, PCR products, plasmids, and viruses including AAV, Adenovirus, Retrovirus, lentivirus, etc. Additional editing templates are also possible. In some embodiments, the recombination is homologous recombination.

In some embodiments, the CRISPR-based system is a CRISPR-Cas9 system. The targeter RNA of the CRISPR-Cas9 system comprises a CRISPR targeting RNA (crRNA) and the activator RNA of the CRISPR-Cas 9 system comprises a trans-activating CRISPR RNA (tracRNA). The Cas protein element of the CRISPR-Cas9 system employs a Cas9 protein. The crRNA and the tracrRNA can be separate or combined into a single RNA construct via a linker loop sequence. This combined RNA construct is called a single-guide RNA (sgRNA; or guide RNA).

With respect to general information on CRISPR-Cas systems, components thereof, and delivery of such components, including methods, materials, delivery vehicles, vectors, particles, AAV, and making and using thereof, including as to amounts and formulations can be found in: U.S. Pat. Nos. 8,999,641, 8,993,233, 8,945,839, 8,932,814, 8,906,616, 8,895,308, 8,889,418, 8,889,356, 8,871,445, 8,865,406, 8,795,965, 8,771,945 and 8,697,359; US Patent Publications US 2014-0310830, US 2014-0287938 A1, US 2014-0273234 A1, US2014-0273232 A1, US 2014-0273231, US 2014-0256046 A1, US 2014-0248702 A1, US 2014-0242700 A1, US 2014-0242699 A1, US 2014-0242664 A1, US 2014-0234972 A1, US 2014-0227787 A1, US 2014-0189896 A1, US 2014-0186958, US 2014-0186919 A1, US 2014-0186843 A1, US 2014-0179770 A1 and US 2014-0179006 A1, US 2014-0170753; European Patents EP 2 784 162 B1 and EP 2 771 468 B1; European Patent Applications EP 2 771 468 (EP13818570.7), EP 2 764 103 (EP13824232.6), and EP 2 784 162 (EP14170383.5); and PCT Patent Publications PCT Patent Publications WO 2014/093661, WO 2014/093694, WO 2014/093595, WO 2014/093718, WO 2014/093709, WO 2014/093622, WO 2014/093635, WO 2014/093655, WO 2014/093712, WO2014/093701, WO2014/018423, WO 2014/204723, WO 2014/204724, WO 2014/204725, WO 2014/204726, WO 2014/204727, WO 2014/204728, WO 2014/204729, and WO2016/028682.

In some embodiments, the CRISPR-based system is a CRISPR-Cpf system. The "CRISPR-Cpf system" comprises: (a) at least one guide RNA element or a nucleic acid comprising a nucleotide sequence(s) encoding the guide RNA element, the guide RNA comprising a targeter RNA having a nucleotide sequence complementary to a nucleotide sequence at a locus of the target nucleic acid; and (b) a Cpf protein element or a nucleic acid comprising a nucleotide sequence encoding the Cpf protein element.

An example of a Cpf protein element includes a Cpf1 nucleases, such as *Francisella* Cpf1 (FnCpf1) and any variants thereof. See, for example, Zetsche et al., "Cpf1 is a single RNA-guided endonuclease of a class 2 CRISPR-Cas system," *Cell*, 163(3): pages 759-71; and Fonfara et al., "The CRISPR-associated DNA-cleaving enzyme Cpf1 also processes precursor CRISPR RNA," *Nature* 532 (7600): pages, 517-21. Cpf1's preferred PAM is 5'-TTN, differing from that of Cas9 (3'-NGG) in both genomic location and GC-content. The CRISPR-Cpf system may not employ an activator RNA (tracrRNA). Both Cpf1 and its guide RNAs are in general smaller than their SpCas9 counterparts. The Cpf1 locus contains a mixed alpha/beta domain, a RuvC-I followed by a helical region, a RuvC-II and a zinc finger-like domain. The Cpf1 protein has a RuvC-like endonuclease domain that is similar to the RuvC domain of Cas9. Furthermore, Cpf1 does not have a HNH endonuclease domain, and the N-terminal of Cpf1 does not have the alfa-helical recognition lobe of Cas9. The Cpf1 loci encode Cas1, Cas2 and Cas4 proteins more similar to types I and III than from type II systems. Cpf1-family proteins can be found in many bacterial species.

Without it being hound to a particular theory, the CRISPR-Cpf system employs a Cpf1-crRNA complex which cleaves target DNA or RNA by identification of a protospacer adjacent motif 5'-YTN-3'-(where "Y" is a pyrimidine and "N" is any nucleobase) or 5'-TTN-3 in contrast to the G-rich PAM targeted by Cas9. After identification of PAM, Cpf1 introduces a sticky-end-like DNA double-stranded break of 4 or 5 nucleotides overhang.

In some embodiments, the genome editing system is a NgAgo-based system. The NgAgo-based system comprises at least one guide DNA element or a nucleic acid comprising a nucleic acid sequence(s) encoding the guide DNA element; and a DNA-guided endonuclease. The NgAgo-based system employs DNA as a guide element. Its working principle is similar to that of CRISPR-Cas9 technology, but its guide element is a segment of guide DNA (dDNA) rather than gRNA in CRISPR-Cas9 technology. An example of DNA-guided endonuclease is an Argonaute endonuclease (NgAgo) from *Natronobacterium gregoryi*. See, for example, Feng Gao et al. "DNA-guided genome editing using the *Natronobacterium gregoryi* Argonaute," *Nature Biotechnology*, (2016): doi:10.1038/nbt.3547.

By "linker," "peptide linker", "peptidic linker" or "peptide spacer" it is intended to mean a peptide sequence that allows the connection of different monomers in a fusion protein and the adoption of the correct conformation for said fusion protein activity and which does not alter the activity of either of the monomers. Peptide linkers can be of various sizes from 1, 2, 3, 4, 5, 10, 15, 20, 30, 40 to 50 amino acids as a non limiting indicative range or any intermediate value within this range.

DNA-PK Inhibitors for Increasing Genomic Editing Efficiency

Targeted genome editing efficiency can be increased by administering to a cell(s) with one or more compounds (e.g., DNA-PK inhibitors) described herein and a genome editing system. Genome editing systems suitable for use include, for example, a meganuclease based system, a zinc finger nuclease (ZFN) based system, a Transcription Activator-Like Effector-based Nuclease (TALEN) system, a CRISPR-based system or NgAgo-based system. The methods, compositions, and kits of the disclosure provide DNA-PK inhibitors and/or a genome editing system for increasing genome editing efficiency. In some embodiments, HDR genome editing efficiency is increased following administering to a cell(s) with a DNA-PK inhibitor.

In some embodiments, the genome editing system is a CRISPR-based genome editing system. The CRISPR-based genome editing system can be a CRISPR-Cas system or variants thereof. The CRISPR-Cas system can use any Cas endonucleases, such as Cas 9 endonucleases and variants thereof. Examples of Cas 9 endonucleases includes Cas9 endonucleases or variants thereof, such as SaCas9, SpCas9, SpCas9n, Cas9-HF, Cas9-H840A, FokI-dCas9, or CasD10A nickase. The Cas endonuclease can be wild type, engineered, or a nickase mutant, or any variations thereof.

In some embodiments, the CRISPR-based genome editing system includes a CRISPR sequence, a trans-activating cr (tracr) sequence, a guide sequence and a Cas endonuclease or any combinations thereof.

In some embodiments, the CRISPR-based genome editing system includes a RNA comprising a CRISPR sequence (crRNA), a RNA comprising a trans-activating cr (tracr) sequence (tracrRNA) and a Cas endonuclease or any combinations thereof.

In some embodiments, the CRISPR-based genome editing system includes a CRISPR sequence sequence, a guide sequence, and a Cas endonuclease or a Cpf endonuclease, or any combinations thereof.

In some embodiments, the CRISPR-based genome editing system is a CRISPR-Cpf system. The Cpf nuclease is a Class 2 CRISPR-Cas system endonuclease. Cpf is a single RNA-guided endonuclease. The Cpf nuclease can be wild type, engineered or a nickase mutant, or any variations thereof. See, for example, Zetsche et al., "CPF1 is a single RNA-guided endonuclease of a Class 2 CRISPR-Cas System," Cell, 163(3): 759-71. In some embodiments, the Cpf nuclease is a Cpf 1 endonuclease.

In some embodiments, the genome editing system is a meganuclease based system. Meganuclease-based genome editing uses sequence-specific endonucleases that recognize large DNA target sites (e.g. typically about >12 bp). See, for example, U.S. Pat. No. 9,365,964. Meganucleases can cleave unique chromosomal sequences without affecting overall genome integrity. In some embodiments, the meganuclease can be a homing endonuclease. In some embodiments, the meganuclease can be an intron endonuclease or an intein endonuclease. The homing endonucleases can belong to the LAGLIDADG family. The meganucleases can be wild type, engineered or a nickase mutant.

In some embodiments, the gene-editing system is a zinc finger nuclease (ZFN) based system. The ZFN is an artificial restriction enzyme engineered based on the fusion between a zing finger DNA-binding domain and a DNA-cleavage domain. See, for example, U.S. Pat. No. 9,145,565.

In some embodiments, the gene-editing system is a Transcription Activator-Like Effector-based Nuclease (TALEN). TALENs are engineered restriction enzymes that are made by the fusion of a TAL effector DNA-binding domain to a DNA cleavage domain. See, for example, U.S. Pat. No. 9,181,535.

In some embodiments, the gene editing system is an Argonaute based system. Argonaute based gene editing systems include an Argonaute derived endonuclease and a 5' phosphorylated ssDNA. In some embodiments, the phosphorylated ssDNA can be 10-40 nucleotides, 15-30 nucleotide or 18-30 nucleotides (e.g, about 24 nucleotides) in length. In some embodiments, the Argonaute endonuclease can be any endonuclease. In some embodiments, the Argonaute endonuclease is derived from *Thermus thermophiles* (TtAgo), *Pyrococcus furiosus* (PfAgo), or *Natronobacterium gregoryi* (NgAgo). In some embodiments, the *Natrobacterium gregoryi* (NgAgo) is strain 2 (i.e. *N. gregoryi* SP2). In some embodiments, the Argonaute endonuclease is NgAgo. See, for example, Gao et al., "DNA-guided genome editing using the *Natronobacterium gregoryi* Argonaute," Nature Biotechnology, May 2016.

The DNA-PK inhibitors can be any DNA-PK inhibitor. The DNA-PK inhibitor can be any compound or substance that causes inhibition of a DNA-PK. The DNA-PK inhibitor can be a compound, small molecule, antibody, or nucleotide sequence. In some embodiments, the DNA-PK inhibitors are compounds represented by Formula (III-E-1) or (III-E-2).

In some embodiments, the disclosure provides a method of editing one or more target genomic regions, the method includes administering to one or more cells that have one or more target genomic regions, a genome editing system and a compound represented by Formula (III-E-1) or (III-E-2):

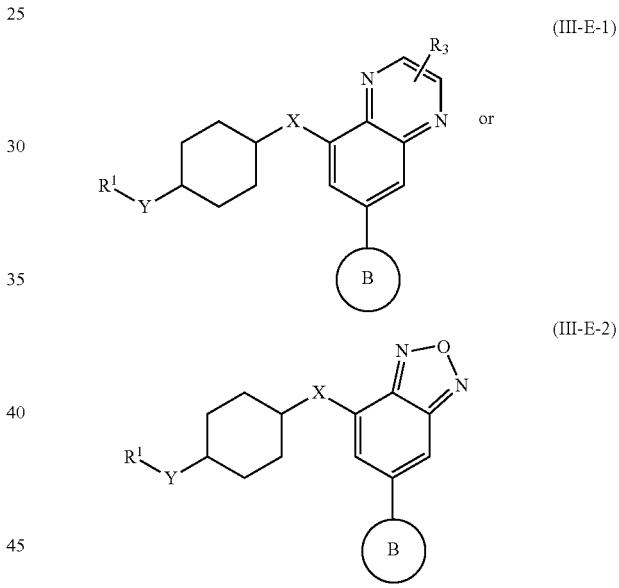

wherein:

X is O or NR; wherein R is H or $C_1$-$C_4$ alkyl;

Y is O, or NR; wherein R is H or $C_1$-$C_4$ alkyl;

$R^3$ is hydrogen, $C_{1-4}$ alkyl, or $OC_{1-2}$ alkyl;

$R^1$ is a 6-membered heteroaromatic ring containing one or two nitrogen atoms wherein the heteroaromatic ring may be substituted by 0, 1, or 2 substituents $R^2$ independently selected from the group consisting of $C_1$-$C_4$-alkyl, $C_1$-$C_4$-haloalkyl, $C(=O)NHR^{2'}$, and $NR^4R^5$; wherein $R^{2'}$ is $C_1$-$C_4$ alkyl, each $R^4$ and $R^5$ is independently H, $C_1$-$C_4$ alkyl, or $C(=O)C_1$-$C_4$ alkyl; or $R^4$ and $R^5$ together with the N atom to which they are attached form a heterocyclic ring comprising 0 or 1 additional N atom wherein said heterocyclic ring may be substituted by $C_1$-$C_4$ alkyl; and Ring B is selected from the group consisting of:

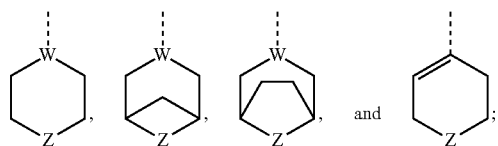

wherein W is N or $CR^3$; and Z is O or S; wherein $R^3$ is H or $C_1$-$C_4$ alkyl.

In some embodiments, the disclosure provides a method of editing one or more target genomic regions, the method includes administering to one or more cells that have one or more target genomic regions, a genome editing system and a compound represented by Formula (III-E-1) or (III-E-2), or pharmaceutically acceptable salts thereof.

In some embodiments, the disclosure also provides a method of repairing a DNA break in one or more target genomic regions via a homology directed repair (HDR) pathway, the method includes administering to one or more cells that have one or more target genomic regions, a genome editing system and a compound represented by Formula (III-E-1) or (III-E-2)), or pharmaceutically acceptable salts thereof.

The genome editing system interacts with a nucleic acid(s) of the target genomic regions, resulting in a DNA break, and wherein the DNA break is repaired at least in part via a HDR pathway.

In some embodiments, the disclosure also provides a method of inhibiting or suppressing repair of a DNA break in one or more target genomic regions via a NHEJ pathway, the method includes administering to one or more cells that have one or more target genomic regions, a genome editing system and a compound represented by Formula (III-E-1) or (III-E-2)), or pharmaceutically acceptable salts thereof.

The genome editing system interacts with a nucleic acid(s) of the one or more target genomic regions, resulting in a DNA break, and wherein repair of the DNA break via a NHEJ pathway is inhibited or suppressed.

In some embodiments, the disclosure also provides a method of modifying expression of one or more genes or proteins, the method includes administering to one or more cells that comprise one or more target genomic regions, a genome editing system and a compound represented by Formula (III-E-1) or (III-E-2), or pharmaceutically acceptable salts thereof.

The genome editing system interacts with a nucleic acid(s) of the one or more target genomic regions of a target gene(s), resulting in editing the one or more target genomic regions and wherein the edit modifies expression of a downstream gene (s) and/or protein(s) associated with the target gene(s).

In some embodiments, the DNA break includes a DNA double strand break (DSB).

In some embodiments, the efficiency of the repair of the DNA break at the target genomic regions in the one or more cells via a HDR pathway is increased as compared to that in otherwise identical cell or cells but without the compound.

In some embodiments, the efficiency of inhibiting or suppressing the repair of the DNA break at the target genomic regions in the one or more cells via a NHEJ pathway is increased as compared to that in otherwise identical cell or cells but without the compound.

In some embodiments, the efficiency is increased by at least 2-fold, 3-fold, 4-fold, 5-fold, 10-fold, 15-fold, 20-fold, 25-fold, 30-fold, 40-fold, 50-fold, or 100-fold as compared to that in otherwise identical cell or cells but without compound.

In some embodiments, the efficiency is measured by frequency of targeted polynucleotide integration. In some embodiments, the efficiency is measured by frequency of targeted mutagenesis. In some embodiments, the targeted mutagenesis comprises point mutations, deletions, and/or insertions.

In some embodiments, the expression of a downstream gene (s) and/or protein(s) associated with the target gene(s) is increased as compared to the baseline expression level in the one or more cells prior to the administration. For example, said expression is increased by at least 10%, 20%, 30%, 40%, 50%, 60%, 70%, 80%, 90%, 1-fold, 1.5-fold, 2-fold, 2.5-fold, 3-fold, 3.5-fold, 4-fold, 4.5-fold, 5-fold, or 10-fold as compared to the baseline expression level in the one or more cells prior to the administration.

In some embodiments, the expression of a downstream gene (s) and/or protein(s) associated with the target gene(s) is decreased as compared to the baseline expression level in the one or more cells prior to the administration. For example, the gene expression is decreased by at least 10%, 20%, 30%, 40%, 50%, 60%, 70%, 80%, 90%, 95%, 96%, 97%, 98%, or 99% as compared to the baseline expression level in the one or more cells prior to the administration.

In some embodiments, the expression of a downstream gene (s) and/or protein(s) associated with the target gene(s) is substantially eliminated in the one or more cells.

In some embodiments, the cell is synchronized at the S or the G2 cell cycle phase.

In some embodiments, the one or more cells that are administered or contacted with said compound have increased survival in comparison to one or more cells that have not been administered or contacted with said compound.

In some embodiments, the genome editing system and the compound are administered into the one or more cells simultaneously. In some embodiments, the genome editing system and the compound are administered into the one or more cells sequentially. In some embodiments, the genome editing system is administered into the one or more cells prior to the compound. In some embodiments, the compound is administered into the one or more cells prior to the genome editing system.

In some embodiments, the one or more cells are cultured cells. In some embodiments, the one or more cells are in vivo cells within an organism. In some embodiments, the one or more cells are ex vivo cells from an organism.

In some embodiments, the organism is a mammal. In some embodiments, the organism is a human.

In some embodiments, the genome editing system and the compound are administered via a same route. In some embodiments, the genome editing system and the compound are administered via a different route. In some embodiments, the genome editing system is administered intravenously and the compound is administered orally.

In some embodiments, the genome editing system is selected from a meganuclease based system, a zinc finger nuclease (ZFN) based system, a Transcription Activator-Like Effector-based Nuclease (TALEN) system, a CRISPR-based system, or a NgAgo-based system.

In some embodiments, the genome editing system is a CRISPR-based system. In some embodiments, the CRISPR-based system is a CRISPR-Cas system or a CRISPR-Cpf system.

In some embodiments, the CRISPR-based system is a CRISPR-Cas system and wherein the CRISPR-Cas system includes: (a) at least one guide RNA element that includes: (i) a targeter RNA that includes a nucleotide sequence substantially complementary to a nucleotide sequence at the one or more target genomic regions or a nucleic acid that includes a nucleotide sequence(s) encoding the targeter RNA; (ii) and an activator RNA that includes a nucleotide sequence that is capable of hybridizing with the targeter RNA or a nucleic acid that includes a nucleotide sequence(s) encoding the activator RNA; and (b) a Cas protein element that includes a Cas protein or a nucleic acid that includes a nucleotide sequence(s) encoding the Cas protein.

In some embodiments, the targeter RNA and activator RNA are fused as a single molecule.

In some embodiments, the Cas protein is a Type-II Cas9 protein. In some embodiments, the Cas9 protein is a SaCas9, SpCas9, SpCas9n, Cas9-HF, Cas9-H840A, FokI-dCas9, or D10A nickase, or any combinations thereof.

In some embodiments, the CRISPR-based system is a CRISPR-Cpf system and the CRISPR-Cpf system includes: (a) at least one guide RNA element or a nucleic acid that includes a nucleotide sequence(s) encoding the guide RNA element, the guide RNA that includes a targeter RNA that that includes a nucleotide sequence substantially complementary to a nucleotide sequence at the one or more target genomic regions; and (b) a Cpf protein element that includes a Cpf protein or a nucleic acid comprising a nucleotide sequence encoding the Cpf protein.

In some embodiments, the genome editing system is delivered by one or more vectors.

In some embodiments, the one or more vectors are selected from viral vectors, plasmids, or ssDNAs.

In some embodiments, the viral vectors are selected from retroviral, lentiviral, adenoviral, adeno-associated and herpes simplex viral vectors.

In some embodiments, the genome editing system is delivered by synthetic RNA.

In some embodiments, the genome editing system is delivered by a nanoformulation.

In some embodiments, a kit or composition is provided for editing one or more target genomic regions. In some embodiments, the kit or composition includes a genome editing system; and a compound represented by formula (III-E-1) or (III-E-2), or pharmaceutically acceptable salts thereof.

In some embodiments, the genome editing system of the kit or composition is a meganuclease based system, a zinc finger nuclease (ZFN) based system, a Transcription Activator-Like Effector-based Nuclease (TALEN) system, a CRISPR-based system, or NgAgo-based system. In some embodiments, the genome editing system of the kit or composition is a CRISPR-based system. In some embodiments, the CRISPR-based system of the kit or composition is a CRISPR-Cas system or a CRISPR-Cpf system.

In some embodiments, the CRISPR-based system of the kit or composition is a CRISPR-Cas system and wherein the CRISPR-Cas system includes: (a) at least one guide RNA element that includes: (i) a targeter RNA that includes a nucleotide sequence substantially complementary to a nucleotide sequence at the one or more target genomic regions or a nucleic acid that includes a nucleotide sequence(s) encoding the targeter RNA; (ii) and an activator RNA that includes a nucleotide sequence that is capable of hybridizing with the targeter RNA, or a nucleic acid that includes a nucleotide sequence(s) encoding the activator RNA; and (b) a Cas protein element that includes a Cas protein or a nucleic acid that includes a nucleotide sequence(s) encoding the Cas protein.

In some embodiments, the Cas protein of the kit or composition is a Type-II Cas9 protein. In some embodiments, the Cas9 protein of the kit or composition is a SaCas9, SpCas9, SpCas9n, Cas9-HF, Cas9-H840A, FokI-dCas9, or D10A nickase, or any combination thereof.

In some embodiments, the CRISPR-based system of the kit or composition is a CRISPR-Cpf system, and wherein the CRISPR-Cpf system includes: (a) a targeter RNA that includes a nucleotide sequence substantially complementary to a nucleotide sequence at the one or more target genomic regions, or a nucleic acid that includes a nucleotide sequence(s) encoding the targeter RNA; and (b) a Cpf protein element that includes a Cpf protein or a nucleic acid that includes a nucleotide sequence(s) encoding the Cpf protein.

In some embodiments, the genome editing system of the kit or composition is included or packaged in one or more vectors. In some embodiments, the one or more vectors are selected from viral vectors, plasmids, or ssDNAs. In some embodiments, the viral vectors are selected from the group consisting of retroviral, lentiviral, adenoviral, adeno-associated and herpes simplex viral vectors.

In some embodiments, the increased genome editing efficiency is about 1-fold, 2-fold, 3-fold, 4-fold, 5-fold, 10-fold, 15-fold, 20-fold, 25-fold, 30-fold, 40-fold, 50-fold, or 100-fold, in comparison to a condition in which a DNA-PK inhibitor and a genome editing system is not administered to a cell(s), or compared to a condition in which only a genome editing system and not a DNA-PK inhibitor is administered to a cell(s).

Use of DNA-PK Inhibitors and Genome Editing System, Kits, and Compositions Thereof Genome editing, in which particular genomic regions are precisely altered, holds great therapeutic potential.

In some embodiments, provided herein are methods for editing one or more target genomic regions, for repairing a DNA break in one or more target genomic regions via a HDR pathway, for inhibiting or suppressing NHEJ-mediated repair of a DNA break in one or more target genomic, and for modifying the expression of one or more genes or proteins via administering to a cell(s) a genome editing system and a DNA-PK inhibitor.

In some embodiments, provided herein are methods of modifying expression of one or more genes or proteins comprising administering to one or more cells that comprise one or more target genomic regions, a genome editing system and a DNA-PK inhibitor described herein, wherein the genome editing system interacts with a nucleic acid(s) of the one or more target genomic regions of a target gene(s), resulting in editing the one or more target genomic regions and wherein the edit modifies expression of a downstream gene (s) and/or protein(s) associated with the target gene(s).

The genome editing system can be any genome editing system that can edit a target genomic region in a cell(s). Exemplary genome editing systems are described in detail above and can include, for example, a meganuclease based system, a zinc finger nuclease (ZFN) based system, a Transcription Activator-Like Effector-based Nuclease (TALEN) system, a CRISPR-based system, or NgAgo-based system Editing of the one or more target genomic regions includes any kind of genetic manipulations or engineering of a cell's genome. The editing of the one or more target genomic regions can include insertions, deletions, or replacements of genomic regions in a cell(s) performed by one or more endonucleases. Genomic regions comprise the genetic material in a cell(s), such as DNA, RNA, polynucleotides, and oligonucleotides. Genomic regions in a cell(s) also comprise the genomes of the mitochondria or chloroplasts contained in a cell(s).

In some embodiments, provided herein are methods of treating a subject having a disease or condition in need of editing one or more target genomic regions in a cell(s) of the subject, comprising administering to one or more cells a genomic editing system and a DNA-PK inhibitor.

In some embodiments, the methods provided herein are used to modify expression of a gene, an RNA molecule, a protein, a group of proteins, or downstream proteins in a pathway. Such modification can be used to treat a disease, a dysfunction, abnormal organismal homeostasis, either acquired or inherited or those due to the aging process. As used herein, the term "modify" or "modifying" includes modulating, enhancing, decreasing, increasing, inserting, deleting, knocking-out, knocking-in, and the like.

One of skill in the art understands that diseases, either acquired or inherited, or otherwise obtained, involve a dysregulation of homeostatic mechanisms including involvement of gene or protein function. To this end, a skilled artisan can use the methods provided herein to modulate, modify, enhance, decrease, or provide an otherwise gene function in a subject.

Modifying expression of gene and consequent protein expression in a cell(s) can be achieved by the methods provided herein, for example, by specific editing (e.g., replacing, inserting or deleting, any combinations thereof) a nucleic acid sequence in any of an exon, an intron, a transcription start site, a promoter region, an enhancer region, a silencer region, an insulator region, an antirepressor, a post translational regulatory element, a polyadenylation signal (e.g. minimal poly A), a conserved region, a transcription factor binding site, or any combinations thereof.

In some embodiments, the methods, kits and compositions provided herein are used to treat a subject that has cancer. The method of treating a subject having a cancer or cancer related condition comprises administering to a cell(s) of the subject a DNA-PK inhibitor and a genome editing system. The administration of the DNA-PK inhibitor and the genome editing system can be in vivo or ex vivo.

The cancer can be of any kind of cancer. Cancer includes solid tumors such as breast, ovarian, prostate, lung, kidney, gastric, colon, testicular, head and neck, pancreas, brain, melanoma, and other tumors of tissue organs and cancers of the blood cells, such as lymphomas and leukemias, including acute myelogenous leukemia, chronic lymphocytic leukemia, T cell lymphocytic leukemia, and B cell lymphomas. The cancers can include melanoma, leukemia, astocytoma, glioblastoma, lymphoma, glioma, Hodgkins lymphoma, chronic lymphocyte leukemia and cancer of the pancreas, breast, thyroid, ovary, uterus, testis, pituitary, kidney, stomach, esophagus and rectum.

In some embodiments, the methods, kits and compositions provided herein are used to treat a subject having any one or more of the following cancers: Acute lymphoblastic leukemia (ALL), Acute myeloid leukemia, Adrenocortical carcinoma, AIDS-related cancers, AIDS-related lymphoma, Anal cancer, Appendix cancer, Astrocytoma, childhood cerebellar or cerebral, Basal-cell carcinoma, Bile duct cancer, extrahepatic (see cholangiocarcinoma), Bladder cancer, Bone tumor, osteosarcoma/malignant fibrous histiocytoma, Brainstem glioma, Brain cancer, Brain tumor, cerebellar astrocytoma, Brain tumor, cerebral astrocytoma/malignant glioma, Brain tumor, ependymoma, Brain tumor, medulloblastoma, Brain tumor, supratentorial primitive neuroectodermal tumors, Brain tumor, visual pathway and hypothalamic glioma, Breast cancer, Bronchial adenomas/carcinoids, Burkitt's lymphoma, Carcinoid tumor, childhood, Carcinoid tumor, gastrointestinal, Carcinoma of unknown primary, Central nervous system lymphoma, primary, Cerebellar astrocytoma, childhood, Cerebral astrocytoma/malignant glioma, childhood, Cervical cancer, Childhood cancers, Chondrosarcoma, Chronic lymphocytic leukemia, Chronic myelogenous leukemia, Chronic myeloproliferative disorders, Colon cancer, Cutaneous T-cell lymphoma, Desmoplastic small round cell tumor, Endometrial cancer, Ependymoma, Epitheliod Hemangioendothelioma (EHE), Esophageal cancer, Ewing's sarcoma in the Ewing family of tumors, Extracranial germ cell tumor, Extragonadal germ cell tumor, Extrahepatic bile duct cancer, Eye cancer, intraocular melanoma, Eye cancer, retinoblastoma, Gallbladder cancer, Gastric (stomach) cancer, Gastrointestinal carcinoid tumor, Gastrointestinal stromal tumor (GIST), Germ cell tumor: extracranial, extragonadal, or ovarian, Gestational trophoblastic tumor, Glioma of the brain stem, Glioma, childhood cerebral astrocytoma, Glioma, childhood visual pathway and hypothalamic, Gastric carcinoid, Hairy cell leukemia, Head and neck cancer, Heart cancer, Hepatocellular (liver) cancer, Hodgkin lymphoma, Hypopharyngeal cancer, Hypothalamic and visual pathway glioma, childhood, Intraocular melanoma, Islet cell carcinoma (endocrine pancreas), Kaposi sarcoma, Kidney cancer (renal cell cancer), Laryngeal cancer, Leukaemias, Leukaemia, acute lymphoblastic (also called acute lymphocytic leukaemia), Leukaemia, acute myeloid (also called acute myelogenous leukemia), Leukaemia, chronic lymphocytic (also called chronic lymphocytic leukemia), Leukemia, chronic myelogenous (also called chronic myeloid leukemia), Leukemia, hairy cell, Lip and oral cavity cancer, Liposarcoma, Liver cancer (primary), Lung cancer, non-small cell, Lung cancer, small cell, Lymphomas, AIDS-related Lymphoma, Burkitt Lymphoma, cutaneous T-Cell Lymphoma, Hodgkin Lymphomas, Non-Hodgkin (an old classification of all lymphomas except Hodgkin's) Lymphoma, primary central nervous system Macroglobulinemia, Waldenström, Male breast cancer, Malignant fibrous histiocytoma of bone/osteosarcoma, Medulloblastoma, childhood Melanoma, Melanoma, intraocular (eye), Merkel cell cancer, Mesothelioma, adult malignant Mesothelioma, childhood Metastatic squamous neck cancer with occult primary, Mouth cancer, Multiple endocrine neoplasia syndrome Multiple myeloma/plasma cell neoplasm, Mycosis fungoides, Myelodysplastic syndromes, Myelodysplastic/myeloproliferative diseases, Myelogenous leukemia, chronic Myeloid leukemia, adult acute Myeloid leukemia, childhood acute Myeloma, multiple (cancer of the bone-marrow), Myeloproliferative disorders, chronic Myxoma, Nasal cavity and paranasal sinus cancer, Nasopharyngeal carcinoma, Neuroblastoma, Non-Hodgkin lymphoma, Non-small cell lung cancer, Oligodendroglioma, Oral cancer, Oropharyngeal cancer, Osteosarcoma/malignant fibrous histiocytoma of bone, Ovarian cancer, Ovarian epithelial cancer (surface epithelial-stromal tumor), Ovarian germ cell tumor, Ovarian low malignant potential tumor, Pancreatic cancer, islet cell Pancreatic cancer, Paranasal sinus and nasal cavity cancer, Parathyroid cancer, Penile cancer, Pharyngeal cancer, Pheochromocytoma, Pineal astrocytoma, Pineal germinoma, Pineoblastoma and supratentorial primitive neuroectodermal tumors, Pituitary adenoma, Plasma cell neoplasia/Multiple myeloma, Pleuropulmonary blastoma, Primary central nervous system lymphoma, Prostate cancer, Rectal cancer, Renal cell carcinoma (kidney cancer), Renal pelvis and ureter caner, transitional cell cancer, Retinoblastoma, Rhabdomyosarcoma, Salivary gland cancer, Sarcoma, Ewing family of tumors, Kaposi Sarcoma, soft tissue Sarcoma, uterine sarcoma, Sézary syndrome, Skin cancer (non-melanoma), Skin cancer (melanoma), Skin carcinoma, Merkel cell, Small cell lung cancer, Small intestine cancer, Soft tissue sarcoma, Squamous cell carcinoma—see skin cancer (non-melanoma), Squamous neck cancer with occult primary, metastatic, Stomach cancer, Supratentorial primitive neuroectodermal tumor, T-Cell lymphoma, cutaneous (Mycosis Fungoides and Sézary syndrome), Testicular cancer, Throat cancer, Thymoma, Thymoma and thymic carcinoma, Thyroid cancer, Thyroid cancer, Transitional cell cancer of the renal pelvis and ureter, Gestational Trophoblastic tumor, Unknown primary site carcinoma of adult, Unknown primary site cancer of, childhood, Ureter and renal pelvis, transitional cell cancer, Urethral cancer, Uterine cancer, endometrial cancer, Uterine sarcoma, Vaginal cancer, Visual pathway and hypothalamic glioma, Vulvar cancer, Waldenström macroglobulinemia, or Wilms tumor (kidney cancer).

In some embodiments, exemplary target genes associated with cancer include ABL1, ABL2, ACSL3, AF15Q14, AF1Q, AF3p21, AF5q31, AKAP9, A T1, AKT2, ALDH2, AL, AL017, APC, ARHGEF12, ARHH, ARID1A, ARID2, ARNT, ASPSCR1, ASXL1, ATF1, ATIC, ATM, ATRX, AXIN1, BAP1, BCL10, BCL11A, BCL11B, BCL2, BCL3, BCLS, BCL6, BCL7A, BCL9, BCOR, BCR, BHD, BIRC3, BLM, BMPRIA, BRAF, BRCA1, BRCA2, BRD3, BRD4, BRIPI, BTG1, BUB1B, Cl2orf9, C15orf21, C15orf55, C16orf75, C2orf44, CAMTA1, CANT1, CARD11, CARS, CBFA2T1, CBFA2T3, C.BFB, CBL, CBLB, CBLC, CCDC6, CCNB1IP1, CCND1, CCND2, CCND3, CCNE1, CD273, CD274, CD74, CD79A, CD79B, CDH1, CDH11, CDK12, CDK4, CDK6, CD N2A, CD N2a(p14), CD N2C, CDX2, CEBPA, CEP1, CHCHD7, CHEK2, CHIC2, CHN1, CIC, Cin A, CLTC, CLTCL1, CMKOR1, CNOT3, COL1 A1, COPEB, COX6C, CREB1, CREB3 L1, CREB3 L2, CREBBP, CRLF2, CRTC3, CTNNB1, CYLD, D10S170, DAXX, DDB2, DDIT3, DDX10, DDX5, DDX6, DEK, D1CER1, DNM2, DNMT3A, DUX4, EBFI, ECT2 L, EGFR, E1F4A2, ELF4, ELK4, ELKS, ELL, ELN, EML4, EP300, EPS 15, ERBB2, ERCC2, ERCC3, ERCC4, ERCC5, ERG, ETV1, ETV4, ETV5, ETV6, EVI1, EWSR1, EXT1, EXT2, EZH2, EZR, FACL6, FAM22A, FAM22B, FAM46C, 1ANCA, EANCC, FANCD2, FANCE, FANCF, FANCG, FBXOl 1, FBXW7, FCGR2B, FEV, FGFR1, FGFRIOP, FGFR2, FGFR3, FTI, FIIIT, FIP1 L1, FLU, FLJ27352, FLT3, FNBP1, FOXL2, FOXOIA, FOX03A, FOXP1, FSTL3, FUBP1, FUS, FVT1, GAS7, GATA1, GATA2, GATA3, GMPS, GNA11, GNAQ, GNAS, GOLGAS, GOPC, GPC3, GPHN, GRAF, H3F3A, IICMOGT-1, IIEAB, HERPUD1, IIEY1, IIIP1, HIST1IT3B, IIIST1II4I, IILF, HLXB9, HMGA1, HMGA2, HNRNPA2BI, HOOK3, HOXA11, HOXA13, HOXA9, HOXC11, HOXC13, HOXD11, HOXD13, HRAS, IIRPT2, HSPCA, HSPCB, IDH1, IDH2, IGH, IGK, IGL, IKZF1, IL2, TL21R, IL6ST, IL7R, IRF4, IRTA1, ITK, JAK1, JAK2, JAK3, JAZF1, JUN, KCNJ5, KDM5A, KDM5C, KDM6A, KDR, KIAA1549, KIF5B, KIT, KLF4, KLK2, KRAS, KTN1, LAF4, LASP1, LCK, LCP1, LCX, LHFP, LIFR, LMO1, LM02, LPP, LRIG3, LYL1, MADH4, MAF, MAFB, MALT1, MAML2, MAP2KL MAP2K2, MλP2K4, MAX, MDM2, MDM4, MDS1, MDS2, MECT1, MED12, MEN1, MET, MITF, MKL1, MLF1, MLII1, MLL, MLL2, MLL3, MLLT1, MLLT10, MLLT2, MLLT3, MLLT4, MLLT6, MLLT7, MN1, MPL, MSF, MSH2, MSH6, MSI2, MSN, MTCP1, MUC1, MUTYH, MYB, MYC, MYCL1, MYCN, MYD88, MYH11, MYH9, MYST4, NACA, NBS1, NCOA1, NCOA2, NCOA4, NDRG1, NF1, NF2, NFE2 L2, NFIB, NFKB2, NIN, NKX2-1, NONO, NOTCH I, NOTCH2, NPM1, NR4A3, NRAS, NSD1, NT5C2, NTRK1, NTRK3, NUMA1, NUP214, NUP98, OLIG2, OMD, P2RY8, PAFAH1B2, PALB 2, PAX3, PAX5, PAX7, PAX8, PBRM1, PBX1, PCM1, PCSK7, PDE4DIP, PDGFB, PDGFRA, PDGFRB, PERI, PIIF6, PHOX2B, PICALM, PIK3CA, PIK3R1, PIM1, PLAG 1, PML, PMS1, PMS2, PMX1, PNUTL1, POT1, POU2AF1, POU5F1, PPARG, PPP2R1A, PRCC, PRDM1, PRDM16, PRF1, PRKAR1 A, PRO1073, PSIP2, PTCH, PTEN, PTPN11, RAB5EP, RAC1, RAD51 L1, RAF1, RALGDS, RANBP17, RAPIGDSI, RARA, RBI, RBM15, RECQL4, REL, RET, RNF43, ROS1, RPL10, RPL22, RPL5, RPN1, RUNDC2A, RUNX1, RUNXBP2, SBDS, SDC4, SDH5, SDHB, SDHC, SDHD, SEPT6, SET, SETBP1, SETD2, SF3B1, SFPQ, SFRS3, SH2B3, SH3GL1, SIL, SLC34A2, SLC45A3, SMARCA4, SMARCB1, SMARCE1, SMO, SOCS1, SOX2, SRGAP3, SRSF2, SSI8, SS18 L1, SSH3BP1, SSX1, SSX2, SSX4, STAT3, STK11, STL, SUFU, SIJZ12, SYK, TAF15, TALI, TAL2, TCEA1, TCF1, TCF12, TCF3, TCF7 L2, TCL1A, TCL6, TERT, TET2, TFE3, TFEB, TFG, TFPT, TFRC, THRAP3, TIF1, TLX1, TLX 3, TMPRSS2, TNFAIP3, TNFRSF14, TNFRSF17, TNFRSF6, TOPI, TP53, TPM3, TPM4, TPR, TRA, TRAF7, TRB, TRD, TRIM27, TRIM33, TRIP11, TSC1, TSC2, TSHR, TTL, U2AF1, USP6, VHL, VTUA, WAS, WHSC1, WHSC1 L1, WIF1, WRN, WT1, WTX, WWTR1, XPA, XPC, XPO1, YWHAE, ZNF145, ZNF198, ZNF278, ZNF331, ZNF384, ZNF521, ZNF9, ZRSR2 or any combinations thereof.

In some embodiments, the methods provided herein are used to treat a subject that has an inherited disorder. The method of treating a subject having a genetic disease or condition or inherited disorder, comprises administering to a cell(s) of the subject a DNA-PK inhibitor and a genome editing system. The administration of or the DNA-PK inhibitor and the genome editing system can be in vivo or ex vivo.

The inherited disorder can result from mutations or duplications in chromosomal regions (e.g. from point mutations, deletions, insertions, frameshift, chromosomal duplications or deletions). The inherited disorder can be any inherited disorder.

In some embodiments, the inherited disorder is 22q11.2 deletion syndrome, Angelman syndrome, Canavan disease, Charcot-Marie-Tooth disease, Color blindness, Cri du chat, Down syndrome, Duchenne muscular dystrophy, Haemochromatosis, Haemophilia, Klinefelter syndrome, Neurofibromatosis, Phenylketonuria, Polycystic kidney disease, Prader-Willi syndrome, Sickle-cell disease, Spinal muscular atrophy, Spinal muscular atrophy, Tay-Sachs disease, Turner syndrome, a hemoglobinopathy, or any combinations thereof.

In some embodiments, the inherited disorder is 1p36 deletion syndrome, 18p deletion syndrome, 21-hydroxylase deficiency, 47 XXX (triple X syndrome), 47 XXY (Klinefelter syndrome), 5-ALA dehydratase-deficient porphyria, ALA dehydratase deficiency, 5-aminolaevulinic dehydratase deficiency porphyria, 5p deletion syndrome, Cri du chat (AKA 5p-syndrome), ataxia telangiectasia (AKA A-T), alpha 1-antitrypsin deficiency (AAT), aceruloplasminemia, achondrogenesis type II (ACG2), achondroplasia (ACH), Acid beta-glucosidase deficiency, Gaucher disease (any type, e.g. type 1, type 2, type 3), Acrocephalosyndactyly (Apert), Apert syndrome, acrocephalosyndactyly (any type, e.g., type 1, type 2, type 3, type 5), Pfeiffer syndrome, Acrocephaly, Acute cerebral Gaucher's disease, acute intermittent porphyria, (AIP) ACY2 deficiency, Alzheimer's disease (AD), Adelaide-type craniosynostosis, Muenke syndrome, Adenomatous Polyposis Coli, familial adenomatous polyposis, Adenomatous Polyposis of the Colon, familial adenomatous polyposis (ADP), adenylosuccinate lyase deficiency, Adrenal gland disorders, Adrenogenital syndrome, Adrenoleukodystrophy, androgen insensitivity syndrome (AIS), alkaptonuria (AKU), ALA dehydratase porphyria, ALA-D porphyria, ALA dehydratase deficiency, Alagille syndrome, Albinism, Alcaptonuria, alkaptonuria, Alexander disease, alkaptonuria, Alkaptonuric ochronosis, alkaptonuria, alpha-1 proteinase inhibitor disease, alpha-1 related emphysema, Alpha-galactosidase A deficiency, Fabry disease, Alström syndrome, Alexander disease (ALX), Amelogenesis imperfecta, Amino levulinic acid dehydratase deficiency, Aminoacylase 2 deficiency, Canavan disease, Anderson-Fabry disease, androgen insensitivity syndrome, Anemia, hereditary sideroblastic, X-linked sideroblastic anemiasplenic and/or familial anemia, Angiokeratoma Corporis Diffusum, Angiokeratoma diffuse, Angiomatosis retinae, von Hippel-Lindau disease, APC resistance, Leiden type, factor V Leiden thrombophilia, Apert syndrome, AR deficiency, androgen insensitivity syndrome, Charcot-Marie-Tooth disease (any type, e.g., CMT1, CMTX, CMT2, CMT4, severe early onset CMT), Arachnodactyly, Marfan syndrome, ARNSHL, Nonsyndromic deafness (autosomal recessive, autosomal dominant, x-linked, or mitochondria), Arthro-ophthalmopathy, hereditary progressive, Stickler syndrome (e.g. COL2A1, COL11A1, COL11A2, COL9A1), Arthrochalasis multiplex congenita, Ehlers-Danlos syndrome (e.g. hypermobility type, arthrochalasia type, classical type, vascular type, kyphoscoliosis type, dermatosparaxis type) Asp deficiency, Aspa deficiency, Aspartoacylase deficiency, ataxia telangiectasia, Autism-Dementia-Ataxia-Loss of Purposeful Hand Use syndrome, Rett syndrome, autosomal dominant juvenile ALS, Autosomal dominant opitz G/BBB syndrome, autosomal recessive form of juvenile ALS type 3, Amyotrophic lateral sclerosis (any type; e.g. ALS1, ALS2, ALS3, ALS4, ALS5, ALS5, ALS6, ALS7, ALS8, ALS9, ALS10, ALS11, ALS12, ALS13, ALS14, ALS15, ALS16, ALS17, ALS18, ALS19, ALS20, ALS21, ALS22, FTDALS1, FTDALS2, FTDALS3, FTDALS4, FTDALS4, IBMPFD2), Autosomal recessive nonsyndromic hearing loss, Autosomal Recessive Sensorineural Hearing Impairment and Goiter, Pendred syndrome, Alexander disease (AxD), Ayerza syndrome, familial pulmonary arterial hypertension, B variant of the Hexosaminidase GM2 gangliosidosis, Sandhoff disease, BANF-related disorder, neurofibromatosis (any type, e.g., NF1, NF2, schwannomatosis), Beare-Stevenson cutis gyrata syndrome, Benign paroxysmal peritonitis, Benjamin syndrome, beta-thalassemia, BH4 Deficiency, tetrahydrobiopterin deficiency, Bilateral Acoustic Neurofibromatosis, biotinidase deficiency, bladder cancer, Bleeding disorders, factor V Leiden thrombophilia, Bloch-Sulzberger syndrome, incontinentia pigmenti, Bloom syndrome, Bone diseases, Bourneville disease, tuberous sclerosis, Brain diseases, prion disease, breast cancer, Birt-Hogg-Dubé syndrome, Brittle bone disease, osteogenesis imperfecta, Broad Thumb-Hallux syndrome, Rubinstein-Taybi syndrome, Bronze Diabetes, hemochromatosis, Bronzed cirrhosis, Bulbospinal muscular atrophy, X-linked Spinal and bulbar muscular atrophy, Burger-Grutz syndrome, lipoprotein lipase deficiency, familial CADASIL syndrome, CGD Chronic granulomatous disorder, Campomelic dysplasia, Cancer Family syndrome, hereditary nonpolyposis colorectal cancer, breast cancer, bladder cancer, Carboxylase Deficiency, Multiple Late-Onset biotinidase deficiency, Cat cry syndrome, Caylor cardiofacial syndrome, Ceramide trihexosidase deficiency, Cerebelloretinal Angiomatosis, familial von Hippel-Lindau disease, Cerebral arteriopathy, CADASIL syndrome, Cerebral autosomal dominant ateriopathy, CADASIL syndrome, Cerebroatrophic Hyperammonemia, Rett syndrome, Cerebroside Lipidosis syndrome, Charcot disease, CHARGE syndrome, Chondrodystrophia, Chondrodystrophy syndrome, Chondrodystrophy with sensorineural deafness, otospondylomegaepiphyseal dysplasia, Chondrogenesis imperfecta, Choreoathetosis self-mutilation hyperuricemia syndrome, Lesch-Nyhan syndrome, Classic Galactosemia, galactosemia, Cleft lip and palate, Stickler syndrome, Cloverleaf skull with thanatophoric dwarfism, Thanatophoric dysplasia (e.g. type 1 or type 2), Coffin-Lowry syndrome (CLS), Cockayne syndrome, Coffin-Lowry syndrome, collagenopathy types II and XI, familial Nonpolyposis, hereditary nonpolyposis colorectal cancer, familial Colon cancer, familial adenomatous polyposis, Colorectal cancer, Complete HPRT deficiency, Lesch-Nyhan syndrome, Complete hypoxanthine-guanine phosphoribosyltransferase deficiency, Compression neuropathy, hereditary neuropathy with liability to pressure palsies, Connective tissue disease, Conotruncal anomaly face syndrome, Cooley's Anemia, beta-thalassemia, Copper storage disease, Wilson's disease, Copper transport disease, Menkes disease, Coproporphyria, hereditary coproporphyria, Coproporphyrinogen oxidase deficiency, Cowden syndrome, CPX deficiency, Craniofacial dysarthrosis, Crouzon syndrome, Craniofacial Dysostosis, Crouzon syndrome, Crohn's disease, fibrostenosing, Crouzon syndrome, Crouzon syndrome with acanthosis nigricans, Crouzonodermoskeletal syndrome, Crouzonodermoskeletal syndrome, Cockayne syndrome (CS), Cowden syndrome, Curschmann-Batten-Steinert syndrome, cutis gyrata syndrome of Beare-Stevenson, Beare-Stevenson cutis gyrata syndrome, D-glycerate dehydrogenase deficiency, hyperoxaluria, primary, Dappled metaphysis syndrome, spondyloepimetaphyseal dysplasia, Strudwick type, Dementia Alzheimer's type (DAT), Genetic hypercalciuria, Dent's disease, muscular dystrophy (e.g. Duchenne and Becker types), Deafness with goiter, Pendred syndrome, Deafness-retinitis pigmentosa syndrome, Usher syndrome, Deficiency disease, Phenylalanine Hydroxylase, Degenerative nerve diseases, de Grouchy syndrome 1, De Grouchy syndrome, Dejerine-Sottas syndrome, Delta-aminolevulinate dehydratase deficiency porphyria, Dementia, CADASIL syndrome, demyelinogenic leukodystrophy, Alexander disease, Dermatosparactic type of Ehlers-Danlos syndrome, Dermatosparaxis, inherited developmental disabilities, distal hereditary motor neuropathy (dHMN), distal hereditary motor neuropathy (e.g. DHMN-V), DHTR deficiency, androgen insensitivity syndrome, Diffuse Globoid Body Sclerosis, Krabbe disease, Di George's syndrome, Dihydrotestosterone receptor deficiency, androgen insensitivity syndrome, distal hereditary motor neuropathy, Myotonic dystrophy (type 1 or type 2), distal spinal muscular atrophy (any type, including e.g. type 1, type 2, type 3, type 4, type 5, type 6), Duchenne/Becker muscular dystrophy, Dwarfism (any kind, e.g. achondroplastic, achondroplasia, thanatophoric dysplasia), Dwarfism-retinal atrophy-deafness syndrome, Cockayne syndrome, dysmyelinogenic leukodystrophy, Alexander disease, Dystrophia myotonica, dystrophia retinae pigmentosa-dysostosis syndrome, Usher syndrome, Early-Onset familial alzheimer disease (EO-FAD), Alzheimer disease (including e.g. type 1, type 2, type 3, or type 4) Ekman-Lobstein disease, osteogenesis imperfecta, Entrapment neuropathy, hereditary neuropathy with liability to pressure palsies, erythropoietic protoporphyria (EPP), Erythroblastic anemia, beta-thalassemia, Erythrohepatic protoporphyria, Erythroid 5-aminolevulinate synthetase deficiency, X-linked sideroblastic anemia, Eye cancer, retinoblastoma FA—Friedreich ataxia, Friedreich's ataxia, FA, fanconi anemia, Facial injuries and disorders, factor V Leiden thrombophilia, FALS, amyotrophic lateral sclerosis, familial acoustic neuroma, familial adenomatous polyposis, familial Alzheimer disease (FAD), familial amyotrophic lateral sclerosis, amyotrophic lateral sclerosis, familial dysautonomia, familial fat-induced hypertriglyceridemia, lipoprotein lipase deficiency, familial, familial hemochromatosis, hemochromatosis, familial LPL deficiency, lipoprotein lipase deficiency, familial, familial nonpolyposis colon cancer, hereditary nonpolyposis colorectal cancer, familial paroxysmal polyserositis, familial PCT, porphyria cutanea tarda, familial pressure-sensitive neuropathy, hereditary neuropathy with liability to pressure palsies, familial primary pulmonary hypertension (FPPH), familial vascular leukoencephalopathy, CADASIL syndrome, FAP, familial adenomatous polyposis, FD, familial dysautonomia, Ferrochelatase deficiency, ferroportin disease, Haemochromatosis (any type, e.g., type 1, type 2A, type 2B, type 3, type 4, neonatal haemochromatosis, acaeruloplasminaemia, congenital atransferrinaemia, gracile syndrome) Periodic fever syndrome, Familial Mediterranean fever (FMF), FG syndrome, FGFR3-associated coronal synostosis, Fibrinoid degeneration of astrocytes, Alexander disease, Fibrocystic disease of the pancreas, Folling disease, fra(X) syndrome, fragile X syndrome, Fragilitas ossium, osteogenesis imperfecta, FRAXA syndrome, Friedreich's ataxia (FRDA), G6PD deficiency, Galactokinase deficiency disease, galactosemia, Galactose-1-phosphate uridyl-transferase deficiency disease, galactosemia, Galactosylceramidase deficiency disease, Krabbe disease, Galactosylceramide lipidosis, Krabbe disease, galactosylcerebrosidase deficiency, galactosylsphingosine lipidosis, GALC deficiency, GALT deficiency, galactosemia, Gaucher-like disease, pseudo-Gaucher disease, GBA deficiency, Genetic brain disorders, genetic emphysema, genetic hemochromatosis, hemochromatosis, Giant cell hepatitis, neonatal, Neonatal hemochromatosis, GLA deficiency, Glioblastoma, retinal, retinoblastoma, Glioma, retinal, retinoblastoma, globoid cell leukodystrophy (GCL, GLD), Krabbe disease, globoid cell leukoencephalopathy, Glucocerebrosidase deficiency, Glucocerebrosidosis, Glucosyl cerebroside lipidosis, Glucosylceramidase deficiency, Glucosylceramide beta-glucosidase deficiency, Glucosylceramide lipidosis, Glyceric aciduria, hyperoxaluria, primary, Glycine encephalopathy, Nonketotic hyperglycinemia, Glycolic aciduria, hyperoxaluria, primary, GM2 gangliosidosis, Tay-Sachs disease, Goiter-deafness syndrome, Pendred syndrome, Graefe-Usher syndrome, Usher syndrome, Gronblad-Strandberg syndrome, pseudoxanthoma elasticum, Haemochromatosis, hemochromatosis, Hallgren syndrome, Usher syndrome, Harlequin type ichthyosis, Hb S disease, hypochondroplasia (HCH), hereditary coproporphyria (HCP), Head and brain malformations, Hearing disorders and deafness, Hearing problems in children, HEF2A, HEF2B, Hematoporphyria, porphyria, Heme synthetase deficiency, Hemochromatoses, hemoglobin M disease, methemoglobinemia beta-globin type, Hemoglobin S disease, hemophilia, hepatoerythropoietic porphyria (HEP), hepatic AGT deficiency, hyperoxaluria, primary, Hepatolenticular degeneration syndrome, Wilson disease, Hereditary arthro-ophthalmopathy, Stickler syndrome, Hereditary dystopic lipidosis, Hereditary hemochromatosis (HHC), hemochromatosis, Hereditary hemorrhagic telangiectasia (HHT), Hereditary Inclusion Body Myopathy, skeletal muscle regeneration, Hereditary iron-loading anemia, X-linked sideroblastic anemia, Hereditary motor and sensory neuropathy, Hereditary motor neuronopathy, type V, distal hereditary motor neuropathy, Hereditary multiple exostoses, Hereditary nonpolyposis colorectal cancer, Hereditary periodic fever syndrome, Hereditary Polyposis Coli, familial adenomatous polyposis, Hereditary pulmonary emphysema, Hereditary resistance to activated protein C, factor V Leiden thrombophilia, Hereditary sensory and autonomic neuropathy type III, familial dysautonomia, Hereditary spastic paraplegia, infantile-onset ascending hereditary spastic paralysis, Hereditary spinal ataxia, Friedreich's ataxia, Hereditary spinal sclerosis, Friedreich's ataxia, Herrick's anemia, Heterozygous OSMED, Weissenbacher-Zweymüller syndrome, Heterozygous otospondylomegaepiphyseal dysplasia, Weissenbacher-Zweymüller syndrome, HexA deficiency, Tay-Sachs disease, Hexosaminidase A deficiency, Tay-Sachs disease, Hexosaminidase alpha-subunit deficiency (any variant, e.g. variant A, variant B), Tay-Sachs disease, HFE-associated hemochromatosis, hemochromatosis, HGPS, Progeria, Hippel-Lindau disease, von Hippel-Lindau disease, hemochromatosis (HLAH), distal hereditary motor neuropathy (HMN V), hereditary nonpolyposis colorectal cancer (HNPCC), hereditary neuropathy with liability to pressure palsies (HNPP), homocystinuria, Homogentisic acid oxidase deficiency, alkaptonuria, Homogentisic acidura, alkaptonuria, Homozygous porphyria cutanea tarda, hepatoerythropoietic porphyria, hyperoxaluria, primary (HP1), hyperoxaluria (HP2), hyperphenylalaninemia (HPA), HPRT—Hypoxanthine-guanine phosphoribosyltransferase deficiency, Lesch-Nyhan syndrome, HSAN type III, familial dysautonomia, familial dysautonomia (HSAN3), Hereditary Sensory Neuropathy (any type, e.g. HSN-1, HSN-II, HSN-III), familial dysautonomia, Human dermatosparaxis, Huntington's disease, Hutchinson-Gilford progeria syndrome, progeria, Hyperandrogenism, nonclassic type due to 21-hydroxylase deficiency, Hyperchylomicronemia, familial lipoprotein lipase deficiency, familial, Hyperglycinemia with ketoacidosis and leukopenia, propionic acidemia, Hyperlipoproteinemia type I, lipoprotein lipase deficiency, familial hyperoxaluria, primary hyperphenylalaninaemia, hyperphenylalaninemia, hyperphenylalaninemia, Hypochondrodysplasia, hypochondroplasia, Hypochondrogenesis, Hypochondroplasia, Hypochromic anemia, X-linked sideroblastic anemia, Hypoxanthine phosphoribosyltransferse (HPRT) deficiency, Lesch-Nyhan syndrome, infantile-onset ascending hereditary spastic paralysis (IAHSP), ICF syndrome, Immunodeficiency, centromere instability and facial anomalies syndrome, Idiopathic hemochromatosis, hemochromatosis, type 3, Idiopathic neonatal hemochromatosis, hemochromatosis, neonatal, Idiopathic pulmonary hypertension, Immune system disorders, X-linked severe combined immunodeficiency, Incontinentia pigmenti, Infantile cerebral Gaucher's disease, Infantile Gaucher disease, infantile-onset ascending hereditary spastic paralysis, Infertility, inherited emphysema, inherited tendency to pressure palsies, hereditary neuropathy with liability to pressure palsies, Insley-Astley syndrome, otospondylomegaepiphyseal dysplasia, Intermittent acute porphyria syndrome, acute intermittent porphyria, Intestinal polyposis-cutaneous pigmentation syndrome, Peutz-Jeghers syndrome, incontinentia pigmenti (IP), Iron storage disorder, hemochromatosis, Isodicentric 15, isodicentric 15, Isolated deafness, nonsyndromic deafness, Jackson-Weiss syndrome, Joubert syndrome, Juvenile Primary Lateral Sclerosis (JPLS), juvenile amyotrophic lateral sclerosis, Juvenile gout, choreoathetosis, mental retardation syndrome, Lesch-Nyhan syndrome, juvenile hyperuricemia syndrome, Lesch-Nyhan syndrome, Jackson-Weiss syndrome (JWS), spinal and bulbar muscular atrophy, Kennedy disease, spinal and bulbar muscular atrophy, Kennedy spinal and bulbar muscular atrophy, spinal and bulbar muscular atrophy, Kerasin histiocytosis, Kerasin lipoidosis, Kerasin thesaurismosis, ketotic glycinemia, propionic acidemia, ketotic hyperglycinemia, propionic acidemia, Kidney diseases, hyperoxaluria, primary, Kniest dysplasia, Krabbe disease, Kugelberg-Welander disease, spinal muscular atrophy, Lacunar dementia, CADASIL syndrome, Langer-Saldino achondrogenesis, Langer-Saldino dysplasia, Late-onset Alzheimer disease, late-onset Krabbe disease (LOKD), Krabbe disease, Learning Disorders, Learning disability, Lentiginosis, perioral, Peutz-Jeghers syndrome, Lesch-Nyhan syndrome, Leukodystrophies, leukodystrophy with Rosenthal fibers, Alexander disease, Leukodystrophy, spongiform, Li-Fraumeni syndrome (LFS), Li-Fraumeni syndrome, Lipase D deficiency, lipoprotein lipase deficiency, familial LIPD deficiency, lipoprotein lipase deficiency, familial Lipidosis, cerebroside, Lipidosis, ganglioside, infantile, Tay-Sachs disease, Lipoid histiocytosis (kerasin type), lipoprotein lipase deficiency, familial Liver diseases, galactosemia, Lou Gehrig disease, Louis-Bar syndrome, ataxia telangiectasia, Lynch syndrome, hereditary nonpolyposis colorectal cancer, Lysyl-hydroxylase deficiency, Machado-Joseph disease, Spinocerebellar ataxia (any type, e.g. SCA1, SCA2, SCA3, SCA 18, SCA20, SCA21, SCA23, SCA26, SCA28, SCA29), Male breast cancer, breast cancer, Male genital disorders, Malignant neoplasm of breast, breast cancer, malignant tumor of breast, breast cancer, Malignant tumor of urinary bladder, bladder cancer, Mammary cancer, breast cancer, Marfan syndrome, Marker X syndrome, fragile X syndrome, Martin-Bell syndrome, fragile X syndrome, McCune-Albright syndrome, McLeod syndrome, MEDNIK syndrome, Mediterranean Anemia, beta-thalassemia, Mega-epiphyseal dwarfism, otospondylomegaepiphyseal dysplasia, Menkea syndrome, Menkes disease, Menkes disease, Mental retardation with osteocartilaginous abnormalities, Coffin-Lowry syndrome, Metabolic disorders, Metatropic dwarfism, type II, Kniest dysplasia, Metatropic dysplasia type II, Kniest dysplasia, Methemoglobinemia (any type, e.g. congenital, beta-globin type, congenital methemoglobinemia type II), methylmalonic acidemia, Marfan syndrome (MFS), MHAM, Cowden syndrome, Micro syndrome, Microcephaly, MMA, methylmalonic acidemia, Menkes disease (AKA MK or MNK), Monosomy 1p36 syndrome, Motor neuron disease, amyotrophic lateral sclerosis, amyotrophic lateral sclerosis, Movement disorders, Mowat-Wilson syndrome, Mucopolysaccharidosis (MPS I), Mucoviscidosis, Multi-Infarct dementia, CADASIL syndrome, Multiple carboxylase deficiency, late-onset, biotinidase deficiency, Multiple hamartoma syndrome, Cowden syndrome, Multiple neurofibromatosis, Muscular dystrophy (any type, including, e.g., Duchenne and Becker type), Myotonia atrophica, myotonic dystrophy, Myotonia dystrophica, Nance-Insley syndrome, otospondylomegaepiphyseal dysplasia, Nance-Sweeney chondrodysplasia, otospondylomegaepiphyseal dysplasia, NBIA1, pantothenate kinase-associated neurodegeneration, Neill-Dingwall syndrome, Cockayne syndrome, Neuroblastoma, retinal, retinoblastoma, Neurodegeneration with brain iron accumulation type 1, pantothenate kinase-associated neurodegeneration, Neurologic diseases, Neuromuscular disorders, distal hereditary motor neuronopathy, Niemann-Pick, Niemann-Pick disease, Noack syndrome, Nonketotic hyperglycinemia, Glycine encephalopathy, Non-neuronopathic Gaucher disease, Non-phenylketonuric hyperphenylalaninemia, tetrahydrobiopterin deficiency, nonsyndromic deafness, Noonan syndrome, Norrbottnian Gaucher disease, Ochronosis, alkaptonuria, Ochronotic arthritis, alkaptonuria, Ogden syndrome, osteogenesis imperfecta (OI), Osler-Weber-Rendu disease, Hereditary hemorrhagic telangiectasia, OSMED, otospondylomegaepiphyseal dysplasia, osteogenesis imperfecta, Osteopsathyrosis, osteogenesis imperfecta, Osteosclerosis congenita, Oto-spondylo-megaepiphyseal dysplasia, otospondylomegaepiphyseal dysplasia, otospondylomegaepiphyseal dysplasia, Oxalosis, hyperoxaluria, primary, Oxaluria, primary, hyperoxaluria, primary, pantothenate kinase-associated neurodegeneration, Patau Syndrome (Trisomy 13), PBGD deficiency, acute intermittent porphyria, PCC deficiency, propionic acidemia, porphyria cutanea tarda (PCT), PDM disease, Pendred syndrome, Periodic disease, Mediterranean fever, Familial Periodic peritonitis, Periorificial lentiginosis syndrome, Peutz-Jeghers syndrome, Peripheral nerve disorders, familial dysautonomia, Peripheral neurofibromatosis, Peroneal muscular atrophy, peroxisomal alanine:glyoxylate aminotransferase deficiency, hyperoxaluria, primary Peutz-Jeghers syndrome, Phenylalanine hydroxylase deficiency disease, Pheochromocytoma, von Hippel-Lindau disease, Pierre Robin syndrome with fetal chondrodysplasia, Weissenbacher-Zweymüller syndrome, Pigmentary cirrhosis, hemochromatosis, Peutz-Jeghers syndrome (PJS), pantothenate kinase-associated neurodegeneration (PKAN), PKU, phenylketonuria, Plumboporphyria, ALA deficiency porphyria, PMA, Polycystic kidney disease, polyostotic fibrous dysplasia, McCune-Albright syndrome, familial adenomatous polyposis, hamartomatous intestinal polyposis, polyps-and-spots syndrome, Peutz-Jeghers syndrome, Porphobilinogen synthase deficiency, ALA deficiency porphyria, porphyrin disorder, PPDX deficiency, variegate porphyria, Prader-Labhart-Willi syndrome, Prader-Willi syndrome, presenile and senile dementia, Primary ciliary dyskinesia (PCD), primary hemochromatosis, hemochromatosis, primary hyperuricemia syndrome, Lesch-Nyhan syndrome, primary senile degenerative dementia, procollagen type EDS VII, mutant, progeria, Hutchinson Gilford Progeria Syndrome, Progeria-like syndrome, Cockayne syndrome, progeroid nanism, Cockayne syndrome, progressive chorea, chronic hereditary (Huntington), Huntington's disease, progressively deforming osteogenesis imperfecta with normal sclerae, Osteogenesis imperfecta (any type, e.g. Type I, Type II, Type III, Type IV, Type V, Type VI, Type VII, Type VIII), proximal myotonic dystrophy (PROMM), propionic acidemia, propionyl-CoA carboxylase deficiency, protein C deficiency, protein S deficiency, protoporphyria, protoporphyrinogen oxidase deficiency, variegate porphyria, proximal myotonic dystrophy, Myotonic dystrophytype 2, proximal myotonic myopathy, pseudo-Gaucher disease, pseudoxanthoma elasticum, psychosine lipidosis, Krabbe disease, pulmonary arterial hypertension, pulmonary hypertension, pseudoxanthoma elasticum (PXE), pseudoxanthoma elasticum, retinoblastoma (Rb), Recklinghausen disease, Recurrent polyserositis, Retinal disorders, Retinitis pigmentosa-deafness syndrome, Usher syndrome, Retinoblastoma, Rett syndrome, RFALS type 3, Ricker syndrome, Riley-Day syndrome, familial dysautonomia, Roussy-Levy syndrome, Rubinstein-Taybi syndrome (RSTS), Rett syndrome (RTS), Rubinstein-Taybi syndrome, Rubinstein-Taybi syndrome, Sack-Barabas syndrome, SADDAN disease, sarcoma family syndrome of Li and Fraumeni, Li-Fraumeni syndrome, SBLA syndrome (sarcoma, breast, leukemia, and adrenal gland syndrome), Li-Fraumeni syndrome, Spinal and bulbar muscular atrophy (SBMA), Schwannoma, acoustic, bilateral, neurofibromatosis type II, Schwartz-Jampel syndrome, X-linked severe combined immunodeficiency (SCIDX1), SED congenita, spondyloepiphyseal dysplasia congenita, SED Strudwick, spondyloepimetaphyseal dysplasia, Strudwick type, spondyloepiphyseal dysplasia congenita (SEDc), Spondyloepimetaphyseal dysplasia (SEMD), Strudwick type SEMD, senile dementia, severe achondroplasia with developmental delay and acanthosis nigricans, SADDAN disease, Shprintzen syndrome, Siderius X-linked mental retardation syndrome caused by mutations in the PHF8 gene, skeleton-skin-brain syndrome, Skin pigmentation disorders, spinal muscular atrophy (SMA), Spondylo-meta-epiphyseal dysplasia (SMED) (any type, e.g. Studwick type, type 1), Smith-Lemli-Opitz syndrome, Smith Magenis Syndrome, South-African genetic porphyria, infantile onset ascending spastic paralysis, infantile-onset ascending hereditary spastic paralysis, Speech and communication disorders, sphingolipidosis, Tay-Sachs, Tay-Sachs disease, spinal and bulbar muscular atrophy, spinal muscular atrophy, spinal muscular atrophy, distal type V, distal hereditary motor neuropathy, spinal muscular atrophy distal with upper limb predominance, distal hereditary motor neuropathy, spinocerebellar ataxia, spondyloepiphyseal dysplasia congenita, spondyloepiphyseal dysplasia, collagenopathy (any type, e.g. types II and XI), spondyloepimetaphyseal dysplasia, spondylometaphyseal dysplasia (SMD), spondyloepimetaphyseal dysplasia, spongy degeneration of central nervous system, spongy degeneration of the brain, spongy degeneration of white matter in infancy, sporadic primary pulmonary hypertension, SSB syndrome, steely hair syndrome, Menkes disease, Steinert disease, myotonic dystrophy, Steinert myotonic dystrophy syndrome, myotonic dystrophy, Stickler syndrome, stroke, CADASIL syndrome, Strudwick syndrome, subacute neuronopathic Gaucher disease, Swedish genetic porphyria, acute intermittent porphyria, acute intermittent porphyria, Swiss cheese cartilage dysplasia, Kniest dysplasia, Tay-Sachs disease, TD—thanatophoric dwarfism, thanatophoric dysplasia, TD with straight femurs and cloverleaf skull, thanatophoric dysplasia Type 2, Telangiectasia, cerebello-oculocutaneous, ataxia telangiectasia, Testicular feminization syndrome, androgen insensitivity syndrome, tetrahydrobiopterin deficiency, testicular feminization syndrome (TFM), androgen insensitivity syndrome, thalassemia intermedia, beta-thalassemia, Thalassemia Major, beta-thalassemia, thanatophoric dysplasia, Thrombophilia due to deficiency of cofactor for activated protein C, Leiden type, factor V Leiden thrombophilia, Thyroid disease, Tomaculous neuropathy, hereditary neuropathy with liability to pressure palsies, Total HPRT deficiency, Lesch-Nyhan syndrome, Total hypoxanthine-guanine phosphoribosyl transferase deficiency, Lesch-Nyhan syndrome, Treacher Collins syndrome, Trias fragilitis ossium, triple X syndrome, Triplo X syndrome, Trisomy 21Trisomy X, Troisier-Hanot-Chauffard syndrome, hemochromatosis, Tay-Sachs disease (TSD), Tuberous Sclerosis Complex (TSC), Tuberous sclerosis, Turner-like syndrome, Noonan syndrome, UDP-galactose-4-epimerase deficiency disease, galactosemia, UDP glucose 4-epimerase deficiency disease, galactosemia, UDP glucose hexose-1-phosphate uridylyltransferase deficiency, galactosemia, Undifferentiated deafness, nonsyndromic deafness, UPS deficiency, acute intermittent porphyria, Urinary bladder cancer, bladder cancer, UROD deficiency, Uroporphyrinogen decarboxylase deficiency, Uroporphyrinogen synthase deficiency, acute intermittent porphyria, Usher syndrome, UTP hexose-1-phosphate uridylyltransferase deficiency, galactosemia, Van Bogaert-Bertrand syndrome, Van der Hoeve syndrome, Velocardiofacial syndrome, VHL syndrome, von Hippel-Lindau disease, Vision impairment and blindness, Alström syndrome, Von Bogaert-Bertrand disease, von Hippel-Lindau disease, Von Recklenhausen-Applebaum disease, hemochromatosis, von Recklinghausen disease, neurofibromatosis type I, Vrolik disease, osteogenesis imperfecta, Waardenburg syndrome, Warburg Sjo Fledelius Syndrome, Micro syndrome, Wilson disease (WD), Weissenbacher-Zweymüller syndrome, Werdnig-Hoffmann disease, spinal muscular atrophy, Williams Syndrome, Wilson disease, Wilson's disease, Wilson disease, Wolf-Hirschhorn syndrome, Wolff Periodic disease, Weissenbacher-Zweymüller syndrome (WZS), Xeroderma pigmentosum, X-linked mental retardation and macroorchidism, fragile X syndrome, X-linked primary hyperuricemia, Lesch-Nyhan syndrome, X-linked severe combined immunodeficiency, X-linked sideroblastic anemia, X-linked spinal-bulbar muscle atrophy, spinal and bulbar muscular atrophy, X-linked uric aciduria enzyme defect, Lesch-Nyhan syndrome, X-SCID, X-linked severe combined immunodeficiency, X-linked sideroblastic anemia (XLSA), X-SCID, X-linked severe combined immunodeficiency, X-linked sideroblastic anemia (XLSA), XSCID, X-linked severe combined immunodeficiency, XXX syndrome, triple X syndrome, XXXX syndrome, XXXXX syndrome, XXXXX, XXY syndrome, XXY trisomy, Klinefelter syndrome, XYY syndrome, triplet repeat disorders, or any combinations thereof.

In embodiments, a specific post-transcriptional control modulator is targeted for modulation, modification, enhancement or decrease in activity by administering a DNA-PK inhibitor and a genomic editing system. For example, post-transcriptional control modulators can include PARN, PAN, CPSF, CstF, PAP, PABP, PAB2, CFI, CFII, RNA triphosphatase, RNA gluanyltransferase, RNA methyltransferase, SAM synthase, ubiquitin-conjugating enzyme E2R, SR proteins SFRS1 through SFR11, hnRNP proteins (e.g. HNRNPA0, HNRNPA1, HNRNPA1 L1, HNRNPA1 L2, HNRNPA2, HNRNPA2B1, HNRNPAB, HNRNPB1, HNRNPC, HNRNPCL1, HNRNPD, HNRPDL, HNRNPF, HNRNHP1, HNRNPH2, HNRNPH3, HNRNPK, HNRNPL, HNRNPLL, HNRNPM, HNRNPR, HNRNPU, HNRNPUL1, HNRNPUL2, HNRNPUL3, ADAR, Mex 67, Mtr2, Nab2, Dead-box helicase, eIF4A, eIF4B, eIF4E, eIF4G, GEF, GCN2, PKR, HRI, PERK, eEF1, eEF2, GCN, eRF3, ARE-specific binding proteins, EXRN1, DCP1, DCP2, RCK/p54, CPEB, eIF4E, microRNAS and siRNAs, DICER, Ago proteins, Nonsense-mediated mRNA decay proteins, UPF3A, UPF3BeIF4A3, MLN51, Y14/MAGOH, MG-1, SMG-5, SMG-6, SMG-7, or any combinations thereof.

In some embodiments, genetic pathways associated with the cell cycle are modulated, enhanced or decreased in activity by administering a DNA-PK inhibitor and a genomic editing system. Exemplary pathways and genes associated with the cell cycle include ATM, PMS2, FAS-L, MRE11, MLH1, FasR, NBS1, MSH6, Trail-L, RAD50, MSH2, Trail-R, 53BP1, RFC, TNF-Ct, P53, PCNA, TNF-R1, CHKE, MSH3, FADD, E2F1, MutS, homolog, TRADD, PML, MutL, homolog, R1P1, FANCD2, Exonuclease, MyD88, SMC1, DNA, Polymerase, delta, IRAK, BLM1, (POLD1, POLD2, POLD3, NIL, BRCA1, and, POLD4, -genes, IKK, H2AX, encoding, subunits), NFKβ, ATR, Topoisomerase, 1, IκBα, RPA, Topoisomerase, 2, IAP, ATRIP, RNAseHl, Caspase, 3, RADS, Ligase, 1, Caspase, 6, RAD1, DNA, polymerase, 1, Caspase, 7, HUS, DNA, polymerase, 3, Caspase, 8, RAD17, Primase, Caspase, 10, RFC, Helicase, HDAC1, CHK1, Single strand, binding, HDAC2, TLK1, proteins, Cytochrome, C, CDC25, Bx1-xL, STAT3, STAT5, DFF45, Vcl-2, ENDO-G, PI3K, Akt, Calpain, Bad, Bax, Ubiqiiitin-mediated proteolysis, Hypoxia, Cell Proliferation, HIF-loc, MAPK, E1, HERC1, TRAF6, HIF-Iβ, MAPKK, E2, UBE2Q, MEKK1, Ref1, MAPKKK, E3, UBE2R, COP!, HSP90, c-Met, UBLE1A, UBE2S, PIFH2, VEGF, HGF, UBLE1B, UBE2Q, cIAP, PAS, ER, S1/2, UBLEIC, UBE2W, PIAS, ARNT, ATK, UBE2A, UBE2Z, SYVN, VHL, PKCs, UBE2B, AFC, LLC, N, NHLRC1, HLF, Paxilin, UBE2C, UBE1, AIRE, EPF, FAK, UBE2A, E6AP, MGRN1, VDU2, Adducin, UBE2E, UBE3B, BRCA1, SUMORESUME, PYK1, UBE2F, Smurf, FANCL, SENP1, RB, UBE2G1, Itch, MIDI, Calcineurin, A, RBI, UBE2G2, HERC2, Cdc20, RACK1, Raf-1, UBE2I, HERC3, Cdhl, PTB, A-Raf, UBE2J1, HERC4, Apcl, Hur, B-raf, UBE2J2, UBE4A, Apc2, PHD2, MEK1/2, UBE2 L3, UBE4B, Apc3, SSAT2, ERK1/2, UBE2 L6, CHIP, Apc4, SSAT1, Ets, UBE2M, CYC4, Apc5, GSK3, Elkl, UBE2N, PPR19, Apc6, CBP, SAP1, UBE20, UIPS, Apc7, FOX04, cPLA2, WWPI, Mdm2, Apc8, F1H-1, WWP2, Parkin, Apc9, TRIP, 12, Trim32, Ape, 10, NEED4, Trim37, Ape, 11, ARF-BP1, SIAH-1, Ape, 12, EDD1, PML, Cell, survival, Cell, cycle, arrest, SMADI, P21, SMADS5, BAX, SAMD8, MDR, LEF1, DRAIL, IGFBP3, TCF3, GADD45, TCF4, P300, HAT1, PI3, Akt, GF1, or any combinations thereof.

In some embodiments, genes associated with angiogenesis are modulated, enhanced or decreased in activity by administering a DNA-PK inhibitor and a genomic editing system to a cell(s). Exemplary genes and genetic pathways associated with angiogenesis, and angiogenesis-related conditions include VEGF, VEGFR2, SHC, E2F7, VEGFB, VEGFR3, PI3, VEGFC, Nrp 1, PIP3, EGFDIP3, DAG, GRB2, SOS, Akt, PB, PKC, Ras, RAF1, DAG, eNOS, NO, ERK1, ER2, cPLA2, ME1, MEK2, or any combinations thereof.

In some embodiments, genetic pathways and/or genes associated with mitochondrial function are modulated, enhanced or decreased in activity by administering a DNA-PK inhibitor and a genomic editing system to a cell(s). Exemplary genes and genetic pathways associated with mitochondrial function include Malate dehydrogenase Aminotransferase, Hydratase, Deacylase, Dehydrogenase, Carboxylase, Mutase, Fatty acid oxidation Leucine Oxidation Isoleucine disorders (enzyme Pathway oxidation pathway deficiencies) Aminotransferase Aminotransferase, OCTN2 Branched chain Branched chain, FATP1-6 aminotransferase 2, aminotransferase 2, CPT-1 mitochondrial mitochondrial, CACT Isobutytyl-CoA 2-methylbutytyl-CoA, CPT-II dehydrogenase Dehydrogenase, SCAD (Branched Chain (Branched Chain, MCAD Keto Acid Keto Acid, VLCAD Dehydrogase Dehydrogenase, ETF-DH Complex) Complex), Alpha-ETF Hydratase Hydratase, Beta-ETF HMG-CoA lyase 2-methyl-3-OH-SCHAD butyryl-CoA, LCHAD dehydrogenase, MTP 3-Oxothiolase, LKAT, DECR 1, HMGCS2, HMGCL, or any combinations thereof.

In some embodiments, genetic pathways and/or genes associated with DNA damage or genomic instability are modulated, enhanced or decreased in activity. Exemplary genes and genetic pathways associated with pathways and/or genes relating to DNA Damage and genomic instability include 53BP1, BLM, MBD2, DNA, ligase, 4, MDC1, H2AX, XLF, SMC1, 53BP1, Rad50, P53, P53, Artemis, Rad27, TdT, APE1, PMS2, APE2, UvrA, RecA, MLH1, NEIL1, UvrB, SSB, MSH6, NEIL2, UvrC, Mrell, MSH2, NEIL3, XPC, Rad50, RFC, XRCC1, Rad23B, Nbsl, PCNA, PNKP, CEN2, CtIP, MSH3, Tdpl, DDB1, RPA, MutS, APTX, XPE, Rad51, MutL, DNA, polymerase β CSA, Rad52, DNA polymerase δ, CSB, Rad54, Topoisomerase, 1, DNA, TFT1H, BRCA1, Topoisomerase, 2, PCNA, XPB, BRCA2, RNAseHl, FEN1, XPD, Exol, Ligase 1, RFC, XPA, BLM, DNA, polymerase, 1, PAR, 1, RPA, Top111a, DNA, Lig1, XPG, GEN1, Primase, Lig3, ERCC1 Yen1 Helicase, UNG, XPF, Slxl, SSBs, MUTY DNA polymerase δ, Slx4, SMUG DNA polymerase ε, Mus8, MBD4, Emel, Dssl, ASH1 L, SETD4, DQT1 L, SETDS, EHMT1, SETD6, EHMT2, SETD7, EZH1, SETD8, EZH2, SETD9, MLL, SETDB1, MLL2, SETDB2, MLL3, SETMAR, MLL4, SMYD, 1, MLLS, SMYD2, NSD, 1, SMYD3, PRDM2, SMYD4, SET, SMYD5, SETBP1, SUV39H1, SETD 1A, SUV39H2, SETD 1B, SUV420H1, SETD2, SUV420 H2, SETD3, or any combinations thereof.

In some embodiments, genes encoding for mammalian transcription factors are modulated, enhanced, decreased or provided to a cell. Exemplary human transcription factors include AFF4, AFF3, AFF2, AFF1, AR, TFAP2B, TFAP2D, TFAP2C, TFAP2E, TFAP2A, JARID2, KDM5D, ARID4A, ARID4B, KDM5A, ARID3A, KDM5B, KDM5C, ARID5B, ARID3B, ARID2, ARID5A, ARID3C, ARID1A, ARID1B, HIF1A, NPAS1, NPAS3, NPAS4, MLXIPL, ARNTL2, MXD1, AHRR, TFE3, HES2, MNT, TCF3, SREBF1, TFAP4, TCFL5, LYL1, USF2, TFEC, AHR, MLX, MYF6, MYF5, SIM1, TFEB, HAND1, HES1, ID2, MYCL1, ID3, TCF21, MXI1, SOHLH2, MYOG, TWIST1, NEUROG3, BHLHE41, NEUROD4, MXD4, BHLHE23, TCF15, MAX, ID1, MYOD1, ARNTL, BHLHE40, MYCN, CLOCK, HEY2, MYC, ASCL1, TCF12, ARNT, HES6, FERD3 L, MSGN1, USF1, TALI, NEUROD1, TCF23, HEYL, HAND2, NEUROD6, HEY1, SOHLH1, MESP1, PTF1A, ATOH8, NPAS2, NEUROD2, NHLH1, ID4, ATOH1, ARNT2, HES3, MLXIP, ASCL3, KIAA2018, OLIG3, NHLH2, NEUROG2, MSC, HES7, ATOH7, BHLHA15, BHLHE22, NEUROG1, FIGLA, ASCL2, OLIG1, TAL2, MITF, SCXB, HELT, ASCL4, MESP2, HES4, SCXA, TCF4, HES5, SREBF2, BHLHA9, OLIG2, MXD3, TWIST2, LOC388553, C13orf38-SOHLH2, CEBPE, XBP1, BATF3, CREB5, CEBPG, ATF3, ATF7, CEBPB, CEBPD, CEBPA, CBFB, CAMTA2, CAMTA1, EBF4, EBF3, EBF1, EBF2, NR2F6, NR2F1, NR2F2, GRHL2, TFCP2 L1, GRHL1, TFCP2, UBP1, GRHL3, YBX2, CSDE1, CSDA, YBX1, LIN28A, CARHSP1, CSDC2, LIN28B, NFIX, NFIC, NFIB, NFIA, CUX2, ONECUT2, CUX1, ONECUT1, SATB1, ONECUT3, SATB2, DMRT3, DMRT1, DMRTC2, DMRTA2, DMRTB1, DMRT2, DMRTA1, E2F2, E2F1, E2F3, TFDP2, E2F8, E2F5, E2F7, E2F6, TFDP3, TFDP1, E2F4, NR1H3, NR1H2, ETV1, ETV7, SPI1, ELF4, ETV2, ERF, ELF2, ELK3, ETV3, ELF1, SPDEF, ELK1, ETS1, EHF, ELF5, ETV6, SPIB, FLI1, GABPA, ERG, ETS2, ELK4, ELF3, FEY, SPIC, ETV4, ETV5, FOXN3, FOXC1, FOXJ2, FOXF1, FOXN1, FOXM1, FOXP1, FOXO3, FOXA2, FOXP2, FOXJ1, FOXP4, FOXF2, FOXN4, FOXK2, FOXO1, FOXH1, FOXQ1, FOXK1, FOXI1, FOXD4, FOXA3, FOXN2, FOXB1, FOXG1, FOXR1, FOXL1, FOXC2, FOXE1, FOXS1, FOXL2, FOXO4, FOXD4 L1, FOXD4 L4, FOXD2, FOXI2, FOXE3, FOXD3, FOXD4 L3, FOXR2, FOXJ3, FOXO6, FOXB2, FOXD4 L5, FOXD4 L6, FOXD4 L2, KIAA0415, FOXA1, FOXP3, GCM2, GCM1, NR3C1, GTF2IRD1, GTF2I, GTF2IRD2B, GTF2IRD2, SOX8, SOX30, PMS1, CIC, TCF7, TOX4, SOX10, HMGXB4, HBP1, TFAM, UBTF, WHSC1, SOX6, HMGXB3, BBX, TOX2, SOX4, SOX21, SOX9, SOX15, SOX5, SOX3, LEF1, HMG20A, SOX13, TCF7 L2, SSRP1, TCF7 L1, SOX17, SOX14, PINX1, SOX7, SOX11, SOX12, SOX2, SOX1, SRY, SOX18, UBTFL1, UBTFL2, TOX, HMGB1, HMGB2, PBRM1, TOX3, SMARCE1, HMG20B, HMGB3, HMGA2, HMGA1, ARX, HOXA11, MEOX1, DLX6, ISL1, HOXC8, BARX2, ALX4, GSC2, DLX3, PITX1, HOXA9, HOXA10, LHX5, LASS4, ZFHX4, SIX4, VSX1, ADNP, RHOXF1, MEIS3, PBX4, DLX5, HOXA1, HOXA2, HOXA3, HOXA5, HOXA6, HOXA13, EVX1, NOBOX, MEOX2, LHX2, LHX6, LHX3, TLX1, PITX3, HOXB6, HNF1B, DLX4, SEBOX, VTN, PHOX2B, NKX3-2, DBX1, NANOG, IRX4, CDX1, TLX2, DLX2, VAX2, PRRX1, TGIF2, VSX2, NKX2-3, HOXB8, HOXB5, HOXB7, HOXB3, HOXB1, MSX2, LHX4, HOXA7, HOXC13, HOXC11, HOXC12, ESX1, BARHL1, NKX2-4, NKX2-2, SIX1, HOXD1, HOXD3, HOXD9, HOXD10, HOXD11, HOXD13, MNX1, CDX4, BARX1, RHOXF2, LHX1, GSC, MEIS2, RAX, EMX1, NKX2-8, NKX2-1, HLX, LMX1B, SIX3, LBX1, PDX1, LASS5, ZFHX3, BARHL2, LHX9, LASS2, MEIS1, DLX1, HMBOX1, ZEB1, VAX1, NKX6-2, VENTX, HHEX, TGIF2 LX, LASS3, ALX3, HOXB13, IRX6, ISL2, PKNOX1, LHX8, LMX1A, EN1, MSX1, NKX6-1, HESX1, PITX2, TLX3, EN2, UNCX, GBX1, NKX6-3, ZHX1, HDX, PHOX2A, PKNOX2, CDX2, DRGX, NKX3-1, PBX3, PRRX2, GBX2, SHOX2, GSX1, HOXD4, HOXD12, EMX2, IRX1, IRX2, SIX2, HOXB9, HOPX, OTP, LASS6, HOXC5, HOXB2, RAX2, EVX2, ZHX3, PROP1, ISX, HOXD8, TGIF2 LY, IRX5, SIX5, TGIF1, IRX3, ZHX2, LBX2, NKX2-6, ALX1, GSX2, HOXC9, HOXC10, HOXB4, NKX2-5, SIX6, MIXL1, DBX2, PBX1, SHOX, ARGFX, HMX3, HMX2, BSX, HOXA4, DMBX1, HOXC6, HOXC4, RHOXF2B, PBX2, DUXA, DPRX, LEUTX, NOTO, HOMEZ, HMX1, DUX4 L5, DUX4 L2, DUX4 L3, DUX4 L6, NKX1-1, HNF1A, HSF4, HSFY2, HSFX1, HSFX2, HSFY1, HSF1, LCORL, LCOR, IRF6, IRF1, IRF3, IRF5, IRF4, IRF8, IRF2, IRF7, IRF9, MBD3, BAZ2B, MBD4, SETDB2, MBD1, MECP2, SETDB1, MBD2, BAZ2A, SMAD7, SMAD5, SMAD9, SMAD6, SMAD4, SMAD3, SMAD1, SMAD2, ZZZ3, RCOR1, CDC5L, MYBL2, DNAJC2, TADA2A, RCOR3, MYB, TERF2, DMTF1, DNAJC1, NCOR1, TERF1, MIER3, MYSM1, SNAPC4, RCOR2, TADA2B, MYBL1, TERF1P2, NCOR2, CCDC79, SMARCC1, SMARCC2, TTF1, C11orf9, NFYA, NFYC, NFYB, NRF1, NR4A3, NR4A1, NR4A2, ESR1, NR0B2, NR0B1, PREB, EAF2, SPZ1, TP63, TP73, TP53, PAX6, PAX7, PAX2, PAX4, PAX8, PAX1, PAX3, PAX5, PAX9, SUB1, POU2F2, POU1F1, POU4F3, POU6F2, POU2F3, POU2F1, POU4F2, POU4F1, POU6F1, POU3F2, POU3F1, POU3F4, POU3F3, POU5F1, POU5F1B, PPARD, PPARG, PPARA, PGR, PROX1, PROX2, NR2E1, NR5A2, NR2C1, NR5A1, NR6A1, ESRRA, NR2C2, RFX3, RFX2, RFX4, RFX1, RFX5, RFX7, RFX6, RFX8, NFATC3, NFKB2, NFATC4, NFATC2, NFAT5, RELB, NFKB1, NFATC1, REL, RELA, RORA, RORC, NR1D2, RORB, RUNX3, RUNX1, SP100, SP140, GMEB2, SP110, AIRE, GMEB1, DEAF1, SP140 L, LOC729991-MEF2B, MEF2A, SRF, MEF2D, MEF2B, STAT1, STAT5A, STAT4, STAT6, STAT3, STAT2, STAT5B, TBX21, TBX5, TBX15, TBX18, TBX2, TBX4, TBX22, TBX3, TBR1, TBX19, TBX6, EOMES, T, TBX20, TBX10, MGA, TBX1, TEAD3, TEAD2, TEAD1, TEAD4, CREBL2, NFE2 L3, CREB3 L3, FOSL2, NFE2 L1, CREM, DBP, CREB3, HLF, BACH2, ATF2, NFE2 L2, ATF6, CREB1, ATF1, NFE2, FOSB, ATF4, NRL, JUND, JDP2, CREB3 L4, BATF, BACH1, CREB3 L1, NFIL3, TEF, BATF2, ATFS, FOS, JUNB, DDIT3, FOSL1, JUN, MAF, CREB3 L2, MAFA, MAFF, MAFG, MAFK, MAFB, ATF6B, CRX, OTX1, OTX2, THAP3, THAP10, THAP1, PRKRIR, THAP8, THAP9, THAP11, THAP2, THAP6, THAP4, THAP5, THAP7, NR1H4, NR2E3, RARB, HNF4A, VDR, ESRRB, THRA, NR1D1, RARA, ESR2, NR1I3, NR1I2, THRB, NR3C2, HNF4G, RARG, RXRA, ESRRG, RXRB, TSC22D1, TSC22D3, TSC22D4, TSC22D2, TULP3, TULP2, TULP1, TULP4, TUB, ZBTB33, ZBTB32, ZBTB11, MYNN, ZBTB25, PATZ1, ZBTB16, ZBTB24, BCL6, ZBTB47, ZBTB17, ZBTB45, GZF1, ZBTB1, ZBTB46, ZBTB8A, ZBTB7B, BCL6B, ZBTB49, ZBTB43, HIC2, ZBTB26, ZNF131, ZNF295, ZBTB4, ZBTB34, ZBTB38, HIC1, ZBTB41, ZBTB7A, ZNF238, ZBTB42, ZBTB2, ZBTB20, ZBTB40, ZBTB7C, ZBTB37, ZBTB3, ZBTB6, ZBTB44, ZFP161, ZBTB12, ZBTB48, ZBTB10, ZBED4, ZBED3, ZBED2, C11orf95, ZBED1, IKZF5, ZNF821, ZNF451, ZNF195, ZFX, ZNF263, ZNF200, HIVEP2, WIZ, ZNF582, SNAI2, ZFP64, IKZF2, ZIC2, ZNF800, PRDM1, PRDM6, ZFP112, ZNF275, ZNF76, ZFAT, KLF6, ZFY, ZXDC, GLI2, ZNF532, ZNF37A, ZNF510, ZNF506, ZNF324, ZNF671, ZNF416, ZNF586, ZNF446, ZNF8, ZNF264, REST, MECOM, ZNF213, ZNF343, ZNF302, ZNF268, ZNF10, HIVEP1, ZNF184, MZF1, SALL4, ZNF516, KLF8, KLF5, ZNF629, ZNF423, CTCF, ZNF500, ZNF174, SALL1, MAZ, ZNF419, OVOL3, ZNF175, ZNF14, ZNF574, ZNF85, SP4, ZKSCAN1, GLI3, GLIS3, KLF3, PRDM4, GLI1, PRDM13, ZNF142, PRDM2, ZNF684, ZNF541, KLF7, PLAGL1, ZNF430, KLF12, KLF9, ZNF410, BCL11A, EGR1, ZFP30, TSHZ3, ZNF549, ZSCAN18, ZNF211, ZNF639, ZSCAN20, GTF3A, ZNF205, ZNF644, EGR2, IKZF4, CTCFL, ZNF831, SNAI1, ZNF576, ZNF45, TRERF1, ZNF391, RREB1, ZNF133, OVOL2, ZNF436, PLAGL2, GLIS2, ZNF384, ZNF484, HIVEP3, BCL11B, KLF2, ZNF780B, FEZF1, KLF16, ZSCAN10, ZNF557, ZNF337, PRDM12, ZNF317, ZNF426, ZNF331, ZNF236, ZNF341, ZNF227, ZNF141, ZNF304, ZSCAN5A, ZNF132, ZNF20, EGR4, ZNF670, VEZF1, KLF4, ZFP37, ZNF189, ZNF193, ZNF280D, PRDM5, ZNF740, ZIC5, ZSCAN29, ZNF710, ZNF434, ZNF287, ZIM3, PRDM15, ZFP14, ZNF787, ZNF473, ZNF614, PRDM16, ZNF697, ZNF687, OSR1, ZNF514, ZNF660, ZNF300, RBAK, ZNF92, ZNF157, ZNF182, ZNF41, ZNF711, PRDM14, ZNF7, ZNF214, ZNF215, SALL3, ZNF827, ZNF547, ZNF773, ZNF776, ZNF256, ZSCAN1, ZNF837, PRDM8, ZNF117, ZIC1, FEZF2, ZNF599, ZNF18, KLF10, ZKSCAN2, ZNF689, ZIC3, ZNF19, ZSCAN12, ZNF276, ZNF283, ZNF221, ZNF225, ZNF230, ZNF222, ZNF234, ZNF233, ZNF235, ZNF362, ZNF208, ZNF714, ZNF394, ZNF333, ZNF382, IKZF3, ZNF577, ZNF653, ZNF75A, GFI1, ZNF281, ZNF496, ZNF2, ZNF513, ZNF148, KLF15, ZNF691, ZNF589, PRDM9, ZNF12, SP8, OSR2, ZNF367, ZNF22, GFI1B, ZNF219, SALL2, ZNF319, ZNF202, ZNF143, ZNF3, ZSCAN21, ZNF606, SP2, ZNF91, ZNF23, ZNF226, ZNF229, ZNF180, ZNF668, ZNF646, ZNF641, ZNF610, ZNF528, ZNF701, ZNF526, ZNF146, ZNF444, ZNF83, ZNF558, ZNF232, E4F1, ZNF597, INSM2, ZNF30, ZNF507, ZNF354A, ZEB2, ZNF32, KLF13, ZFPM2, ZNF764, ZNF768, ZNF35, ZNF778, ZNF212, ZNF282, PRDM10, SP7, SCRT1, ZNF16, ZNF296, ZNF160, ZNF415, ZNF672, ZNF692, ZNF439, ZNF440, ZNF581, ZNF524, ZNF540, ZNF562, ZNF561, ZNF584, ZNF274, ZIK1, ZNF540, ZNF570, KLF17, ZNF217, ZNF57, ZNF556, ZNF554, KLF11, HINFP, ZNF24, ZNF596, OVOL1, SP3, ZNF621, ZNF680, BNC2, ZNF483, ZNF449, INSM1, ZNF417, ZNF791, ZNF80, GLIS1, ZNF497, KLF14, ZNF266, ZIC4, ZNF408, ZNF519, ZNF25, ZNF77, ZNF169, ZNF613, ZNF683, ZNF135, ZSCAN2, ZNF575, ZNF491, ZNF620, ZNF619, ZNF354C, ZNF114, ZNF366, ZNF454, ZNF543, ZNF354B, ZNF223, ZNF713, ZNF852, ZNF552, ZFP42, ZNF664, EGR3, ZFPM1, ZNF784, ZNF648, FIZ1, ZNF771, TSHZ1, ZNF48, ZNF816, ZNF571, ZSCAN4, ZNF594, ZFP3, ZNF443, ZNF792, ZNF572, ZNF707, ZNF746, ZNF322A, ZNF467, ZNF678, ZFP41, HKR1, PLAG1, ZNF329, ZNF101, ZNF716, ZNF708, ZSCAN22, ZNF662, ZNF320, ZNF623, ZNF530, ZNF285, ZFP1, WT1, ZFP90, ZNF479, ZNF445, ZNF74, SP1, SNAI3, ZNF696, IKZF1, ZNF267, ZNF566, ZNF224, ZNF529, ZNF284, ZNF749, ZNF17, ZNF555, ZNF75D, ZNF501, ZNF197, ZNF396, ZFP91, ZNF732, ZNF397, ZSCAN30, ZNF546, ZNF286A, ZKSCAN4, ZNF70, ZNF643, ZNF642, ZSCAN23, ZNF490, ZNF626, ZNF793, ZNF383, ZNF669, ZNF559, ZNF177, ZNF548, MTF1, ZNF322B, ZNF563, ZNF292, ZNF567, SP6, ZNF573, ZNF527, ZNF33A, ZNF600, ZKSCAN3, ZNF676, ZNF699, ZNF250, ZNF79, ZNF681, ZNF766, ZNF107, ZNF471, ZNF836, ZNF493, ZNF167, ZNF565, ZNF34, ZNF781, ZNF140, ZNF774, ZNF658, ZNF765, ZNF124, ZNF569, ZNF777, ZNF775, ZNF799, ZNF782, ZNF846, ZNF136, ZKSCANS, ZNF502, ZFP62, ZNF33B, ZNF512B, ZNF431, ZNF418, ZNF700, ZNF239, ZSCAN16, ZFP28, ZNF705A, ZNF585A, ZNF138, ZNF429, ZNF470, ZNF100, ZNF398, ZNF498, ZNF441, ZNF420, ZNF763, ZNF679, ZNF682, ZNF772, ZNF257, ZNF785, ZSCAN5B, ZNF165, ZNF655, ZNF98, ZNF786, ZNF517, ZNF675, ZNF860, ZNF628, ZNF665, ZNF624, ZNF841, ZNF615, ZNF350, ZNF432, ZNF433, ZNF460, ZNF81, ZNF780A, ZNF461, ZNF181, LOC100287841, ZNF44, ZNF790, ZNF677, ZNF823, ZNF311, ZNF347, ZNF71, ZNF121, ZNF335, ZNF560, ZNF273, ZNF84, ZNF667, ZNF649, ZNF248, ZNF544, ZNF770, ZNF737, ZNF251, ZNF607, ZNF334, ZXDA, ZNF485, ZIM2, PEG3, ZNF192, ZNF442, ZNF813, ZNF26, ZNF69, ZNF583, ZNF568, ZXDB, ZNF480, ZNF587, ZNF808, ZNF43, ZNF28, ZNF627, ZNF789, ZNF536, ZNF534, ZNF652, ZNF521, ZNF358, ZFP2, SP5, ZNF814, ZNF551, ZNF805, ZSCAN5C, ZNF468, ZNF616, ZFP57, ZNF155, ZNF783, ZNF425, ZNF580, ZNF611, ZNF254, ZNF625, ZNF134, ZNF845, ZNF99, ZNF253, ZNF90, ZNF93, ZNF486, REPIN1, LOC100131539, ZNF705D, LOC100132396, ZNF705G, SCRT2, ZNF407, SP9, ZNF579, ZNF880, ZNF630, ZNF844, ZNF469, ZNF717, ZNF865, ZNF492, ZNF688, YY2, ZNF878, ZNF879, ZNF736, ZNF323, ZNF709, ZNF512, ZNF585B, ZNF154, ZNF324B, ZNF564, ZFP82, GLI4, ZNF674, ZNF345, ZNF550, KLF1, YY1, MYST2, ST18, L3MBTL4, MYT1 L, MYT1, L3MBTL1, MTA3, GATA1, TRPS1, GATA3, GATA5, GATA4, GATA6, GATAD2B, GATAD1, GATA2, MTA1, ZGLP1, MTA2, RERE, C16orf5, LITAF, PIAS1, PIAS2, PIAS4, ZMIZ1, ZMIZ2, PIAS3, RNF138, NFX1, NFXL1, or any combinations thereof.

In some embodiments, cells are manipulated (e.g., converted or differentiated) from one cell type to another. In some embodiments, a pancreatic cell is manipulated into a beta islet cell. In some embodiments, a fibroblast is manipulated into an iPS cell. In some embodiments, a preadipocyte is manipulated into a brown fat cell. Other exemplary cells include, e.g., muscle cells, neural cells, leukocytes, and lymphocytes.

In some embodiments, the cell is a diseased or mutant-bearing cell. Such cells can be manipulated to treat the disease, e.g., to correct a mutation, or to alter the phenotype of the cell, e.g., to inhibit the growth of a cancer cell. For example, a cell is associated with one or more diseases or conditions described herein.

In some embodiments, the manipulated cell is a normal cell.

In some embodiments, the manipulated cell is a stem cell or progenitor cell (e.g., iPS, embryonic, hematopoietic, adipose, germline, lung, or neural stem or progenitor cells). In some embodiments, the manipulated cell can be a cell from any of the three germ layers (i.e. mesodermal, endodermal or ectodermal. In some embodiments, the manipulated cell can be from an extraembryonic tissue, for example, from the placenta.

In some embodiments, the cell being manipulated is selected from fibroblasts, monocytic-precursors, B cells, exocrine cells, pancreatic progenitors, endocrine progenitors, hepatoblasts, myoblasts, or preadipocytes. In some embodiments, the cell is manipulated (e.g., converted or differentiated) into muscle cells, erythroid-megakaryocytic cells, eosinophils, iPS cells, macrophages, T cells, islet beta-cells, neurons, cardiomyocytes, blood cells, endocrine progenitors, exocrine progenitors, ductal cells, acinar cells, alpha cells, beta cells, delta cells, PP cells, hepatocytes, cholangiocytes, angioblast, mesoangioblast or brown adipocytes.

In some embodiments, the cell is a muscle cell, erythroid-megakaryocytic cell,
   eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or white or brown adipocyte.

In some embodiments, the cell is a precursor cell, a pluripotent cell, a totipotent cell, an adult stem cell, an inner cell mass cell, an embryonic stem cell, or an iPS cell.

In some embodiments, the manipulated cell is a cancer cell. In some embodiments, the cancer cell can be a lung cancer cell, a breast cancer cell, a skin cancer cell, a brain cancer cell, a pancreatic cancer cell, a hematopoietic cancer cell, a liver cancer cell, a kidney cancer cell, an ovarian cancer cell, a prostate cancer cell, a skin cancer cell.

In some embodiments, the cell is a muscle cell, erythroid-megakaryocytic cell, eosinophil, iPS cell, macrophage, T cell, islet beta-cell, neuron, cardiomyocyte, blood cell, endocrine progenitor, exocrine progenitor, ductal cell, acinar cell, alpha cell, beta cell, delta cell, PP cell, hepatocyte, cholangiocyte, or white or brown adipocyte.

Administration of DNA-PK Inhibitors and Gene-Editing System to a Cell(s)

Administering to a cell(s) a genome editing system and a DNA-PK inhibitor can be performed by any method known in the art. The administering can be in vitro, ex vivo or in vivo. The administering to a cell(s) a genome editing system and a DNA-PK inhibitor can occur simultaneously or sequentially. In some embodiments, the administering results in the DNA-PK inhibitor and the genome editing system components to enter the cell membrane. In some embodiments, the administering results in the DNA-PK inhibitor and the genome editing system components to enter into the cell nucleus. In some embodiments, the administering includes incubating the cell in the presence of the DNA-PK inhibitor and genome editing system.

The gene editing system can be administered to a cell(s) by any method known in the art. For example, any nucleic acid or protein delivery methods known in the art can be used. The gene editing system is administered (e.g., delivered) to a cell by way of a nucleic acid encoding the gene editing system components. The gene editing system can be administered to a cell by either viral vectors or non-viral vectors. In some embodiments, viral vectors are used. The viral vectors can be retroviral (e.g. murine leukemia, HIV, or lentiviral) or DNA viruses (e.g. adenovirus, herpes simplex, and adeno-associated). In some embodiments, transfection methods (e.g. non-viral delivery methods) are used to introduce the genome editing system into a cell. Transfection methods include contacting the cell with DEAE-Dextran, calcium phosphate, liposomes or electroporation of a plasmid into a cell. Additional methods of non-viral delivery include electroporation, lipofection, microinjection, biolistics, virosomes, liposomes, immunoliposomes, polycation or lipid: nucleic acid conjugates, naked DNA, naked RNA, artificial virions, and agent-enhanced uptake of DNA. Sonoporation using, e.g., the Sonitron 2000 system (RichMar) can also be used for delivery of nucleic acids. In some embodiments, one or more nucleic acids are delivered as mRNA. In some embodiments, capped mRNAs are used to increase translational efficiency and/or mRNA stability. In some embodiments, ARCA (anti-reverse cap analog) caps or variants thereof are used. See US patents US7074596 and U.S. Pat. No. 8,153,773.

In embodiments, the endonuclease (e.g. Cas, Cpf1 and the like) and the gRNA, are transcribed from DNA.

In embodiments, the endonuclease (e.g. Cas, Cpf1 and the like) is transcribed from DNA and the gRNA is provided as RNA.

In embodiments, the endonuclease (e.g. Cas, Cpf1 and the like) and the gRNA are provided as RNA.

In embodiments, the endonuclease (e.g. Cas, Cpf1 and the like) is provided as a protein and the gRNA is provided as DNA.

In embodiments, the endonuclease (e.g. Cas, Cpf1 and the like) is provided as protein and the gRNA is provided as RNA.

Additional nucleic acid delivery systems include those provided by Amaxa Biosystems (Cologne, Germany), Maxcyte, Inc. (Rockville, Maryland), BTX Molecular Delivery Systems (Holliston, MA) and Copernicus Therapeutics Inc, (see for example U.S. Pat. No. 6,008,336). Lipofection is described in e.g., U.S. Pat. Nos. 5,049,386; 4,946,787; and 4,897,355) and lipofection reagents are sold commercially (e.g., Transfectam™ and Lipofectin™ and Lipofectamine™ RNAiMAX). Cationic and neutral lipids that are suitable for efficient receptor-recognition lipofection of polynucleotides include those of Feigner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995);

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiarmid et al (2009) Nature Biotechnology 27(7):643) Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

In some embodiments, the transfection can be transient in which the transfected genome editing system containing plasmid enters the nucleus but does not become incorporated into the genome of the cell during replication. The transfection can be stable in which the transfected plasmid will become integrated into a genomic region of the cell.

In some embodiments in which transient expression is used, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Kotin, Human Gene Therapy 5:793-801 (1994); Muzyczka, J. Clin. Invest. 94: 1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol Cell. Biol. 4:2072-2081 (1984); Hermonat & Muzyczka, PNAS 81:6466-6470 (1984); and Samulski et al., J. Virol 63:03822-3828 (1989).

In some embodiments, the administering to a cell(s) of a DNA-PK inhibitor is performed by culturing an isolated cell(s) in the presence of the DNA-PK inhibitor and any suitable medium that allows for the DNA-PK inhibitor to enter the cell membrane and/or the cell nucleus.

In some embodiments, the DNA-PK inhibitors are administered to a cell (s) in vitro, in vivo or ex vivo. In some embodiment, the DNA-PK inhibitor is contacted with a cell(s) for about 5 hours, 10 hours, 15 hours, 20 hours, 21 hours, 22 hours, 23 hours, 24 hours, 25 hours, 30 hours, 35 hours, 40 hours, 45 hours, 50 hours, 55 hours, 60 hours, 65 hours, 70 hours, 85 hours, 90 hours, 100 hours, 125 hours, 150 hours, 200 hours, or for any period of time in between. In some embodiments, the DNA-PK inhibitor is contacted with a cell(s) for about 1.5 weeks, 2.0 weeks, 2.5 weeks, 3.0 weeks, 3.5 weeks, 4 weeks, or any period of time in between. The DNA-PK inhibitor may be re-administered with cell culture medium changes. The DNA-PK inhibitor can be contacted with the cell either before, during or after introduction of genome editing system components.

In some embodiments, the DNA-PK inhibitor is administered to a cell(s) at a concentration of about 0.1 µM, 0.25 µM, 0.5 µM, 0.75 µM, 1.0 µM, 1.25 µM, 1.50 µM, 1.75 µM, 2.0 µM, 2.5 µM, 3.0 µM, 3.5 µM, 4.0 µM, 4.5 µM, 5.0 µM, 5.5 µM, 6.0 µM, 6.5 µM, 7.0 µM, 7.5 µM, 8.0 µM, 8.5 µM, 9.0 µM, 9.5 µM, 10 µM, 10.5 µM, 11.0 µM, 11.5 µM, 12 µM, or any concentrations in between. The DNA-PK inhibitor concentration can be modified during the course of administration.

In some embodiments, the gene-editing components are delivered into a cell(s) by one or more vectors or in the form of RNA, mRNA or in the case of the endonuclease component as purified protein or mRNA (e.g. Cas9 protein). The one or more vectors can include viral vectors, plasmids or ssDNAs. Viral vectors can include retroviral, lentiviral, adenoviral, adeno-associated, and herpes simplex viral vectors, or any combinations thereof. In some embodiments, the gene-editing components are delivered via RNA or synthetic RNA.

In some embodiments, administration of the DNA-PK inhibitors to a cell along with a gene-editing system results in increased amounts of homologous directed repair gene-editing outcome in comparison to a baseline condition in which the cell is not administered a DNA-PK inhibitor. In some embodiments, administration of the DNA-PK inhibitors to a cell(s) along with a gene-editing system results in suppression of indels (from NHEJ) either on-target or off-target. In some embodiments, administration of the DNA-PK inhibitors to a cell(s) along with a gene-editing system results in increased or decreased expression of a gene of interest. Administration of the DNA-PK inhibitors to a cell(s) along with a gene-editing system can result in the expression of a gene not endogenous to a cell. In some embodiments, administration of the DNA-PK inhibitors to a cell(s) along with a gene-editing system results in the complete or partial removal, or a modification of a gene from a cell(s). In some embodiments, administration of the DNA-PK inhibitors to a cell(s) along with gene-editing system result(s) in the complete or partial removal, or a modification of an intron and/or an exon in a cell(s). In some embodiments, administration of the DNA-PK inhibitors to a cell(s) along with gene-editing system result(s) in the complete or partial removal, or a modification of a non-coding region in a cell(s). In some embodiments, administration of the DNA-PK inhibitors to a cell along with gene-editing system result(s) in simultaneous or sequential, complete or partial removal, or a modification of a coding and/or non-coding genetic region in a cell(s). In some embodiments, administration of the DNA-PK inhibitors to a cell(s) along with gene-editing system results in simultaneous or sequential, complete or partial removal, or a modification of a coding and/or non-coding genetic region in a cell(s), including extrachromosomal DNA or RNA. The Extrachromosomal DNA can be mitochondrial DNA, chloroplast DNA, extrachromosomal circular DNA, or viral extra chromosomal DNA.

In some embodiments, administration of DNA-PK inhibitors to a cell along with genome editing system results in increased expression or decreased expression of a gene of interest. In some embodiments, the increase or decrease in expression of a gene of interest can be about or between, 2.5%, 5%, 10%, 20%, 30%, 40%, 50%, 60%, 70%, 80%, 90% in comparison to a baseline condition in which the cell is not administered a DNA-PK inhibitor. In some embodiments, the increase or decrease of a gene of interest can be about or between, 0.5-fold, 1.0-fold, 1.5-fold, 2.0-fold, 2.5-fold, 3.0-fold, 3.5-fold, 4-fold, 4.5-fold, 5-fold or 10-fold in comparison to the baseline expression level in which the cell is not administered a DNA-PK inhibitor.

In some embodiments, administration of DNA-PK inhibitors to a cell along with a genome editing system results in an increase in genome editing. In some embodiments, the increase in genome editing can be about or between 2.5%, 5%, 10%, 20%, 30%, 40%, 50%, 60%, 70%, 80%, 90% in comparison to a baseline condition in which the cell is not administered a DNA-PK inhibitor. In some embodiments, the increase in genome editing can be about or between 0.5-fold, 1.0-fold, 1.5-fold, 2.0-fold, 2.5-fold, 3.0-fold, 3.5-fold, 4-fold, 4.5-fold, 5-fold or 10-fold in comparison to the baseline expression level in which the cell is not administered a DNA-PK inhibitor.

In some embodiments, administration of a DNA-PK inhibitor and a gene editing system to a cell population results in greater cell survival in comparison to a baseline condition in which a cell population only administered a gene editing system and is not administered a DNA-PK inhibitor. In some embodiments, the DNA-PK inhibitor that results in greater cell survival is a compound of formula (III-E-1) or (III-E-2), or pharmaceutically acceptable salts thereof.

In some embodiments, the cell is synchronized at the S or G2 cell cycle phase, either before, after or during administration of the DNA-PK inhibitor. In some embodiments, the cell is synchronized at the S or G2 cell cycle phase, either before, after or during introduction of the gene-editing components. Synchronization of the cell at the S or G2 cell cycle phase can be achieved by any method known in the art. As a non-limiting example, agents that can be used to synchronize a cell at the S or G2 cell cycle phase include aphidicolin, dyroxyurea, lovastatin, mimosine, nocodazole, thymidine, or any combinations thereof. (See, Lin et al. Elife. 2014 Dec. 15; 32014). In some embodiments, the agents for cell synchronization can be administered at any time during the gene-editing process.

In some embodiments, the DNA-PK inhibitor and/or the genome editing system can be included in a container, pack, or dispenser together with instructions for use. In some embodiments, the DNA-PK inhibitor agent and/or the genome editing system included in a container, pack or dispenser together with instructions for use is a kit.

In some embodiments, the DNA-PK inhibitors and/or the genome editing system are included in a kit with instructions for use. The kit can contain any genome editing system, and/or DNA-PK inhibitor and instructions for use. In some embodiments the DNA-PK inhibitor is any of compounds represented by Structural Formula (III-E-1) or (III-E-2). In some embodiments, the genome editing system is a selected from a meganuclease based system, a zinc finger nuclease (ZFN) based system, a Transcription Activator-Like Effector-based Nuclease (TALEN) system, a CRISPR-based system, or a NgAgo-based system. The genome editing system can be provided in the kit in any form, for example as a plasmid, vector, DNA, or RNA construct.

In some embodiments, the DNA-PK inhibitor and/or a genome editing system is administered in vivo. The DNA-PK inhibitor and the gene-editing system is formulated to be compatible with its intended route of administration. Examples of routes of administration are described above.

In some embodiments, the formulation can also contain more than one active compound as necessary for the particular indication being treated, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In some embodiments, the DNA-PK inhibitor agent and/or the genome editing system are administered in combination therapy, i.e., combined with other agents, e.g., therapeutic agents, that are useful for treating pathological conditions or disorders, such as various forms of cancer and inflammatory diseases. The term "in combination" in this context means that the agents are given substantially contemporaneously, either simultaneously or sequentially. If given sequentially, at the onset of administration of the second compound, the first of the two compounds is preferably still detectable at effective concentrations at the site of treatment.

Genome Editing Screening Methods

Any method known in the art can be used to screen cells for genome-editing efficiency, including the efficiency of NHEJ and/or HDR. For example, screening methods can include PCR based amplification of targeted regions followed by sequencing or deep sequencing of the amplified regions to confirm genome editing. PCR genotyping permits the quantification and ranking of compounds in stimulating HDR. Other screening methods can include next-generation sequencing. See, for example Bell et al., "A high-throughput screening strategy for detecting CRISPR-Cas9 induced mutations using next-generation sequencing," *BMC Genomics*, 15:1002 (2014).

PCR primers can be engineered to selectively amplify both unmodified and modified genetic regions, resulting in amplicons of different lengths depending on the genetic modification status. The amplicons can then be resolved on a gel, and the HDR efficiency estimated by densitometry using a Bio-Imager. Alternatively, a new PCR technology, the rapid digital droplet PCR (DDPCR) can be used to simultaneously measure HDR and NHEJ events in genome-edited samples. See, for example, Miyaoka et al., "Systematic quantification of HDR and NHEJ reveals effects of locus, nuclease, and cell type on genome-editing," *Scientific Reports*, 6, 2016. Other methods that can be used for screening cells for genomic modiciations including, Sanger sequencing, deep sequencing, and RT-PCR.

Preparation of Compounds of the Invention

As used herein, all abbreviations, symbols and conventions are consistent with those used in the contemporary scientific literature. See, e.g., Janet S. Dodd, ed., *The ACS Style Guide: A Manual for Authors and Editors*, 2nd Ed., Washington, D.C.: American Chemical Society, 1997. The following definitions describe terms and abbreviations used herein:

BPin pinacol boronate ester
Brine a saturated NaCl solution in water
DCM dichloromethane
DIAD diisopropylazodicarboxylate
DIEA diisopropylethylamine
DMA dimethylacetamide
DMF dimethylformamide
DMSO dimethylsulfoxide
DTT dithiothreitol
ESMS electrospray mass spectrometry
Et$_2$O ethyl ether
EtOAc ethyl acetate
EtOH ethyl alcohol
HEPES 4-(2-hydroxyethyl)-1-piperazineethanesulfonic acid
HPLC high performance liquid chromatography
IPA isopropanol
LAH lithium aluminum hydride
LC-MS liquid chromatography-mass spectrometry
LDA lithium diisoproylethylamide
Me methyl
MeOH methanol
MsCl methanesulfonyl chloride
MTBE methyl t-butyl ether
NMP N-methylpyrrolidine
Pd$_2$(dba)$_3$ tris(dibenzylideneacetone)dipalladium(0)
Pd(dppf)Cl$_2$ 1,1'bis(diphenylphosphino)-ferrocene dichloro-palladium
PG protecting group
Ph phenyl
(rac)-BINAP racemic 2,2'-bis(diphenylphosphino)-1,1'-binaphthyl
RockPhos di-tert-butyl(2',4',6'-triisopropyl-3,6-dimethoxy-[1,1'-biphenyl]-2-yl)phosphine
RT or rt room temperature
SFC supercritical fluid chromatography
SPhos 2-dicyclohexylphosphino-2',6'-dimethoxybiphenyl
TBAI tetrabutylammonium iodide
tBu tertiary butyl
THF tetrahydrofuran
TEA triethylamine
TMEDA tetramethylethylenediamine
VPhos [3-(2-dicyclohexylphosphanylphenyl)-2,4-dimethoxy-phenyl]sulfonyloxysodium General Synthetic Procedures In general, the compounds of this invention may be prepared by methods described herein or by other methods known to those skilled in the art.

Example 1. General Preparation of the Compounds of Formula G

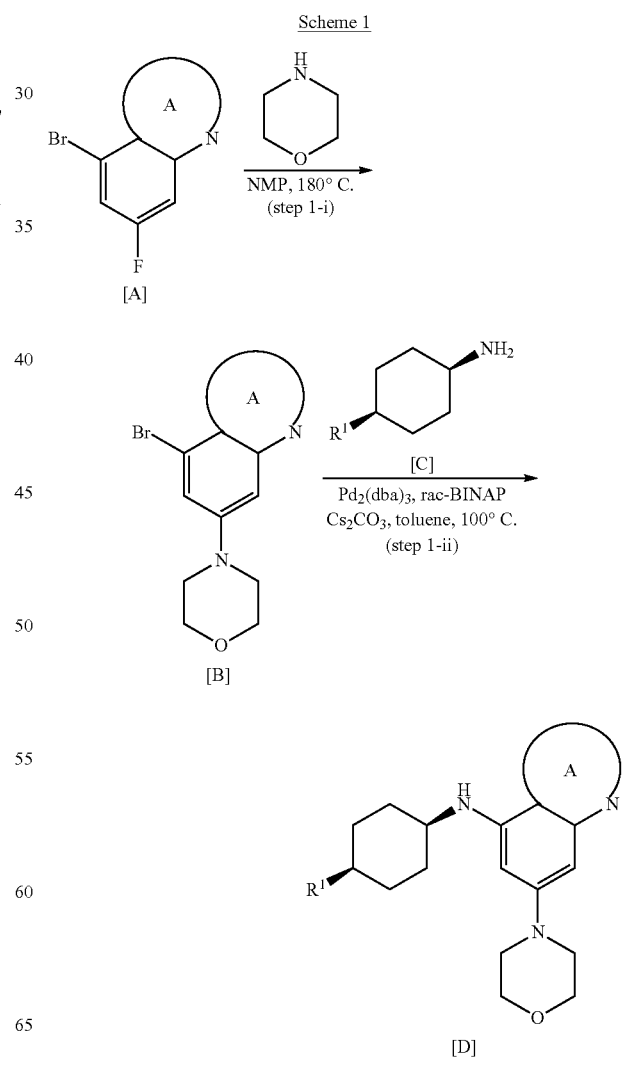

-continued

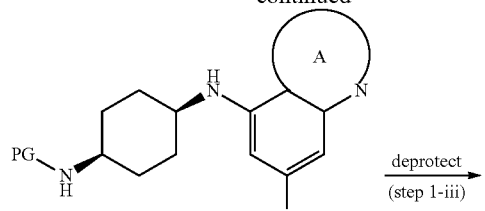

[E]

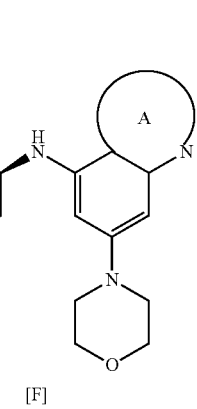

[F]

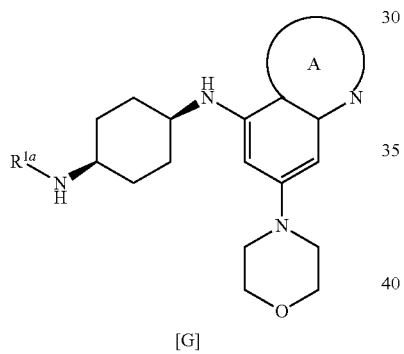

[G]

Example 2. General Preparation of the Compounds of Formula M, N, R, and S

Scheme 2a

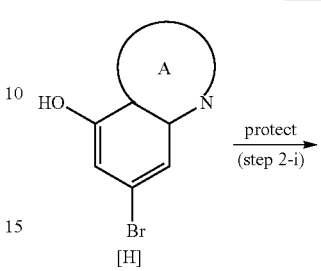

[H]

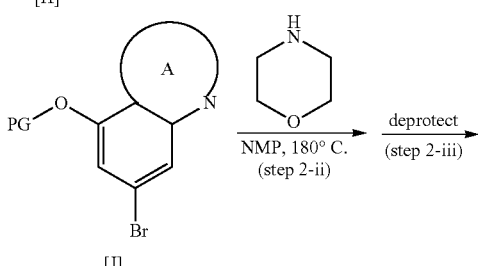

[J]

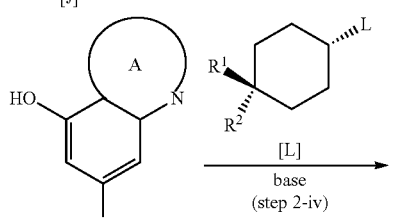

[K]

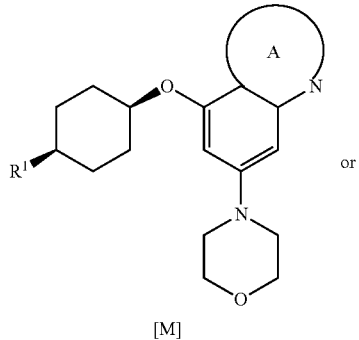

[M]

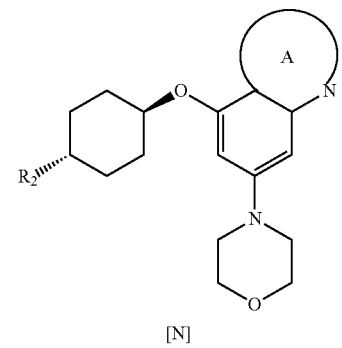

[N]

Compounds of formula (III-E-1) or (III-E-2), wherein X is NH can be prepared as outlined below in Scheme 1. Accordingly, as shown in step 1-i of Scheme 1, heteroaryl compounds of formula A can be reacted with morpholine or a morpholine analog by heating the mixture in a polar, non-protic solvent to produce compounds of formula B. Utilizing a palladium-catalyzed, phosphine ligand-assisted Buchwald/Hartwig-type coupling, as shown in step 1-ii of Scheme 1, a compound of formula B can be reacted with aminocyclohexanes of formula C to produce compounds of formula D, wherein $R^1$ and $R^2$ are as described elsewhere herein. In one example, when monoprotected meso cyclohexane-1,4-diamines of formula E are prepared, removal of the protecting group forms compounds of formula F, as shown in step 1-iii of Scheme 1. The resulting free amine can then be reacted with various moieties having groups reactive towards amines (e.g., $R^{1a}$-L, where L is a leaving group such as chloro, bromo, iodo, toluenesulfonate, methanesulfonate, or trifluoromethanesulfonate; or where L is a reactive carbonyl-containing moiety such as an active ester or an isocyanato group) to produce a compound of formula G, as shown in step 1-iv of Scheme 1.

Compounds of (III-E-1) or (III-E-2), wherein X is O can be prepared as outlined below in Schemes 2a and 2b. Accordingly, as shown in step 2-i of Scheme 2a, the hydroxyl group of heteroaryl compounds of formula H can be protected to produce compounds of formula J, which can then be reacted with morpholine or a morpholine analog by heating the mixture in a polar, non-protic solvent to produce compounds of formula K after removal of the protecting group, as shown in steps 2-ii and 2-iii of Scheme 2a. Subsequently, as shown in step 2-iv of Scheme 2a, a compound of formula K can be reacted with a compound of formula L under conditions sufficient to affect the SN2 displacement of its leaving group (e.g., where L is a leaving group such as chloro, bromo, iodo, toluenesulfonate, methanesulfonate, or trifluoromethanesulfonate) to produce a compound of formula M or formula M, depending on whether $R^1$ or $R^2$ is hydrogen. In those instances when $R^1$ or $R^2$ are protected nitrogen or oxygen moieties, compounds of the invention can be produced by removal of the protecting group and subsequent synthetic manipulation of the resulting free amine/alcohol.

Alternatively, as shown in Scheme 2b, the hydroxyl group of a compound of formula O can be reacted with a compound of formula L to produce a fused bicycloheteroaryl bromide of formula P, which can subsequently be reacted with morpholine or a morpholine analog to produce a compound of formula M or formula N.

Scheme 2b

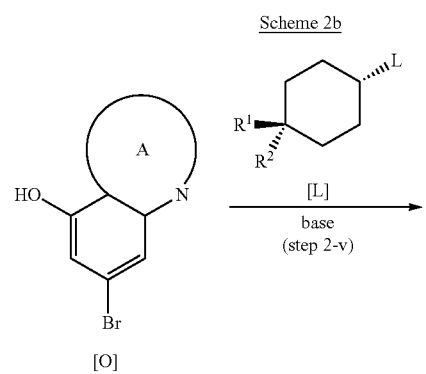

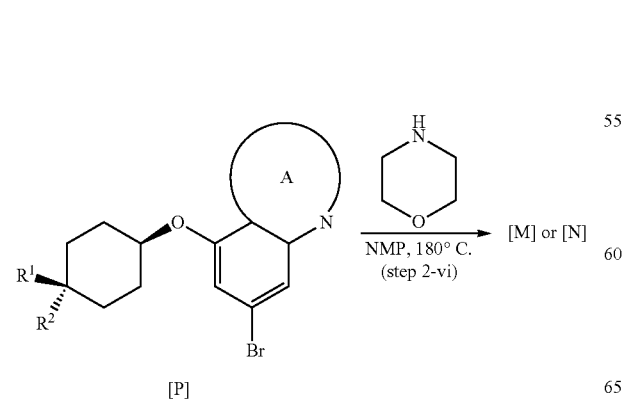

Alternatively, as shown in Scheme 2c, compounds of the invention in which Ring B is a dihydropyran ring can be prepared by reacting compounds of formula Q with dialkyl (3,6-dihydro-2H-pyran-4-yl)boronates to produce compounds of formula R. Compounds of formula R can then be subsequently reduced to form compounds of formula S.

Scheme 2c

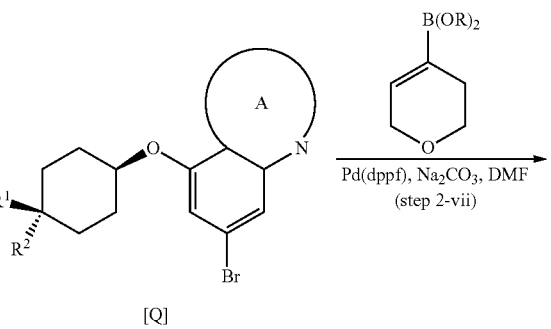

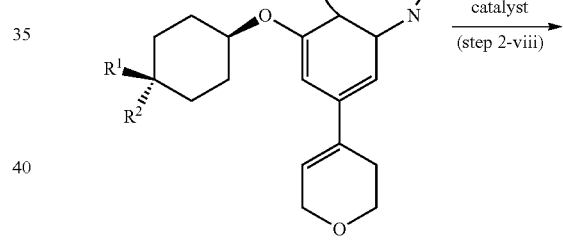

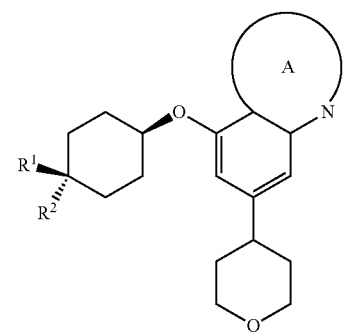

Example 3. Preparation of ethyl (4-((7-morpholino-quinoxalin-5-yl)amino)cyclohexyl)carbamate (Compound 6) and $N^1$-(7-morpholinoquinoxalin-5-yl)-$N^4$-(pyrimidin-2-yl)cyclohexane-1,4-diamine (Compound 18)

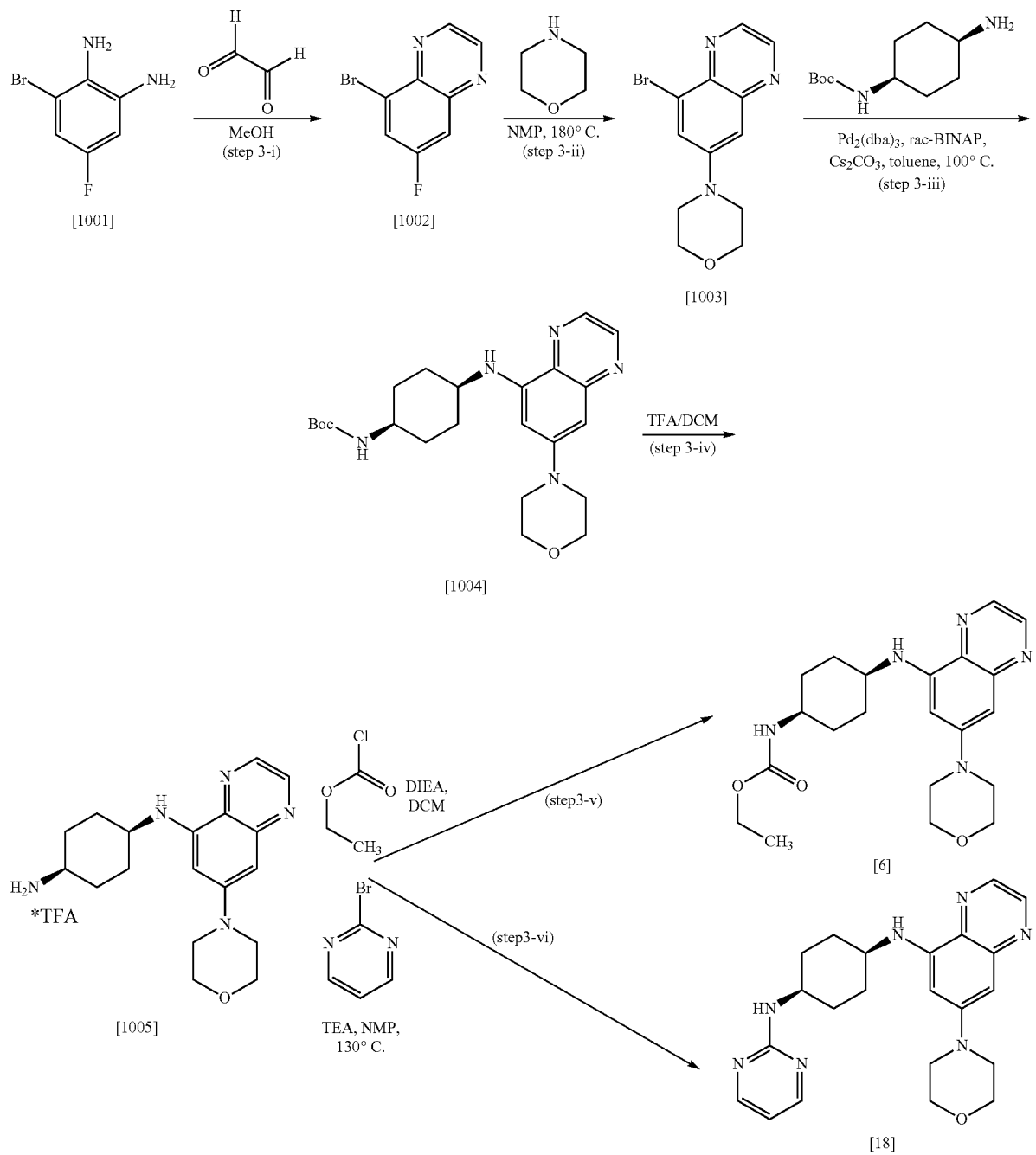

As shown in step 3-i of Scheme 3, to a solution of 3-bromo-5-fluoro-benzene-1,2-diamine (compound 1001, 1.11 g, 5.41 mmol) in methanol (11 mL) was added oxaldehyde (1.57 mL of 40% w/v, 10.8 mmol). The reaction mixture was stirred at room temperature under nitrogen. After 2 hours a yellow solid precipitated. The reaction mixture was diluted with water (20 mL), stirred an additional 5 minutes, filtered, and the collected solid dried under high vacuum to produce 5-bromo-7-fluoroquinoxaline (compound 1002, 868 mg, 70.6% yield): $^1$H-NMR (300 MHz, DMSO-$d_6$) δ 9.06 (s, 2H), 8.36 (dd, J=8.5, 2.7 Hz, 1H), 8.00 (dd, J=9.2, 2.7 Hz, 1H); ESMS (M+H$^+$)=227.14.

As shown in step 3-ii of Scheme 3, to a solution of 5-bromo-7-fluoroquinoxaline (4.5 g, 19.8 mmol) in NMP (67.5 mL) was added morpholine (3.1 mL, 35.6 mmol). The reaction mixture was heated to 140° C. and stirred for 15 hours. After cooling, the mixture was poured into water (200 mL), extracted with ethyl acetate (2×100 mL), dried over magnesium sulfate, filtered, evaporated under reduced pressure, and purified by medium pressure silica gel chromatography (10 to 80% EtOAc/hexanes gradient) to provide 4-(8-bromoquinoxalin-6-yl)morpholine (compound 1003, 3.86 g, 66% yield) as a yellow solid: $^1$H-NMR (400 MHz, DMSO-d$_6$) δ 8.82 (d, J=1.6 Hz, 1H), 8.73 (d, J=1.6 Hz, 1H), 8.12 (d, J=2.5 Hz, 1H), 7.27 (d, J=2.4 Hz, 1H), 3.87-3.69 (m, 4H), 3.44-3.34 (m, 4H); ESMS (M+H$^+$)=227.14.

As shown in step 3-iii of Scheme 3, a mixture of 4-(8-bromoquinoxalin-6-yl)morpholine (1.57 g, 5.34 mmol), tert-butyl-N-(4-aminocyclohexyl)carbamate (1.37 g, 6.40 mmol), (rac)-BINAP (664 mg, 1.07 mmol), cesium carbonate (5.22 g, 16.0 mmol), and Pd$_2$(dba)$_3$ (489 mg, 0.534 mmol) in toluene (50 mL) was heated at 100° C. for 12 hours. After cooling, the mixture was diluted with ethyl acetate (150 mL) and water (25 mL), then filtered through diatomaceous earth which was subsequently washed with ethyl acetate. The combined organics were washed with brine, dried over sodium sulfate, concentrated under reduced pressure, and purified by medium pressure silica gel chromatography (0 to 60% EtOAc/hexanes gradient) to provide tert-butyl(-4-((7-morpholinoquinoxalin-5-yl)amino)cyclohexyl)carbamate (compound 1004, 1.83 g, 83.2% yield): $^1$H-NMR (300 MHz, CDCl$_3$) δ 8.65 (d, J=2.0 Hz, 1H), 8.35 (d, J=2.0 Hz, 1H), 6.60 (d, J=2.4 Hz, 1H), 6.34 (d, J=2.4 Hz, 1H), 6.11 (d, J=7.8 Hz, 1H), 4.60 (s, 1H), 3.97-3.86 (m, 4H), 3.67 (s, 2H), 3.41-3.25 (m, 4H), 1.85 (d, J=3.0 Hz, 5H), 1.74-1.57 (m, 3H), 1.45 (s, 9H).

As shown in step 3-iv of Scheme 3, to a solution of tert-butyl (-4-((7-morpholinoquinoxalin-5-yl)amino)cyclohexyl)carbamate (900 mg, 2.00 mmol) in dichloromethane (16 mL) was added trifluoroacetic acid (3 mL, 38.9 mmol). The resulting black reaction mixture was stirred under an atmosphere of nitrogen at room temperature for 2 hours. Saturated aqueous sodium bicarbonate (150 mL) was added slowly until the color turned from black to orange. The mixture was extracted with dichloromethane (2×100 mL) and the combined organics washed with brine (50 mL), dried over sodium sulfate, and concentrated under reduced pressure to provide-N$^1$-(7-morpholinoquinoxalin-5-yl)cyclohexane-1,4-diamine, trifluoroacetate (compound 1005): $^1$H NMR (300 MHz, CDCl$_3$) δ 8.64 (d, J=1.9 Hz, 1H), 8.36 (d, J=1.9 Hz, 1H), 6.59 (d, J=2.3 Hz, 1H), 6.34 (d, J=2.3 Hz, 1H), 6.20 (d, J=7.9 Hz, 1H), 3.95-3.84 (m, 4H), 3.69 (s, 1H), 3.41-3.25 (m, 4H), 2.93 (d, J=8.9 Hz, 1H), 2.09-1.87 (m, 2H), 1.90-1.68 (m, 6H), 1.58 (dd, J=11.2, 8.7 Hz, 2H); ESMS (M+H$^+$)=328.34. This compound was used as is without further purification.

As shown in step 3-v of Scheme 3, to solution of N$^1$-(7-morpholinoquinoxalin-5-yl)cyclohexane-1,4-diamine (25 mg, 0.07 mmol) and diisopropylethylamine (18.0 mg, 24.3 μL, 0.14 mmol) in dichloromethane (750 μL) was added ethyl chloroformate (11.4 mg, 10.0 μL, 0.105 mmol). The reaction mixture was stirred for 12 hours, diluted with dichloromethane (10 mL), washed with saturated aqueous sodium bicarbonate (5 mL), dried over sodium sulfate, and concentrated under reduced pressure. The resulting residue was purified by HPLC preparative chromatography using a 10-90% acetonitrile/water (0.1% TFA) gradient as eluant to provide ethyl (4-((7-morpholinoquinoxalin-5-yl)amino)cyclohexyl)carbamate (compound 6, 14 mg, 50% yield): $^1$H-NMR (300 MHz, CDCl$_3$) δ 8.65 (d, J=2.0 Hz, 1H), 8.36 (d, J=2.0 Hz, 1H), 6.61 (d, J=2.4 Hz, 1H), 6.35 (d, J=2.4 Hz, 1H), 6.10 (d, J=7.6 Hz, 1H), 4.72 (s, 1H), 4.12 (q, J=7.0 Hz, 2H), 3.96-3.82 (m, 4H), 3.68 (s, 2H), 3.42-3.23 (m, 4H), 1.93-1.78 (m, 6H), 1.69 (dd, J=15.0, 6.3 Hz, 2H), 1.25 (t, J=7.1 Hz, 3H); ESMS (M+H$^+$)=400.17.

As shown in step 3-vi of Scheme 3, A mixture of N$^1$-(7-morpholinoquinoxalin-5-yl)cyclohexane-1,4-diamine (185 mg, 0.56 mmol), 2-bromopyrimidine (93 mg, 0.58 mmol), and triethylamine (143 mg, 197 μL, 1.41 mmol) in 1-methylpyrrolidin-2-one (3 mL) was heated to 130° C. and stirred for 15 hours. After cooling to room temperature, the mixture was diluted with ethyl acetate (70 mL) and methyl tert-butyl ether (20 mL), washed with water (3×20 mL), washed with brine (15 mL), dried over sodium sulfate, concentrated under reduced pressure, and purified by medium pressure silica gel chromatography (10 to 100% EtOAc/hexanes gradient) to provide N$^1$-(7-morpholinoquinoxalin-5-yl)-N$^4$-(pyrimidin-2-yl)cyclohexane-1,4-diamine (compound 18, 102 mg, 45% yield): $^1$H-NMR (300 MHz, CDCl$_3$) δ 8.65 (d, J=2.0 Hz, 1H), 8.37 (d, J=2.0 Hz, 1H), 8.27 (d, J=4.8 Hz, 2H), 6.60 (d, J=2.4 Hz, 1H), 6.51 (t, J=4.8 Hz, 1H), 6.36 (d, J=2.4 Hz, 1H), 6.15 (d, J=7.8 Hz, 1H), 5.20 (d, J=7.7 Hz, 1H), 4.04 (d, J=7.9 Hz, 1H), 3.96-3.82 (m, 4H), 3.70 (s, 1H), 3.39-3.24 (m, 4H), 1.94 (dd, J=13.7, 4.4 Hz, 6H), 1.78 (dt, J=28.8, 16.1 Hz, 2H); ESMS (M+H$^+$)=328.34.

Example 4. Preparation of 1-(4-((7-(8-oxa-3-azabicyclo[3.2.1]octan-3-yl)quinoxalin-5-yl)amino)cyclohexyl)-3-ethylurea (Compound 22)\

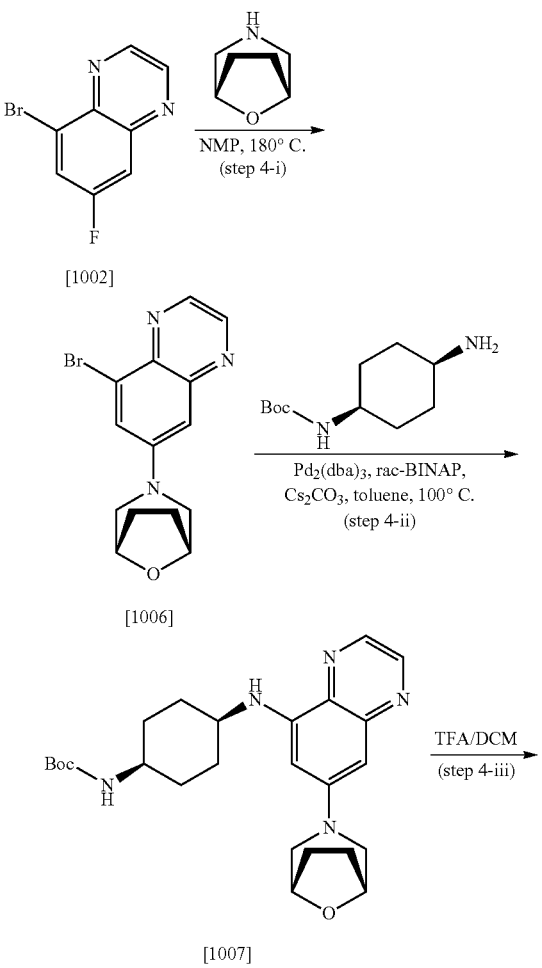

-continued

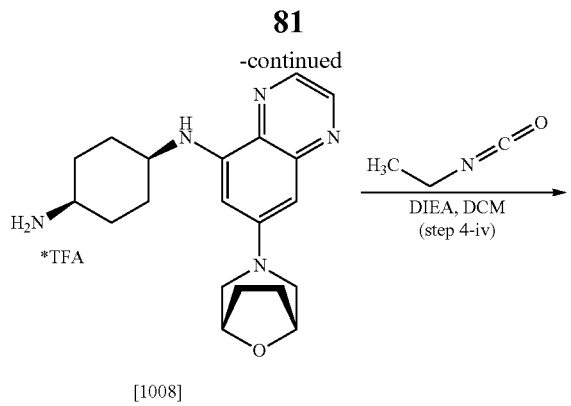

[1008]

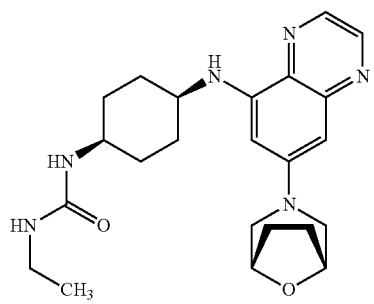

[22]

As shown in step 4-i of Scheme 4, to a solution of 5-bromo-7-fluoroquinoxaline (compound 1002, 150 mg, 0.66 mmol) in NMP (2.3 mL) was added 8-oxa-3-azabicyclo[3.2.1]octane (178 mg, 1.2 mmol) at RT. The reaction mixture was sealed in a microwave vial and heated at 180° C. for 20 minutes. After cooling to RT and pouring into water, the aqueous phase was extracted with EtOAc (3×). The combined extracts were dried over MgSO$_4$, filtered, concentrated under reduced pressure, and purified by medium pressure silica gel chromatography (0 to 100% EtOAc/hexanes gradient) to provide 3-(8-bromoquinoxalin-6-yl)-8-oxa-3-azabicyclo[3.2.1]octane (compound 1006, 87 mg, 41% yield) as a dark orange oil: ESMS (M+H$^+$)= 320.07.

As shown in step 4-ii of Scheme 4, a degassed solution of 3-(8-bromoquinoxalin-6-yl)-8-oxa-3-azabicyclo[3.2.1]octane (261 mg, 0.815 mmol), tert-butyl N-(4-aminocyclohexyl)carbamate (210 mg, 0.98 mmol), rac-BINAP (102 mg, 0.163 mmol), Cs$_2$CO$_3$ (797 mg, 2.45 mmol), and Pd$_2$(dba)$_3$ (75 mg, 0.0815 mmol) in toluene (10.5 mL) was heated at 100° C. (oil bath temp) in a sealed microwave tube for 15 hours. After cooling, the mixture was applied directly to a chromatography column and purified by medium pressure silica gel chromatography (0 to 100% EtOAc/hexanes gradient) to afford tert-butyl (4-((7-(8-oxa-3-azabicyclo[3.2.1]octan-3-yl)quinoxalin-5-yl)amino)cyclohexyl)carbamate (compound 1007, 141 mg, 36% yield) as a white solid: $^1$H-NMR (400 MHz, CDCl$_3$) δ 8.49 (s, 1H), 8.23 (d, J=1.5 Hz, 1H), 6.48 (s, 1H), 6.18 (d, J=1.9 Hz, 1H), 6.06 (s, 1H), 4.52 (s, 1H), 4.47 (s, 2H), 3.60 (s, 2H), 3.45 (d, J=11.6 Hz, 2H), 3.14-3.12 (m, 2H), 1.96-1.84 (m, 4H), 1.79 (s, 5H), 1.54 (s, 3H) and 1.38 (s, 9H) ppm; ESMS (M+H$^+$)=453.96.

As shown in step 4-iii of Scheme 4, to a solution of compound 1007 (141 mg, 0.295 mmol) in CH$_2$Cl$_2$ (2.5 mL) was added TFA (656 mg, 443 μL, 5.75 mmol) at RT. The resulting black solution was stirred for 2 hours and then the reaction was quenched by the addition of saturated NaHCO$_3$ until the black color gradually turned into an orange color. The reaction mixture was extracted with CH$_2$Cl$_2$ (3×) and the combined organic extracts were dried over Na$_2$SO$_4$ and evaporated to dryness to provide N$^1$-(7-(8-oxa-3-azabicyclo[3.2.1]octan-3-yl)quinoxalin-5-yl)cyclohexane-1,4-diamine, trifluoroacetate (compound 1008): ESMS (M+H$^+$)= 354.20. This material was used in subsequent reactions without any further purification.

As shown in step 4-iv of Scheme 4, to a solution of compound 1008 (45 mg, 0.071 mmol) and DIEA (36.5 mg, 49.0 μL, 0.28 mmol) in CH$_2$Cl$_2$ (1.4 mL) was added ethyl isocyanate (20 mg, 0.28 mmol) at RT. The solution was stirred at this temperature for 15 hours and then applied directly to a chromatography column and purified by medium pressure silica gel chromatograph (0 to 100% EtOAc/hexanes gradient) to afford 1-(4-((7-(8-oxa-3-azabicyclo[3.2.1]octan-3-yl)quinoxalin-5-yl)amino)cyclohexyl)-3-ethylurea (compound 22, 8 mg, 27% yield) as a white solid: $^1$H-NMR (400 MHz, CDCl$_3$) δ 8.54 (s, 1H), 8.22 (s, 1H), 6.43 (s, 1H), 6.19 (s, 1H), 6.02 (s, 1H), 4.47 (s, 2H), 4.38 (d, J=5.2 Hz, 1H), 4.28 (s, 1H), 3.74 (s, 1H), 3.60 (s, 1H), 3.42 (s, 4H), 3.14-3.09 (m, 4H), 2.05-1.87 (m, 3H), 1.79 (s, 3H), 1.55 (d, J=7.1 Hz, 2H) and 1.21-1.05 (m, 5H) ppm; ESMS (M+H$^+$)=425.35.

Example 5. Preparation of N$^1$-(6-morpholinobenzo[c][1,2,5]oxadiazol-4-yl)-N$^4$-(pyrimidin-2-yl)cyclohexane-1,4-diamine (Compound 23)

Scheme 5

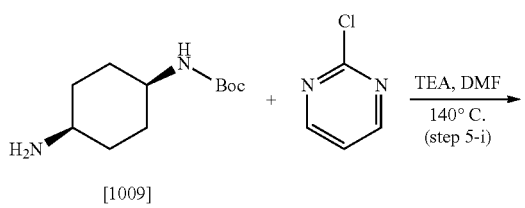

[1009]

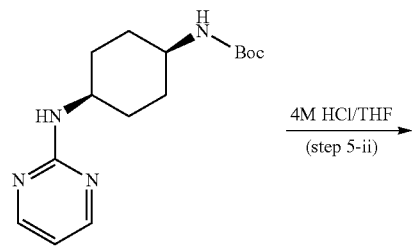

[1010]

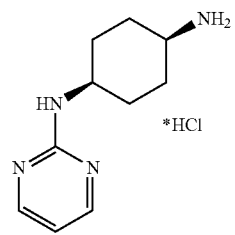

[1011]

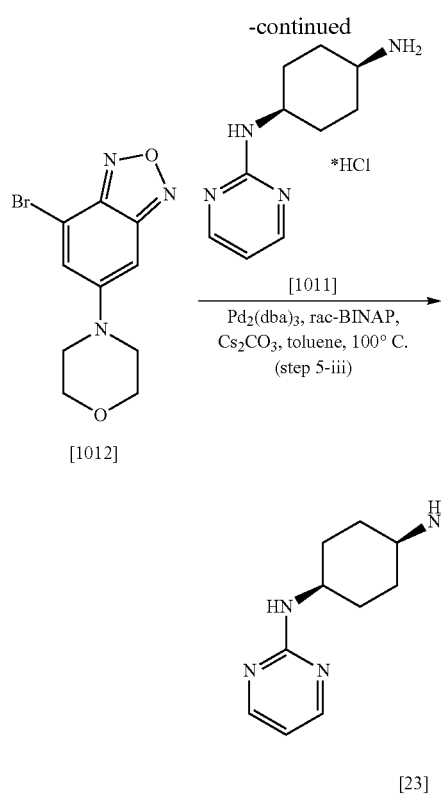

As shown in step 5-i of Scheme 5, a mixture of tert-butyl ((cis)-4-aminocyclohexyl)carbamate (compound 1009, 490 mg, 2.3 mmol), 2-chloropyrimidine (262 mg, 2.3 mmol) and TEA (463 mg, 637 µL, 4.6 mmol) in DMF (10 mL) was subjected to microwave irradiation for 20 minutes at 150° C. The reaction mixture was diluted with EtOAc, washed with H$_2$O, dried over Na$_2$SO$_4$, concentrated under reduced pressure, and purified by medium pressure silica gel chromatography (0 to 50% EtOAc/hexanes gradient) to provide tert-butyl ((cis)-4-(pyrimidin-2-ylamino)cyclohexyl)carbamate (compound 1010) as a white solid: $^1$H-NMR (300 MHz, CDCl$_3$) δ 8.28 (d, J=4.8 Hz, 2H), 6.53 (t, J=4.8 Hz, 1H), 5.12 (s, 1H), 4.56 (s, 1H), 3.99 (dq, J=7.0, 3.5 Hz, 1H), 3.65 (s, 1H), 1.83 (tq, J=10.2, 3.6 Hz, 5H), 1.66 (s, 8H), 8.13-7.91 (m, 3H), 1.47 (s, 9H).

As shown in step 5-ii of Scheme 5, HCl (3 mL, 4M in THF, 12 mmol) was added to compound 1010. The mixture was stirred for 30 min and concentrated under reduced pressure to produce (cis)-N$^1$-(pyrimidin-2-yl)cyclohexane-1,4-diamine hydrochloride (compound 1011). This material was used in subsequent reactions as is without further purification.

As shown in step 5-iii of Scheme 5, a mixture of 4-bromo-6-morpholinobenzo[c][1,2,5]oxadiazole (compound 1012, 147 mg, 0.5 mmol), (cis)-N$^1$-(pyrimidin-2-yl)cyclohexane-1,4-diamine hydrochloride (120 mg, 0.6 mmol), (rac)-BINAP (32 mg, 0.05 mmol), Pd$_2$(dba)$_3$ (24 mg, 0.026 mmol), and cesium carbonate (506 mg, 1.55 mmol) in toluene (5 mL) was flushed with nitrogen gas and stirred overnight at 90° C. under an atmosphere of nitrogen. The mixture was filtered though a layer of diatomaceous earth, concentrated under reduced pressure, and purified by medium pressure silica gel chromatography (0 to 80% EtOAc/hexanes gradient) to provide (cis)-N$^1$-(6-morpholinobenzo[c][1,2,5]oxadiazol-4-yl)-N$^4$-(pyrimidin-2-yl)cyclohexane-1,4-diamine (compound 23) as an orange solid: $^1$H-NMR (300 MHz, CDCl$_3$) δ 8.20 (d, J=4.9 Hz, 2H), 6.46 (t, J=4.8 Hz, 1H), 6.05 (d, J=1.6 Hz, 1H), 5.82 (s, 1H), 5.24 (s, 1H), 4.82 (d, J=7.0 Hz, 1H), 3.98 (s, 1H), 3.85-3.72 (m, 4H), 3.60 (s, 1H), 3.23-3.06 (m, 4H), 1.95-1.62 (m, 8H).

Example 6. Preparation of 5-methoxy-N-((cis)-4-((7-morpholinoquinoxalin-5-yl)oxy)cyclohexyl)pyrimidin-2-amine (Compound 134)

Scheme 6

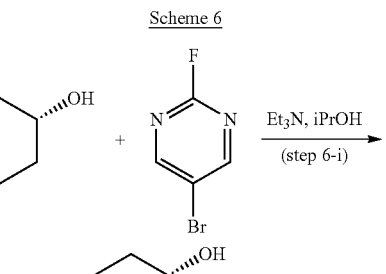

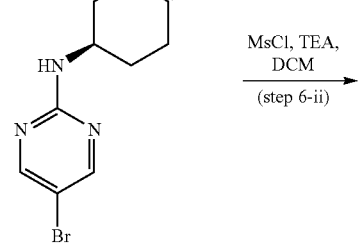

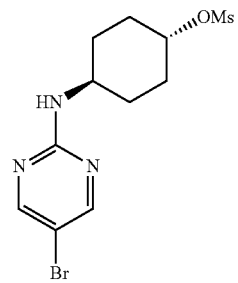

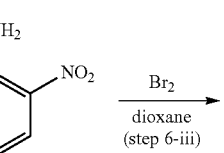

-continued

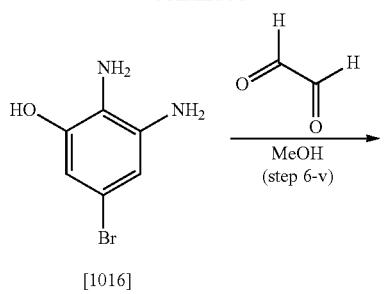

[1016]

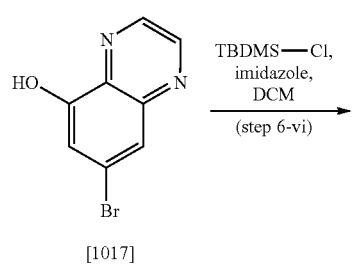

[1017]

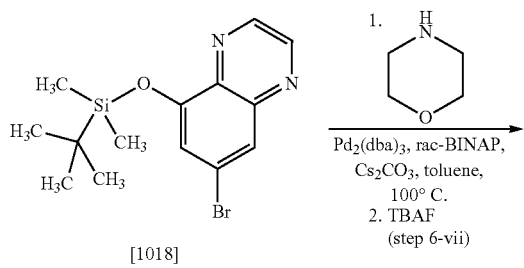

[1018]

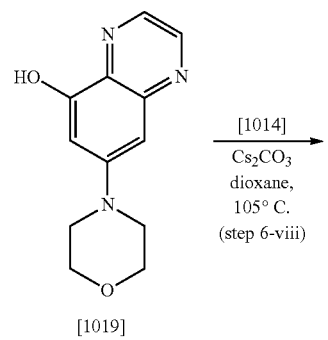

[1019]

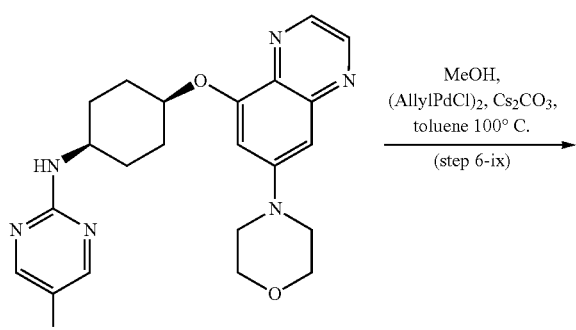

[1020]

-continued

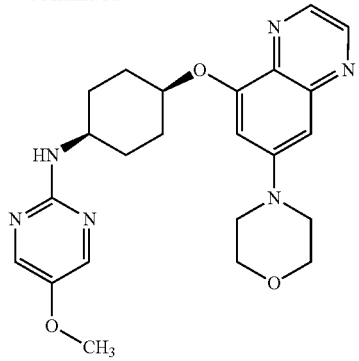

[134]

As shown in step 6-i of Scheme 6, to a mixture of 5-bromo-2-fluoro-pyrimidine (1 g, 5.651 mmol) in iPrOH (10 mL) was added TEA (1.143 g, 1.574 mL, 11.30 mmol) and trans-4-aminocyclohexan-1-ol (650.8 mg, 5.651 mmol). The mixture was microwaved for 20 min at 150° C., concentrated under reduced pressure, diluted with EtOAc, washed with water, and dried over $Na_2SO_4$. After removal of the volatiles under reduced pressure, the residue was purified by medium pressure silica gel chromatography (0-80% EtOAc/hexanes gradient) to provide (trans)-4-((5-bromopyrimidin-2-yl)amino)cyclohexanol (compound 1013, 1.2 g): $^1$H-NMR (300 MHz, $CDCl_3$) δ 8.28 (s, 2H), 5.03 (d, J=8.1 Hz, 1H), 3.91-3.49 (m, 2H), 2.31-1.90 (m, 4H), 1.56-1.19 (m, 4H).

As shown in step 6-ii of Scheme 6, to compound 1013 (1.2 g, 4.41 mmol) in DCM (20 mL) was added TEA (1.134 g, 1.84 mL, 13.2 mmol) and MsCl (505 mg, 341 μL, 4.41 mmol). The reaction mixture was stirred for 1 hour, concentrated under reduced pressure, and purified by medium pressure silica gel chromatography (0 to 80% EtOAc/hexanes gradient) to provide trans-4-((5-bromopyrimidin-2-yl)amino)cyclohexyl methanesulfonate (compound 1014): $^1$H-NMR (300 MHz, $CDCl_3$) δ 8.29 (s, 2H), 5.03 (d, J=7.8 Hz, 1H), 4.70 (tt, J=10.6, 3.9 Hz, 1H), 3.80 (dtt, J=11.2, 7.6, 3.7 Hz, 1H), 3.04 (s, 3H), 2.30-2.12 (m, 4H), 1.93-1.69 (m, 2H), 1.51-1.33 (m, 2H).

As shown in step 6-iii of Scheme 6, to a solution of 2-amino-3-nitrophenol (5.00 g, 32.4 mmol) in dioxane (50 mL) was added bromine (6.22 g, 2.01 mL, 38.9 mmol). The mixture was stirred for 2 hours and a precipitate formed, which was collected and washed with dioxane and ether. The resulting yellow solid treated with a saturated $NaHCO_3$ solution, which was extracted with EtOAc (3×). The combined organics were dried over $Na_2SO_4$, filtered, and concentrated under reduced pressure to yield 2-amino-5-bromo-3-nitrophenol (compound 1015) as a brown solid. This material was carried on as is in subsequent reactions without further purification.

As shown in step 6-iv of Scheme 6, to a solution of 2-amino-5-bromo-3-nitrophenol (7.5 g, 31.8 mmol) in ethyl acetate (60 mL) was added Raney Nickel™ (1.90 g, 214 μL, 32.4 mmol) and the reaction mixture was shaken for 2 hours under an atmosphere of $H_2$ at 30 p.s.i. After filtering and drying over $Na_2SO_4$, the mixture was concentrated under reduced pressure to provide 2,3-diamino-5-bromophenol (compound 1016), which was used as is in subsequent reactions without further purification.

As shown in step 6-v of Scheme 6, 2,3-diamino-5-bromophenol (6.0 g, 29.5 mmol) was dissolved in methanol and to this solution was added glyoxal (3.77 g, 2.98 mL, 64.9 mmol) and stirred overnight. The reaction mixture was concentrated under reduced pressure to a minimum volume and the resulting tan solid collected by filtration and dried under high vacuum to produce 7-bromoquinoxalin-5-ol (compound 1017), which was used as is in subsequent reactions without further purification.

As shown in step 6-vi of Scheme 6, a solution of 7-bromoquinoxalin-5-ol (2.0 g, 8.89 mmol) in DCM (20 mL) was added imidazole (1.82 g, 26.7 mmol) and tert-butyldimethylsilyl chloride (1.34 g, 1.65 mL, 8.89 mmol). The reaction mixture was stirred overnight at RT, concentrated under reduced pressure, and purified by medium pressure silica gel chromatography (0 to 20% EtOAc/hexanes gradient) to provide 7-bromo-5-((tert-butyldimethylsilyl)oxy)quinoxaline (compound 1018) as a colorless oil: $^1$H-NMR (300 MHz, CDCL$_3$) δ 8.69 (q, J=1.8 Hz, 2H), 7.80 (d, J=2.1 Hz, 1H), 7.22 (d, J=2.1 Hz, 1H), 0.96 (s, 9H), 0.81 (s, 7H).

As shown in step 6-vii of Scheme 6, a mixture of 7-bromo-5-((tert-butyldimethylsilyl)oxy)quinoxaline (700 mg, 2.06 mmol), morpholine (270 mg, 270 L, 3.09 mmol), Pd$_2$(dba)$_3$ (94.50 mg, 0.1032 mmol), (rac)-BINAP (129 mg, 0.206 mmol), cesium carbonate (2.02 g, 6.19 mmol) in toluene (7 mL) was flushed with nitrogen for 10 minutes. The mixture was then heated overnight at 100° C. After cooling, the reaction mixture was diluted with EtOAc, filtered through a layer of diatomaceous earth, concentrated under reduced pressure, and purified by medium pressure silica gel chromatography (0 to 30% EtOAc/hexanes gradient) to provide 7-morpholinoquinoxalin-5-ol. This compound (450 mg, 1.3 mmol) was dissolved in THF (20 mL) and tetra-n-butylammonium fluoride (539 mg, 2.06 mmol) was added. The reaction mixture was stirred for 0.5 hour, concentrated under reduced pressure, and purified by medium pressure silica gel chromatography (0 to 100% EtOAc/hexanes gradient) to provide 7-morpholinoquinoxalin-5-ol (compound 1019) as a yellow solid: $^1$H-NMR (300 MHz, CDCl$_3$) δ 8.75 (d, J=2.0 Hz, 1H), 8.46 (d, J=2.0 Hz, 1H), 7.70 (d, J=41.8 Hz, 1H), 7.01 (d, J=2.6 Hz, 1H), 6.89 (d, J=2.5 Hz, 1H), 4.12-3.78 (m, 4H), 3.51-3.24 (m, 4H).

As shown in step 6-viii of Scheme 6, a solution of 7-morpholinoquinoxalin-5-ol (100 mg, 0.432 mmol), (trans)-4-((5-bromopyrimidin-2-yl)amino)cyclohexyl methanesulfonate (compound 1014, 303 mg, 0.865 mmol), and CsCO$_3$ (282 mg, 0.865 mmol) in dioxane (1.0 mL was stirred for 16 hours at 105° C. After cooling, the reaction mixture was diluted with EtOAc, filtered through diatomaceous earth, concentrated under reduced pressure, and purified by medium pressure silica gel chromatography (0 to 5% MeOH/DCM gradient) to produce 5-bromo-N-((cis)-4-((7-morpholinoquinoxalin-5-yl)oxy)cyclohexyl)pyrimidin-2-amine (compound 1020, 110 mg) as a yellow foam: $^1$H-NMR (400 MHz, CDCl$_3$) δ 8.70 (d, J=2.0 Hz, 1H), 8.64 (d, J=1.9 Hz, 1H), 8.29 (s, 2H), 6.98 (d, J=2.5 Hz, 1H), 6.92 (d, J=2.5 Hz, 1H), 5.29 (d, J=8.3 Hz, 1H), 4.81 (s, 1H), 4.04-3.84 (m, 4H), 3.42-3.31 (m, 4H), 2.22 (s, 2H), 1.92 (d, J=4.9 Hz, 6H).

As shown in step 6-ix of Scheme 6, to a mixture 5-bromo-N-((cis)-4-((7-morpholinoquinoxalin-5-yl)oxy)cyclohexyl) pyrimidin-2-amine (75 mg, 0.155 mmol), cesium carbonate (101 mg, 0.309 mmol), allylpalladium(II) chloride dimer (0.28 mg, 0.0015 mmol), RockPhos (2.17 mg, 0.0046 mmol) and MeOH (9.9 mg, 12.5 µL, 0.31 mmol) in toluene (2 mL) was flushed with nitrogen gas and heated to 100° C. for 18 hours. The reaction mixture was diluted with EtOAc, filtered though a layer of diatomaceous earth, and concentrated under reduced pressure. Purification by medium pressure silica gel chromatography (0-8% MeOH/DCM gradient) yielded 5-methoxy-N-((cis)-4-((7-morpholinoquinoxalin-5-yl)oxy)cyclohexyl)pyrimidin-2-amine (compound 134, 43 mg): $^1$H-NMR (300 MHz, CDCl$_3$) δ 8.70 (d, J=1.9 Hz, 1H), 8.63 (d, J=1.9 Hz, 1H), 8.07 (s, 2H), 6.96 (d, J=2.5 Hz, 1H), 6.92 (d, J=2.5 Hz, 1H), 5.01 (d, J=8.1 Hz, 1H), 4.80 (q, J=5.6, 4.2 Hz, 1H), 4.03-3.87 (m, 5H), 3.80 (s, 3H), 3.42-3.27 (m, 4H), 2.29-2.10 (m, 2H), 1.99-1.82 (m, 6H).

Example 7. Preparation of 4-(8-(((trans)-4-(pyrimidin-2-yloxy)cyclohexyl)oxy)quinoxalin-6-yl)morpholine (Compound 34) and 4-(8-(((cis)-4-(pyrimidin-2-yloxy)cyclohexyl)oxy)-quinoxalin-6-yl) morpholine (Compound 42)

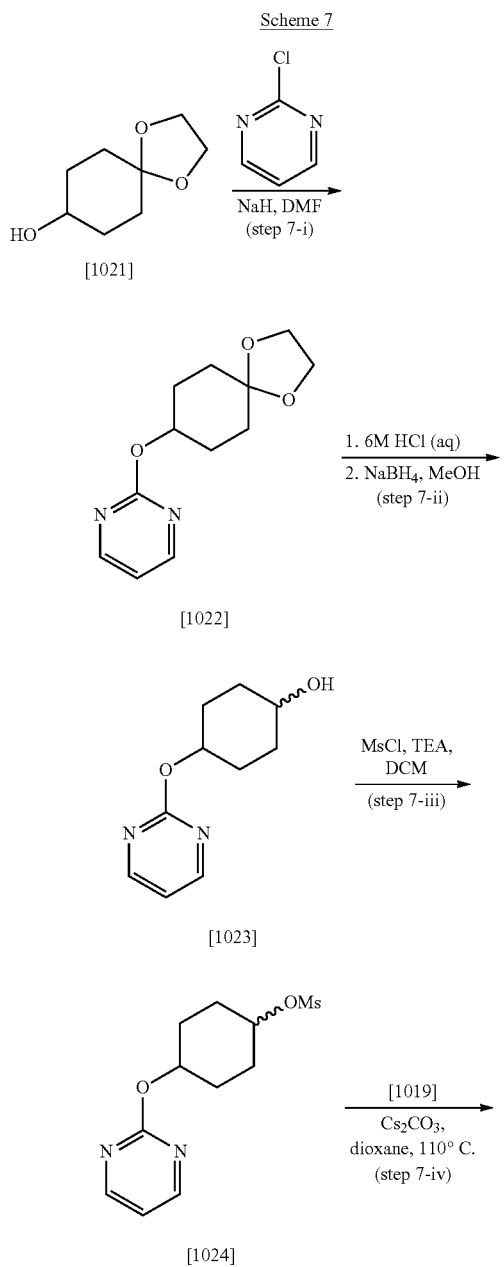

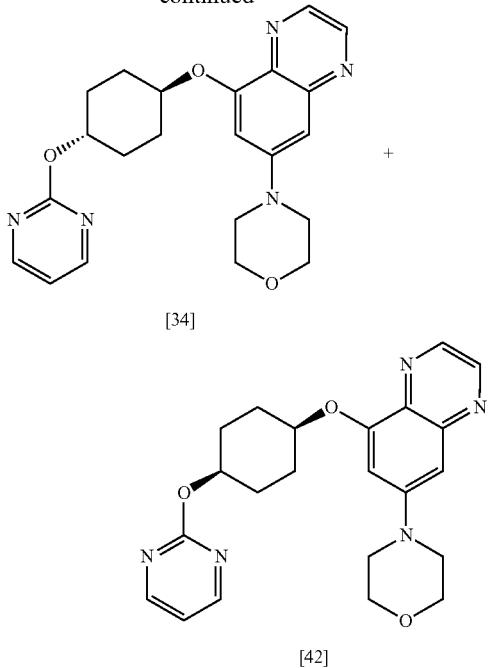

[34]

[42]

As shown in step 7-i of Scheme 7, to a solution of 1,4-dioxaspiro[4.5]decan-8-ol (compound 1021, 1.0 g, 6.32 mmol) in DMF (10 mL) was added NaH (370 mg, 9.25 mmol). The reaction mixture was stirred for 20 minutes before the addition of 2-chloropyrimidine (869 mg, 7.59 mmol). The mixture was stirred for 30 minute at RT and then heated to 100° C. for 9 hours. After cooling, the mixture was diluted with EtOAc, washed with H$_2$O, dried over Na$_2$SO$_4$, concentrated under reduced pressure, and purified by medium pressure silica gel chromatography (0-40% EtOAc/hexanes) to produce 2-(1,4-dioxaspiro[4.5]decan-8-yloxy) pyrimidine (compound 1022) as a colorless oil: $^1$H NMR (300 MHz, Chloroform-d) δ 8.52 (d, J=4.8 Hz, 2H), 6.92 (t, J=4.8 Hz, 1H), 5.15 (ddd, J=10.7, 6.5, 4.2 Hz, 1H), 4.05-3.87 (m, 4H), 2.14-1.85 (m, 6H), 1.79-1.65 (m, 2H); ESMS (M+H$^+$)=237.12.

As shown in step 7-ii of Scheme 7, to 2-(1,4-dioxaspiro [4.5]decan-8-yloxy)pyrimidine (620 mg, 2.624 mmol) was added HCl (4.0 mL of 6 M, 8.86 mmol) and the reaction mixture was stirred for 2 hours. The pH of the mixture was neutralized with with sat. NaHCO$_3$(aq) and the mixture was concentrated under reduced pressure as a methanol azeotrope. To the residue was added DCM (30 mL) to produce a precipitate, followed by stirring for an additional 20 minutes. The solids were filtered off and the mother liquor was concentrated under reduced pressure. The resulting residue was dissolved in methanol and sodium borohydride (151 mg, 3.99 mmol) was added as a solid. The mixture was stirred for 1 hour and the reaction quenched with HCl (6M, 0.70 mL). Stirring was continued until gas evolution ceased. The pH of the mixture was adjusted to about 8 with 1N sodium hydroxide and extracted with EtOAc (20 mL). The organics were dried over sodium sulfate and concentrated under reduced pressure to produce 4-(pyrimidin-2-yloxy) cyclohexanol (compound 1023, 248 mg, 64% yield) as a mixture of (cis)- and (trans)-isomers. A 12 mg aliquot of the sample was purified via HPLC preparative reversed-phase chromatography (10-90% CH$_3$CN/water gradient containing 0.1% TFA) to separate the isomers: (trans)-4-pyrimidin-2-yloxycyclohexanol-$^1$H NMR (300 MHz, Chloroform-d) δ 8.54 (d, J=4.8 Hz, 2H), 6.95 (t, J=4.8 Hz, 1H), 5.05 (tt, J=9.4, 4.0 Hz, 1H), 3.91-3.75 (m, 1H), 2.26-1.99 (m, 4H), 1.76-1.41 (m, 4H); ESMS (M+H$^+$)=195.07, (cis)-4-pyrimidin-2-yloxycyclohexanol NMR (300 MHz, Chloroform-d) δ 8.62 (d, J=4.9 Hz, 2H), 7.04 (t, J=4.9 Hz, 1H), 5.21 (tt, J=5.3, 2.6 Hz, 1H), 4.56 (s, 1H), 3.85 (p, J=5.9 Hz, 1H), 2.17-2.02 (m, 2H), 1.88-1.67 (m, 6H); ESMS (M+H$^+$) =195.07. The remaining material was used in subsequent reactions as the cis/trans mixture.

As shown in step 7-iii of Scheme 7, to a solution of a cis/trans mixture of 4-pyrimidin-2-yloxycyclohexanol (244 mg, 1.256 mmol) and triethylamine (350 µL, 2.51 mmol) in dichloromethane (5 mL) was added methane sulfonyl chloride (145 µL, 1.87 mmol). The reaction mixture was stirred for 2 hours, concentrated under reduced pressure, and purified by medium pressure silica gel chromatography (0-20% EtOAc/dichloromethane gradient) to provide 4-pyrimidin-2-yloxycyclohexyl) methanesulfonate (compound 1024, 239 mg, 70% yield) as a mixture of cis/trans isomers: $^1$H NMR (300 MHz, Chloroform-d) δ 8.51 (d, J=4.8 Hz, 2H), 6.93 (t, J=4.8 Hz, 1H), 5.13 (dq, J=9.9, 3.0 Hz, 1H), 4.87 (p, J=3.8 Hz, 1H), 3.04 (d, J=2.4 Hz, 3H), 2.28-1.99 (m, 4H), 1.99-1.74 (m, 4H); ESMS (M+H$^+$)=273.52.

As shown in step 7-iv of Scheme 7, a mixture of (4-pyrimidin-2-yloxycyclohexyl) methanesulfonate (105 mg, 0.386 mmol), 7-morpholinoquinoxalin-5-ol (178.3 mg, 0.7712 mmol), and Cs$_2$CO$_3$ (125.6 mg, 0.3856 mmol) in dioxane (1.5 mL) was sealed in a 5 mL microwave tube and heated to 110° C. for 14 hours using an oil bath. The reaction mixture was cooled to room temperature, diluted with EtOAc, and filtered through diatomaceous earth which was subsequently washed with ethyl acetate. The filtrate was concentrated under reduced pressure and the residue purified via preparative reversed-phase HPLC (10-90% CH$_3$CN/ water gradient containing 0.1% TFA). Fractions containing a mixture of cis and trans isomers were further purified via SFC using a chiral OJ column and eluting with 40% MeOH in CO$_2$ to provide 21 mg of 4-(8-(((trans)-4-(pyrimidin-2-yloxy)cyclohexyl)oxy)quinoxalin-6-yl)morpholine (compound 34): $^1$H NMR (300 MHz, Chloroform-d) δ 8.69 (dd, J=3.4, 1.9 Hz, 1H), 8.62 (dd, J=3.6, 1.9 Hz, 1H), 8.51 (dd, J=4.8, 2.2 Hz, 2H), 7.01-6.83 (m, 3H), 5.18 (tt, J=7.0, 3.4 Hz, 1H), 4.79 (tt, J=6.9, 3.1 Hz, 1H), 4.00-3.85 (m, 4H), 3.34 (dq, J=4.8, 2.6 Hz, 4H), 2.44-2.16 (m, 4H), 1.92 (tdd, J=16.4, 7.7, 2.8 Hz, 4H); ESMS (M+H$^+$)=408.56, and 22 mg of 4-(8-(((cis)-4-(pyrimidin-2-yloxy)cyclohexyl)oxy)-quinoxalin-6-yl)morpholine (compound 42): $^1$H NMR (300 MHz, Chloroform-d) δ 8.70 (d, J=1.9 Hz, 1H), 8.63 (d, J=1.9 Hz, 1H), 8.52 (d, J=4.8 Hz, 2H), 7.01-6.87 (m, 3H), 5.17 (ddt, J=8.7, 6.7, 3.4 Hz, 1H), 4.76-4.58 (m, 1H), 4.00-3.87 (m, 4H), 3.40-3.27 (m, 4H), 2.43-2.22 (m, 4H), 2.05-1.87 (m, 2H), 1.86-1.71 (m, 2H); ESMS (M+H$^+$)=408.56.

Example 8. N-[(cis)-4-[7-(3,6-dihydro-2H-pyran-4-yl)quinoxalin-5-yl]oxycyclohexyl]pyrimidin-2-amine (Compound 36)

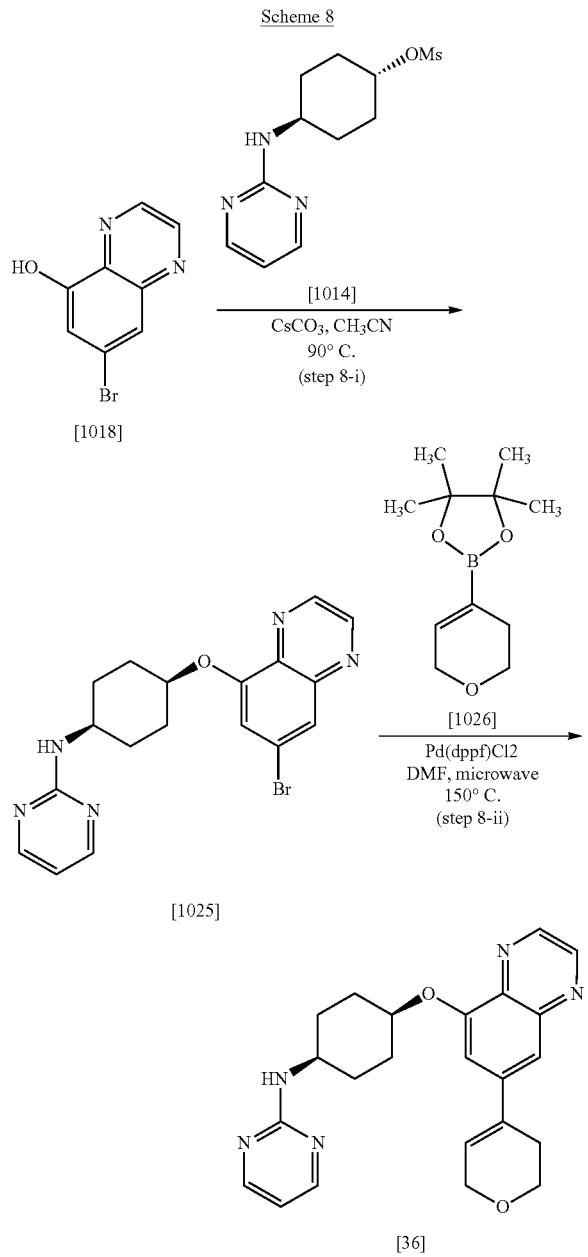

[36]

As shown in step 8-i of Scheme 8, to a mixture of 7-bromoquinoxalin-5-ol (compound 1018, 200 mg, 0.89 mmol) and cesium carbonate (579 mg, 1.78 mmol) in NMP (4.0 mL) was added (trans)-4-(pyrimidin-2-ylamino)cyclohexyl methanesulfonate (compound 1014, 241.1 mg, 0.8887 mmol). The mixture was stirred for 18 hours at 90° C., at which time an additional 0.5 eq of compound 1014 (241 mg, 0.89 mmol) was added. After stirring at 90° C. for an additional 6 hours, the reaction mixture was diluted with EtOAc, washed with H₂O, dried over Na₂SO₄, concentrated, and purified by medium pressure silica gel chromatography (0-5% MeOH/DCM) to provide N-((cis)-4-((7-bromoquinoxalin-5-yl)oxy)cyclohexyl)pyrimidin-2-amine (compound 1025): $^1$H-NMR (300 MHz, CDCl$_3$) δ 9.01-8.77 (m, 2H), 8.29 (d, J=4.8 Hz, 2H), 7.89 (d, J=1.9 Hz, 1H), 7.25 (d, J=2.0 Hz, 1H), 6.53 (t, J=4.8 Hz, 1H), 5.43-5.22 (m, 1H), 4.79 (td, J=5.2, 2.5 Hz, 1H), 4.18-3.95 (m, 1H), 3.51 (s, 1H), 2.22 (td, J=10.2, 9.6, 5.4 Hz, 2H), 2.09-1.86 (m, 6H).

As shown in step 8-ii of Scheme 8, a mixture of N-((cis)-4-((7-bromoquinoxalin-5-yl)oxy)cyclohexyl)pyrimidin-2-amine (compound 1025, 52 mg, 0.1299 mmol), Pd(dppf)Cl₂ (10.61 mg, 0.01299 mmol), 2-(3,6-dihydro-2H-pyran-4-yl)-4,4,5,5-tetramethyl-1,3,2-dioxaborolane (compound 1026, 27.3 mg, 0.13 mmol), Na₂CO₃ (195 µL of 2M (aq) solution, 0.39 mmol) in DMF (1 mL) was flushed with nitrogen gas for 10 minutes. The mixture was subjected to microwave radiation for 20 min at 150° C. After cooling, the mixture was diluted with EtOAc, washed with H₂O, dried over Na₂SO₄, concentrated under reduced pressure and purified by medium pressure silica gel chromatography (0-5% MeOH/DCM) to provide N-[(cis)-4-[7-(3,6-dihydro-2H-pyran-4-yl)quinoxalin-5-yl]oxycyclohexyl]pyrimidin-2-amine (compound 36) as an off-white solid: $^1$H-NMR (300 MHz, CDCl$_3$) δ 8.94-8.76 (m, 2H), 8.29 (d, J=4.8 Hz, 2H), 7.67 (d, J=1.7 Hz, 1H), 6.53 (t, J=4.8 Hz, 1H), 6.37 (tt, J=3.1, 1.5 Hz, 1H), 5.30 (d, J=7.9 Hz, 1H), 4.87 (dt, J=7.5, 3.6 Hz, 1H), 4.43 (q, J=2.8 Hz, 2H), 4.02 (t, J=5.5 Hz, 3H), 2.68 (dqd, J=6.0, 3.4, 3.0, 1.8 Hz, 2H), 2.35-2.11 (m, 2H), 2.07-1.84 (m, 6H); ESMS (M+H⁺)=404.2.

Example 9. N-((cis)-4-((7-morpholinoquinoxalin-5-yl)oxy)cyclohexyl)pyrimidin-2-amine (Compound 28)

Scheme 9

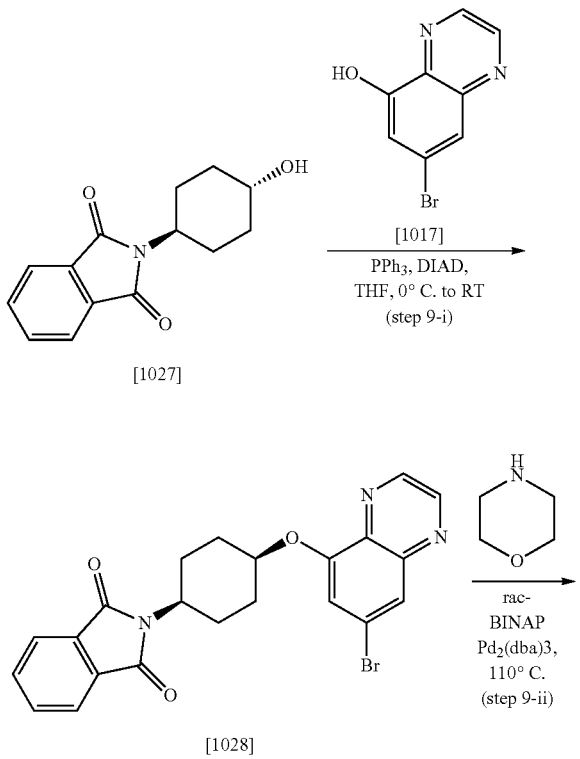

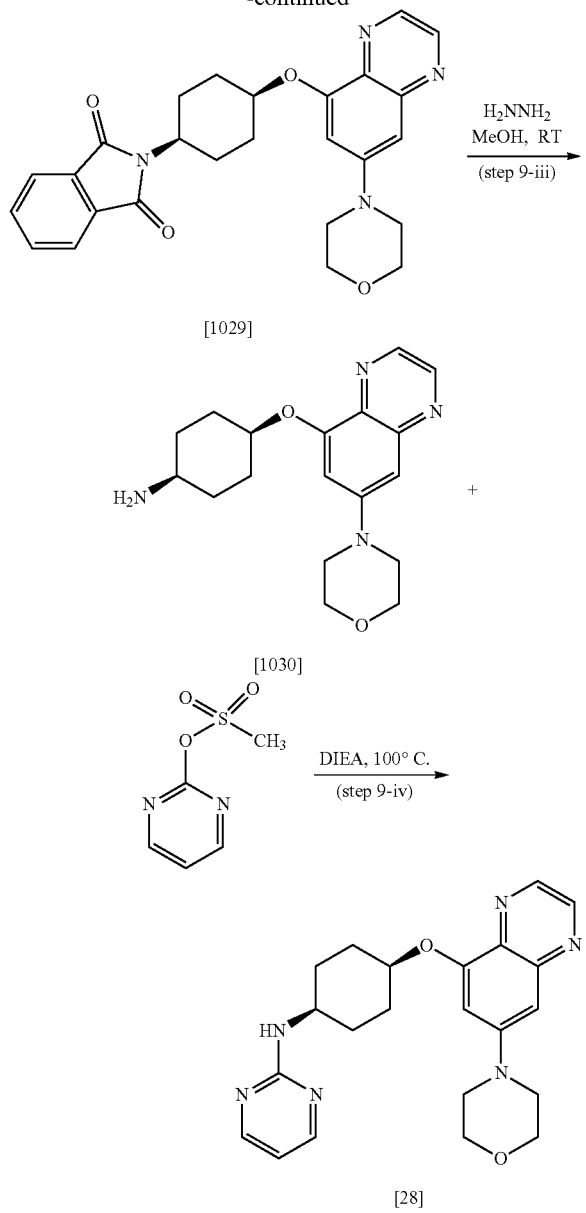

[1029]

[1030]

[28]

As shown in step 9-i of Scheme 9, 7-bromoquinoxalin-5-ol (compound 1017, 5.4 g, 24.0 mmol), 2-((trans)-4-hydroxycyclohexyl)isoindoline-1,3-dione (5.607 g, 22.86 mmol), and triphenylphosphine (8.994 g, 7.945 mL, 34.29 mmol) were dissolved in anhydrous THF and the flask was cooled in an ice bath. DIAD (6.93 g, 6.64 mL, 34.3 mmol) was added dropwise and the reaction was stirred at 0° C. for 5 minutes, then warmed to room temperature and stirred for 18 hours. The reaction mixture was concentrated under reduced pressure, the residue was treated with Et$_2$O and stirred for 0.5 hour at RT, the precipitates filtered off, the filtrate concentrated under reduced pressure, and the residue purified by medium pressure silica gel chromatography (0-50% EtOAc/hexanes gradient) to produce 2-[(cis)-4-(7-bromoquinoxalin-5-yl)oxycyclohexyl]isoindoline-1,3-dione (compound 1028, 6.2 g, 60% yield): $^1$H-NMR (300 MHz, CDCl$_3$) δ 8.95 (d, J=1.8 Hz, 1H), 8.86 (d, J=1.8 Hz, 1H), 7.91 (d, J=2.0 Hz, 1H), 7.88-7.80 (m, 2H), 7.77-7.68 (m, 2H), 7.31 (d, J=2.0 Hz, 1H), 4.96 (t, J=2.9 Hz, 1H), 4.29 (tt, J=12.5, 3.8 Hz, 1H), 2.88 (qd, J=12.9, 3.6 Hz, 2H), 2.54-2.32 (m, 2H), 1.94-1.61 (m, 4H).

As shown in step 9-ii of Scheme 9, In a round bottom flask fitted with a condenser, a mixture of 2-[4-(7-bromoquinoxalin-5-yl)oxycyclohexyl]isoindoline-1,3-dione (6.2 g, 12.34 mmol), morpholine (1.61 g, 1.62 mL, 18.5 mmol), and Cs$_2$CO$_3$ (12.06 g, 37.0 mmol) in anhydrous toluene (73 mL) was treated with rac-BINAP (768.4 mg, 1.234 mmol) and Pd$_2$(dba)$_3$ (565 mg, 0.617 mmol). The reaction mixture was heated at 110° C. for 18 hours. After cooling to room temperature, the mixture was filtered through diatomaceous earth and concentrated under reduced pressure. The residue was triturated with Et$_2$O and the solids collected by filtration and washed with Et$_2$O to produce 2-((cis)-4-((7-morpholinoquinoxalin-5-yl)oxy)cyclohexyl)isoindoline-1,3-dione (compound 1029, 4.2 g) as yellow solid. The filterate was concentrated under reduced pressure and purified by medium pressure silica gel chromatography (0-100% EtOAc/hexanes gradient) to produce an additional 300 mg of compound 1029: $^1$H-NMR (300 MHz, CDCl$_3$) δ 8.76-8.63 (m, 2H), 7.85 (dd, J=5.4, 3.1 Hz, 2H), 7.79-7.60 (m, 2H), 7.09 (d, J=2.6 Hz, 1H), 6.99 (d, J=2.5 Hz, 1H), 5.06 (t, J=2.8 Hz, 1H), 4.27 (tt, J=12.3, 3.8 Hz, 1H), 4.02-3.85 (m, 4H), 3.49-3.27 (m, 4H), 3.03-2.75 (m, 2H), 2.37 (d, J=14.0 Hz, 2H), 1.83-1.56 (m, 4H).

As shown in step 9-iii of Scheme 9, to a suspension of 2-[(cis)-4-(7-morpholinoquinoxalin-5-yl)oxycyclohexyl]isoindoline-1,3-dione (2.3 g, 5.02 mmol) in MeOH (25 mL) was added hydrazine (321 mg, 315 μL, 10.0 mmol) and the reaction mixture stirred for 18 hours at RT, over which time the initial suspension became homogeneous followed by the appearance of a precipitate. Et$_2$O (30 mL) was added and the reaction mixture stirred an additional 30 minutes. The precipitates were filtered off, the filtrate concentrated under reduced pressure, the residue treated with DCM (30 mL), and any remaining solids removed by filtration. The filtrate was concentrated under reduced pressure to provide (cis)-4-((7-morpholinoquinoxalin-5-yl)oxy)cyclohexanamine (compound 1030), which was used as is in subsequent reactions: $^1$H-NMR (300 MHz, CDCl$_3$) δ 8.69 (d, J=1.9 Hz, 1H), 8.62 (d, J=1.9 Hz, 1H), 6.95 (d, J=2.5 Hz, 1H), 6.90 (d, J=2.5 Hz, 1H), 5.00-4.67 (m, 3H), 4.03-3.81 (m, 4H), 3.49 (s, 1H), 3.43-3.25 (m, 4H), 2.88 (q, J=6.2 Hz, 2H), 2.36-1.96 (m, 6H).

As shown in step 9-iv of Scheme 9, to a solution so (cis) 4-(7-morpholinoquinoxalin-5-yl)oxycyclohexanamine (415 mg, 1.264 mmol) and 2-methylsulfonylpyrimidine (400 mg, 2.53 mmol) was added DIEA (490 mg, 661 μL, 3.79 mmol) and the reaction mixture was sealed in a vessel and heated to 100° C. for 16 hours. After this time, the volatiles were removed under a stream of nitrogen gas and the crude residue dissolved in minimal amount of DCM. Purification by medium pressure silica gel chromatography (0-10% MeOH/DCM, 1% Et$_3$N produced N-((cis)-4-((7-morpholinoquinoxalin-5-yl)oxy)cyclohexyl)pyrimidin-2-amine containing triethylamine hydrochloride as an impurity. Dissolved product in DCM and stirred with a silica-supported amine (Silabond Amine® 40-63 μm). The scavenger mixture was filtered, concentrated under reduced pressure, and dried under high vacuum to provide N-((cis)-4-((7-morpholinoquinoxalin-5-yl)oxy)cyclohexyl)pyrimidin-2-amine (Compound 28, 435 mg): $^1$H-NMR (400 MHz, CDCl$_3$) δ 8.68 (d, J=1.9 Hz, 1H), 8.61 (d, J=1.9 Hz, 1H), 8.27 (s, 1H), 8.26 (s, 1H), 6.94 (d, J=2.4 Hz, 1H), 6.90 (d, J=2.4 Hz, 1H), 6.50 (t, J=4.8 Hz, 1H), 4.78 (s, 1H), 4.08-3.97 (m, 1H), 3.94-3.86 (m, 4H), 3.37-3.28 (m, 4H), 2.20 (d, J=9.1 Hz, 2H), 1.95-1.85 (m, 6H).

Example 10. Preparation of N-[4-[7-(6-oxa-3-azabi-cyclo[3.1.1]heptan-3-yl)quinoxalin-5-yl]oxycyclo-hexyl]pyrimidin-2-amine (Compound 291)

Scheme 10a

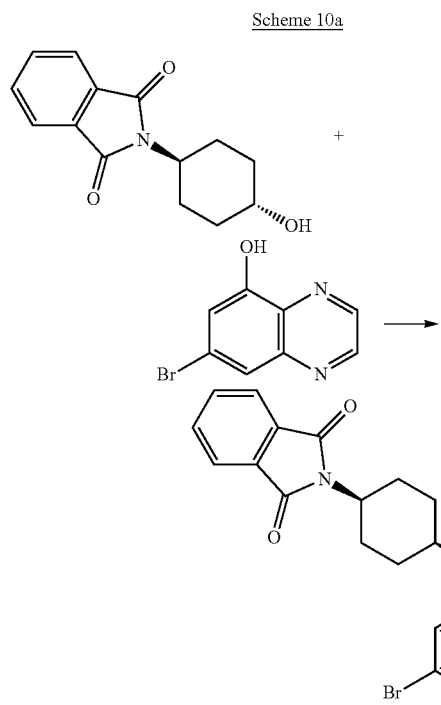

Scheme 10b

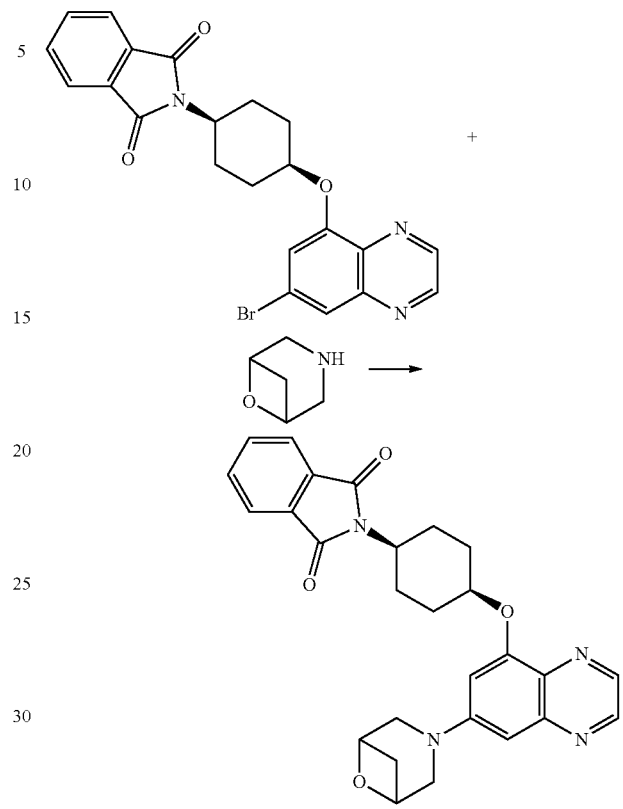

To a mixture of 7-bromoquinoxalin-5-ol (47.53 g, 211.2 mmol), 2-(4-hydroxycyclohexyl)isoindoline-1,3-dione (52.41 g, 213.7 mmol), and PPh3 (87.31 g, 332.9 mmol) in THF (740 mL) at 21° C. was added tert-butyl (NZ)-N-tert-butoxycarbonyliminocarbamate (DTBAD) (79.51 g, 328.0 mmol) in portions over 40 min so as to maintain the temperature below 30° C. and the resultant reaction mixture was stirred at room temperature for a further 20 h.

The reaction was evaporated in vacuo. The residual reddish-brown viscous oil was dissolved in CH2Cl2 and filtered through a plug of silica in a glass column using applied air pressure (plug was made with 1 L of dry silica suspended in CH2Cl2). The plug was eluted with CH2Cl2, the fractions were combined and evaporated in vacuo to afford a red-brown viscous oil/foam, that was then dissolved in 700 mL of MeOH before precipitating. The mixture was stirred at room temperature for 1 h, filtered, washed with cold MeOH (500 mL) and Et2O (100 mL), then dried in vacuo to yield a tan solid that was suspended in 300 mL MeOH and brought to reflux for 10 min The suspension was cooled to room temperature and filtered, washed with a further MeOH and Et2O (4:1), and dried in vacuo to provide 2-[4-(7-bromoquinoxalin-5-yl)oxycyclohexyl]isoindoline-1,3-dione (58.43 g, 126.6 mmol, 59.94%). 1H NMR (400 MHz, CDCl$_3$) δ 8.96 (d, J=1.8 Hz, 1H), 8.86 (d, J=1.8 Hz, 1H), 7.91 (d, J=1.9 Hz, 1H), 7.89-7.82 (m, 2H), 7.78-7.67 (m, 2H), 7.30 (d, J=1.9 Hz, 1H), 4.95 (s, 1H), 4.29 (tt, J=12.5, 3.7 Hz, 1H), 2.87 (qd, J=13.1, 3.5 Hz, 2H), 2.44 (d, J=15.2 Hz, 2H), 1.80 (t, J=14.1 Hz, 2H), 1.67 (d, 2H). ESI-MS m/z calc. 451.05316, found 452.19 (M+1)+; Retention time: 0.92 minutes.

A mixture of 2-[4-(7-bromoquinoxalin-5-yl)oxycyclohexyl]isoindoline-1,3-dione (1 g, 2.211 mmol), 6-oxa-3-azabicyclo[3.1.1]heptane HCl (180 mg, 1.328 mmol), cesium carbonate (2.161 g, 6.633 mmol), Pd2(dba)3 (202.5 mg, 0.2211 mmol) and rac-BINAP (275.3 mg, 0.4422 mmol) in dioxane (5 mL) was stirred overnight at 70° C., then heated in a microwave reactor for 15 min at 150° C. The reaction was then diluted with methylene chloride, filtered though Celite, and concentrated. Silica gel flash column chromatography (0-5% MeOH/DCM) yielded 2-[4-[7-(6-oxa-3-azabicyclo[3.1.1]heptan-3-yl)quinoxalin-5-yl]oxycy-clohexyl]isoindoline-1,3-dione (750 mg, 72.1%) as a yellow solid that was carried on to the next reaction.

Scheme 10c

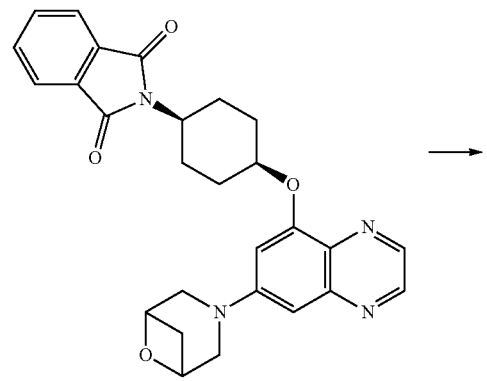

-continued

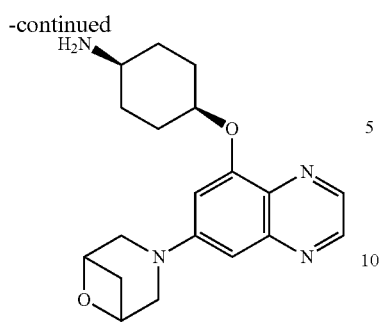

To a solution of 2-[4-[7-(6-oxa-3-azabicyclo[3.1.1]heptan-3-yl)quinoxalin-5-yl]oxycyclohexyl]isoindoline-1,3-dione (800 mg, 1.700 mmol) in EtOH (10 mL) was added hydrazine monohydrate (85.10 mg, 83.35 µL, 1.700 mmol) and the reaction was stirred at reflux overnight, then concentrated, diluted with DCM, and filtered. The filtrate was concentrated, and purified on a 40 g silica gel cartridge with 0-50% (20% NH3/MeOH) to yield 4-[7-(6-oxa-3-azabicyclo[3.1.1]heptan-3-yl)quinoxalin-5-yl]oxycyclohexanamine (450 mg, 77.8%) as a yellow solid. 1H NMR (300 MHz, Chloroform-d) δ 8.65 (d, J=1.9 Hz, 1H), 8.53 (d, J=1.9 Hz, 1H), 6.83 (q, J=2.6 Hz, 2H), 4.83 (t, J=6.0 Hz, 4H), 3.87-3.60 (m, 5H), 3.34 (dt, J=8.7, 6.6 Hz, 1H), 3.01-2.83 (m, 1H), 2.23 (dq, J=11.3, 5.8, 4.8 Hz, 2H), 2.07 (d, J=8.7 Hz, 1H), 1.92-1.62 (m, 6H).

Scheme 10d

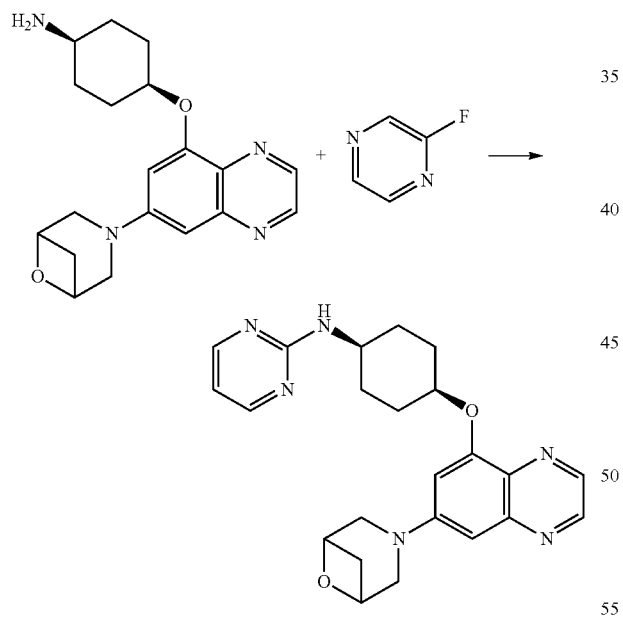

A mixture of 4-[7-(6-oxa-3-azabicyclo[3.1.1]heptan-3-yl)quinoxalin-5-yl]oxycyclohexanamine (190 mg, 0.5581 mmol), 2-fluoropyrimidine (60 mg, 0.6118 mmol) and DIEA (200 µL, 1.148 mmol) in 2-propanol (2 mL) was heated in a microwave reactor for 20 min at 150° C. The reaction mixture was concentrated, and then purified from 12 g silica gel cartridge with 0-6% MeOH/DCM to yield N-[4-[7-(6-oxa-3-azabicyclo[3.1.1]heptan-3-yl)quinoxalin-5-yl]oxycyclohexyl]pyrimidin-2-amine (120.2 mg, 48.9%) as a yellow solid. Mass+1: 419.23; Retention Time: 0.72; NMR Annotation: 1H NMR (400 MHz, Chloroform-d) δ 8.42 (d, J=1.9 Hz, 1H), 8.30 (d, J=1.9 Hz, 1H), 8.04 (d, J=4.8 Hz, 2H), 6.65-6.56 (m, 2H), 6.28 (t, J=4.8 Hz, 1H), 4.99 (d, J=8.1 Hz, 1H), 4.60 (d, J=6.5 Hz, 3H), 3.79 (dd, J=8.2, 4.0 Hz, 0H), 3.62-3.38 (m, 4H), 3.17-3.03 (m, 1H), 2.07-1.90 (m, 2H), 1.89-1.59 (m, 7H).

Example 11. Preparation of 4-methyl-N-[4-[(6-morpholino-2,1,3-benzoxadiazol-4-yl)oxy]cyclohexyl]pyrimidin-2-amine (Compound 665)

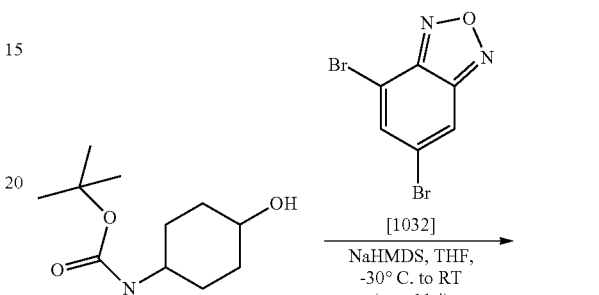

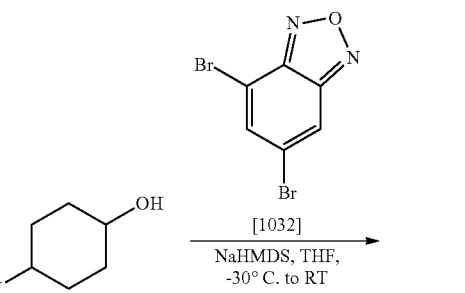

[1032]
NaHMDS, THF,
-30° C. to RT
(step 11-i)

[1031]

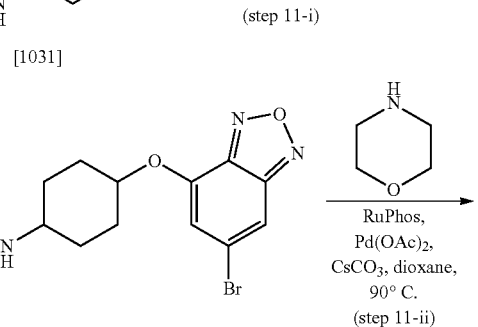

RuPhos,
Pd(OAc)2,
CsCO3, dioxane,
90° C.
(step 11-ii)

[1033]

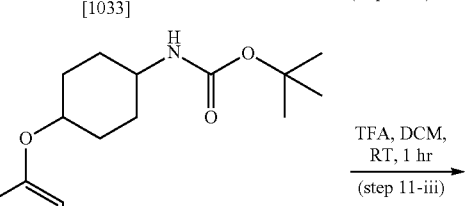

TFA, DCM,
RT, 1 hr
(step 11-iii)

1034]

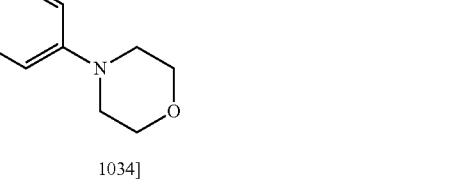

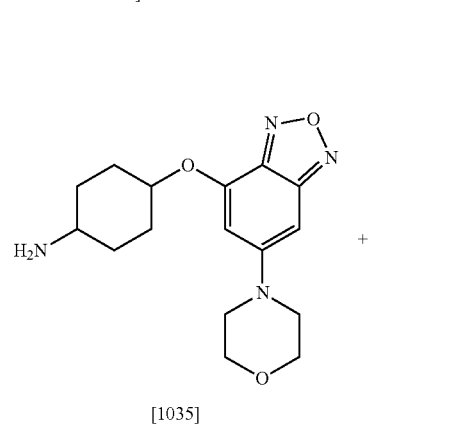

+

[1035]

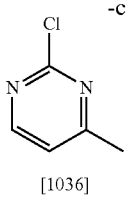

[1036]

-continued

RuPhos, NaOtBu,
dioxane, 70° C.

(step 11-iv)

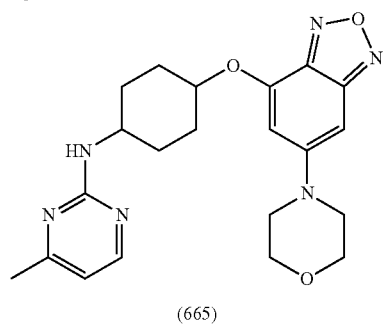 [SMILES: Cc1ccnc(NC2CCC(Oc3cc(N4CCOCC4)cc4nonc34)CC2)n1]

(665)

A mixture of 4,6-dibromo-2,1,3-benzoxadiazole (3 g, 10.80 mmol) and tert-butyl N-(4-hydroxycyclohexyl)carbamate (2.5 g, 11.61 mmol) was dissolved in THF (60 mL) and cooled down to −30° C. To the mixture was dropwise added sodium bis(trimethylsilyl)amide (NaHMDS, 23 mL of 1 M, 23.00 mmol) over 10 min and the solution became dark blue. The mixture was stirred for 30 min −20 to 0° C. and 30 min at rt. LC-MS showed desired product peak only with no starting material. Cooled down to 0° C., quenched with 10% citric acid solution, extracted with EtOAc, dried over Na2SO4, and concentrated. Purified by 0-40% EtOAc/heptane. Recovered 1.9 g (42%) of tert-butyl ((1s,4s)-4-((6-bromobenzo[c][1,2,5]oxadiazol-4-yl)oxy)cyclohexyl)carbamate (C17H22BrN3O4).

A mixture of tert-butyl N-[4-[(6-morpholino-2,1,3-benzoxadiazol-4-yl)oxy]cyclohexyl]carbamate (2.6 g, 6.306 mmol), cesium carbonate (4 g, 12.28 mmol), diacetoxypalladium (140 mg, 0.6236 mmol), RuPhos (580 mg, 1.243 mmol) and morpholine (900 μL, 10.32 mmol) in dioxane (30 mL) purged with N2 for 5 minutes. The mixture was stirred for 3 h at 90° C. LC-MS showed desired product. The mixture was diluted with DCM, filtered though a layer of celite, concentrated and purified with a 80 g silica gel cartridge eluting with 0-80% EtOAc/heptane, recovering tert-butyl N-[4-[(6-morpholino-2,1,3-benzoxadiazol-4-yl)oxy]cyclohexyl]carbamate (2.1 g, 80%). 1H NMR (400 MHz, Chloroform-d) δ 6.42 (dd, J=12.3, 1.7 Hz, 2H), 4.86 (s, 1H), 4.58 (s, 1H), 4.00-3.86 (m, 4H), 3.38-3.18 (m, 4H), 2.28-2.08 (m, 2H), 1.94-1.62 (m, 6H), 1.42 (s, 9H).

tert-butyl N-[4-[(6-morpholino-2,1,3-benzoxadiazol-4-yl)oxy]cyclohexyl]carbamate A solution of tert-butyl N-[4-[(6-morpholino-2,1,3-benzoxadiazol-4-yl)oxy]cyclohexyl]carbamate (3.5 g, 8.363 mmol) i n DCM (30 mL) was added TFA (approximately 953.6 mg, 644.3 μL, 8.363 mmol) and stirred for 1 hr. The mixture was concentrated and purified with 40 g silica gel cartridge eluting with 0-10% (7N NH3/MeOH/DCM). Recovered 4-[(6-morpholino-2,1,3-benzoxadiazol-4-yl)oxy]cyclohexanamine (2.5 g, 94%) ESI-MS m/z calc. 318.1692, found 319.2 (M+1)+; Retention time: 0.55 minutes.

A microwave vial was charged with 4-[(6-morpholino-2,1,3-benzoxadiazol-4-yl)oxy]cyclohexanamine (1 g, 3.141 mmol), 2-chloro-4-methyl-pyrimidine (600 mg, 4.667 mmol), RockPhos G3 (80 mg, 0.3175 mmol) and dioxane (10 mL). NaOtBu (4 mL of 2 M, 8.000 mmol) was added to the mixture. The mixture was stirred for 15 minutes at 70° C. LC-MS showed a conversion, affording 4-methyl-N-[4-[(6-morpholino-2,1,3-benzoxadiazol-4-yl)oxy]cyclohexyl] pyrimidin-2-amine The mixture was diluted with DCM, filtered though a layer of celite, concentrated, and purified with 40 g silica gel cartridge eluting with 0-10% MeOH/DCM. recovered the product. The product was triturated with Et2O and dried under vacuum. 4-methyl-N-[4-[(6-morpholino-2,1,3-benzoxadiazol-4-yl)oxy]cyclohexyl]pyrimidin-2-amine (795.3 mg, 59%), 1H NMR (400 MHz, Chloroform-d) δ 8.16 (d, J=5.1 Hz, 1H), 6.49 (d, J=1.7 Hz, 1H), 6.47-6.40 (m, 2H), 5.07 (d, J=8.0 Hz, 1H), 4.95 (s, 1H), 3.96-3.85 (m, 4H), 3.32-3.24 (m, 4H), 2.34 (s, 3H), 2.25-2.08 (m, 2H), 2.04-1.74 (m, 6H). ESI-MS m/z calc. 410.20663, found 411.3 (M+1)+; Retention time: 0.63 minutes.

Preparation of N-methyl-2-((4-((6-morpholinobenzo[c][1,2,5]oxadiazol-4-yl)oxy)cyclohexyl)amino)pyrimidine-4-carboxamide (Compound (666))

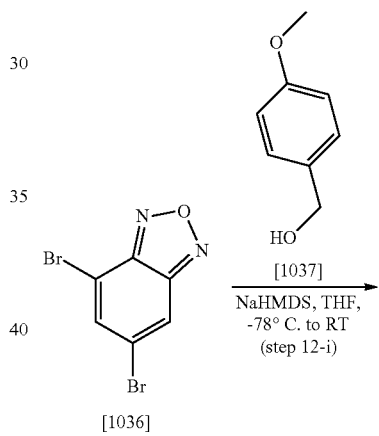

[1036]

NaHMDS, THF,
-78° C. to RT
(step 12-i)

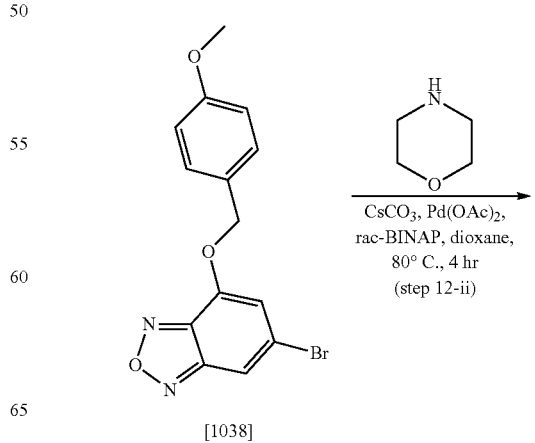

[1038]

CsCO3, Pd(OAc)2,
rac-BINAP, dioxane,
80° C., 4 hr
(step 12-ii)

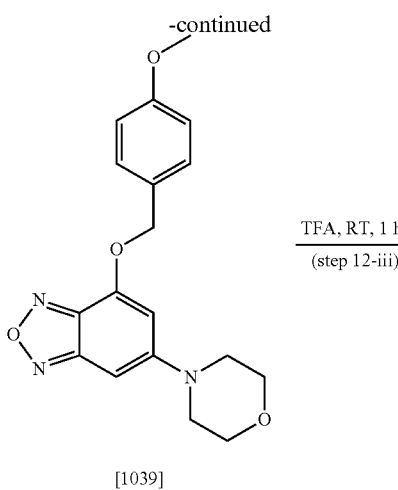

[1039]

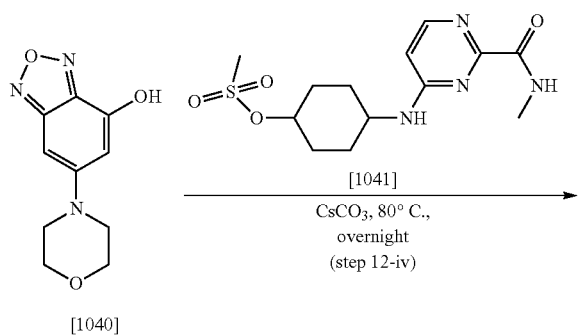

[1040]

[1041]
CsCO₃, 80° C.,
overnight
(step 12-iv)

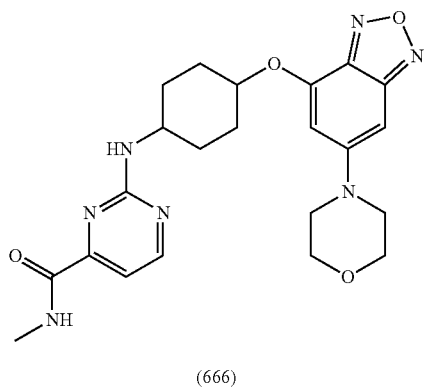

(666)

To a mixture of 4,6-dibromo-2,1,3-benzoxadiazole (1 g, 3.598 mmol), (4-methoxyphenyl)methanol (500 μL, 4.010 mmol) in THF (20 mL) at −78° C. was dropwise added NaHMDS (4 mL of 1 M, 4.000 mmol). The solution became blue. The mixture was stirred at −78° C. for 30 minutes. The mixture was allowed to warm up to RT and was stirred for 1 h at RT. LC-MS showed a product peak and no starting material. TLC showed a spot slightly less polar than the starting material. The reaction was quenched with sat. NH₄Cl, extracted with EtOAc, washed with H₂O, and dried over Na₂SO₄, concentrated. The product was purified with 40 g silica gel cartridge eluting with 0-30% EtOAc, recovering 6-bromo-4-[(4-methoxyphenyl)methoxy]-2,1,3-benzoxadiazole (850 mg, 70%) as slightly yellow solid. 1H NMR (300 MHz, CDCl3) δ 7.48 (d, J=1.2 Hz, 1H), 7.38-7.19 (m, 2H), 6.94-6.74 (m, 2H), 6.57 (d, J=1.1 Hz, 1H), 5.11 (s, 2H), 3.68 (d, J=9.4 Hz, 3H).

A mixture of 6-bromo-4-[(4-methoxyphenyl)methoxy]-2,1,3-benzoxadiazole (830 mg, 2.476 mmol), cesium carbonate (2.4 g, 7.366 mmol), Pd(OAc)2 (50 mg, 0.2227 mmol), rac-BINAP (300 mg, 0.4818 mmol) and morpholine (300 μL, 3.440 mmol) in dioxane (10 mL) was bubbled with N₂ for 10 minutes. The mixture was heated to 80° C. The mixture was stirred for 4.5 h at 80° C. LC-MS showed a clean product. The mixture was cooled to rt, diluted with DCM, filtered though a layer of celite, and concentrated. The product was purified with 4 0 g silica gel cartridge with 0-70% EtOAc/DCM, recovered 4-[(4-methoxyphenyl)methoxy]-6-morpholino-2,1,3-benzoxadiazole (750 mg, 89%). 1H NMR (300 MHz, CDCl3) δ 7.42 (d, J=8.7 Hz, 2H), 7.03-6.87 (m, 2H), 6.48 (d, J=1.6 Hz, 1H), 6.40 (d, J=1.6 Hz, 1H), 5.30 (d, J=13.5 Hz, 2H), 3.99-3.75 (m, 7H), 3.31-3.17 (m, 4H).

A solution of 4-[(4-methoxyphenyl)methoxy]-6-morpholino-2,1,3-benzoxadiazole (750 mg, 2.197 mmol) in DCM (10 mL) was added TFA (2 mL, 25.96 mmol) and stirred for 1 h. The mixture was concentrated and the product purified with 12 g silica gel cartridge eluting with 0-10% MeOH/DCM. 6-Morpholino-2,1,3-benzoxadiazol-4-ol (400 mg, 82%) is recovered as a yellow foam.

A mixture of 6-morpholino-2,1,3-benzoxadiazol-4-ol (50 mg, 0.2260 mmol), [4-[[4-(methylcarbamoyl)pyrimidin-2-yl]amino]DMF, hexyl] methanesulfonate (240 mg, 0.7308 mmol), and cesium carbonate (250 mg, 0.7673 mmol) in DMF (1 mL) was stirred overnight at 80° C. LC-MS showed the desired product. The mixture was diluted with DCM and H₂O, extracted with DCM, dried over Na₂SO₄, concentrated. The product was purified with a 4 g silica gel cartridge eluting with 0-5% MeOH/DCM, recovering the desired product N-methyl-2-((4-((6-morpholinobenzo[c][1,2,5]oxadiazol-4-yl)oxy)cyclohexyl)amino)pyrimidine-4-carboxamide (41.8 mg, 39%). 1H NMR (300 MHz, CDCl₃) δ 8.50 (d, J=4.9 Hz, 1H), 7.76 (s, 1H), 7.34 (d, J=4.9 Hz, 1H), 6.50 (d, J=1.3 Hz, 1H), 6.43 (d, J=1.5 Hz, 1H), 5.21 (d, J=7.2 Hz, 1H), 4.96 (s, 1H), 4.04 (s, 1H), 3.94-3.81 (m, 4H), 3.33-3.17 (m, 4H), 3.01 (t, J=9.9 Hz, 3H), 2.19 (d, J=8.2 Hz, 2H), 2.06-1.78 (m, 6H). ESI-MS m/z calc. 453.21246, found 454.39 (M+1)⁺; Retention time: 0.72 minutes.

Tables 1 and 2 provides analytical characterization data for certain compounds of formula (III-E-1 and III-E-2) (blank cells indicate that the test was not performed).

Table 1

| Cmpd. No. | Compound Structure | ESMS (M + H) | ¹H NMR (300 MHz, unless indicated otherwise) NMR peaks given as δ values |
|---|---|---|---|
| 18 | 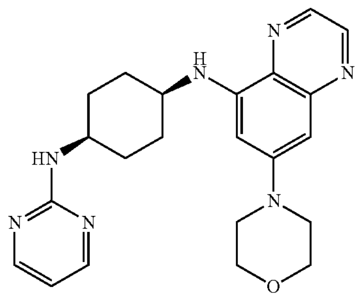 [SMILES: c1cnc(N[C@H]2CC[C@@H](Nc3cc(N4CCOCC4)cc4nccnc34)CC2)nc1] | 406.48 | (CDCl₃) δ 8.65 (d, J = 2.0 Hz, 1H), 8.37 (d, J = 2.0 Hz, 1H), 8.27 (d, J = 4.8 Hz, 2H), 6.60 (d, J = 2.4 Hz, 1H), 6.51 (t, J = 4.8 Hz, 1H), 6.36 (d, J = 2.4 Hz, 1H), 6.15 (d, J = 7.8 Hz, 1H), 5.20 (d, J = 7.7 Hz, 1H), 4.04 (d, J = 7.9 Hz, 1H), 3.96-3.82 (m, 4H), 3.70 (s, 1H), 3.39-3.24 (m, 4H), 1.94 (dd, J = 13.7, 4.4 Hz, 6H), 1.78 (dt, J = 28.8, 16.1 Hz, 2H) |
| 23 | 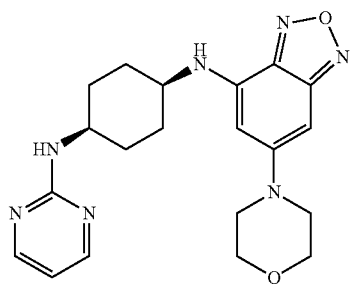 [SMILES: c1cnc(N[C@H]2CC[C@@H](Nc3cc(N4CCOCC4)cc4nonc34)CC2)nc1] | 396.2 | (CDCl₃) δ 8.20 (d, J = 4.9 Hz, 2H), 6.46 (t, J = 4.8 Hz, 1H), 6.05 (d, J = 1.6 Hz, 1H), 5.82 (s, 1H), 5.24 (s, 1H), 4.82 (d, J = 7.0 Hz, 1H), 3.98 (s, 1H), 3.85-3.72 (m, 4H), 3.60 (s, 1H), 3.23-3.06 (m, 4H), 1.95-1.62 (m, 8H). [2] |
| 24 | 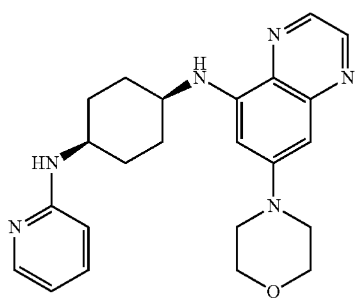 [SMILES: c1ccc(N[C@H]2CC[C@@H](Nc3cc(N4CCOCC4)cc4nccnc34)CC2)nc1] | 405.59 | (400 MHz, CDCl₃) δ 8.65 (s, 1H), 8.37 (d, J = 1.8 Hz, 1H), 8.08 (d, J = 4.9 Hz, 1H), 7.41 (t, J = 7.7 Hz, 1H), 6.61 (s, 1H), 6.58-6.53 (m, 1H), 6.46-6.30(m, 2H), 6.15 (d, J = 7.3 Hz, 1H), 4.56 (s, 1H), 3.98-3.78 (m, 5H), 3.76-3.61 (m, 1H), 3.42-3.24 (m, 4H), 1.97 (d, J = 29.6 Hz, 6H), 1.86-1.66 (m, 2H) |
| 27 | 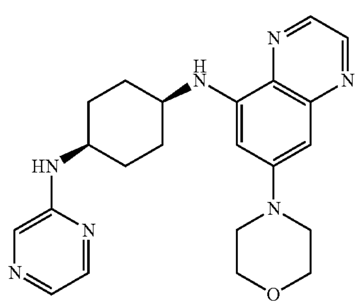 [SMILES: c1cnc(N[C@H]2CC[C@@H](Nc3cc(N4CCOCC4)cc4nccnc34)CC2)cn1] | 406.58 | (CDCl₃) δ 8.65 (d, J = 2.0 Hz, 1H), 8.36 (d, J = 2.0 Hz, 1H), 7.98 (dd, J = 2.8, 1.5 Hz, 1H), 7.88 (d, J = 1.5 Hz, 1H), 7.79 (d, J = 2.8 Hz, 1H), 6.62 (d, J = 2.4 Hz, 1H), 6.37 (d, J = 2.4 Hz, 1H), 6.17 (s, 1H), 8.69-8.61 (m, 1H), 4.60 (d, J = 7.7 Hz, 1H), 4.08-3.83 (m, 5H), 8.71-8.57 (m, 1H), 3.73 (t, J = 6.9 Hz, 1H), 3.40-3.25 (m, 4H), 1.96 (h, J = 4.9 Hz, 6H), 1.77 (q, J = 7.4, 6.1 Hz, 2H) |
| 28 | 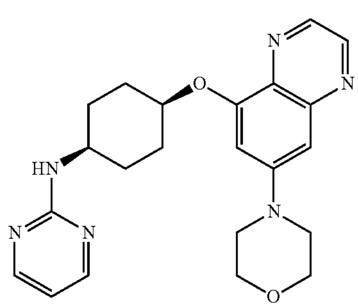 | 407.3 | (400 MHz, CDCl₃) δ 8.77-8.59 (m, 2H), 8.29 (d, J = 4.9 Hz, 2H), 7.01-6.87 (m, 2H), 6.61-6.48 (m, 1H), 4.82 (s, 1H), 4.05 (s, 1H), 3.93 (t, J = 4.8 Hz, 4H), 3.35 (t, J = 4.8 Hz, 4H), 2.23 (d, J = 13.1 Hz, 2H), 2.05-1.82 (m, 6H) |

Table 1-continued

| Cmpd. No. | Compound Structure | ESMS (M + H) | 1H NMR (300 MHz, unless indicated otherwise) NMR peaks given as δ values |
|---|---|---|---|
| 29 | 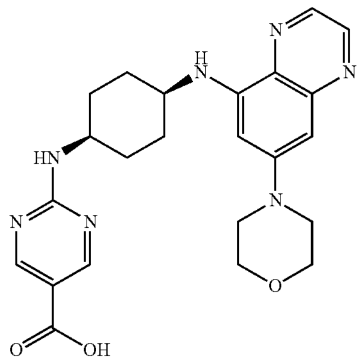 [SMILES: O=C(O)c1cnc(N[C@H]2CC[C@@H](Nc3cc(N4CCOCC4)cc4nccnc34)CC2)nc1] | 450.61 | (DMSO-d6) δ 12.65 (s, 1H), 8.69 (d, J = 2.0 Hz, 2H), 8.43 (d, J = 2.0 Hz, 1H), 8.00 (d, J = 7.9 Hz, 1H), 6.54 (d, J = 2.5 Hz, 1H), 6.48 (d, J = 2.3 Hz, 1H), 6.17 (d, J = 8.2 Hz, 1H), 4.06 (s, 1H), 3.77 (dd, J = 5.9, 3.8 Hz, 4H), 3.29 (s, 5H), 2.04-1.46 (m, 8H) |
| 30 | 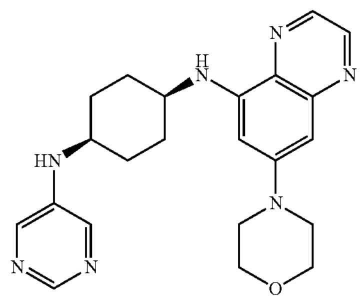 [SMILES: c1ncc(N[C@H]2CC[C@@H](Nc3cc(N4CCOCC4)cc4nccnc34)CC2)cn1] | 406.52 | (CDCl3) δ 8.66 (d, J = 2.0 Hz, 1H), 8.58 (s, 1H), 8.37 (d, J = 2.0 Hz, 1H), 8.13 (s, 2H), 6.63 (d, J = 2.4 Hz, 1H), 6.37 (d, J = 2.4 Hz, 1H), 6.14 (d, J = 7.6 Hz, 1H), 3.96-3.86 (m, 4H), 3.76 (d, J = 7.7 Hz, 2H), 3.54 (d, J = 8.3 Hz, 1H), 3.39-3.29 (m, 4H), 2.02-1.86 (m, 6H), 1.76 (q, J = 8.9, 8.3 Hz, 2H) |
| 32 | 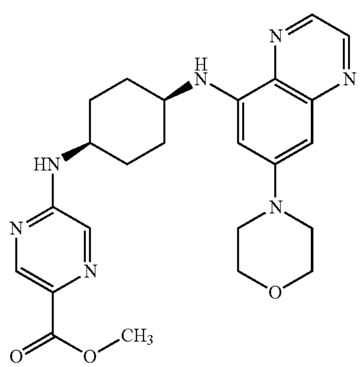 [SMILES: COC(=O)c1cnc(N[C@H]2CC[C@@H](Nc3cc(N4CCOCC4)cc4nccnc34)CC2)cn1] | 464.6 | (CDCl3) δ 8.78 (d, J = 1.3 Hz, 1H), 8.66 (d, J = 2.0 Hz, 1H), 8.37 (d, J = 2.0 Hz, 1H), 7.91 (d, J = 1.3 Hz, 1H), 6.62 (d, J = 2.4 Hz, 1H), 6.37 (d, J = 2.4 Hz, 1H), 6.16 (d, J = 7.6 Hz, 1H), 5.13 (d, J = 7.6 Hz, 1H), 4.10 (s, 1H), 3.99-3.86 (m, 7H), 3.76 (s, 1H), 3.39-3.28 (m, 4H), 1.98 (h, J = 4.8 Hz, 6H), 1.80 (t, J = 8.7 Hz, 2H) |
| 33 | 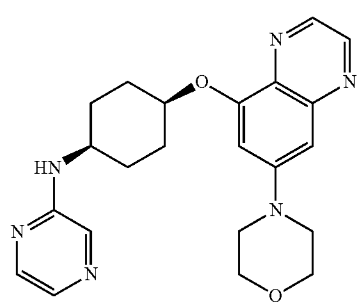 [SMILES: c1cnc(N[C@H]2CC[C@@H](Oc3cc(N4CCOCC4)cc4nccnc34)CC2)cn1] | 407.3 | (CDCl3) δ 8.63 (d, J = 1.9 Hz, 1H), 7.99 (dd, J = 2.8, 1.5 Hz, 1H), 7.94-7.85 (m, 1H), 7.79 (d, J = 2.8 Hz, 1H), 7.14 (d, J = 1.0 Hz, 1H), 7.03-6.87 (m, 2H), 4.82 (d, J = 5.7 Hz, 1H), 4.70 (d, J = 8.0 Hz, 1H), 4.03-3.86 (m, 4H), 3.51 (s, 1H), 3.43-3.30 (m, 4H), 2.35-1.81 (m, 8H) |

Table 1-continued

| Cmpd. No. | Compound Structure | ESMS (M + H) | ¹H NMR (300 MHz, unless indicated otherwise) NMR peaks given as δ values |
|---|---|---|---|
| 34 | 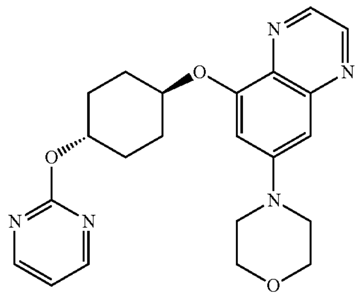 [SMILES: c1cnc(O[C@H]2CC[C@H](Oc3cc(N4CCOCC4)cc4nccnc34)CC2)nc1] | 408.5 | (CDCl₃) δ 8.69 (dd, J = 3.4, 1.9 Hz, 1H), 8.62 (dd, J = 3.6, 1.9 Hz, 1H), 8.51 (dd, J = 4.8, 2.2 Hz, 2H), 7.01-6.83 (m, 3H), 5.18 (tt, J = 7.0, 3.4 Hz, 1H), 4.79 (tt, J = 6.9, 3.1 Hz, 1H), 4.00-3.85 (m, 4H), 3.34 (dq, J = 4.8, 2.6 Hz, 4H), 2.44-2.16 (m, 4H), 1.92 (tdd, J = 16.4, 7.7, 2.8 Hz, 4H) |
| 36 | 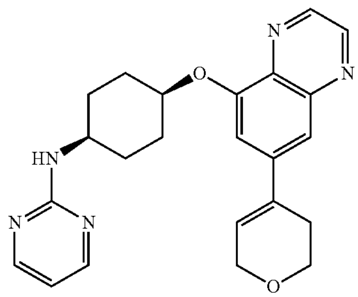 [SMILES: C1=C(c2cc(O[C@H]3CC[C@@H](Nc4ncccn4)CC3)c3nccnc3c2)CCOC1] | 404.2 | (CDCl₃) δ 8.94-8.76 (m, 2H), 8.29 (d, J = 4.8 Hz, 2H), 7.67 (d, J = 1.7 Hz, 1H), 6.53 (t, J = 4.8 Hz, 1H), 6.37 (tt, J = 3.1, 1.5 Hz, 1H), 5.30 (d, J = 7.9 Hz, 1H), 4.87 (dt, J = 7.5, 3.6 Hz, 1H), 4.43 (q, J = 2.8 Hz, 2H), 4.02 (t, J = 5.5 Hz, 3H), 2.68 (dqd, J = 6.0, 3.4, 3.0, 1.8 Hz, 2H), 2.35-2.11 (m, 2H), 2.07-1.84 (m, 6H) |
| 37 | 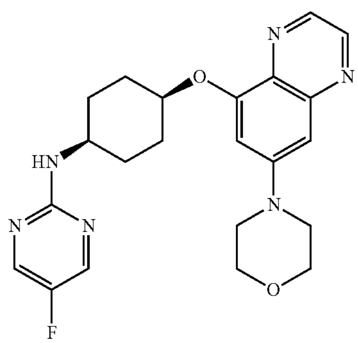 [SMILES: Fc1cnc(N[C@H]2CC[C@@H](Oc3cc(N4CCOCC4)cc4nccnc34)CC2)nc1] | 425.25 | (CDCl₃) δ 8.71 (d, J = 1.9 Hz, 1H), 8.63 (d, J = 1.9 Hz, 1H), 8.18 (dd, J = 3.7, 0.8 Hz, 2H), 7.01-6.85 (m, 2H), 5.37-5.20 (m, 1H), 4.79 (d, J = 5.5 Hz, 1H), 4.02-3.85 (m, 4H), 3.43-3.29 (m, 4H), 2.31-2.15 (m, 2H), 2.02-1.85 (m, 6H) |
| 38 | 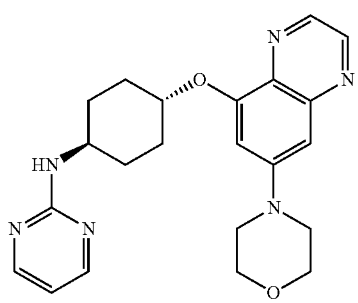 [SMILES: c1cnc(N[C@H]2CC[C@H](Oc3cc(N4CCOCC4)cc4nccnc34)CC2)nc1] | 407.25 | (CDCl₃) δ 8.61 (d, J = 2.0 Hz, 1H), 8.55 (d, J = 1.9 Hz, 1H), 8.20 (d, J = 4.8 Hz, 2H), 6.87 (d, J = 2.5 Hz, 1H), 6.81 (d, J = 2.5 Hz, 1H), 6.46 (t, J = 4.8 Hz, 1H), 4.95 (s, 1H), 4.45 (tt, J = 10.7, 3.6 Hz, 1H), 3.95-3.77 (m, 5H), 3.32-3.19 (m, 4H), 2.34-2.10 (m, 4H), 1.82 (dt, J = 12.9, 10.0 Hz, 2H), 1.45-1.20 (m, 2H) |
| 39 | 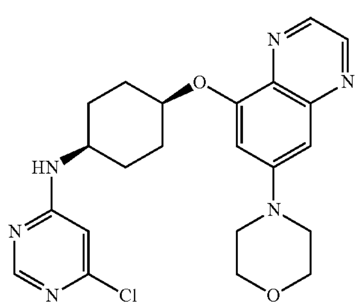 [SMILES: Clc1cc(N[C@H]2CC[C@@H](Oc3cc(N4CCOCC4)cc4nccnc34)CC2)ncn1] | 441.28 | (CDCl₃) δ 8.72 (d, J = 1.9 Hz, 1H), 8.62 (d, J = 1.9 Hz, 1H), 8.37 (s, 1H), 6.98 (d, J = 2.5 Hz, 1H), 6.36 (d, J = 1.0 Hz, 1H), 4.91-4.76 (m, 1H), 4.00-3.88 (m, 4H), 3.45-3.24 (m, 4H), 2.34-2.17 (m, 2H), 2.03-1.84 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 40 | 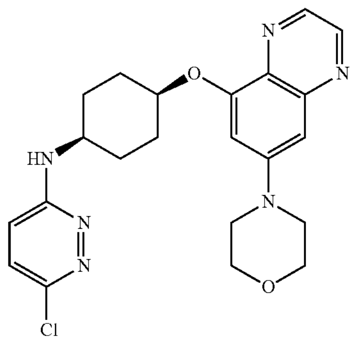 [SMILES: Clc1ccc(N[C@H]2CC[C@@H](Oc3cc(N4CCOCC4)cc4nccnc34)CC2)nn1] | 441.3 | (CDCl$_3$) δ 8.71 (d, J = 1.9 Hz, 1H), 8.61 (d, J = 1.9 Hz, 1H), 7.15 (d, J = 9.3 Hz, 1H), 7.00-6.87 (m, 2H), 6.64 (d, J = 9.3 Hz, 1H), 4.89-4.76 (m, 2H), 4.11-4.03 (m, 1H), 4.00-3.83 (m, 4H), 3.40-3.24 (m, 4H), 2.23 (dq, J = 12.9, 6.3, 5.6 Hz, 2H), 2.02-1.79 (m, 6H) |
| 41 | 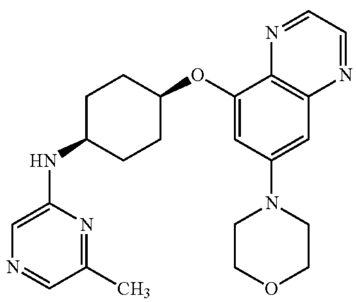 | 421.43 | (CDCl$_3$) δ 8.63 (d, J = 1.9 Hz, 1H), 8.55 (d, J = 1.9 Hz, 1H), 7.58 (d, J = 23.6 Hz, 2H), 6.89 (d, J = 2.4 Hz, 1H), 6.84 (d, J = 2.5 Hz, 1H), 4.73 (s, 2H), 3.93-3.72 (m, 5H), 3.34-3.18 (m, 4H), 2.29 (s, 3H), 2.15 (m, 2H), 1.84 (m, 6H) |
| 42 | 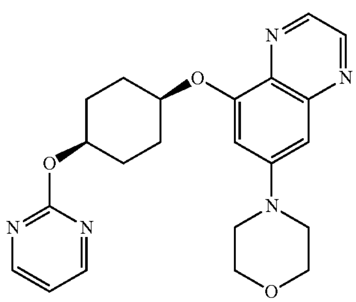 [SMILES: c1cnc(O[C@H]2CC[C@@H](Oc3cc(N4CCOCC4)cc4nccnc34)CC2)nc1] | 408.56 | (CDCl$_3$) δ 8.70 (d, J = 1.9 Hz, 1H), 8.63 (d, J = 1.9 Hz, 1H), 8.52 (d, J = 4.8 Hz, 2H), 7.01-6.87 (m, 3H), 5.17 (ddt, J = 8.7, 6.7, 3.4 Hz, 1H), 4.76-4.58 (m, 1H), 4.00-3.87 (m, 4H), 3.40-3.27 (m, 4H), 2.43-2.22 (m, 4H), 2.05-1.87 (m, 2H), 1.86-1.71 (m, 2H) |
| 44 | 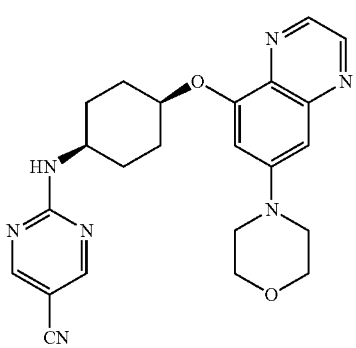 | 432.6 | (CDCl$_3$) δ 8.71 (d, J = 2.0 Hz, 1H), 8.64 (d, J = 2.0 Hz, 1H), 8.54 (d, J = 2.9 Hz, 1H), 8.47 (d, J = 3.0 Hz, 1H), 6.99 (d, J = 2.4 Hz, 1H), 6.92 (d, J = 2.5 Hz, 1H), 5.81 (d, J = 8.3 Hz, 1H), 4.84 (dt, J = 5.3, 2.8 Hz, 1H), 4.13-4.05 (m, 1H), 4.00-3.84 (m, 4H), 3.43-3.30 (m, 4H), 2.32-2.17 (m, 2H), 2.02-1.85 (m, 6H) |

Table 1-continued

| Cmpd. No. | Compound Structure | ESMS (M + H) | $^1$H NMR (300 MHz, unless indicated otherwise) NMR peaks given as δ values |
|---|---|---|---|
| 45 | 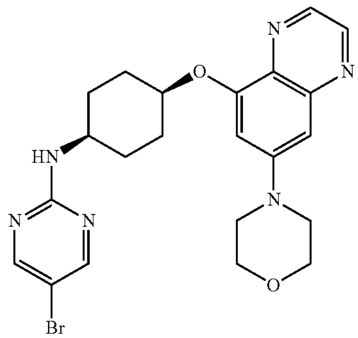 | 485.26 | (CDCl$_3$) δ 8.70 (d, J = 2.0 Hz, 1H), 8.64 (d, J = 1.9 Hz, 1H), 8.29 (s, 2H), 6.98 (d, J = 2.5 Hz, 1H), 6.92 (d, J = 2.5 Hz, 1H), 5.29 (d, J = 8.3 Hz, 1H), 4.81 (s, 1H), 4.04-3.84 (m, 4H), 3.42-3.31 (m, 4H), 2.22 (s, 2H), 1.92 (d, J = 4.9 Hz, 6H) |
| 46 | 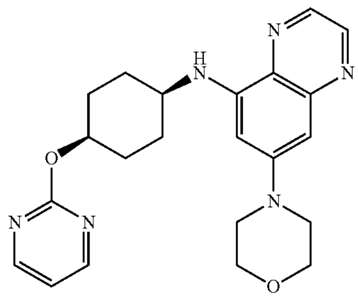 [SMILES: c1cnc(O[C@H]2CC[C@@H](Nc3cc(N4CCOCC4)cc4nccnc34)CC2)nc1] | 407.57 | (CDCl$_3$) δ 8.63 (d, J = 2.0 Hz, 1H), 8.52 (d, J = 4.8 Hz, 2H), 8.37 (d, J = 2.0 Hz, 1H), 6.92 (t, J = 4.8 Hz, 1H), 6.62 (d, J = 2.4 Hz, 1H), 6.38 (d, J = 2.4 Hz, 1H), 6.16 (s, 1H), 5.27 (s, 1H), 4.06-3.78 (m, 4H), 3.64 (s, 1H), 3.48-3.20 (m, 4H), 2.14 (s, 2H), 2.04-1.80 (m, 4H) |
| 49 | 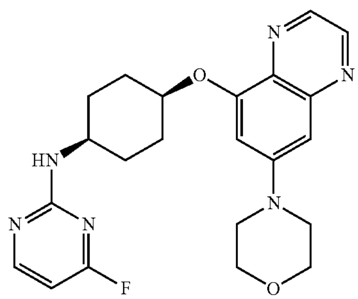 [SMILES: Fc1ccnc(N[C@H]2CC[C@@H](Oc3cc(N4CCOCC4)cc4nccnc34)CC2)n1] | 425.39 | (400 MHz, CDCl$_3$) δ 8.70 (d, J = 1.9 Hz, 1H), 8.60 (d, J = 1.9 Hz, 1H), 7.99 (s, 1H), 6.96 (d, J = 2.4 Hz, 1H), 6.89 (d, J = 2.3 Hz, 1H), 6.20 (s, 1H), 5.19 (bs, 1H), 4.81 (bs, 1H), 3.96-3.84 (m, 4H), 3.40-3.27 (m, 4H), 2.29-2.14 (m, 2H), 1.99-1.81 (m, 6H) |
| 50 | 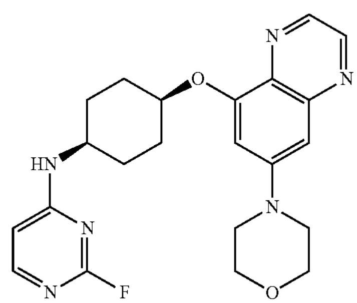 [SMILES: Fc1nccc(N[C@H]2CC[C@@H](Oc3cc(N4CCOCC4)cc4nccnc34)CC2)n1] | 425.39 | (400 MHz, CDCl$_3$) δ 8.69 (d, J = 1.9 Hz, 1H), 8.60 (d, J = 1.9 Hz, 1H), 8.30 (d, J = 2.1 Hz, 1H), 6.95 (d, J = 2.4 Hz, 1H), 6.89 (d, J = 2.4 Hz, 1H), 5.84 (s, 1H), 5.42 (s, 1H), 4.81 (s, 1H), 3.99-3.82 (m, 4H), 3.39-3.24 (m, 4H), 2.31-2.19 (m, 2H), 2.08-1.72 (m, 8H) |
| 51 | 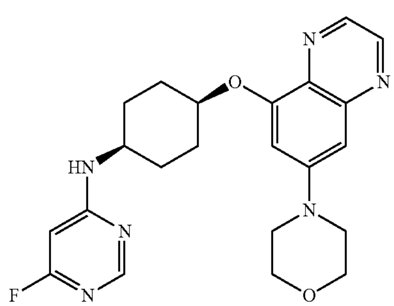 [SMILES: Fc1cc(N[C@H]2CC[C@@H](Oc3cc(N4CCOCC4)cc4nccnc34)CC2)ncn1] | 425.33 | (400 MHz, CDCl$_3$) δ 8.69 (d, J = 1.9 Hz, 1H), 8.60 (d, J = 1.9 Hz, 1H), 8.30 (d, J = 2.1 Hz, 1H), 6.95 (d, J = 2.4 Hz, 1H), 6.89 (d, J = 2.4 Hz, 1H), 5.84 (s, 1H), 5.42 (s, 1H), 4.81 (s, 1H), 3.99-3.82 (m, 4H), 3.39-3.24 (m, 4H), 2.31-2.19 (m, 2H), 2.08-1.72 (m, 8H) |

TABLE 1-continued

| Cmpd. No. | Compound Structure | ESMS (M + H) | ¹H NMR (300 MHz, unless indicated otherwise) NMR peaks given as δ values |
|---|---|---|---|
| 52 | 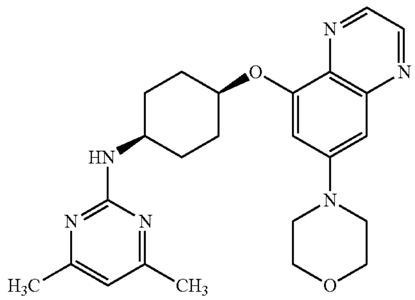 [SMILES: Cc1cc(C)nc(N[C@H]2CC[C@@H](Oc3cc(N4CCOCC4)cc4nccnc34)CC2)n1] | 435.19 | (400 MHz, CDCl₃) δ 8.68 (d, J = 1.4 Hz, 1H), 8.60 (d, J = 1.5 Hz, 1H), 6.93 (s, 1H), 6.90 (s, 1H), 6.28 (s, 1H), 5.06 (d, J = 7.9 Hz, 1H), 4.77 (s, 1H), 4.06 (bs, 1H), 3.97-3.84 (m, 4H), 3.38-3.25 (m, 4H), 2.27 (s, 6H), 2.18-2.09 (m, 2H), 1.94-1.83 (m, 7H) |
| 53 | 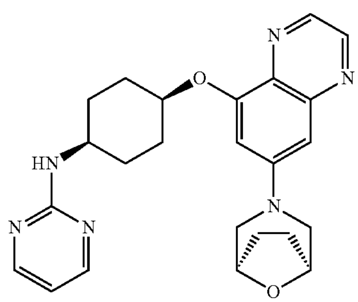 [SMILES: c1cnc(N[C@H]2CC[C@@H](Oc3cc(N4C[C@H]5CC[C@@H](C4)O5)cc4nccnc34)CC2)nc1] | 433.25 | (CDCl₃) δ 9 Hz, 1H), 8.28 (d, J = 4.8 Hz, 2H), 6.85 (t, J = 1.9 Hz, 2H), 6.51 (t, J = 4.8 Hz, 1H), 5.29 (d, J = 6.3 Hz, 1H), 4.80 (dq, J = 5.5, 2.8 Hz, 1H), 4.57 (d, J = 3.9 Hz, 2H), 4.02 (t, J = 6.2 Hz, 1H), 3.54-3.43 (m, 2H), 3.19 (dd, J = 11.6, 2.6 Hz, 2H), 2.27-2.14 (m, 2H), 2.08-1.85 (m, 10H) |
| 54 | 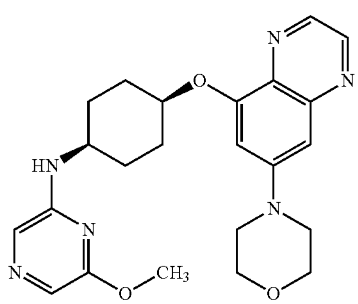 [SMILES: COc1cncc(N[C@H]2CC[C@@H](Oc3cc(N4CCOCC4)cc4nccnc34)CC2)n1] | 437.27 | (CDCl₃) δ 8.70 (d, J = 1.9 Hz, 1H), 8.62 (d, J = 1.9 Hz, 1H), 7.45 (d, J = 7.8 Hz, 2H), 7.02-6.81 (m, 2H), 4.78 (ddd, J = 7.3, 5.6, 3.1 Hz, 1H), 4.66 (d, J = 7.9 Hz, 1H), 4.01-3.78 (m, 7H), 3.41-3.25 (m, 4H), 2.30-2.08 (m, 2H), 1.94 (h, J = 8.8, 8.2 Hz, 6H) |
| 55 | 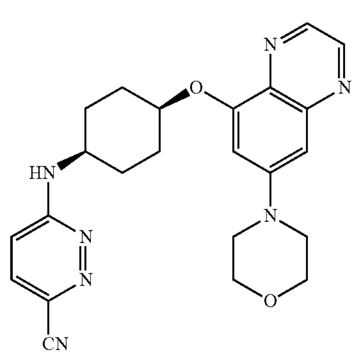 [SMILES: N#Cc1ccc(N[C@H]2CC[C@@H](Oc3cc(N4CCOCC4)cc4nccnc34)CC2)nn1] | 432.3 | (CDCl₃) δ 8.73 (d, J = 2.0 Hz, 1H), 8.63 (d, J = 2.0 Hz, 1H), 7.42 (d, J = 9.3 Hz, 1H), 6.96 (dd, J = 19.6, 2.5 Hz, 2H), 6.65 (d, J = 9.3 Hz, 1H), 5.40 (s, 1H), 4.86 (s, 1H), 3.94 (dd, J = 5.9, 3.8 Hz, 4H), 3.37 (dd, J = 6.0, 3.7 Hz, 4H), 2.27 (d, J = 12.7 Hz, 2H), 2.05-1.80 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 59 | 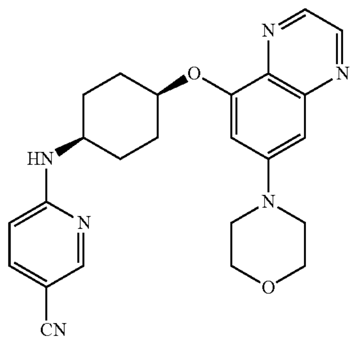 [SMILES: N#Cc1ccc(N[C@H]2CC[C@@H](Oc3cc(N4CCOCC4)cc4nccnc34)CC2)nc1] | 431.19 | (400 MHz, CDCl₃) δ 8.70 (d, J = 1.9 Hz, 1H), 8.61 (d, J = 1.9 Hz, 1H), 8.36 (d, J = 1.8 Hz, 1H), 7.54 (dd, J = 8.8, 2.2 Hz, 1H), 6.96 (d, J = 2.4 Hz, 1H), 6.90 (d, J = 2.4 Hz, 1H), 6.37 (d, J = 8.7 Hz, 1H), 5.11 (s, 1H), 4.80 (s, 1H), 3.94 (s, 1H), 3.94-3.79 (m, 4H), 3.38-3.25 (m, 4H), 2.32-2.12 (m, 2H), 2.02-1.78 (m, 6H) |
| 60 | 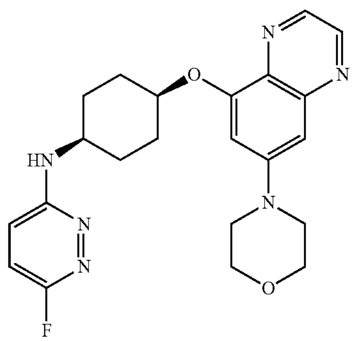 [SMILES: Fc1ccc(N[C@H]2CC[C@@H](Oc3cc(N4CCOCC4)cc4nccnc34)CC2)nn1] | 425.23 | (CDCl₃) δ 8.71 (d, J = 1.9 Hz, 1H), 8.62 (d, J = 1.9 Hz, 1H), 7.06-6.88 (m, 3H), 6.80 (dd, J = 9.4, 6.3 Hz, 1H), 4.97-4.71 (m, 2H), 4.14 (q, J = 7.1 Hz, 1H), 4.01-3.85 (m, 4H), 3.44-3.24 (m, 4H), 2.23 (d, J = 10.7 Hz, 2H), 1.96 (dt, J = 11.0, 7.6 Hz, 6H) |
| 61 | 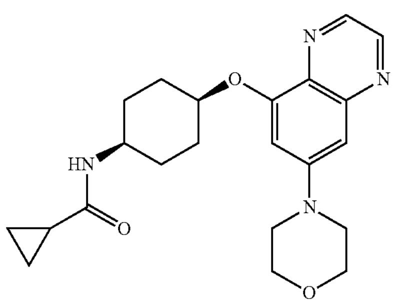 [SMILES: O=C(N[C@H]1CC[C@@H](Oc2cc(N3CCOCC3)cc3nccnc23)CC1)C1CC1] | 397.15 | (400 MHz, CDCl₃) δ 8.69 (d, J = 1.8 Hz, 1H), 8.61 (d, J = 1.9 Hz, 1H), 6.94 (d, J = 2.3 Hz, 1H), 6.87 (s, 1H), 5.78-5.64 (m, 1H), 4.73 (s, 1H), 4.01 (s, 1H), 3.97-3.78 (m, 4H), 3.43-3.18 (m, 4H), 2.26-2.05 (m, 2H), 1.98-1.73 (m, 6H), 1.36-1.26 (m, 1H), 1.01-0.92 (m, 2H), 0.78-0.67 (m, 2H) |
| 63 | 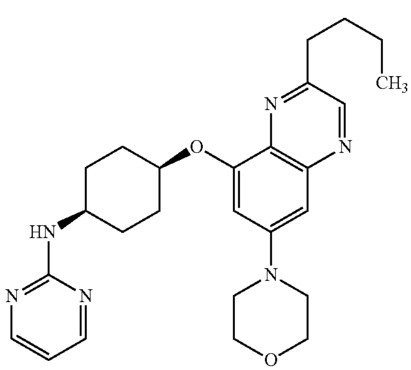 [SMILES: CCCCc1cnc2cc(N3CCOCC3)cc(O[C@H]3CC[C@@H](Nc4ncccn4)CC3)c2n1] | 463.54 | (CDCl₃) δ 8.53 (s, 1H), 8.29 (d, J = 4.8 Hz, 2H), 6.92 (d, J = 2.5 Hz, 1H), 6.85 (d, J = 2.5 Hz, 1H), 6.52 (t, J = 4.8 Hz, 1H), 5.25 (d, J = 8.3 Hz, 1H), 4.79 (s, 1H), 4.07 (d, J = 20.4 Hz, 1H), 3.98-3.85 (m, 4H), 3.43-3.21 (m, 4H), 3.05-2.83 (m, 2H), 2.30-2.14 (m, 1H), 2.03-1.71 (m, 7H), 1.45 (dq, J = 14.5, 7.3 Hz, 2H), 0.98 (t, J = 7.3 Hz, 3H) |

Table 1-continued

| Cmpd. No. | Compound Structure | ESMS (M + H) | ¹H NMR (300 MHz, unless indicated otherwise) NMR peaks given as δ values |
|---|---|---|---|
| 64 | 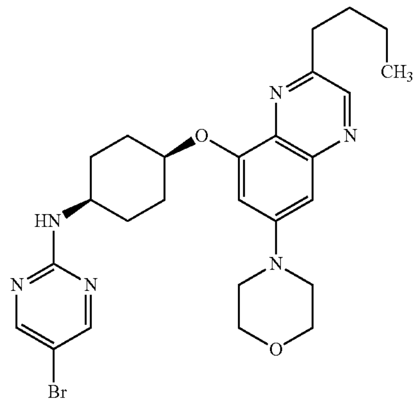 [SMILES: CCCCc1cnc2cc(N3CCOCC3)cc(O[C@H]3CC[C@@H](Nc4ncc(Br)cn4)CC3)c2n1] | 541.26 | (CDCl₃) δ 8.55 (s, 1H), 8.29 (d, J = 1.5 Hz, 2H), 7.05-6.93 (m, 1H), 6.85 (d, J = 2.5 Hz, 1H), 5.49 (d, J = 8.0 Hz, 1H), 4.80 (d, J = 5.8 Hz, 1H), 4.03-3.81 (m, 5H), 3.45-3.27 (m, 4H), 2.98 (dd, J = 8.5, 7.0 Hz, 2H), 2.32-2.09 (m, 2H), 2.00-1.71 (m, 8H), 1.56-1.34 (m, 2H), 0.98 (td, J = 7.3, 3.3 Hz, 3H) |
| 65 | 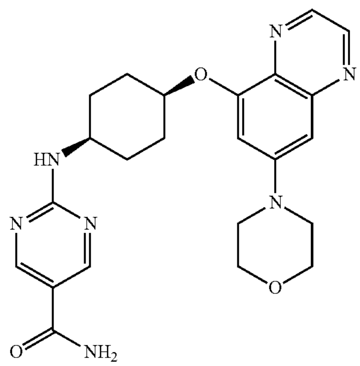 [SMILES: NC(=O)c1cnc(N[C@H]2CC[C@@H](Oc3cc(N4CCOCC4)cc4nccnc34)CC2)nc1] | 450.49 | (CDCl₃) δ 8.76-8.66 (m, 3H), 8.61 (d, J = 1.9 Hz, 1H), 6.99-6.87 (m, 2H), 5.71 (d, J = 8.1 Hz, 1H), 4.81 (s, 1H), 4.11 (s, 1H), 3.92 (t, J = 4.9 Hz, 4H), 3.34 (t, J = 4.9 Hz, 4H), 2.22 (d, J = 10.2 Hz, 2H), 2.02-1.85 (m, 6H) |
| 66 | 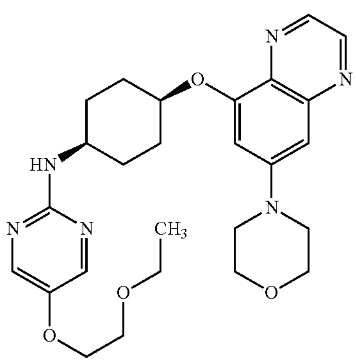 [SMILES: CCOCCOc1cnc(N[C@H]2CC[C@@H](Oc3cc(N4CCOCC4)cc4nccnc34)CC2)nc1] | 495.23 | (CDCl₃) δ 8.77 (d, J = 2.3 Hz, 1H), 8.72 (d, J = 2.3 Hz, 1H), 7.12 (d, J = 2.4 Hz, 1H), 7.02 (d, J = 2.4 Hz, 1H), 4.92 (s, 1H), 4.18-4.08 (m, 2H), 3.93 (t, J = 4.9 Hz, 4H), 3.85-3.76 2H), 3.47 (t, J = 4.9 Hz, 4H), 2.26 (d, J = 13.3 Hz, 2H), 2.07 (t, J = 10.5 Hz, 2H), 2.01-1.72 (m, 2H), 1.26 (t, J = 7.0 Hz, |
| 67 | 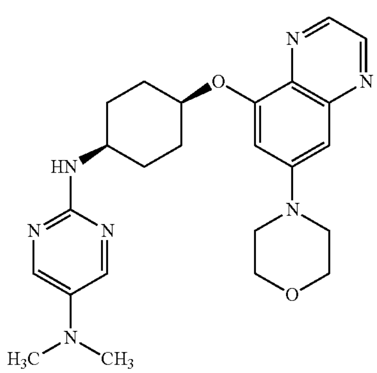 | 450.3 | (CDCl₃) δ 8.71 (d, J = 2.0 Hz, 1H), 8.64 (d, J = 1.9 Hz, 1H), 8.02 (s, 1H), 6.94 (dd, J = 12.2, 2.5 Hz, 2H), 5.32 (s, 2H), 4.87 (d, J = 8.1 Hz, 1H), 4.79 (s, 1H), 4.01-3.86 (m, 4H), 3.36 J = 5.4, 4.7 Hz, 4H), 2.83 (s, 6H), 2.19 (s, 2H), 1.92 (d, J = 4.8 Hz, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 69 | 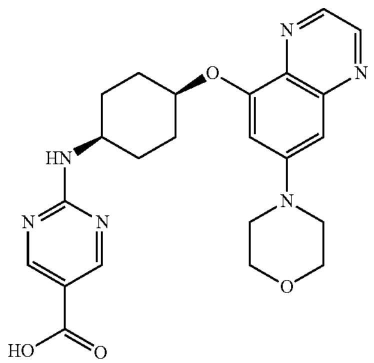 [SMILES: O=C(O)c1cnc(N[C@H]2CC[C@@H](Oc3cc(N4CCOCC4)cc4nccnc34)CC2)nc1] | 451.21 | (CDCl$_3$) δ 9.05 (s, 1H), 8.88-8.71 (m, 3H), 8.49 (s, 1H), 7.06 (d, J = 2.3 Hz, 1H), 6.96 (d, J = 2.3 Hz, 1H), 4.85 (s, 1H), 4.17 (s, 1H), 3.93 (t, J = 4.8 Hz, 4H), 3.42 (t, J = 4.9 Hz, 4H), 2.25-2.10 (m, 2H), 1.95 (d, J = 11.9 Hz, 4H) |
| 71 | 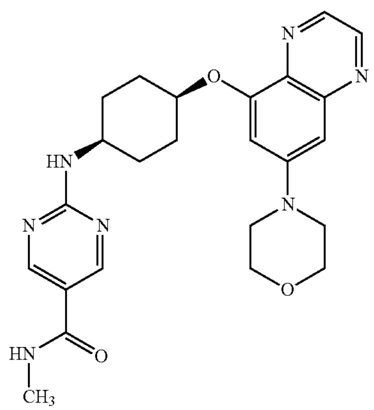 [SMILES: CNC(=O)c1cnc(N[C@H]2CC[C@@H](Oc3cc(N4CCOCC4)cc4nccnc34)CC2)nc1] | 464.4 | (CDCl$_3$) δ 8.79 - 8.64 (m, 3H), 8.59 (d, J = 1.9 Hz, 1H), 6.99-6.88 (m, 2H), 6.19 (q, J = 4.7 Hz, 1H), 5.90 (d, J = 8.2 Hz, 1H), 4.81 (dq, J = 5.3, 2.7 Hz, 1H), 4.08 (qd, J = 8.2, 6.5, 2.3 Hz, 1H), 3.97-3.87 (m, 4H), 3.39-3.29 (m, 4H), 2.93 (d, J = 4.8 Hz, 3H), 2.27-2.14 (m, 2H), 2.06-1.79 (m, 6H) |
| 72 | 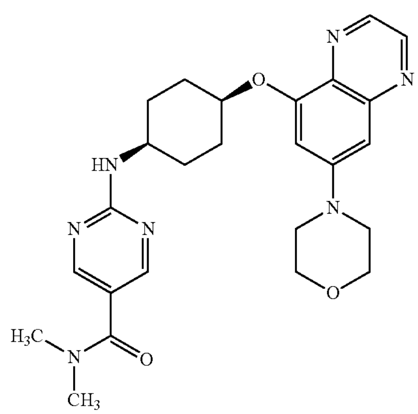 [SMILES: CN(C)C(=O)c1cnc(N[C@H]2CC[C@@H](Oc3cc(N4CCOCC4)cc4nccnc34)CC2)nc1] | 478.39 | (CDCl$_3$) δ 3.97-3.87 (m, 4H), 3.39-3.29 (m, 4H), 3.10 (s, 6H), 2.22 (dt, J = 11.3, 5.1 Hz, 2H), 1.94 (dd, J = 8.3, 3.9 Hz, 6H), 4.12-4.01 (m, 1H), 8.70 (d, J = 1.9 Hz, 1H), 8.62 (d, J = 1.9 Hz, 1H), 8.46 (s, 2H), 7.00-6.87 (m, 2H), 5.57 (d, J = 8.1 Hz, 1H), 4.81 (dq, J = 5.1, 2.4 Hz, 1H) |
| 84 | 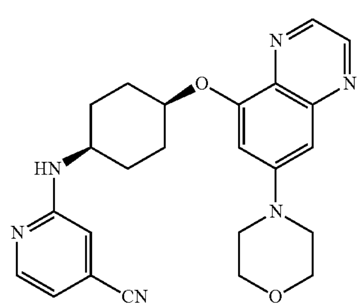 [SMILES: N#Cc1ccnc(N[C@H]2CC[C@@H](Oc3cc(N4CCOCC4)cc4nccnc34)CC2)c1] | 431.19 | (400 MHz, CDCl$_3$) δ 8.69 (d, J = 1.9 Hz, 1H), 8.61 (d, J = 1.9 Hz, 1H), 8.19 (d, J = 4.8 Hz, 1H), 6.95 (d, J = 2.3 Hz, 1H), 6.90 (d, J = 2.4 Hz, 1H), 6.70 (dd, J = 5.1, 1.2 Hz, 1H), 6.56 (s, 1H), 4.87 (d, J = 7.6 Hz, 1H), 4.80 (s, 1H), 3.96-3.88 (m, 4H), 3.85 (s, 1H), 3.38-3.28 (m, 4H), 2.28-2.14 (m, 2H), 2.00-1.85 (m, 6H) |

Table 1-continued

| Cmpd. No. | Compound Structure | ESMS (M + H) | 1 H NMR (300 MHz, unless indicated otherwise) NMR peaks given as δ values |
|---|---|---|---|
| 87 | 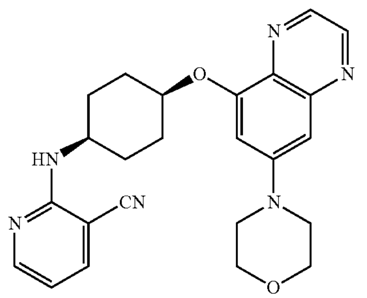 [SMILES: N#Cc1cccnc1N[C@H]1CC[C@@H](Oc2cc(N3CCOCC3)cc3nccnc23)CC1] | 431.2 | (CDCl₃) δ 8.63 (d, J = 1.9 Hz, 1H), 8.57 (d, J = 1.9 Hz, 1H), 8.20 (dd, J = 5.0, 1.9 Hz, 1H), 7.57 (dd, J = 7.6, 1.9 Hz, 1H), 6.89 (d, J = 2.5 Hz, 1H), 6.85 (d, J = 2.5 Hz, 1H), 6.51 (dd, J = 7.6, 4.9 Hz, 1H), 5.12 (d, J = 7.7 Hz, 1H), 4.83-4.71 (m, 0H), 4.24-4.03 (m, 1H), 3.92-3.77 (m, 4H), 3.35-3.19 (m, 4H), 2.28-2.10 (m, 2H), 1.88 (td, J = 8.3, 6.8, 3.9 Hz, 6H) |
| 93 | 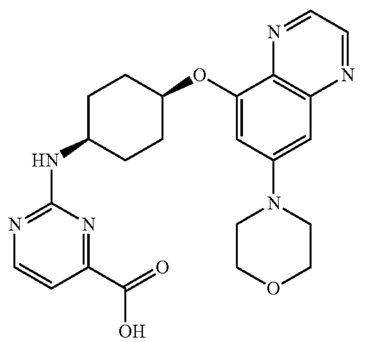 [SMILES: O=C(O)c1ccnc(N[C@H]2CC[C@@H](Oc3cc(N4CCOCC4)cc4nccnc34)CC2)n1] | 451.21 | (methanol-d₄) δ 8.69 (d, J = 2.2 Hz, 1H), 8.59 (d, J = 2.2 Hz, 1H), 8.53 (d, J = 4.9 Hz, 1H), 7.19 (d, J = 5.0 Hz, 1H), 7.15 (d, J = 2.3 Hz, 1H), 6.87 (d, J = 2.4 Hz, 1H), 4.95 (d, J = 7.7 Hz, 1H), 4.10 (s, 1H), 3.95-3.82 (m, 4H), 3.47-3.37 (m, 4H), 2.20 (d, J = 10.1 Hz, 2H), 2.04-1.81 (m, 6H) |
| 94 | 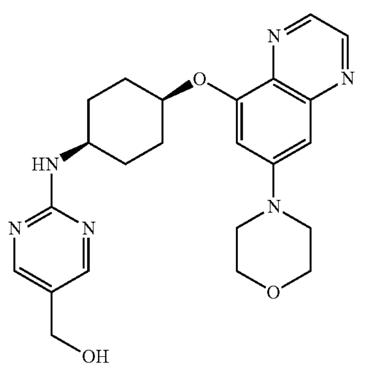 [SMILES: OCc1cnc(N[C@H]2CC[C@@H](Oc3cc(N4CCOCC4)cc4nccnc34)CC2)nc1] | 437.44 | (CDCl₃) δ 8.68 (d, J = 2.0 Hz, 1H), 8.60 (d, J = 1.9 Hz, 1H), 8.29 (s, 2H), 6.98-6.87 (m, 2H), 5.36 (d, J = 8.1 Hz, 1H), 4.79 (q, J = 5.2, 4.0 Hz, 1H), 4.52 (s, 2H), 4.01 (dd, J = 8.1, 4.3 Hz, 1H), 3.95-3.84 (m, 4H), 3.39-3.28 (m, 4H), 2.25-2.12 (m, 2H), 1.99-1.82 (m, 6H) |
| 104 | 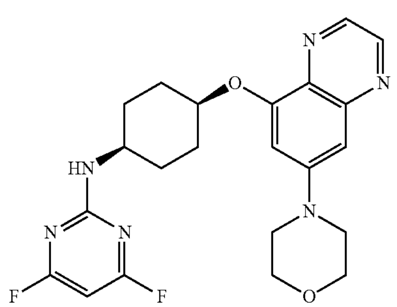 [SMILES: Fc1cc(F)nc(N[C@H]2CC[C@@H](Oc3cc(N4CCOCC4)cc4nccnc34)CC2)n1] | 443.38 | (CDCl₃) δ 8.73 (s, 1H), 8.68 (d, J = 2.4 Hz, 1H), 6.99 (d, J = 2.4 Hz, 1H), 6.85 (d, J = 2.4 Hz, 1H), 5.69 (d, J = 2.5 Hz, 1H), 4.76 (s, 1H), 3.84 (dd, J = 5.9, 3.9 Hz, 4H), 3.38 (dd, J = 6.0, 3.9 Hz, 4H), 2.15 (d, J = 11.1 Hz, 2H), 1.96-1.67 (m, 6H) |

TABLE 1-continued

| Cmpd. No. | Compound Structure | ESMS (M + H) | ¹H NMR (300 MHz, unless indicated otherwise) NMR peaks given as δ values |
|---|---|---|---|
| 108 | 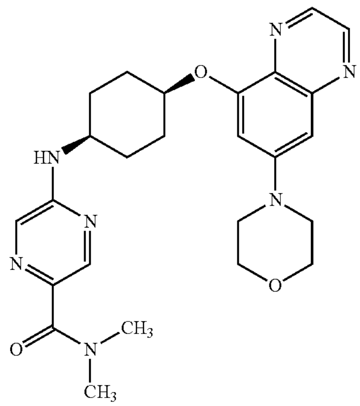 [SMILES: CN(C)C(=O)c1cnc(N[C@H]2CC[C@@H](Oc3cc(N4CCOCC4)cc4nccnc34)CC2)cn1] | 478.26 | (CDCl₃) δ 8.69 (d, J = 1.9 Hz, 1H), 8.61 (d, J = 2.0 Hz, 1H), 8.49 (d, J = 1.4 Hz, 1H), 7.77 (d, J = 1.4 Hz, 1H), 6.93 (dd, J = 16.1, 2.5 Hz, 2H), 5.03 (d, J = 7.9 Hz, 1H), 4.81 (td, J = 5.3, 2.6 Hz, 1H), 4.09-3.98 (m, 1H), 3.98-3.87 (m, 4H), 3.39-3.26 (m, 4H), 3.19 (s, 3H), 3.12 (s, 3H), 2.22 (dt, J = 11.2, 4.9 Hz, 2H), 2.02-1.82 (m, 6H) |
| 109 | 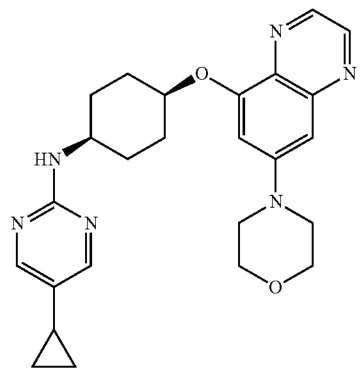 [SMILES: c1cnc2c(O[C@H]3CC[C@@H](Nc4ncc(C5CC5)cn4)CC3)cc(N3CCOCC3)cc2n1] | 447.02 | (CDCl₃) δ 8.70 (d, J = 1.9 Hz, 1H), 8.63 (d, J = 1.9 Hz, 1H), 8.10 (d, J = 0.5 Hz, 2H), 6.97 (d, J = 2.5 Hz, 1H), 6.92 (d, J = 2.5 Hz, 1H), 5.13 (d, J = 8.3 Hz, 1H), 4.80 (s, 1H), 4.06-3.86 (m, 5H), 3.35 (dd, J = 5.9, 3.8 Hz, 4H), 2.27-2.14 (m, 2H), 1.92 (d, J = 5.1 Hz, 6H), 1.79-1.44 (m, 6H), 1.28 (t, J = 7.1 Hz, 1H), 1.03-0.83 (m, 2H), 0.68-0.51 (m, 2H) |
| 134 | 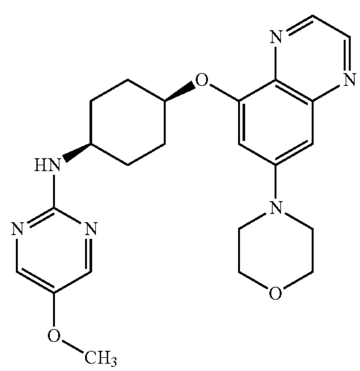 [SMILES: COc1cnc(N[C@H]2CC[C@@H](Oc3cc(N4CCOCC4)cc4nccnc34)CC2)nc1] | 437.3 | (CDCl₃) δ 8.70 (d, J = 1.9 Hz, 1H), 8.63 (d, J = 1.9 Hz, 1H), 8.07 (s, 2H), 6.97 (d, J = 2.5 Hz, 1H), 6.92 (d, J = 2.6 Hz, 1H), 4.99 (d, J = 8.0 Hz, 1H), 4.81 (d, J = 5.9 Hz, 1H), 3.93 (dd, J = 6.0, 3.7 Hz, 5H), 3.81 (s, 3H), 3.45-3.24 (m, 4H), 2.21 (d, J = 8.6 Hz, 2H), 2.05-1.78 (m, 6H) |
| 135 | 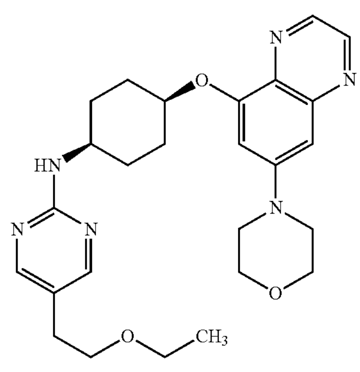 [SMILES: CCOCCc1cnc(N[C@H]2CC[C@@H](Oc3cc(N4CCOCC4)cc4nccnc34)CC2)nc1] | 479.2 | (CDCl₃) δ 8.70 (d, J = 1.9 Hz, 1H), 8.63 (d, J = 1.9 Hz, 1H), 8.19 (s, 2H), 6.96 (d, J = 2.5 Hz, 1H), 6.92 (d, J = 2.5 Hz, 1H), 5.12 (d, J = 8.1 Hz, 1H), 4.81 (d, J = 5.6 Hz, 1H), 4.09-3.85 (m, 5H), 3.63-3.41 (m, 4H), 3.43-3.26 (m, 4H), 2.69 (t, J = 6.6 Hz, 2H), 2.33-2.13 (m, 2H), 2.03-1.83 (m, 6H), 1.21 (t, J = 7.0 Hz, 3H) |

| Cmpd. No. | Compound Structure | ESMS (M + H) | ¹H NMR (300 MHz, unless indicated otherwise) NMR peaks given as δ values |
|---|---|---|---|
| 139 | 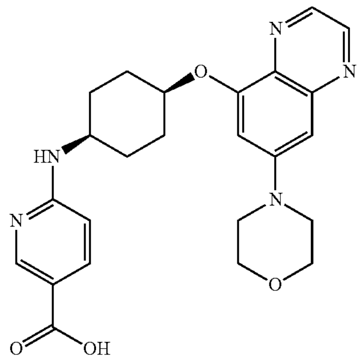 [SMILES: O=C(O)c1ccc(N[C@H]2CC[C@@H](Oc3cc(N4CCOCC4)cc4nccnc34)CC2)nc1] | 450.17 | (400 MHz, CDCl₃) δ 8.74 (d, J = 1.9 Hz, 2H), 8.70 (d, J = 1.9 Hz, 1H), 8.03 (dd, J = 8.9, 2.0 Hz, 1H), 6.97 (d, J = 2.4 Hz, 1H), 6.92 (d, J = 2.4 Hz, 1H), 6.37 (d, J = 8.9 Hz, 1H), 6.05 (s, 1H), 4.81 (s, 1H), 3.99-3.88 (m, 4H), 3.84 (s, 1H), 3.39-3.27 (m, 4H), 2.31-2.17 (m, 2H), 2.08-1.98 (m, 2H), 1.98-1.82 (m, 4H) |
| 140 | 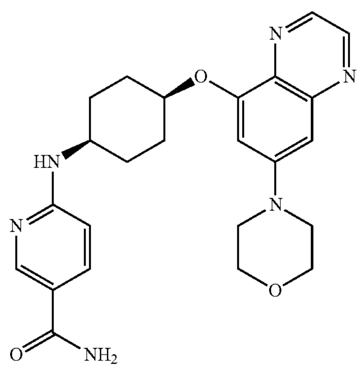 | 449.19 | (400 MHz, CDCl₃) δ 8.70 (d, J = 1.9 Hz, 1H), 8.61 (d, J = 1.9 Hz, 1H), 8.53 (d, J = 2.1 Hz, 1H), 7.88 (dd, J = 8.8, 2.4 Hz, 1H), 6.95 (d, J = 2.4 Hz, 1H), 6.90 (d, J = 2.4 Hz, 1H), 6.39 (d, J = 8.7 Hz, 1H), 5.61 (s, 2H), 4.97 (d, J = 7.9 Hz, 1H), 4.80 (s, 1H), 4.02-3.82 (m, 5H), 3.42-3.26 (m, 4H), 2.27-2.14 (m, 2H), 2.00-1.81 (m, 6H) |
| 142 | 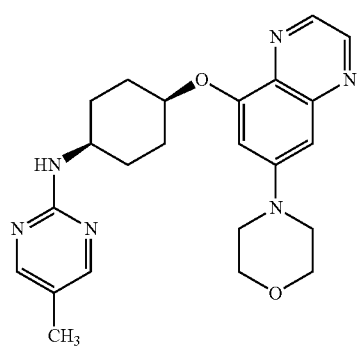 [SMILES: Cc1cnc(N[C@H]2CC[C@@H](Oc3cc(N4CCOCC4)cc4nccnc34)CC2)nc1] | 421.2 | (CDCl₃) δ 8.70 (d, J = 1.9 Hz, 1H), 8.63 (d, J = 1.9 Hz, 1H), 8.14 (d, J = 0.8 Hz, 2H), 7.01-6.90 (m, 2H), 4.81 (td, J = 5.6, 2.7 Hz, 1H), 4.08-3.84 (m, 5H), 3.43-3.26 (m, 4H), 2.25-2.10 (m, 5H), 2.02-1.83 (m, 6H) |
| 143 | 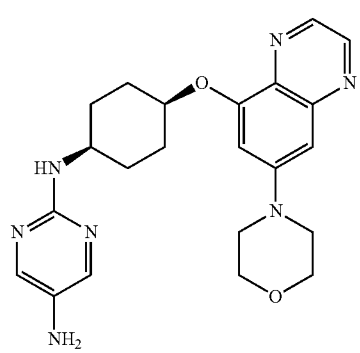 [SMILES: Nc1cnc(N[C@H]2CC[C@@H](Oc3cc(N4CCOCC4)cc4nccnc34)CC2)nc1] | 422.25 | (CDCl₃) δ 8.70 (d, J = 1.9 Hz, 1H), 8.63 (d, J = 1.9 Hz, 1H), 8.02 (s, 2H), 6.95 (dd, J = 11.8, 2.5 Hz, 2H), 4.81 (s, 2H), 4.08-3.85 (m, 5H), 3.41-3.30 (m, 4H), 2.20 (d, J = 10.1 Hz, 2H), 1.95 (d, J = 19.7 Hz, 6H), 1H NMR (300 MHz, Methanol-d4) 8.68 (d, J = 2.0 Hz, 1H), 8.56 (d, J = 2.1 Hz, 1H), 7.93 (s, 2H), 7.11 (d, J = 2.5 Hz, 1H), 6.88 (d, J = 2.4 Hz, 1H), 3.96-3.71 (m, 5H), 3.37 (dd, J = 5.8, 3.9 Hz, 4H), 2.27-2.04 (m, 2H), 1.98-1.74 (m, 6H). [2] |

Table 1-continued

| Cmpd. No. | Compound Structure | ESMS (M + H) | ¹H NMR (300 MHz, unless indicated otherwise) NMR peaks given as δ values |
|---|---|---|---|
| 144 | 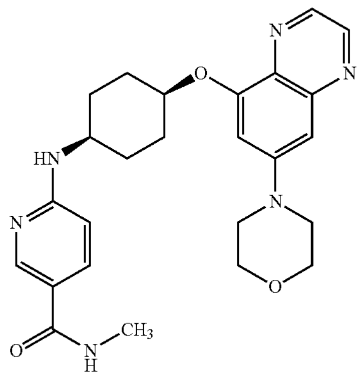 [SMILES: CNC(=O)c1ccc(N[C@H]2CC[C@@H](Oc3cc(N4CCOCC4)cc4nccnc34)CC2)nc1] | 463.2 | (400 MHz, CDCl$_3$) δ 8.69 (d, J = 1.9 Hz, 1H), 8.61 (d, J = 1.9 Hz, 1H), 8.47 (d, J = 2.1 Hz, 1H), 7.84 (dd, J = 8.7, 2.4 Hz, 1H), 6.95 (d, J = 2.4 Hz, 1H), 6.90 (d, J = 2.4 Hz, 1H), 6.37 (d, J = 8.7 Hz, 1H), 5.94 (d, J = 3.9 Hz, 1H), 4.92 (d, J = 7.8 Hz, 1H), 4.79 (s, 1H), 3.98-3.84 (m, 5H), 3.39-3.26 (m, 4H), 2.98 (d, J = 4.8 Hz, 3H), 2.27-2.12 (m, 2H), 1.97-1.83 (m, 6H) |
| 145 | 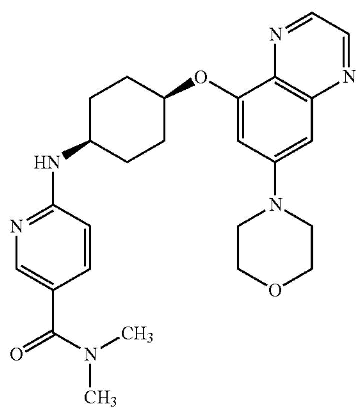 [SMILES: CN(C)C(=O)c1ccc(N[C@H]2CC[C@@H](Oc3cc(N4CCOCC4)cc4nccnc34)CC2)nc1] | 477.2 | (400 MHz, CDCl$_3$) δ 8.69 (d, J = 1.9 Hz, 1H), 8.61 (d, J = 1.9 1H), 8.20 (s, 1H), 7.61 (d, J = 8.2 Hz, 1H), 6.95 (d, J = 2.4 Hz, 1H), 6.91 (d, J = 2.4 Hz, 1H), 6.43 (d, J = 7.9 Hz, 1H), 4.81 (s, 1H), 3.98-3.81 (m, 5H), 3.40-3.27 (m, 4H), 3.09 (s, 6H), 2.27-2.15 (m, 2H), 1.99-1.83 (m, 6H) |
| 146 | 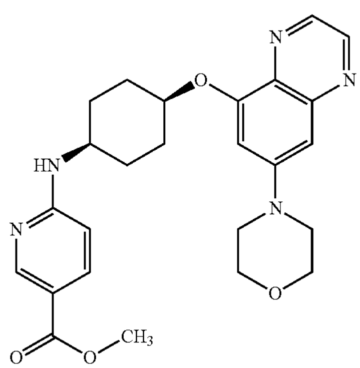 [SMILES: COC(=O)c1ccc(N[C@H]2CC[C@@H](Oc3cc(N4CCOCC4)cc4nccnc34)CC2)nc1] | 464.17 | (CDCl$_3$) δ 8.76 (d, J = 2.0 Hz, 1H), 8.71 (d, J = 1.9 Hz, 1H), 8.63 (d, J = 1.9 Hz, 1H), 7.99 (dd, J = 8.8, 2.2 Hz, 1H), 6.97 (d, J = 2.5 Hz, 1H), 6.92 (d, J = 2.5 Hz, 1H), 6.38 (d, J = 8.9 Hz, 1H), 5.13 (s, 1H), 4.82 (s, 1H), 4.11-3.73 (m, 8H), 3.44-3.27 (m, 4H), 2.30-2.17 (m, 2H), 2.07-1.79 (m, 6H) |
| 152 | 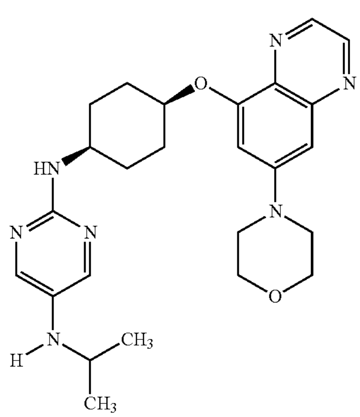 [SMILES: CC(C)Nc1cnc(N[C@H]2CC[C@@H](Oc3cc(N4CCOCC4)cc4nccnc34)CC2)nc1] | 464.21 | (CDCl$_3$) δ 8.70 (d, J = 1.9 Hz, 1H), 8.64 (d, J = 1.9 Hz, 1H), 7.94 (s, 2H), 6.99-6.90 (m, 2H), 4.82 (s, 1H), 4.05-3.87 (m, 5H), 3.44 (q, J = 6.3 Hz, 1H), 3.39-3.26 (m, 4H), 2.23 (d, J = 12.4 Hz, 2H), 2.03-1.82 (m, 6H), 1.23 (d, J = 6.3 Hz, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 155 | 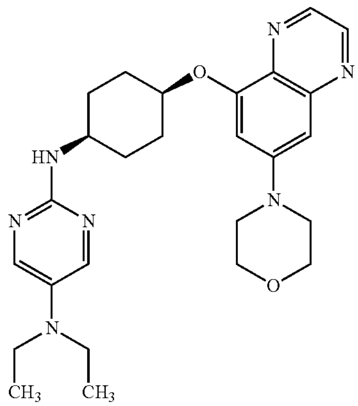 [SMILES: CCN(CC)c1cnc(N[C@H]2CC[C@@H](Oc3cc(N4CCOCC4)cc4nccnc34)CC2)nc1] | 478.3 | (CDCl₃) δ 8.71 (d, J = 1.9 Hz, 1H), 8.64 (d, J = 1.9 Hz, 1H), 7.02-6.89 (m, 2H), 4.83 (s, 1H), 4.08-3.87 (m, 5H), 3.44-3.33 (m, 4H), 3.27 (d, J = 26.0 Hz, 4H), 2.23 (d, J = 9.8 Hz, 2H), 2.05-1.80 (m, 6H), 1.14 (s, 6H) |
| 158 | 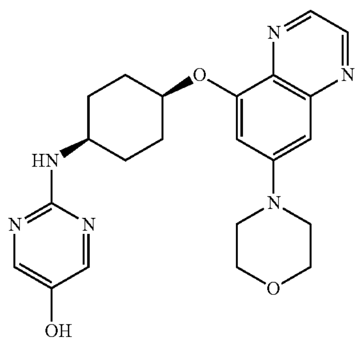 [SMILES: Oc1cnc(N[C@H]2CC[C@@H](Oc3cc(N4CCOCC4)cc4nccnc34)CC2)nc1] | | (CDCl₃) δ 8.71 (d, J = 2.0 Hz, 1H), 8.64 (d, J = 1.9 Hz, 1H), 8.41 (s, 2H), 6.97 (d, J = 2.4 Hz, 1H), 6.93 (d, J = 2.5 Hz, 1H), 5.32 (d, J = 8.1 Hz, 1H), 4.82 (s, 1H), 4.07 (s, 1H), 4.00-3.88 (m, 4H), 3.43-3.29 (m, 4H), 2.22 (s, 2H), 2.06-1.81 (m, 6H) |
| 160 | 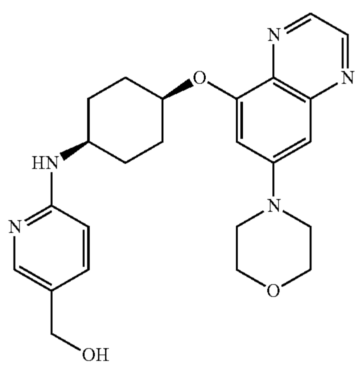 [SMILES: OCc1ccc(N[C@H]2CC[C@@H](Oc3cc(N4CCOCC4)cc4nccnc34)CC2)nc1] | 436.2 | (400 MHz, CDCl₃) δ 8.69 (d, J = 1.9 Hz, 1H), 8.61 (d, J = 1.9 Hz, 1H), 8.05 (d, J = 2.2 Hz, 1H), 7.46 (dd, J = 8.5, 2.3 Hz, 1H), 6.94 (d, J = 2.4 Hz, 1H), 6.90 (d, J = 2.4 Hz, 1H), 6.39 (d, J = 8.6 Hz, 1H), 4.77 (s, 1H), 4.53 (s, 2H), 3.95-3.87 (m, 5H), 3.36-3.32 (m, 4H), 2.25-2.12 (m, 2H), 1.90 (d, J = 4.4 Hz, 6H) |
| 161 | 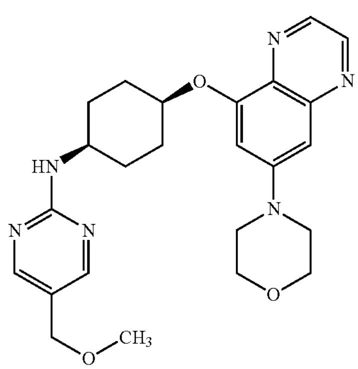 [SMILES: COCc1cnc(N[C@H]2CC[C@@H](Oc3cc(N4CCOCC4)cc4nccnc34)CC2)nc1] | 451.28 | (CDCl₃) δ 8.69 (d, J = 1.9 Hz, 1H), 8.61 (d, J = 1.9 Hz, 1H), 8.26 (s, 2H), 6.95 (d, J = 2.5 Hz, 1H), 6.90 (d, J = 2.6 Hz, 1H), 5.23 (d, J = 8.1 Hz, 1H), 4.80 (d, J = 5.8 Hz, 1H), 4.26 (s, 2H), 4.03 (s, 1H), 3.97-3.85 (m, 4H), 3.44-3.21 (m, 7H), 2.32-2.09 (m, 2H), 2.06-1.70 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 162 | 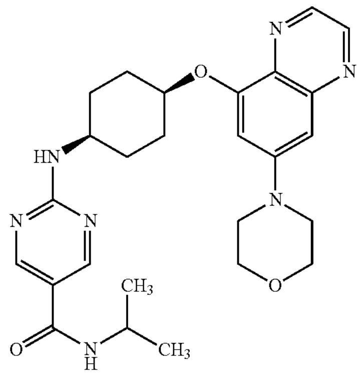 [SMILES: CC(C)NC(=O)c1cnc(N[C@H]2CC[C@@H](Oc3cc(N4CCOCC4)cc4nccnc34)CC2)nc1] | 492.29 | (DMSO-d$_6$) δ 8.81-8.64 (m, 3H), 8.58 (d, J = 1.9 Hz, 1H), 7.99 (d, J = 7.6 Hz, 1H), 7.76 (d, J = 7.4 Hz, 1H), 7.14 (d, J = 2.5 Hz, 1H), 6.84 (d, J = 2.3 Hz, 1H), 4.92 (s, 1H), 3.98-3.84 (m, 1H), 4.05 (dq, J = 13.5, 6.7 Hz, 1H), 3.79 (d, J = 9.6 Hz, 4H), 3.32 (d, J = 8.2 Hz, 4H), 2.06 (d, J = 11.8 Hz, 2H), 1.96-1.66 (m, 6H), 1.14 (d, J = 6.6 Hz, 6H) |
| 164 | 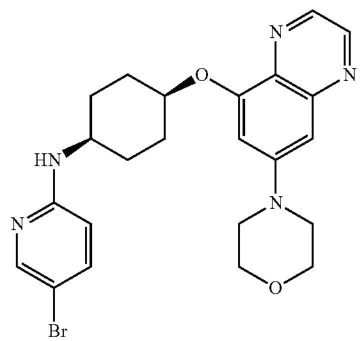 [SMILES: Brc1ccc(N[C@H]2CC[C@@H](Oc3cc(N4CCOCC4)cc4nccnc34)CC2)nc1] | 484.12 | (400 MHz, CDCl$_3$) δ 8.60 (d, J = 1.9 Hz, 1H), 8.52 (d, J = 1.9 Hz, 1H), 8.01 (d, J = 2.1 Hz, 1H), 7.35 (dd, J = 8.8, 2.5 Hz, 1H), 6.86 (d, J = 2.5 Hz, 1H), 6.80 (d, J = 2.5 Hz, 1H), 6.20 (d, J = 8.4 Hz, 1H), 4.68 (s, 1H), 4.47 (d, J = 8.0 Hz, 1H), 3.92-3.80 (m, 4H), 3.74 (s, 1H), 3.34-3.14 (m, 4H), 2.18-2.02 (m, 2H), 1.94-1.67 (m, 6H) |
| 187 | 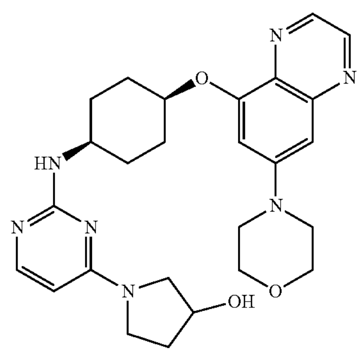 [SMILES: OC1CCN(c2ccnc(N[C@H]3CC[C@@H](Oc4cc(N5CCOCC5)cc5nccnc45)CC3)n2)C1] | 492.26 | (CDCl$_3$) δ 8.70 (d, J = 1.9 Hz, 1H), 8.63 (d, J = 1.9 Hz, 1H), 7.70 (s, 1H), 6.96 (q, J = 2.6 Hz, 2H), 5.75 (d, J = 6.5 Hz, 1H), 4.82 (s, 1H), 4.65 (s, 1H), 3.93 (dd, J = 5.9, 3.8 Hz, 4H), 3.63 (s, 4H), 3.36 (dd, J = 6.1, 3.7 Hz, 4H), 2.14 (s, 2H), 1.95 (d, J = 31.2 Hz, 6H) |
| 189 | 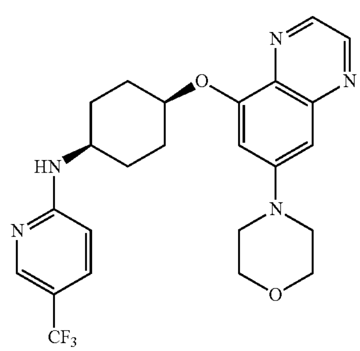 [SMILES: FC(F)(F)c1ccc(N[C@H]2CC[C@@H](Oc3cc(N4CCOCC4)cc4nccnc34)CC2)nc1] | 474.147 | (400 MHz, CDCl$_3$) δ 8.69 (d, J = 1.6 Hz, 1H), 8.61 (d, J = 1.7 Hz, 1H), 8.32 (s, 1H), 7.56 (d, J = 6.7 Hz, 1H), 6.96 (d, J = 2.2 Hz, 1H), 6.90 (d, J = 2.3 Hz, 1H), 6.40 (d, J = 8.7 Hz, 1H), 4.96 (s, 1H), 4.80 (s, 1H), 4.01-3.84 (m, 5H), 3.42-3.24 (m, 4H), 2.21 (d, J = 8.4 Hz, 2H), 1.92 (d, J = 6.4 Hz, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 190 | 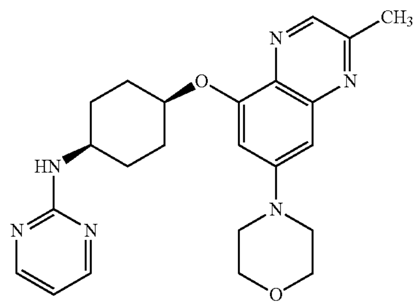 [SMILES: Cc1cnc2c(O[C@H]3CC[C@@H](Nc4ncccn4)CC3)cc(N3CCOCC3)cc2n1] | | (CDCl₃) δ 8.52 (s, 1H), 8.29 (d, J = 4.8 Hz, 2H), 6.90 (d, J = 2.5 Hz, 1H), 6.85 (d, J = 2.5 Hz, 1H), 6.52 (t, J = 4.8 Hz, 1H), 5.36 (s, 1H), 4.79 (dq, J = 5.6, 2.9 Hz, 1H), 4.04 (dp, J = 8.0, 3.8 Hz, 1H), 3.97-3.85 (m, 4H), 3.38-3.26 (m, 4H), 2.70 (s, 3H), 2.29-2.11 (m, 2H), 2.00-1.78 (m, 6H) |
| 191 | 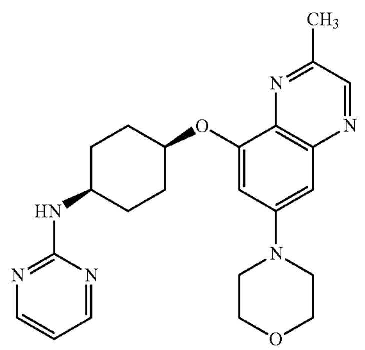 [SMILES: Cc1cnc2cc(N3CCOCC3)cc(O[C@H]3CC[C@@H](Nc4ncccn4)CC3)c2n1] | 421.24 | (CDCl₃) δ 8.52 (s, 1H), 8.29 (d, J = 4.8 Hz, 2H), 6.90 (d, J = 2.5 Hz, 1H), 6.85 (d, J = 2.5 Hz, 1H), 6.53 (t, J = 4.8 Hz, 1H), 5.42 (d, J = 7.9 Hz, 1H), 4.80 (dq, J = 5.9, 2.9 Hz, 1H), 4.11-3.98 (m, 1H), 3.91 (dd, J = 5.9, 3.8 Hz, 4H), 3.42-3.21 (m, 4H), 2.71 (s, 3H), 2.31-2.07 (m, 2H), 2.04-1.77 (m, 6H) |
| 193 | 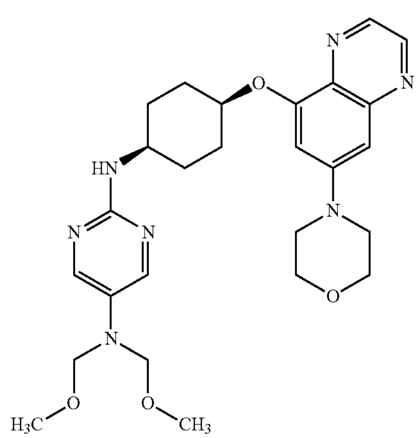 [SMILES: COCN(COC)c1cnc(N[C@H]2CC[C@@H](Oc3cc(N4CCOCC4)cc4nccnc34)CC2)nc1] | 524.21 | (CDCl₃) δ 8.70 (d, J = 1.9 Hz, 1H), 8.63 (d, J = 1.9 Hz, 1H), 7.95 (s, 2H), 7.05-6.88 (m, 2H), 4.92 (s, 1H), 4.79 (s, 1H), 3.93 (t, J = 4.8 Hz, 5H), 3.60-3.44 (m, 4H), 3.37 (d, J = 10.5 Hz, 9H), 2.20 (d, J = 6.9 Hz, 2H), 1.91 (d, J = 4.6 Hz, 6H) |
| 194 | 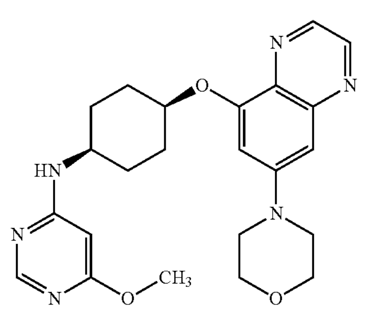 [SMILES: COc1cc(N[C@H]2CC[C@@H](Oc3cc(N4CCOCC4)cc4nccnc34)CC2)ncn1] | 437.23 | (CDCl₃) δ 8.70 (d, J = 1.9 Hz, 1H), 8.62 (d, J = 1.9 Hz, 1H), 8.28 (d, J = 0.9 Hz, 1H), 6.97 (d, J = 2.5 Hz, 1H), 6.91 (d, J = 2.5 Hz, 1H), 5.74-5.58 (m, 1H), 5.16 (d, J = 8.0 Hz, 1H), 4.82 (dq, J = 5.4, 2.7 Hz, 1H), 4.06-3.85 (m, 7H), 3.70 (d, J = 14.0 Hz, 1H), 3.42-3.28 (m, 4H), 2.30-2.16 (m, 2H), 1.99-1.75 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 195 | 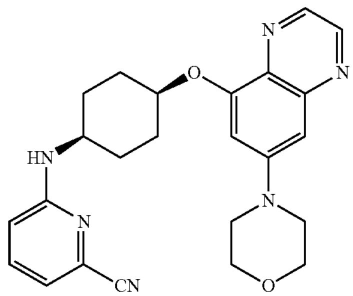 [SMILES: N#Cc1cccc(N[C@H]2CC[C@@H](Oc3cc(N4CCOCC4)cc4nccnc34)CC2)n1] | 431.22 | (CDCl₃) δ 8.70 (d, J = 1.9 Hz, 1H), 8.62 (d, J = 2.0 Hz, 1H), 7.43 (dd, J = 8.6, 7.2 Hz, 1H), 7.02-6.86 (M, 3H), 6.55 (dd, J = 8.6, 0.8 Hz, 1H), 4.80 (d, J = 6.6 Hz, 2H), 4.10-3.81 (m, 5H), 3.47-3.25 (m, 4H), 2.30-2.11 (m, 2H), 1.99-1.81 (m, 6H) |
| 196 | 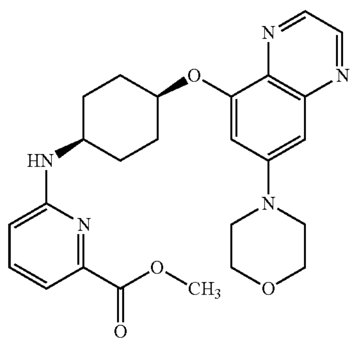 [SMILES: COC(=O)c1cccc(N[C@H]2CC[C@@H](Oc3cc(N4CCOCC4)cc4nccnc34)CC2)n1] | 463.27 | (CDCl₃) δ 8.71 (d, J = 1.9 Hz, 1H), 8.63 (d, J = 1.9 Hz, 1H), 7.61 (d, J = 9.4 Hz, 1H), 7.41 (d, J = 7.2 Hz, 1H), 7.05-6.87 (m, 2H), 6.65 (s, 1H), 4.86 (s, 1H), 4.04-3.87 (m, 7H), 3.74 (s, 1H), 3.43-3.27 (m, 4H), 2.21 (d, J = 10.8 Hz, 2H), 1.98 (d, J = 23.5 Hz, 6H) |
| 197 | 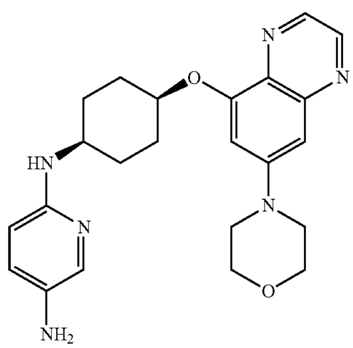 [SMILES: Nc1ccc(N[C@H]2CC[C@@H](Oc3cc(N4CCOCC4)cc4nccnc34)CC2)nc1] | 421.69 | (400 MHz, CDCl₃) δ 8.68 (d, J = 1.9 Hz, 1H), 8.61 (d, J = 1.9 Hz, 1H), 8.13-8.04 (m, 1H), 7.67 (d, J = 2.4 Hz, 1H), 6.99-6.93 (m, 2H), 6.90 (d, J = 2.4 Hz, 1H), 6.33 (d, J = 8.7 Hz, 1H), 4.77 (s, 1H), 3.99-3.65 (m, 7H), 3.39-3.27 (m, 4H), 2.25-2.10 (m, 2H), 1.96-1.82 (m, 6H) |
| 198 | 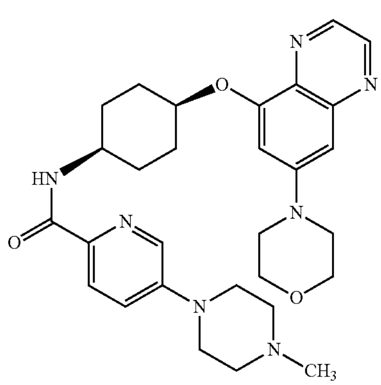 [SMILES: CN1CCN(c2ccc(C(=O)N[C@H]3CC[C@@H](Oc4cc(N5CCOCC5)cc5nccnc45)CC3)nc2)CC1] | 532.11 | (400 MHz, CDCl₃) δ 8.69 (d, J = 1.6 Hz, 1H), 8.61 (d, J = 1.7 Hz, 1H), 8.57 (d, J = 2.1 Hz, 1H), 7.89 (dd, J = 8.9, 2.3 Hz, 1H), 6.95 (s, 1H), 6.90 (s, 1H), 6.62 (d, J = 9.0 Hz, 1H), 5.99 (d, J = 7.7 Hz, 1H), 4.78 (s, 1H), 4.18 (s, 1H), 4.03-3.81 (m, 4H), 3.76-3.60 (m, 4H), 3.42-3.25 (m, 4H), 2.62-2.44 (m, 4H), 2.36 (s, 3H), 2.29-2.14 (m, 2H), 1.99-1.84 (m, 6H) |

TABLE 1-continued

| Cmpd. No. | Compound Structure | ESMS (M + H) | [1] H NMR (300 MHz, unless indicated otherwise) NMR peaks given as δ values |
|---|---|---|---|
| 199 | 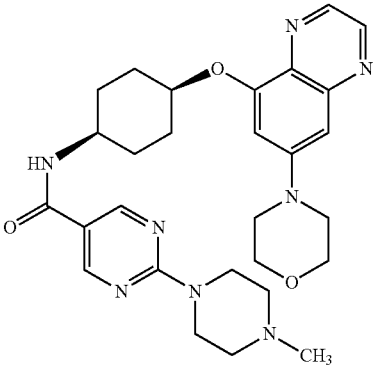 [SMILES: CN1CCN(c2ncc(C(=O)N[C@H]3CC[C@@H](Oc4cc(N5CCOCC5)cc5nccnc45)CC3)cn2)CC1] | 533.01 | (400 MHz, CDCl$_3$) δ 8.73-8.65 (m, 3H), 8.60 (d, J = 1.9 Hz, 1H), 6.95 (d, J = 2.4 Hz, 1H), 6.89 (d, J = 2.4 Hz, 1H), 5.93 (d, J = 8.0 Hz, 1H), 4.79 (s, 1H), 4.23-4.09 (m, 1H), 3.97-3.88 (m, 8H), 3.40-3.25 (m, 4H), 2.53-2.42 (m, 4H), 2.34 (s, 3H), 2.26-2.18 (m, 2H), 1.97-1.83 (m, 6H) |
| 200 | 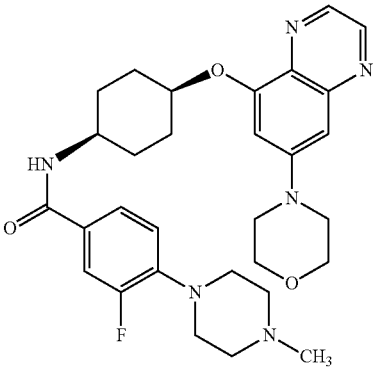 [SMILES: CN1CCN(c2ccc(C(=O)N[C@H]3CC[C@@H](Oc4cc(N5CCOCC5)cc5nccnc45)CC3)cc2F)CC1] | 549.17 | (400 MHz, CDCl$_3$) δ 8.69 (d, J = 1.9 Hz, 1H), 8.61 (d, J = 1.9 Hz, 1H), 7.51-7.42 (m, 2H), 6.98-6.85 (m, 3H), 6.07 (d, J = 8.0 Hz, 1H), 4.77 (s, 1H), 4.25-4.11 (m, 1H), 3.99-3.85 (m, 4H), 3.40-3.27 (m, 4H), 3.26-3.14 (m, 4H), 2.67-2.52 (m, 4H), 2.36 (s, 3H), 2.28-2.13 (m, 2H), 1.98-1.84 (m, 6H) |
| 201 | 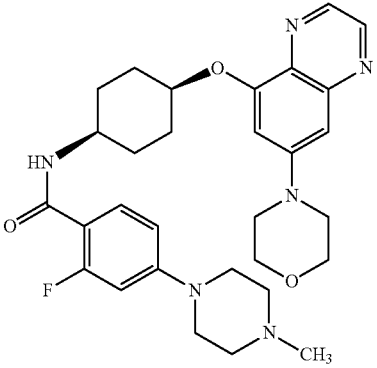 [SMILES: CN1CCN(c2ccc(C(=O)N[C@H]3CC[C@@H](Oc4cc(N5CCOCC5)cc5nccnc45)CC3)c(F)c2)CC1] | 549.1 | (400 MHz, CDCl$_3$) δ 9.47 (s, 1H), 8.68 (d, J = 1.7 Hz, 1H), 8.56 (d, J = 1.7 Hz, 1H), 8.21-8.11 (m, 1H), 6.97-6.85 (m, 4H), 4.82 (s, 1H), 4.23-4.07 (m, 1H), 3.96-3.87 (m, 4H), 3.38-3.29 (m, 4H), 3.03 (s, 4H), 2.65 (s, 4H), 2.37-2.25 (m, 5H), 2.02-1.84 (m, 6H) |
| 202 | 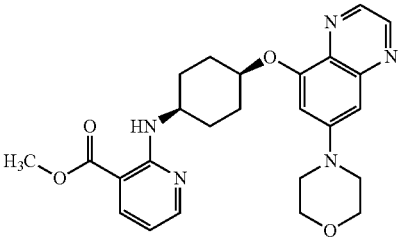 [SMILES: COC(=O)c1cccnc1N[C@H]1CC[C@@H](Oc2cc(N3CCOCC3)cc3nccnc23)CC1] | 464.13 | (400 MHz, CDCl$_3$) δ 8.69 (d, J = 1.8 Hz, 1H), 8.63 (d, J = 1.9 Hz, 1H), 8.27 (dd, J = 4.7, 1.9 Hz, 1H), 8.19 (s, 1H), 8.11 (d, J = 6.8 Hz, 1H), 6.95 (d, J = 2.4 Hz, 1H), 6.92 (d, J = 2.3 Hz, 1H), 6.51 (dd, J = 7.4, 4.9 Hz, 1H), 4.76 (s, 1H), 4.30 (s, 1H), 4.02-3.90 (m, 4H), 3.88 (s, 3H), 3.41-3.26 (m, 4H), 2.29-2.11 (m, 2H), 2.11-1.85 (m, 6H) |

TABLE 1-continued

| Cmpd. No. | Compound Structure | ESMS (M + H) | ¹H NMR (300 MHz, unless indicated otherwise) NMR peaks given as δ values |
|---|---|---|---|
| 203 | 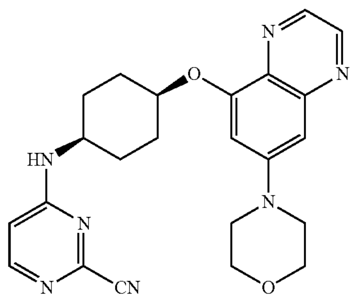 [SMILES: N#Cc1nccc(N[C@H]2CC[C@@H](Oc3cc(N4CCOCC4)cc4nccnc34)CC2)n1] | 432.58 | (CDCl₃) δ 8.70 (d, J = 1.9 Hz, 1H), 8.60 (d, J = 1.9 Hz, 1H), 8.15 (s, 1H), 6.93 (dd, J = 17.9, 2.5 Hz, 2H), 6.43 (d, J = 6.1 Hz, 1H), 5.20 (s, 1H), 4.82 (s, 1H), 4.00-3.82 (m, 4H), 3.44-3.25 (m, 4H), 2.23 (d, J = 11.2 Hz, 2H), 1.91 (s, 6H) |
| 204 | 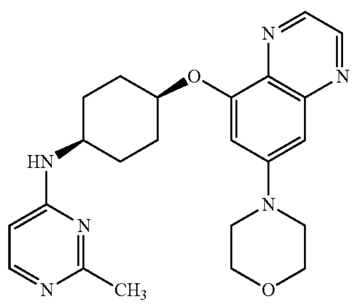 [SMILES: Cc1nccc(N[C@H]2CC[C@@H](Oc3cc(N4CCOCC4)cc4nccnc34)CC2)n1] | 421.65 | (CDCl₃) δ 8.70 (d, J = 1.9 Hz, 1H), 8.61 (d, J = 1.9 Hz, 1H), 8.09 (d, J = 6.0 Hz, 1H), 6.93 (dd, J = 16.1, 2.5 Hz, 2H), 6.15 8.0 Hz, 1H), 4.81 (td, J = 5.5, 2.7 Hz, 1H), 3.97-3.87 (m, 4H), 3.49 (s, 1H), 3.39-3.27 (m, 4H), 2.49 (s, 3H), 2.27-2.14 (m, 2H), 2.03-1.80 (m, 6H) |
| 205 | 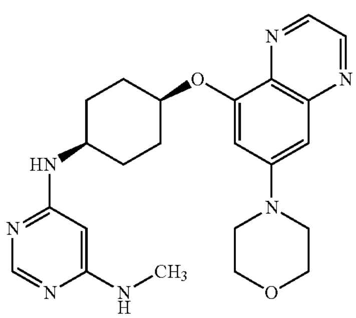 [SMILES: CNc1cc(N[C@H]2CC[C@@H](Oc3cc(N4CCOCC4)cc4nccnc34)CC2)ncn1] | 436.63 | (CDCl₃) δ 8.70 (d, J = 1.9 Hz, 1H), 8.61 (dd, J = 5.3, 1.9 Hz, 1H), 8.19-8.06 (m, 1H), 6.99-6.84 (m, 2H), 5.34-5.21 (m, 1H), 4.76 (d, J = 9.7 Hz, 3H), 3.92 (t, J = 4.9 Hz, 4H), 3.81 (s, 1H), 3.33 (dd, J = 5.7, 4.1 Hz, 4H), 2.87 (d, J = 5.2 Hz, 3H), 2.19 (d, J = 8.5 Hz, 2H), 1.88 (dd, J = 13.3, 5.1 Hz, 6H) |
| 206 | 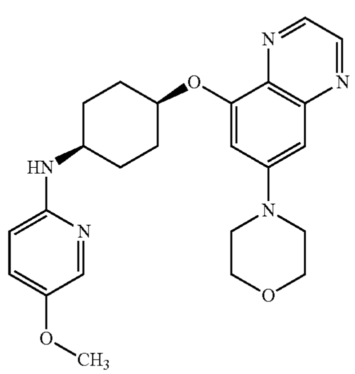 [SMILES: COc1ccc(N[C@H]2CC[C@@H](Oc3cc(N4CCOCC4)cc4nccnc34)CC2)nc1] | 436.18 | (400 MHz, CDCl₃) δ 8.68 (d, J = 1.9 Hz, 1H), 8.61 (d, J = 1.9 Hz, 1H), 7.82 (d, J = 2.8 Hz, 1H), 7.09 (dd, J = 8.9, 3.0 Hz, 1H), 6.94 (d, J = 2.5 Hz, 1H), 6.90 (d, J = 2.5 Hz, 1H), 6.37 (d, J = 8.8 Hz, 1H), 4.77 (s, 1H), 4.29 (bs, 1H), 3.98-3.87 (m, 4H), 3.85-3.79 (m, 1H), 3.77 (s, 3H), 3.41-3.24 (m, 4H), 2.27-2.12 (m, 2H), 1.97-1.79 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 207 | 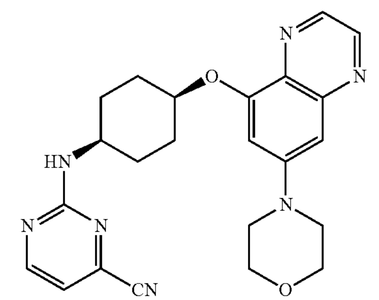 [SMILES: N#Cc1ccnc(N[C@H]2CC[C@@H](Oc3cc(N4CCOCC4)cc4nccnc34)CC2)n1] | | (CDCl₃) δ 8.71 (d, J = 2.0 Hz, 1H), 8.64 (d, J = 1.9 Hz, 1H), 8.44 (s, 1H), 6.98 (d, J = 2.5 Hz, 1H), 6.92 (d, J = 2.5 Hz, 1H), 6.82 (d, J = 4.7 Hz, 1H), 5.56 (d, J = 30.8 Hz, 1H), 4.83 (d, J = 5.2 Hz, 1H), 4.04 (s, 2H), 3.97-3.84 (m, 4H), 3.44-3.29 (m, 4H), 2.23 (d, J = 8.2 Hz, 2H), 2.02-1.77 (m, 6H) |
| 208 | 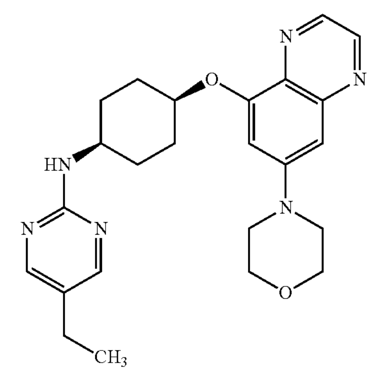 [SMILES: CCc1cnc(N[C@H]2CC[C@@H](Oc3cc(N4CCOCC4)cc4nccnc34)CC2)nc1] | 435.6 | (CDCl₃) δ 8.70 (d, J = 1.9 Hz, 1H), 8.64 (d, J = 1.9 Hz, 1H), 8.16 (s, 2H), 7.00-6.84 (m, 2H), 5.32 (s, 1H), 4.81 (s, 1H), 4.03 (s, 1H), 3.96-3.85 (m, 4H), 3.43-3.32 (m, 4H), 2.49 (q, J = 7.6 Hz, 2H), 2.21 (d, J = 8.8 Hz, 2H), 2.06-1.75 (m, 6H), 1.21 (t, J = 7.6 Hz, 3H) |
| 209 | 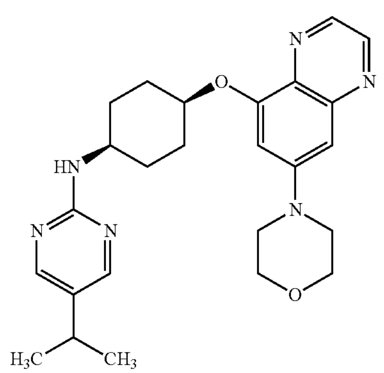 [SMILES: CC(C)c1cnc(N[C@H]2CC[C@@H](Oc3cc(N4CCOCC4)cc4nccnc34)CC2)nc1] | | (CDCl₃) δ 8.70 (d, J = 1.9 Hz, 1H), 8.63 (d, J = 1.9 Hz, 1H), 8.18 (s, 2H), 7.01-6.88 (m, 2H), 5.30 (d, J = 9.0 Hz, 1H), 4.81 (d, J = 5.9 Hz, 1H), 4.02 (s, 1H), 3.96-3.85 (m, 4H), 3.42-3.29 (m, 4H), 2.78 (p, J = 6.9 Hz, 1H), 2.31-2.14 (m, 2H), 2.01-1.83 (m, 6H), 1.25 (d, J = 6.9 Hz, 6H) |
| 210 | 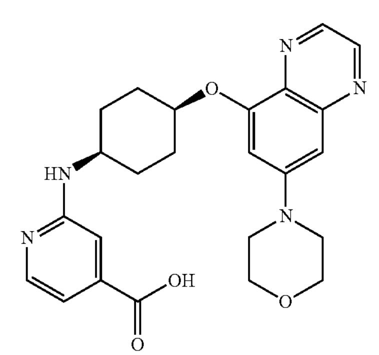 [SMILES: O=C(O)c1ccnc(N[C@H]2CC[C@@H](Oc3cc(N4CCOCC4)cc4nccnc34)CC2)c1] | 450.17 | (400 MHz, methanol-d₄) δ 8.69 (d, J = 2.0 Hz, 1H), 8.57 (d, J = 2.0 Hz, 1H), 7.92 (d, J = 6.2 Hz, 1H), 7.17-7.10 (m, 2H), 7.02 (d, J = 7.1 Hz, 1H), 6.90 (d, J = 2.5 Hz, 1H), 4.93 (s, 1H), 3.93-3.87 (m, 4H), 3.84-3.79 (m, 1H), 3.44-3.37 (m, 4H), 2.24-2.15 (m, 2H), 1.97-1.82 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 215 | 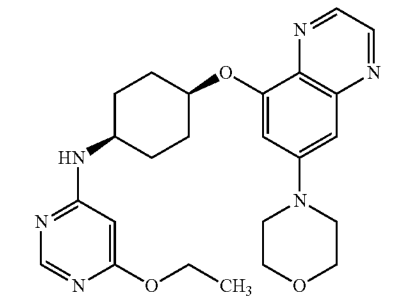 [SMILES: CCOc1cc(N[C@H]2CC[C@@H](Oc3cc(N4CCOCC4)cc4nccnc34)CC2)ncn1] | 451.21 | (CDCl₃) δ 8.70 (d, J = 1.9 Hz, 1H), 8.61 (d, J = 1.9 Hz, 1H), 8.25 (d, J = 0.9 Hz, 1H), 6.93 (dd, J = 17.1, 2.5 Hz, 2H), 5.64 (d, J = 0.9 Hz, 1H), 5.00 (d, J = 8.1 Hz, 1H), 4.80 (dq, J = 5.5, 2.7 Hz, 1H), 4.33 (q, J = 7.1 Hz, 2H), 3.97-3.87 (m, 4H), 3.71 (s, 1H), 3.38-3.29 (m, 4H), 2.27-2.14 (m, 2H), 2.03-1.80 (m, 6H), 1.37 (t, J = 7.1 Hz, 3H) |
| 219 | 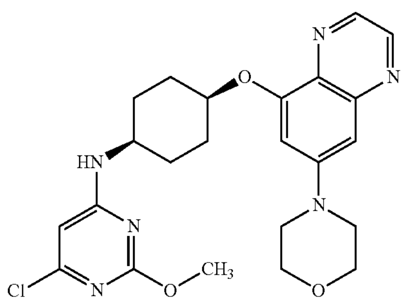 [SMILES: COc1nc(Cl)cc(N[C@H]2CC[C@@H](Oc3cc(N4CCOCC4)cc4nccnc34)CC2)n1] | 471.06 | (CDCl₃) δ 8.70 (d, J = 1.9 Hz, 1H), 8.61 (d, J = 1.9 Hz, 1H), 6.96 (d, J = 2.5 Hz, 1H), 6.89 (d, J = 2.5 Hz, 1H), 6.03 (s, 1H), 5.00 (s, 1H), 4.79 (s, 1H), 3.92 (d, J = 9.3 Hz, 7H), 3.41-3.25 (m, 4H), 2.28-2.13 (m, 2H), 1.92 (d, J = 18.6 Hz, 6H) |
| 223 | 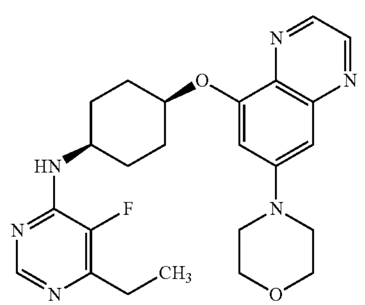 [SMILES: CCc1ncnc(N[C@H]2CC[C@@H](Oc3cc(N4CCOCC4)cc4nccnc34)CC2)c1F] | 435.18 | (CDCl₃) δ 8.71 (d, J = 1.9 Hz, 1H), 8.61 (d, J = 1.9 Hz, 1H), 6.94 (dd, J = 15.2, 2.5 Hz, 2H), 6.07 (s, 1H), 4.82 (dt, J = 5.8, 3.0 Hz, 1H), 4.02-3.83 (m, 4H), 3.77-3.57 (m, 1H), 3.43-3.28 (m, 4H), 2.52 (s, 3H), 2.37 (s, 3H), 2.30-2.16 (m, 2H), 2.05-1.78 (m, 6H) |
| 224 | 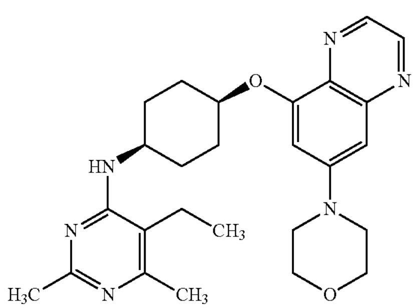 [SMILES: CCc1c(C)nc(C)nc1N[C@H]1CC[C@@H](Oc2cc(N3CCOCC3)cc3nccnc23)CC1] | 475.02 | (CDCl₃) δ 8.72 (d, J = 1.9 Hz, 1H), 8.63 (d, J = 1.9 Hz, 1H), 8.27 (s, 1H), 6.98 (d, J = 2.4 Hz, 1H), 6.92 (d, J = 2.6 Hz, 1H), 6.44 (d, J = 6.0 Hz, 1H), 4.84 (s, 1H), 3.93 (dd, J = 6.0, 3.7 Hz, 4H), 3.43-3.25 (m, 4H), 2.23 (s, 2H), 2.08-1.83 (m, 6H) |
| 225 | 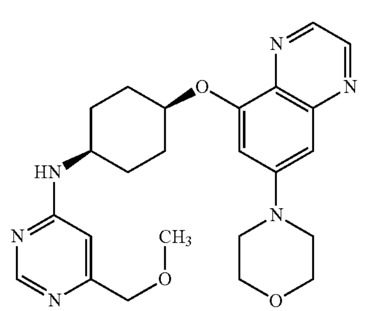 [SMILES: COCc1cc(N[C@H]2CC[C@@H](Oc3cc(N4CCOCC4)cc4nccnc34)CC2)ncn1] | 451.16 | (CDCl₃) δ 8.70 (d, J = 1.9 Hz, 1H), 8.62 (d, J = 1.9 Hz, 1H), 8.49 (d, J = 1.1 Hz, 1H), 6.93 (dd, J = 16.7, 2.5 Hz, 2H), 6.45 (d, J = 1.2 Hz, 1H), 5.01 (s, 1H), 4.81 (s, 1H), 4.39 (d, J = 0.9 Hz, 2H), 3.97-3.87 (m, 4H), 3.49 (s, 3H), 3.39-3.29 (m, 4H), 2.22 (d, J = 9.4 Hz, 2H), 1.99-1.87 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 226 | 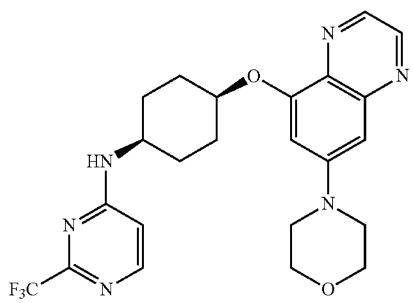 [SMILES: FC(F)(F)c1nccc(N[C@H]2CC[C@@H](Oc3cc(N4CCOCC4)cc4nccnc34)CC2)n1] | 463.18 | (CDCl₃) δ 8.70 (d, J = 2.0 Hz, 1H), 8.63 (d, J = 1.9 Hz, 1H), 6.95 (d, J = 2.5 Hz, 1H), 6.91 (d, J = 2.5 Hz, 1H), 4.75 (d, J = 5.6 Hz, 1H), 4.66 (s, 1H), 4.32 (s, 1H), 4.00-3.83 (m, 4H), 3.43-3.22 (m, 4H), 2.46 (d, J = 15.1 Hz, 5H), 2.36 (s, 3H), 2.19 (q, J = 6.3, 3.9 Hz, 2H), 1.12 (t, J = 7.6 Hz, 3H) |
| 227 | 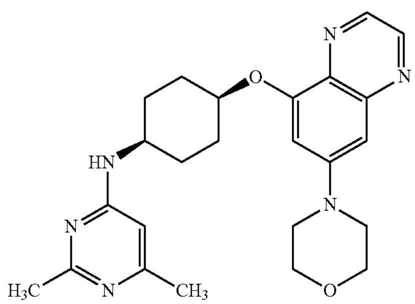 | 453.2 | (CDCl₃) δ 8.72 (d, J = 1.9 Hz, 1H), 8.64 (d, J = 1.9 Hz, 1H), 8.33 (d, J = 1.8 Hz, 1H), 7.04-6.87 (m, 2H), 5.15 (s, 1H), 4.82 (dq, J = 5.2, 2.6 Hz, 1H), 4.24 (dt, J = 8.3, 4.7 Hz, 1H), 4.03-3.86 (m, 4H), 3.44-3.28 (m, 4H), 2.74 (qd, J = 7.6, 2.3 Hz, 2H), 2.24 (dq, J = 9.6, 4.6 Hz, 2H), 2.09-1.85 (m, 6H), 1.29 (t, J = 7.6 Hz, 3H) |
| 233 | 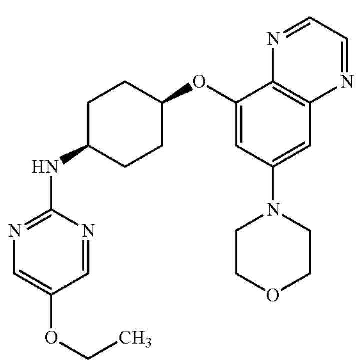 [SMILES: CCOc1cnc(N[C@H]2CC[C@@H](Oc3cc(N4CCOCC4)cc4nccnc34)CC2)nc1] | 451.2 | (CDCl₃) δ 8.70 (d, J = 1.9 Hz, 1H), 8.63 (d, J = 1.9 Hz, 1H), 8.06 (s, 2H), 7.01-6.86 (m, 2H), 5.00 (d, J = 8.1 Hz, 1H), 4.80 (d, J = 5.6 Hz, 1H), 4.10-3.82 (m, 7H), 3.42-3.26 (m, 5H), 2.20 (d, J = 8.2 Hz, 2H), 2.01-1.80 (m, 6H), 1.39 (t, J = 7.0 Hz, 3H) |
| 234 | 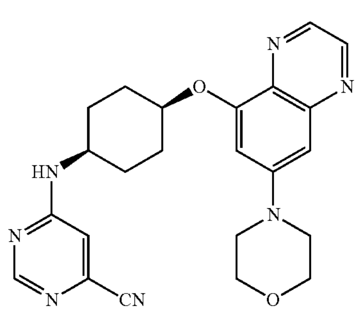 [SMILES: N#Cc1cc(N[C@H]2CC[C@@H](Oc3cc(N4CCOCC4)cc4nccnc34)CC2)ncn1] | 432.17 | (CDCl₃) δ 8.72 (d, J = 1.9 Hz, 1H), 8.60 (t, J = 1.9 Hz, 2H), 6.97 (d, J = 2.5 Hz, 1H), 6.91 (d, J = 2.5 Hz, 1H), 6.70 (d, J = 1.2 Hz, 1H), 4.85 (d, J = 4.9 Hz, 1H), 3.98-3.84 (m, 4H), 3.42-3.26 (m, 4H), 2.33-2.17 (m, 2H), 2.01-1.77 (m, 5H) |

TABLE 1-continued

| Cmpd. No. | Compound Structure | ESMS (M + H) | ¹H NMR (300 MHz, unless indicated otherwise) NMR peaks given as δ values |
|---|---|---|---|
| 235 | 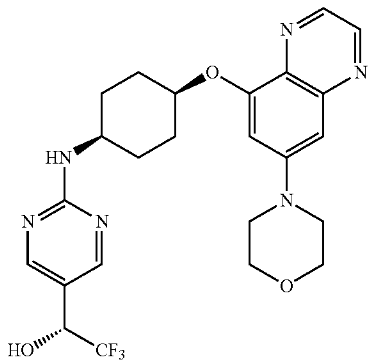 [SMILES: O[C@H](c1cnc(N[C@H]2CC[C@@H](Oc3cc(N4CCOCC4)cc4nccnc34)CC2)nc1)C(F)(F)F] | 505.04 | (CDCl₃) δ 8.68 (d, J = 2.0 Hz, 1H), 8.59 (d, J = 1.9 Hz, 1H), 8.36 (s, 2H), 6.97-6.86 (m, 2H), 5.53 (d, J = 8.1 Hz, 1H), 4.96-4.72 (m, 3H), 4.09-3.86 (m, 5H), 3.33 (dd, J = 5.8, 4.0 Hz, 4H), 2.28-2.10 (m, 2H), 1.98-1.78 (m, 6H) |
| 236 | 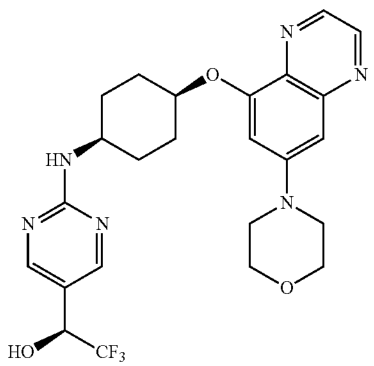 [SMILES: O[C@@H](c1cnc(N[C@H]2CC[C@@H](Oc3cc(N4CCOCC4)cc4nccnc34)CC2)nc1)C(F)(F)F] | 505.17 | (CDCl₃) δ 8.68 (d, J = 2.0 Hz, 1H), 8.59 (d, J = 1.9 Hz, 1H), 8.36 (s, 2H), 6.97-6.86 (m, 2H), 5.53 (d, J = 8.1 Hz, 1H), 4.96-4.72 (m, 3H), 4.09-3.86 (m, 5H), 3.33 (dd, J = 5.8, 4.0 Hz, 4H), 2.28-2.10 (m, 2H), 1.98-1.78 (m, 6H) |
| 237 | 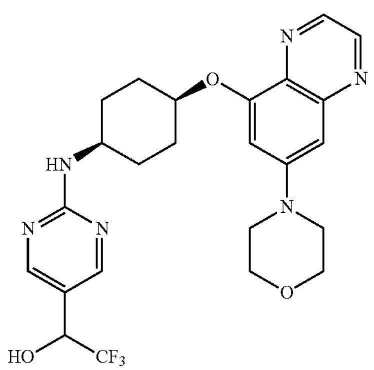 [SMILES: OC(c1cnc(N[C@H]2CC[C@@H](Oc3cc(N4CCOCC4)cc4nccnc34)CC2)nc1)C(F)(F)F] | 451.16 | (CDCl₃) δ 8.69 (d, J = 1.9 Hz, 1H), 8.61 (d, J = 1.9 Hz, 1H), 8.31 (s, 2H), 6.99-6.87 (m, 2H), 5.34 (d, J = 8.1 Hz, 1H), 4.87-4.73 (m, 2H), 4.06-3.87 (m, 6H), 3.38-3.29 (m, 4H), 2.20 (q, J = 5.8 Hz, 2H), 2.04-1.84 (m, 6H), 1.51 (d, J = 6.5 Hz, 3H) |
| 241 | 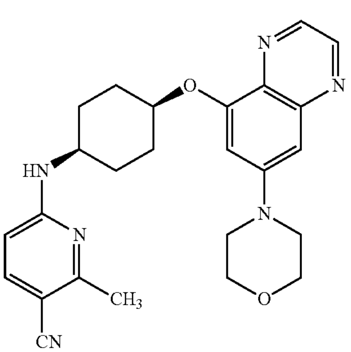 [SMILES: Cc1nc(N[C@H]2CC[C@@H](Oc3cc(N4CCOCC4)cc4nccnc34)CC2)ccc1C#N] | 445.54 | (400 MHz, CDCl₃) δ 8.69 (d, J = 1.9 Hz, 1H), 8.61 (d, J = 1.9 Hz, 1H), 7.52 (d, J = 8.7 Hz, 1H), 6.96 (d, J = 2.5 Hz, 1H), 6.90 (d, J = 2.5 Hz, 1H), 6.23 (d, J = 8.7 Hz, 1H), 5.09 (s, 1H), 4.80 (s, 1H), 4.00-3.78 (m, 5H), 3.40-3.24 (m, 4H), 2.56 (s, 3H), 2.29-2.14 (m, 2H), 2.01-1.80 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 242 | 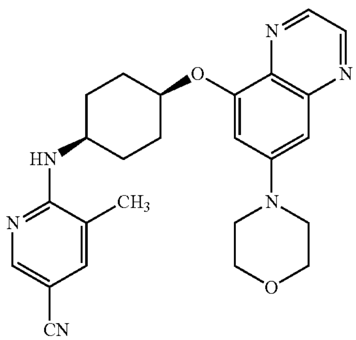 [SMILES: Cc1cc(C#N)cnc1N[C@H]1CC[C@@H](Oc2cc(N3CCOCC3)cc3nccnc23)CC1] | 445.54 | (400 MHz, CDCl₃) δ 8.70 (d, J = 1.8 Hz, 1H), 8.62 (d, J = 1.9 Hz, 1H), 8.30 (d, J = 1.8 Hz, 1H), 7.37 (s, 1H), 6.96 (d, J = 2.3 Hz, 1H), 6.91 (d, J = 2.3 Hz, 1H), 4.79 (s, 1H), 4.74 (s, 1H), 4.28 (s, 1H), 4.01-3.83 (m, 4H), 3.40-3.25 (m, 4H), 2.30-2.17 (m, 2H), 2.11 (s, 3H), 1.99-1.87 (m, 6H) |
| 243 | 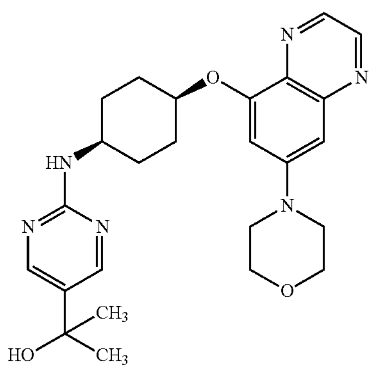 [SMILES: CC(C)(O)c1cnc(N[C@H]2CC[C@@H](Oc3cc(N4CCOCC4)cc4nccnc34)CC2)nc1] | 465.2 | (CDCl₃) δ 8.69 (d, J = 2.0 Hz, 1H), 8.62 (d, J = 1.9 Hz, 1H), 5.36 (s, 1H), 4.03 (s, 1H), 1.57 (s, 6H), 2.02-1.80 (m, 6H), 8.42 (s, 2H), 6.99-6.87 (m, 2H), 4.80 (s, 1H), 3.92 (dd, J = 6.0, 3.7 Hz, 4H), 3.39-3.29 (m, 4H), 2.20 (d, J = 9.0 Hz, 2H) |
| 245 | 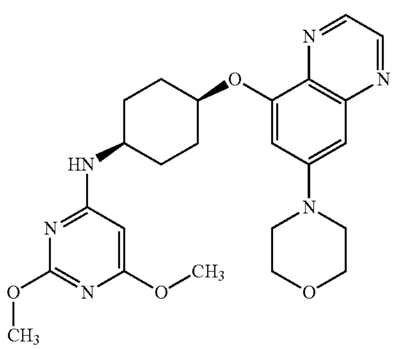 [SMILES: COc1cc(N[C@H]2CC[C@@H](Oc3cc(N4CCOCC4)cc4nccnc34)CC2)nc(OC)n1] | 467.14 | (CDCl₃) δ 8.61 (d, J = 1.9 Hz, 1H), 8.53 (d, J = 1.9 Hz, 1H), 6.84 (dd, J = 18.2, 2.5 Hz, 2H), 5.26 (s, 1H), 4.78 (d, J = 8.0 Hz, 1H), 4.68 (d, J = 5.6 Hz, 1H), 3.82 (t, J = 4.0 Hz, 10H), 3.30-3.15 (m, 4H), 2.10 (q, J = 6.2, 5.7 Hz, 2H), 1.94-1.69 (m, 6H) |
| 246 | 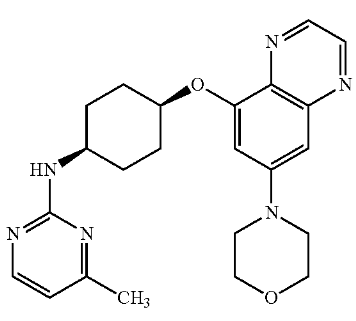 | 421.23 | (CDCl₃) δ 8.61 (d, J = 1.9 Hz, 1H), 8.54 (d, J = 1.9 Hz, 1H), 8.06 (d, J = 5.0 Hz, 1H), 6.94-6.78 (m, 2H), 6.32 (d, J = 5.0 Hz, 1H), 5.09 (s, 1H), 4.70 (d, J = 6.0 Hz, 1H), 3.95 (s, 1H), 3.91-3.77 (m, 5H), 3.37-3.13 (m, 4H), 2.20-2.00 (m, 2H), 1.94-1.71 (m, 6H) |

Table 1-continued

| Cmpd. No. | Compound Structure | ESMS (M + H) | $^1$H NMR (300 MHz, unless indicated otherwise) NMR peaks given as δ values |
|---|---|---|---|
| 247 | 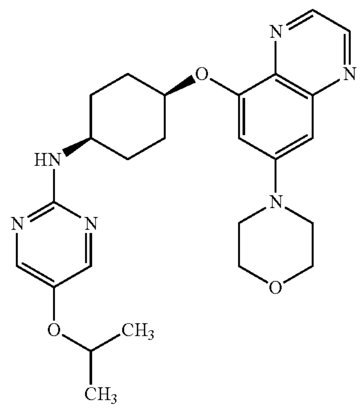 [SMILES: CC(C)Oc1cnc(N[C@H]2CC[C@@H](Oc3cc(N4CCOCC4)cc4nccnc34)CC2)nc1] | 465.1 | (CDCl$_3$) δ 8.71 (d, J = 1.9 Hz, 1H), 8.64 (t, J = 2.4 Hz, 1H), 8.05 (s, 2H), 7.04-6.87 (m, 2H), 5.20 (s, 1H), 4.80 (s, 1H), 4.30 (p, J = 6.1 Hz, 1H), 4.05-3.81 (m, 4H), 3.44-3.27 (m, 4H), 2.22 (t, J = 7.3 Hz, 2H), 1.93 (d, J = 4.6 Hz, 6H), 1.33 (d, J = 6.1 Hz, 6H) |
| 254 | 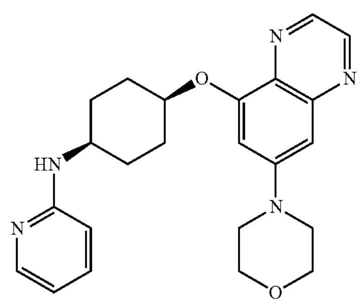 [SMILES: c1ccc(N[C@H]2CC[C@@H](Oc3cc(N4CCOCC4)cc4nccnc34)CC2)nc1] | 406.57 | (400 MHz, CDCl$_3$) δ 8.71 (d, J = 1.9 Hz, 1H), 8.63 (d, J = 1.9 Hz, 1H), 8.15-8.04 (m, 1H), 7.46-7.39 (m, 1H), 6.97 (d, J = 2.5 Hz, 1H), 6.93 (d, J = 2.5 Hz, 1H), 6.60-6.52 (m, 1H), 6.41 (d, J = 8.4 Hz, 1H), 4.80 (s, 1H), 4.68 (s, 1H), 3.98-3.85 (m, 5H), 3.41-3.30 (m, 4H), 2.27-2.15 (m, 2H), 1.97- 1.86 (m, 6H) |
| 256 | 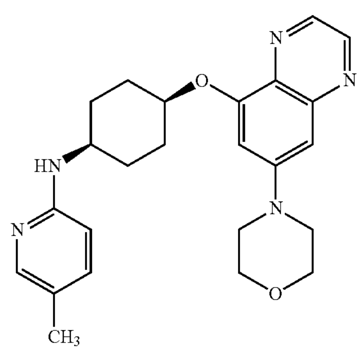 | 420.1 | (CDCl$_3$) δ 8.71 (d, J = 1.9 Hz, 1H), 8.64 (d, J = 1.9 Hz, 1H), 7.80 (d, J = 1.5 Hz, 1H), 7.47 (d, J = 1.5 Hz, 1H), 7.02-6.86 (m, 2H), 4.80 (s, 1H), 4.27 (d, J = 8.3 Hz, 1H), 4.00-3.72 (m, 7H), 3.35 (dd, J = 6.0, 3.8 Hz, 4H), 2.23 (s, 2H), 2.02-1.80 (m, 6H) |
| 257 | 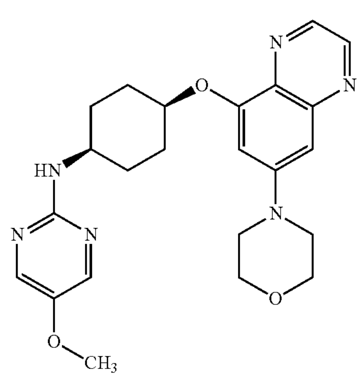 [SMILES: COc1cnc(N[C@H]2CC[C@@H](Oc3cc(N4CCOCC4)cc4nccnc34)CC2)nc1] | 437.1 | (CDCl$_3$) δ 8.71 (d, J = 1.9 Hz, 1H), 8.63 (dd, J = 1.9, 0.7 Hz, 1H), 7.99-7.88 (m, 1H), 7.02-6.87 (m, 2H), 6.34 (d, J = 8.4 Hz, 1H), 4.78 (s, 1H), 4.40 (d, J = 8.2 Hz, 1H), 4.03-3.75 (m, 5H), 3.35 (dd, J = 6.0, 3.7 Hz, 4H), 2.18 (s, 5H), 2.03-1.81 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 260 | 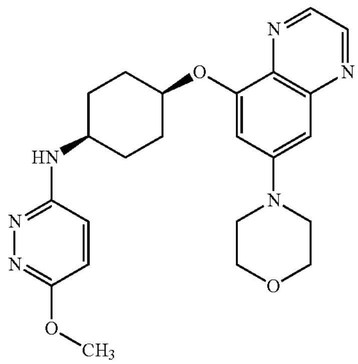 [SMILES: COc1ccc(N[C@H]2CC[C@@H](Oc3cc(N4CCOCC4)cc4nccnc34)CC2)nn1] | 437.24 | (CDCl₃) δ 8.70 (d, J = 1.9 Hz, 1H), 8.62 (d, J = 1.9 Hz, 1H), 6.93 (dd, J = 14.5, 2.5 Hz, 2H), 6.79 (d, J = 9.4 Hz, 1H), 6.64 (d, J = 9.4 Hz, 1H), 4.80 (d, J = 5.5 Hz, 1H), 4.27 (d, J = 7.5 Hz, 1H), 4.14 (s, 1H), 4.02 (s, 3H), 3.98-3.88 (m, 4H), 3.42-3.29 (m, 4H), 2.31-2.12 (m, 2H), 1.95 (ddd, J = 17.2, 9.2, 6.0 Hz, 6H) |
| 263 | 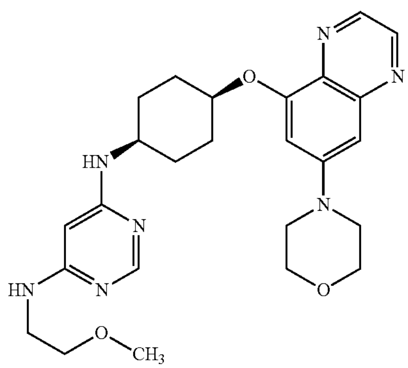 [SMILES: COCCNc1cc(N[C@H]2CC[C@@H](Oc3cc(N4CCOCC4)cc4nccnc34)CC2)ncn1] | 480.22 | (CDCl₃) δ 8.70 (d, J = 1.9 Hz, 1H), 8.61 (d, J = 1.9 Hz, 1H), 8.11 (d, J = 0.9 Hz, 1H), 6.93 (dd, J = 15.5, 2.5 Hz, 2H), 5.30 (d, J = 1.0 Hz, 1H), 5.16 (s, 1H), 4.95 (s, 1H), −0.17--0.23 (m, 0H), 4.80 (s, 1H), 3.92 (dd, J = 5.9, 3.7 Hz, 4H), 3.74 (s, 1H), 3.57 (dd, J = 5.6, 4.6 Hz, 2H), 3.50-3.29 (m, 9H), 2.20 (d, J = 9.1 Hz, 2H), 1.93 (d, J = 13.1 Hz, 6H) |
| 264 | 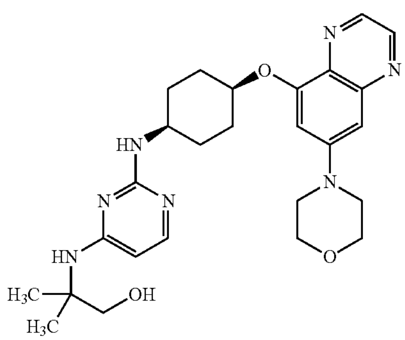 [SMILES: CC(C)(CO)Nc1ccnc(N[C@H]2CC[C@@H](Oc3cc(N4CCOCC4)cc4nccnc34)CC2)n1] | 494.1 | (CDCl₃) δ 8.69 (d, J = 1.9 Hz, 1H), 8.62 (d, J = 2.0 Hz, 1H), 7.76 (d, J = 5.8 Hz, 1H), 7.02-6.86 (m, 2H), 5.66 (d, J = 5.9 Hz, 1H), 4.80 (d, J = 5.5 Hz, 1H), 4.63 (s, 1H), 3.97-3.84 (m, 5H), 1.30-1.20 (m, 1H), 3.64 (s, 2H), 3.38-3.28 (m, 4H), 1.37 (s, 6H), 5.16-4.86 (m, 1H), 2.24-2.13 (m, 2H), 1.96-1.82 (m, 6H) |
| 265 | 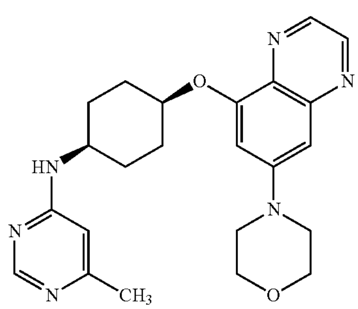 [SMILES: Cc1cc(N[C@H]2CC[C@@H](Oc3cc(N4CCOCC4)cc4nccnc34)CC2)ncn1] | 421.18 | (CDCl₃) δ 8.70 (d, J = 1.9 Hz, 1H), 8.61 (d, J = 1.9 Hz, 1H), 8.47 (d, J = 1.1 Hz, 1H), 6.93 (dd, J = 16.7, 2.5 Hz, 2H), 6.17 (t, J = 0.9 Hz, 1H), 4.95 (s, 1H), 4.81 (td, J = 5.3, 2.5 Hz, 1H), 4.07-3.83 (m, 5H), 3.39-3.29 (m, 4H), 2.34 (s, 3H), 2.21 (dt, J = 11.1, 5.1 Hz, 2H), 2.04-1.76 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 267 | 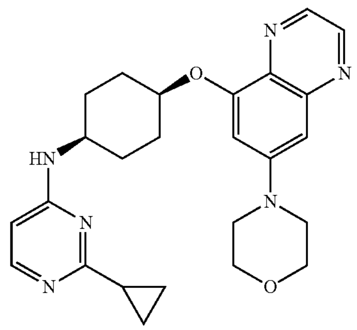 [SMILES: c1cc(N[C@H]2CC[C@@H](Oc3cc(N4CCOCC4)cc4nccnc34)CC2)nc(C2CC2)n1] | 447.11 | (CDCl$_3$) δ 8.70 (d, J = 1.9 Hz, 1H), 8.60 (d, J = 1.9 Hz, 1H), 8.03 (d, J = 6.1 Hz, 1H), 6.93 (dd, J = 18.6, 2.5 Hz, 2H), 6.13 (d, J = 6.1 Hz, 1H), 5.09 (s, 1H), 4.79 (s, 1H), 4.03-3.78 (m, 5H), 3.34 (dd, J = 6.0, 3.8 Hz, 4H), 2.20 (d, J = 8.1 Hz, 2H), 1.96 (s, 7H), 1.10 (d, J = 2.8 Hz, 2H), 1.00 (d, J = 8.0 Hz, 2H) |
| 268 | 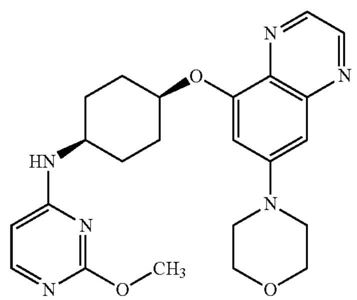 [SMILES: COc1nccc(N[C@H]2CC[C@@H](Oc3cc(N4CCOCC4)cc4nccnc34)CC2)n1] | 437.19 | (CDCl$_3$) δ 8.69 (d, J = 1.9 Hz, 1H), 8.60 (d, J = 1.9 Hz, 1H), 7.95 (d, J = 5.8 Hz, 1H), 6.92 (dd, J = 17.9, 2.5 Hz, 2H), 5.99 (d, J = 5.9 Hz, 1H), 5.01 (s, 1H), 4.79 (dt, J = 6.9, 3.4 Hz, 1H), 3.91 (d, J = 8.7 Hz, 8H), 3.43-3.25 (m, 4H), 2.32-2.09 (m, 2H), 2.05-1.74 (m, 6H) |
| 269 | 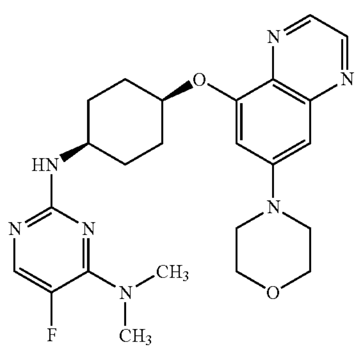 [SMILES: CN(C)c1nc(N[C@H]2CC[C@@H](Oc3cc(N4CCOCC4)cc4nccnc34)CC2)ncc1F] | 468.13 | (CDCl$_3$) δ 8.69 (d, J = 1.9 Hz, 1H), 8.62 (d, J = 1.9 Hz, 1H), 7.70 (d, J = 6.8 Hz, 1H), 6.92 (dd, J = 14.4, 2.5 Hz, 2H), 4.86 (d, J = 8.1 Hz, 1H), 4.75 (dt, J = 8.6, 4.0 Hz, 1H), 3.97-3.87 (m, 5H), 3.38-3.28 (m, 4H), 3.14 (d, J = 2.2 Hz, 6H), 2.24-2.07 (m, 2H), 2.02-1.79 (m, 6H) |
| 272 | 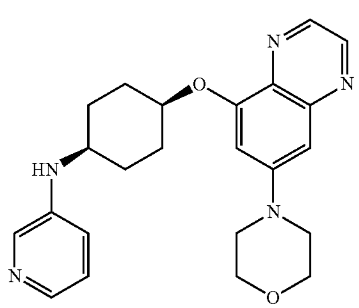 [SMILES: c1cncc(N[C@H]2CC[C@@H](Oc3cc(N4CCOCC4)cc4nccnc34)CC2)c1] | 406.53 | (CDCl$_3$) δ 8.69 (d, J = 1.9 Hz, 1H), 8.61 (d, J = 1.9 Hz, 1H), 8.04 (d, J = 2.8 Hz, 1H), 7.94 (dd, J = 4.7, 1.3 Hz, 1H), 7.11 (dd, J = 8.3, 4.7 Hz, 1H), 7.00-6.84 (m, 3H), 4.78 (s, 1H), 3.98-3.88 (m, 4H), 3.85 (d, J = 8.1 Hz, 1H), 3.38-3.28 (m, 4H), 2.27-2.15 (m, 2H), 1.97-1.84 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 273 | 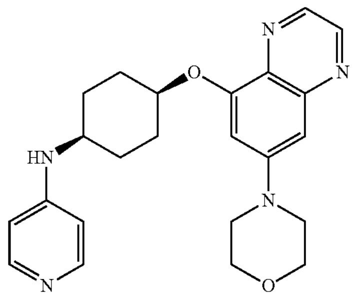 [SMILES: c1cc(N[C@H]2CC[C@@H](Oc3cc(N4CCOCC4)cc4nccnc34)CC2)ccn1] | 406.57 | (CDCl$_3$) δ 8.70 (d, J = 1.9 Hz, 1H), 8.61 (d, J = 1.9 Hz, 1H), 8.18 (d, J = 6.3 Hz, 2H), 6.96 (d, J = 2.4 Hz, 1H), 6.90 (d, J = 2.4 Hz, 1H), 6.51-6.42 (m, 2H), 4.79 (s, 1H), 4.47 (d, J = 7.7 Hz, 1H), 3.98-3.86 (m, 4H), 3.56 (s, 1H), 3.39-3.26 (m, 4H), 2.27-2.15 (m, 2H), 2.01-1.79 (m, 6H) |
| 275 | 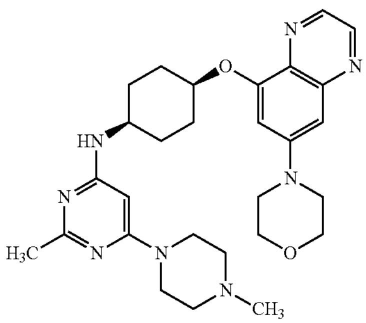 [SMILES: Cc1nc(N[C@H]2CC[C@@H](Oc3cc(N4CCOCC4)cc4nccnc34)CC2)cc(N2CCN(C)CC2)n1] | 519.2 | (CDCl$_3$) δ 8.62 (d, J = 1.9 Hz, 1H), 8.54 (d, J = 1.9 Hz, 1H), 6.93-6.77 (m, 2H), 5.20 (s, 1H), 4.78-4.60 (m, 2H), 3.92-3.79 (m, 5H), 3.64 (s, 0H), 3.51 (t, J = 5.1 Hz, 4H), 3.36-3.16 (m, 4H), 2.40 (t, J = 5.1 Hz, 4H), 2.27 (d, J = 4.8 Hz, 6H), 2.16-2.02 (m, 2H), 1.81 (q, J = 8.1, 5.7 Hz, 6H) |
| 276 | 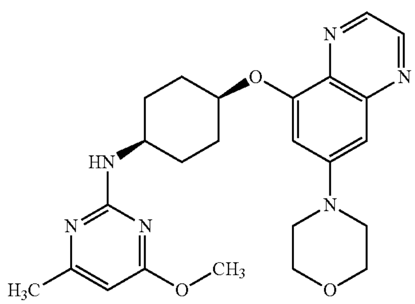 [SMILES: COc1cc(C)nc(N[C@H]2CC[C@@H](Oc3cc(N4CCOCC4)cc4nccnc34)CC2)n1] | 451.53 | (CDCl$_3$) δ 8.69 (d, J = 1.8 Hz, 1H), 8.61 (d, J = 1.9 Hz, 1H), 6.94 (d, J = 2.3 Hz, 1H), 6.90 (d, J = 2.3 Hz, 1H), 5.87 (s, 1H), 5.13 (s, 1H), 4.76 (s, 1H), 4.04 (s, 1H), 3.98-3.89 (m, 4H), 3.87 (s, 3H), 3.41-3.23 (m, 4H), 2.25 (s, 3H), 2.23-2.09 (m, 2H), 1.99-1.80 (m, 6H) |
| 277 | 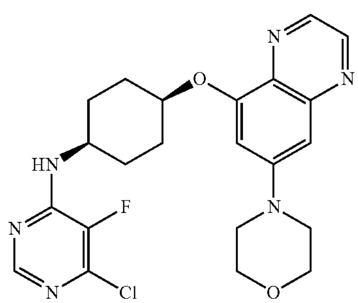 [SMILES: Fc1c(Cl)ncnc1N[C@H]1CC[C@@H](Oc2cc(N3CCOCC3)cc3nccnc23)CC1] | 459.08 | (CDCl$_3$) δ 8.71 (d, J = 1.9 Hz, 1H), 8.62 (d, J = 1.9 Hz, 1H), 8.17 (d, J = 0.9 Hz, 1H), 6.94 (dd, J = 15.8, 2.5 Hz, 2H), 5.31 (s, 1H), 4.83 (dp, J = 4.6, 2.5 Hz, 1H), 4.22 (qt, J = 8.5, 4.9 Hz, 1H), 4.03-3.87 (m, 4H), 3.39-3.29 (m, 4H), 2.25 (td, J = 7.9, 6.6, 3.9 Hz, 2H), 2.09-1.80 (m, 6H) |
| 282 | 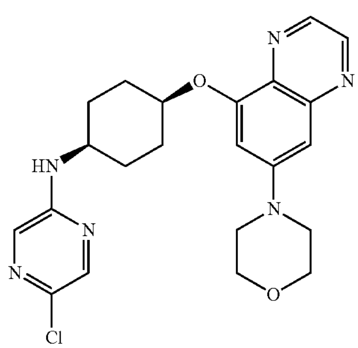 [SMILES: Clc1cnc(N[C@H]2CC[C@@H](Oc3cc(N4CCOCC4)cc4nccnc34)CC2)cn1] | 421.2 | (CDCl$_3$) δ 8.71 (d, J = 1.9 Hz, 1H), 8.63 (d, J = 1.9 Hz, 1H), 7.93-7.74 (m, 2H), 7.04-6.82 (m, 2H), 4.80 (s, 1H), 4.50 (d, J = 8.1 Hz, 1H), 3.93 (dd, J = 6.4, 3.4 Hz, 5H), 3.41-3.25 (m, 4H), 2.51-2.33 (m, 3H), 2.23 (s, 2H), 2.04-1.82 (m, 6H) |

Table 1-continued

| Cmpd. No. | Compound Structure | ESMS (M + H) | ¹H NMR (300 MHz, unless indicated otherwise) NMR peaks given as δ values |
|---|---|---|---|
| 283 | 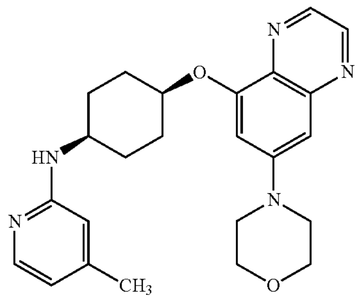 [SMILES: Cc1ccnc(N[C@H]2CC[C@@H](Oc3cc(N4CCOCC4)cc4nccnc34)CC2)c1] | 420.2 | (CDCl₃) δ 6 8.62 (d, J = 1.9 Hz, 1H), 8.55 (d, J = 1.9 Hz, 1H), 7.88 (dd, J = 5.3, 0.7 Hz, 1H), 6.95-6.79 (m, 2H), 6.32 (ddd, J = 5.2, 1.5, 0.7 Hz, 1H), 6.12 (dt, J = 1.6, 0.8 Hz, 1H), 4.71 (d, J = 5.9 Hz, 1H), 4.40 (d, J = 8.2 Hz, 1H), 3.98-3.67 (m, 4H), 3.35-3.17 (m, 4H), 2.15 (s, 4H), 1.83 (d, J = 5.2 Hz, 5H) |
| 285 | 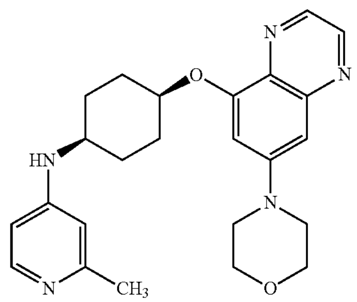 | 420.57 | (400 MHz, CDCl₃) δ 8.69 (d, J = 1.9 Hz, 1H), 8.61 (d, J = 1.9 Hz, 1H), 8.08 (d, J = 5.7 Hz, 1H), 6.96 (d, J = 2.4 Hz, 1H), 6.90 (d, J = 2.4 Hz, 1H), 6.30 (s, 1H), 6.28 (dd, J = 5.7, 2.2 Hz, 1H), 4.78 (s, 1H), 4.19 (d, J = 7.7 Hz, 1H), 3.97-3.82 (m, 4H), 3.53 (s, 1H), 3.40-3.24 (m, 4H), 2.41 (s, 3H), 2.27-2.11 (m, 2H), 1.92-1.84 (m, 6H) |
| 286 | 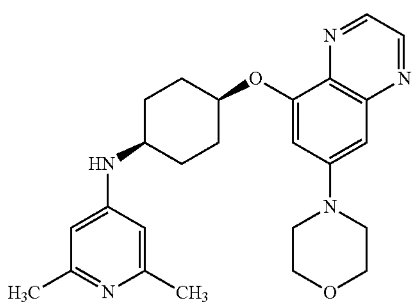 [SMILES: Cc1cc(N[C@H]2CC[C@@H](Oc3cc(N4CCOCC4)cc4nccnc34)CC2)cc(C)n1] | 434.56 | (400 MHz, CDCl₃) δ 8.69 (d, J = 1.9 Hz, 1H), 8.60 (d, J = 1.9 Hz, 1H), 6.95 (d, J = 2.4 Hz, 1H), 6.89 (d, J = 2.4 Hz, 1H), 6.15 (s, 2H), 4.77 (s, 1H), 4.12 (d, J = 7.8 Hz, 1H), 3.99-3.81 (m, 4H), 3.53 (s, 1H), 3.40-3.23 (m, 4H), 2.36 (d, J = 14.5 Hz, 6H), 2.25-2.14 (m, 2H), 1.89 (t, J = 7.8 Hz, 6H) |

TABLE 2

| Cmpd. No. | Compound Structure | ESMS (M + H) | ¹H NMR |
|---|---|---|---|
| 287 | 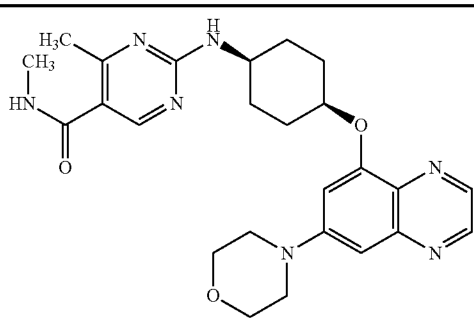 | 478.3 | 1H NMR (300 MHz, Chloroform-d) δ 8.70 (d, J = 1.9 Hz, 1H), 8.62 (d, J = 1.9 Hz, 1H), 8.33 (s, 1H), 6.94 (dd, J = 14.3, 2.5 Hz, 2H), 5.80 (d, J = 4.9 Hz, 1H), 5.42 (d, J = 8.1 Hz, 1H), 4.88-4.74 (m, 1H), 4.08 (s, 2H), 3.99-3.86 (m, 4H), 3.50 (s, 3H), 3.42-3.28 (m, 4H), 3.01 (dd, J = 18.4, 5.0 Hz, 3H), 2.54 (s, 3H), 2.28-2.08 (m, 2H), 2.03-1.79 (m, 6H). |

| Cmpd. No. | Compound Structure | ESMS (M + H) | 1H NMR |
|---|---|---|---|
| 291 | 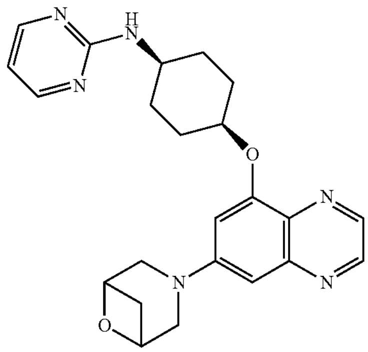 [SMILES: c1cnc(N[C@H]2CC[C@@H](Oc3cc(N4CC5CC(C4)O5)cc4nccnc34)CC2)nc1] | 419.23 [1] | 1H NMR (400 MHz, Chloroform-d) δ 8.42 (d, J = 1.9 Hz, 1H), 8.30 (d, J = 1.9 Hz, 1H), 8.04 (d, J = 4.8 Hz, 2H), 6.65-6.56 (m, 2H), 6.28 (t, J = 4.8 Hz, 1H), 4.99 (d, J = 8.1 Hz, 1H), 4.60 (d, J = 6.5 Hz, 3H), 3.79 (dd, J = 8.2, 4.0 Hz, 0H), 3.62-3.38 (m, 4H), 3.17-3.03 (m, 1H), 2.07-1.90 (m, 2H), 1.89-1.59 (m, 7H). |
| 294 | 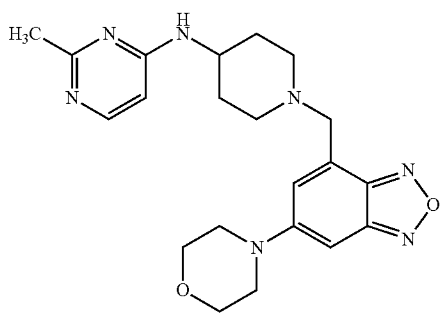 [SMILES: Cc1nccc(NC2CCN(Cc3cc(N4CCOCC4)cc4nonc34)CC2)n1] | 410.35 | 1H NMR (300 MHz, Chloroform-d) δ 8.10 (d, J = 6.0 Hz, 1H), 7.36-7.28 (m, 1H), 6.65 (d, J = 2.0 Hz, 1H), 6.13 (d, J = 6.0 Hz, 1H), 4.81 (d, J = 8.0 Hz, 1H), 4.00-3.80 (m, 6H), 3.80-3.56 (m, 1H), 3.29 (dd, J = 5.8, 3.8 Hz, 4H), 3.02-2.84 (m, 2H), 2.48 (s, 3H), 2.36 (td, J = 11.4, 10.9, 2.5 Hz, 2H), 2.14-1.98 (m, 2H), 1.70-1.46 (m, 2H). |
| 295 | 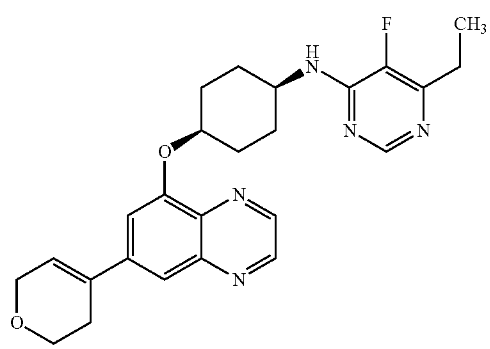 [SMILES: CCc1ncnc(N[C@H]2CC[C@@H](Oc3cc(C4=CCOCC4)cc4nccnc34)CC2)c1F] | 450.2 | 1H NMR (300 MHz, Chloroform-d) δ 8.98-8.78 (m, 2H), 8.33 (d, J = 1.9 Hz, 1H), 7.67 (d, J = 1.8 Hz, 1H), 7.30 (d, J = 1.8 Hz, 1H), 6.49-6.31 (m, 1H), 5.07 (d, J = 7.6 Hz, 1H), 4.87 (d, J = 5.5 Hz, 1H), 4.43 (q, J = 2.8 Hz, 2H), 4.24 (s, 1H), 4.02 (t, J = 5.4 Hz, 2H), 2.71 (dtd, J = 13.1, 7.7, 2.7 Hz, 4H), 2.26 (dt, J = 10.4, 5.3 Hz, 2H), 1.97 (d, J = 5.3 Hz, 6H), 1.28 (t, J = 7.6 Hz, 3H). |
| 297 | 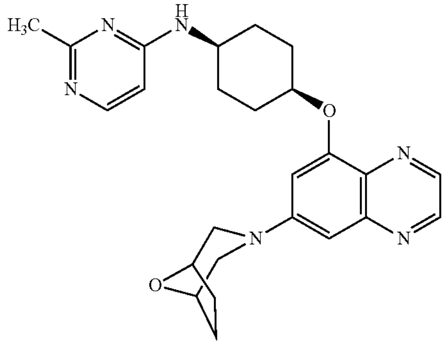 [SMILES: Cc1nccc(N[C@H]2CC[C@@H](Oc3cc(N4CC5CCC(C4)O5)cc4nccnc34)CC2)n1] | 447 | 1H NMR (400 MHz, CDCl3) δ 8.60 (d, J = 1.9 Hz, 1H), 8.49 (d, J = 1.9 Hz, 1H), 8.02 (d, J = 6.0 Hz, 1H), 6.78 (dd, J = 10.1, 2.5 Hz, 2H), 6.08 (d, J = 6.0 Hz, 1H), 4.96 (s, 1H), 4.74 (d, J = 2.4 Hz, 1H), 4.49 (d, J = 2.3 Hz, 2H), 3.41 (t, J = 5.4 Hz, 2H), 3.12 (dd, J = 11.6, 2.5 Hz, 2H), 2.43 (s, 3H), 2.14 (dd, J = 9.6, 4.9 Hz, 2H), 1.98-1.68 (m, 10H). |

TABLE 2-continued

| Cmpd. No. | Compound Structure | ESMS (M + H) | 1H NMR |
|---|---|---|---|
| 298 | 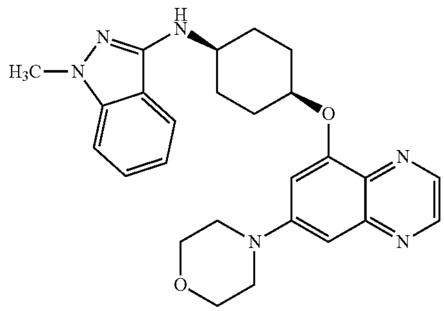 [SMILES: Cn1nc(N[C@H]2CC[C@@H](Oc3cc(N4CCOCC4)cc4nccnc34)CC2)c2ccccc21] | 459.4 | 1H NMR (300 MHz, Chloroform-d) δ 8.71 (d, J = 1.9 Hz, 1H), 8.65 (d, J = 1.9 Hz, 1H), 7.53 (dt, J = 8.1, 1.0 Hz, 1H), 7.35 (ddd, J = 8.1, 6.8, 1.1 Hz, 1H), 7.20 (dt, J = 8.5, 0.9 Hz, 1H), 7.07-6.89 (m, 3H), 4.79 (td, J = 6.1, 3.1 Hz, 1H), 4.02-3.91 (m, 4H), 3.87 (s, 3H), 3.43-3.25 (m, 4H), 2.34-2.15 (m, 2H), 2.10-1.88 (m, 6H). |
| 308 | 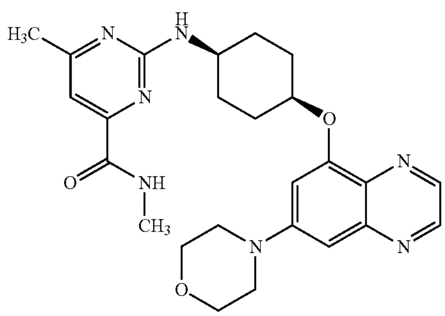 [SMILES: CNC(=O)c1cc(C)nc(N[C@H]2CC[C@@H](Oc3cc(N4CCOCC4)cc4nccnc34)CC2)n1] | 478.64 | 1H NMR (300 MHz, Chloroform-d) δ 8.71 (d, J = 1.9 Hz, 1H), 8.64 (d, J = 1.9 Hz, 1H), 7.79 (s, 1H), 7.23 (s, 1H), 6.95 (dd, J = 14.0, 2.5 Hz, 2H), 5.23 (d, J = 8.1 Hz, 1H), 4.80 (s, 1H), 4.09 (s, 1H), 3.94 (dd, J = 6.1, 3.6 Hz, 4H), 3.43-3.23 (m, 4H), 3.02 (d, J = 5.1 Hz, 3H), 2.43 (s, 3H), 2.31-2.12 (m, 2H), 1.95 (p, J = 10.0 Hz, 6H). |
| 309 | 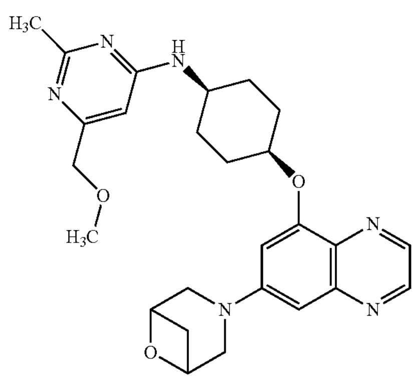 [SMILES: COCc1cc(N[C@H]2CC[C@@H](Oc3cc(N4CC5CC(C4)O5)cc4nccnc34)CC2)nc(C)n1] | 477.54 | 1H NMR (300 MHz, Chloroform-d) δ 8.68 (d, J = 1.9 Hz, 1H), 8.54 (d, J = 1.9 Hz, 1H), 6.85 (s, 2H), 6.30 (s, 1H), 5.06 (d, J = 16.2 Hz, 1H), 4.85 (d, J = 6.5 Hz, 3H), 4.44-4.30 (m, 2H), 4.14 (q, J = 7.1 Hz, 1H), 3.89-3.60 (m, 5H), 3.50 (s, 3H), 3.35 (q, J = 7.2 Hz, 1H), 2.49 (s, 3H), 2.24 (d, J = 8.7 Hz, 2H), 2.08 (d, J = 7.7 Hz, 2H), 1.92 (q, J = 9.6, 6.9 Hz, 6H), 1.28 (t, J = 7.1 Hz, 2H). |
| 312 | 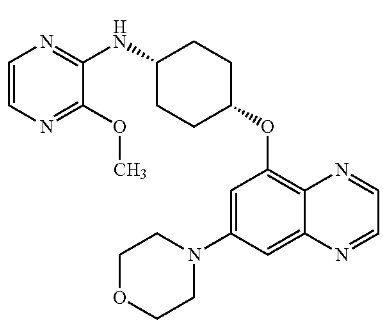 [SMILES: COc1nccnc1N[C@H]1CC[C@@H](Oc2cc(N3CCOCC3)cc3nccnc23)CC1] | 437.33 | 1H NMR (300 MHz, CDCl3) δ 8.71 (d, J = 1.9 Hz, 1H), 8.65 (d, J = 1.9 Hz, 1H), 7.57 (d, J = 3.2 Hz, 1H), 7.35-7.28 (m, 2H), 6.97 (d, J = 2.4 Hz, 1H), 6.91 (d, J = 2.4 Hz, 1H), 5.23 (s, 1H), 4.76 (s, 1H), 4.20 (s, 1H), 4.01 (s, 3H), 3.98-3.84 (m, 4H), 3.44-3.29 (m, 4H), 2.27-2.14 (m, 2H), 2.05-1.85 (m, 6H). |

| Cmpd. No. | Compound Structure | ESMS (M + H) | ¹H NMR |
|---|---|---|---|
| 314 | 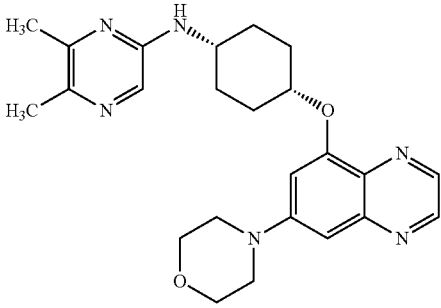 [SMILES: Cc1ncc(N[C@H]2CC[C@@H](Oc3cc(N4CCOCC4)cc4nccnc34)CC2)nc1C] | 435.32 | 1H NMR (300 MHz, CDCl3) δ 8.71 (d, J = 1.9 Hz, 1H), 8.63 (d, J = 1.9 Hz, 1H), 7.66 (s, 1H), 6.94 (dd, J = 14.9, 2.4 Hz, 2H), 4.84-4.74 (m, 1H), 4.47 (s, 1H), 4.02-3.87 (m, 4H), 3.87-3.75 (m, 1H), 3.47-3.21 (m, 4H), 2.38 (d, J = 4.0 Hz, 6H), 2.26-2.13 (m, 2H), 2.01-1.78 (m, 6H). |
| 315 | 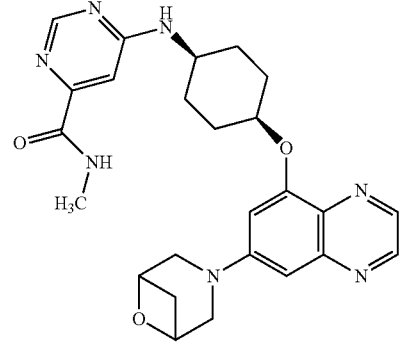 [SMILES: CNC(=O)c1cc(N[C@H]2CC[C@@H](Oc3cc(N4CC5CC(C4)O5)cc4nccnc34)CC2)ncn1] | 476.23 | 1H NMR (300 MHz, Chloroform-d) δ 8.86 (d, J = 1.9 Hz, 1H), 8.59-8.46 (m, 2H), 7.98 (s, 1H), 7.18 (s, 1H), 6.85 (s, 2H), 4.85 (d, J = 6.6 Hz, 2H), 3.90-3.62 (m, 5H), 3.35 (d, J = 8.2 Hz, 1H), 3.03 (d, J = 5.1 Hz, 3H), 2.27 (s, 2H), 2.13-1.80 (m, 7H), 10.58 (s, 2H) |
| 316 | 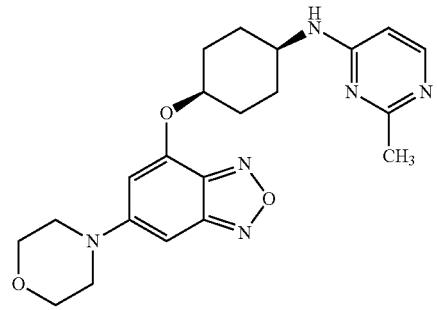 [SMILES: Cc1nccc(N[C@H]2CC[C@@H](Oc3cc(N4CCOCC4)cc4nonc34)CC2)n1] | 411.34 | 1H NMR (300 MHz, Chloroform-d) δ 8.14 (d, J = 6.2 Hz, 1H), 6.50 (d, J = 1.7 Hz, 1H), 6.43 (d, J = 1.6 Hz, 1H), 6.21 (d, J = 6.2 Hz, 1H), 4.98 (s, 1H), 4.01-3.81 (m, 5H), 3.37-3.18 (m, 5H), 2.54 (s, 3H), 2.20 (d, J = 9.1 Hz, 3H), 2.05-1.71 (m, 6H). |
| 317 | 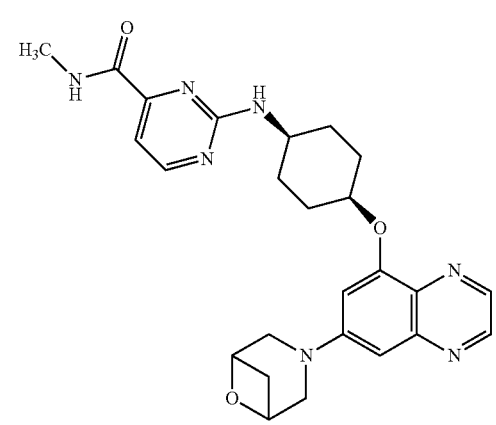 [SMILES: CNC(=O)c1ccnc(N[C@H]2CC[C@@H](Oc3cc(N4CC5CC(C4)O5)cc4nccnc34)CC2)n1] | 476.55 | 1H NMR (300 MHz, Chloroform-d) δ 8.68 (d, J = 1.9 Hz, 1H), 8.62-8.41 (m, 2H), 7.79 (s, 1H), 7.33 (d, J = 4.9 Hz, 1H), 6.85 (q, J = 2.6 Hz, 3H), 4.85 (d, J = 6.3 Hz, 4H), 4.08 (s, 0H), 3.88-3.58 (m, 5H), 3.35 (q, J = 6.8 Hz, 1H), 3.03 (d, J = 5.1 Hz, 3H), 2.36-2.13 (m, 2H), 2.15-1.84 (m, 6H). |

TABLE 2-continued

| Cmpd. No. | Compound Structure | ESMS (M + H) | ¹H NMR |
|---|---|---|---|
| 318 | 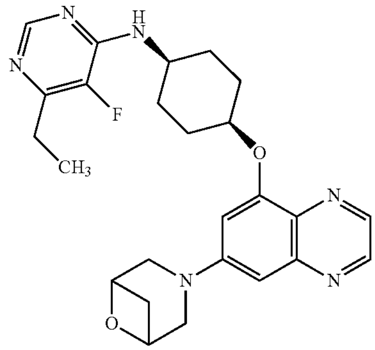 [SMILES: CCc1ncnc(N[C@H]2CC[C@@H](Oc3cc(N4CC5CC(C4)O5)cc4nccnc34)CC2)c1F] | 465.3 | 1H NMR (300 MHz, Chloroform-d) δ 8.68 (d, J = 1.9 Hz, 1H), 8.56 (d, J = 1.9 Hz, 1H), 8.33 (d, J = 1.9 Hz, 1H), 6.85 (s, 2H), 5.07 (d, J = 8.1 Hz, 1H), 4.86 (d, J = 6.4 Hz, 4H), 4.23 (s, 2H), 3.90-3.62 (m, 4H), 3.35 (q, J = 7.1 Hz, 1H), 2.73 (qd, J = 7.6, 2.3 Hz, 2H), 2.27 (d, J = 10.1 Hz, 3H), 2.12-1.82 (m, 6H), 1.28 (t, J = 7.6 Hz, 3H). |
| 319 | 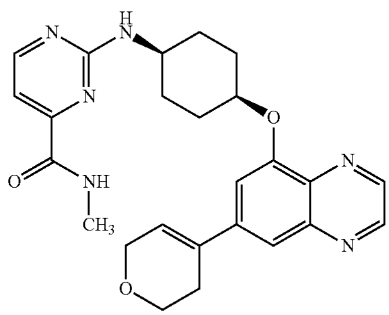 [SMILES: CNC(=O)c1ccnc(N[C@H]2CC[C@@H](Oc3cc(C4=CCOCC4)cc4nccnc34)CC2)n1] | 461.38 | 1H NMR (300 MHz, Chloroform-d) δ 8.83 (dt, J = 6.4, 1.4 Hz, 2H), 8.51 (d, J = 4.7 Hz, 1H), 7.78 (s, 1H), 7.68 (d, J = 1.7 Hz, 1H), 7.34 (dd, J = 4.9, 0.9 Hz, 1H), 6.38 (s, 1H), 5.32 (d, J = 0.9 Hz, 1H), 4.87 (s, 1H), 4.43 (q, J = 2.8 Hz, 2H), 4.17-3.94 (m, 3H), 3.03 (dd, J = 5.1, 1.0 Hz, 3H), 2.76-2.59 (m, 2H), 2.23 (d, J = 12.7 Hz, 2H), 1.98 (d, J = 7.7 Hz, 6H). |
| 321 | 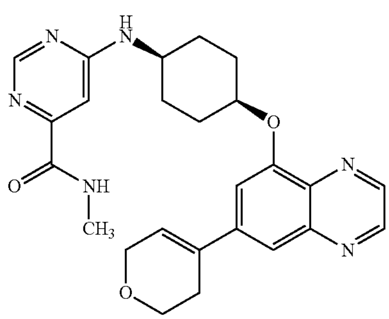 [SMILES: CNC(=O)c1cc(N[C@H]2CC[C@@H](Oc3cc(C4=CCOCC4)cc4nccnc34)CC2)ncn1] | 461.63 | 1H NMR (300 MHz, Chloroform-d) δ 8.81-8.67 (m, 2H), 8.42 (s, 1H), 7.89 (s, 1H), 7.58 (d, J = 1.8 Hz, 1H), 7.09 (s, 1H), 6.28 (dq, J = 3.0, 1.6 Hz, 1H), 4.81 (s, 1H), 4.33 (q, J = 2.8 Hz, 2H), 3.92 (t, J = 5.4 Hz, 2H), 2.93 (d, J = 5.1 Hz, 3H), 2.67-2.48 (m, 2H), 2.18 (d, J = 11.3 Hz, 2H), 1.98-1.73 (m, 6H). |
| 323 | 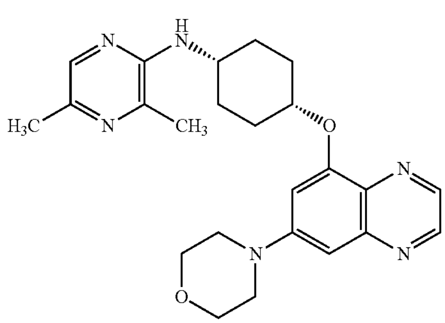 [SMILES: Cc1cnc(N[C@H]2CC[C@@H](Oc3cc(N4CCOCC4)cc4nccnc34)CC2)c(C)n1] | 435.33 | |

TABLE 2-continued

| Cmpd. No. | Compound Structure | ESMS (M + H) | $^1$H NMR |
|---|---|---|---|
| 324 | 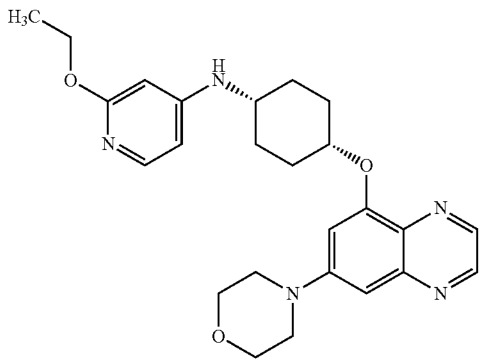 [SMILES: CCOc1cc(N[C@H]2CC[C@@H](Oc3cc(N4CCOCC4)cc4nccnc34)CC2)ccn1] | 450.35 | 1H NMR (300 MHz, CDCl3) δ 8.71 (d, J = 1.9 Hz, 1H), 8.63 (d, J = 1.9 Hz, 1H), 7.79 (d, J = 5.9 Hz, 1H), 6.97 (d, J = 2.4 Hz, 1H), 6.91 (d, J = 2.4 Hz, 1H), 6.13 (dd, J = 5.9, 2.1 Hz, 1H), 5.87 (d, J = 2.0 Hz, 1H), 4.87-4.70 (m, 1H), 4.32 (q, J = 7.1 Hz, 2H), 4.21 (d, J = 7.8 Hz, 1H), 4.05-3.81 (m, 4H), 3.60-3.45 (m, 1H), 3.45-3.24 (m, 4H), 2.33-2.10 (m, 2H), 2.02-1.77 (m, 6H), 1.39 (t, J = 7.1 Hz, 3H). [2] |
| 332 | 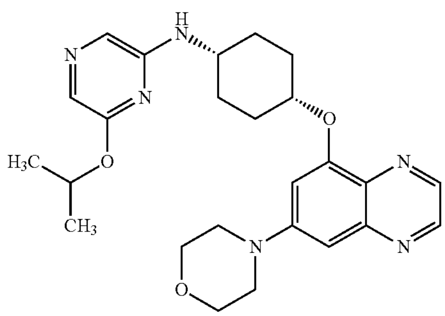 [SMILES: CC(C)Oc1cncc(N[C@H]2CC[C@@H](Oc3cc(N4CCOCC4)cc4nccnc34)CC2)n1] | 465.36 | |
| 333 | 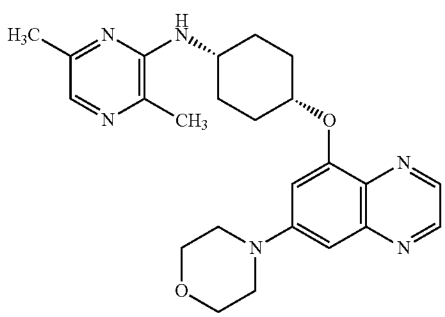 [SMILES: Cc1cnc(C)c(N[C@H]2CC[C@@H](Oc3cc(N4CCOCC4)cc4nccnc34)CC2)n1] | 435.33 | |
| 334 | 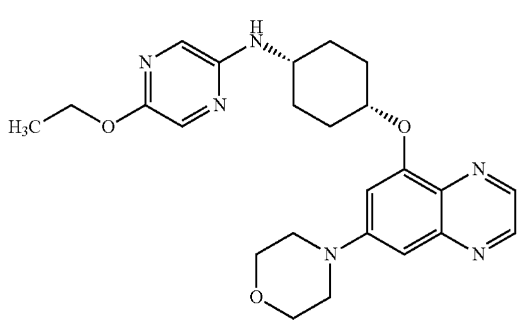 [SMILES: CCOc1cnc(N[C@H]2CC[C@@H](Oc3cc(N4CCOCC4)cc4nccnc34)CC2)cn1] | 451.36 | |

| Cmpd. No. | Compound Structure | ESMS (M + H) | ¹H NMR |
|---|---|---|---|
| 335 | 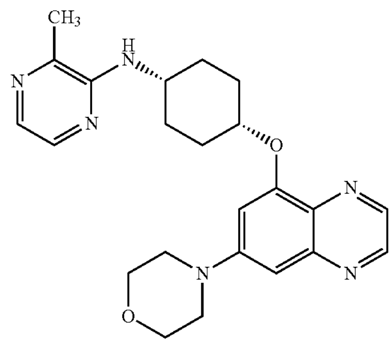 [SMILES: Cc1nccnc1N[C@H]1CC[C@@H](Oc2cc(N3CCOCC3)cc3nccnc23)CC1] | 421.37 | |
| 336 | 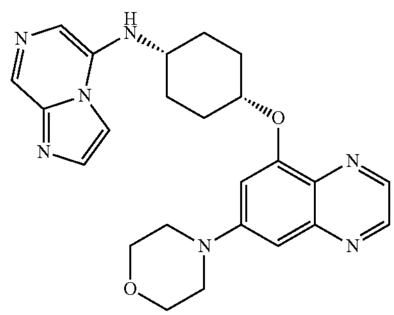 [SMILES: c1cnc2c(O[C@H]3CC[C@@H](Nc4cncc5nccn45)CC3)cc(N3CCOCC3)cc2n1] | 446.35 | |
| 340 | 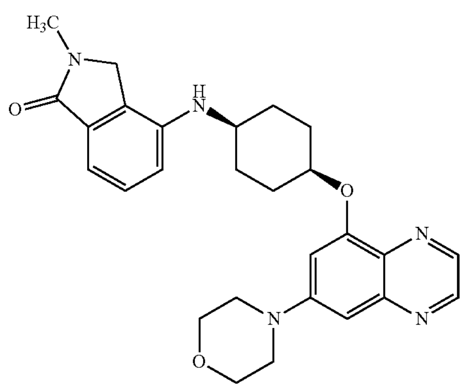 [SMILES: CN1Cc2c(N[C@H]3CC[C@@H](Oc4cc(N5CCOCC5)cc5nccnc45)CC3)cccc2C1=O] | 474.48 | 1H NMR (300 MHz, DMSO-d6) δ 8.73 (d, J = 1.9 Hz, 1H), 8.59 (d, J = 1.9 Hz, 1H), 7.25 (m, 1H), 7.14 (d, J = 2.4 Hz, 1H), 6.89-6.78 (m, 3H), 5.47 (d, J = 7.7 Hz, 1H), 4.94 (m, 1H), 4.29 (s, 2H), 3.79 (m, 4H), 3.51 (m, 1H), 3.06 (s, 3H), 2.09 (m, 2H), 1.81 (m, 6H). |
| 341 | 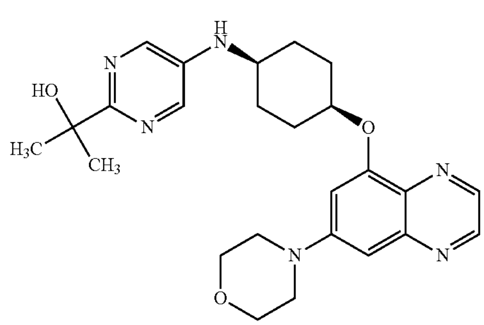 [SMILES: CC(C)(O)c1ncc(N[C@H]2CC[C@@H](Oc3cc(N4CCOCC4)cc4nccnc34)CC2)cn1] | 465.57 | 1H NMR (300 MHz, DMSO-d6) δ 8.72 (d, J = 1.9 Hz, 1H), 8.58 (d, J = 1.9 Hz, 1H), 8.17 (s, 2H), 7.15 (d, J = 2.4 Hz, 1H), 6.83 (d, J = 2.3 Hz, 1H), 6.06 (d, J = 7.8 Hz, 1H), 4.92 (m, 1H), 4.77 (s, 1H), 3.79 (m, 4H), 3.50 (m, 1H), 3.30 (m, 4H), 2.02 (m, 2H), 1.80 (m, 6H), 1.42 (s, 6H). |

TABLE 2-continued

| Cmpd. No. | Compound Structure | ESMS (M + H) | 1H NMR |
|---|---|---|---|
| 351 | 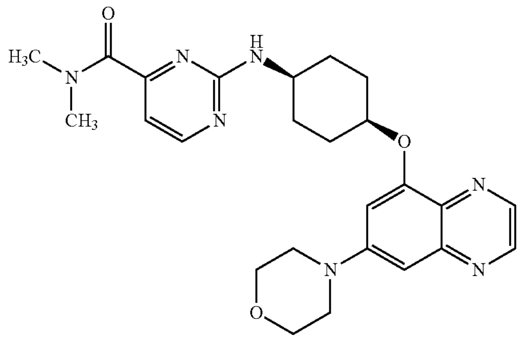 [SMILES: CN(C)C(=O)c1ccnc(N[C@H]2CC[C@@H](Oc3cc(N4CCOCC4)cc4nccnc34)CC2)n1] | 478.38 | 1H NMR (300 MHz, Chloroform-d) δ 8.70 (d, J = 1.9 Hz, 1H), 8.62 (d, J = 2.0 Hz, 1H), 8.38 (d, J = 4.9 Hz, 1H), 6.93 (dd, J = 14.5, 2.4 Hz, 2H), 6.68 (d, J = 4.9 Hz, 1H), 5.28 (s, 1H), 4.79 (s, 1H), 4.22-3.86 (m, 5H), 3.34 (t, J = 4.8 Hz, 4H), 3.17-2.97 (m, 6H), 2.20 (s, 2H), 1.91 (d, J = 5.1 Hz, 6H). |
| 352 | 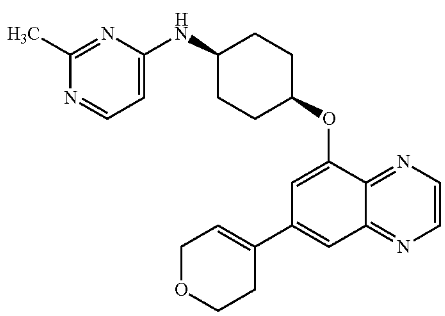 [SMILES: Cc1nccc(N[C@H]2CC[C@@H](Oc3cc(C4=CCOCC4)cc4nccnc34)CC2)n1] | 418.5 | 1H NMR (300 MHz, Chloroform-d) δ 8.91-8.75 (m, 2H), 8.11 (d, J = 5.9 Hz, 1H), 7.68 (d, J = 1.8 Hz, 1H), 6.37 (tt, J = 3.0, 1.5 Hz, 1H), 6.16 (d, J = 6.0 Hz, 1H), 4.99 (s, 1H), 4.88 (d, J = 6.0 Hz, 1H), 4.43 (q, J = 2.8 Hz, 2H), 4.02 (t, J = 5.4 Hz, 2H), 3.85 (s, 1H), 2.77-2.64 (m, 2H), 2.51 (s, 3H), 2.23 (d, J = 13.2 Hz, 2H), 2.03-1.82 (m, 6H). |
| 353 | 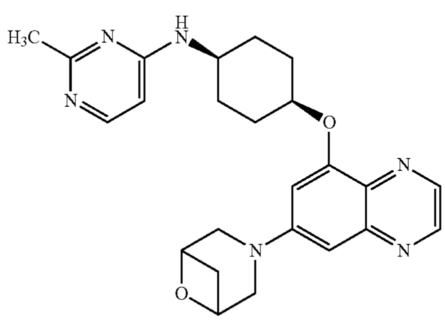 [SMILES: Cc1nccc(N[C@H]2CC[C@@H](Oc3cc(N4CC5CC(C4)O5)cc4nccnc34)CC2)n1] | 433.62 | 1H NMR (300 MHz, Chloroform-d) δ 8.67 (d, J = 1.9 Hz, 1H), 8.54 (d, J = 1.9 Hz, 1H), 8.11 (d, J = 6.0 Hz, 1H), 6.85 (s, 2H), 6.16 (d, J = 6.0 Hz, 1H), 5.00 (s, 1H), 4.85 (d, J = 6.5 Hz, 3H), 3.93-3.57 (m, 5H), 3.35 (q, J = 7.1 Hz, 1H), 2.62 (d, J = 8.0 Hz, 1H), 2.50 (s, 3H), 2.24 (d, J = 8.9 Hz, 2H), 2.01-1.81 (m, 6H). |
| 354 | 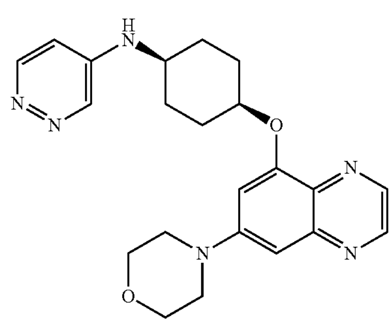 [SMILES: c1cc(N[C@H]2CC[C@@H](Oc3cc(N4CCOCC4)cc4nccnc34)CC2)cnn1] | 407.56 | 1H NMR (300 MHz, DMSO-d6) δ 8.73 (d, J = 1.9 Hz, 1H), 8.61 (d, J = 3.1 Hz, 1H), 8.58 (d, J = 2.0 Hz, 1H), 8.47 (d, J = 6.2 Hz, 1H), 7.15 (d, J = 2.4 Hz, 1H), 6.99 (d, J = 7.8 Hz, 1H), 6.83 (d, J = 2.3 Hz, 1H), 6.65 (m, 1H), 4.94 (m, 1H), 3.79 (m, 4H), 3.55 (m, 1H), 3.35 (m, 4H), 2.03 (m, 2H), 1.78 (m, 6H). |

TABLE 2-continued

| Cmpd. No. | Compound Structure | ESMS (M + H) | ¹H NMR |
|---|---|---|---|
| 366 | 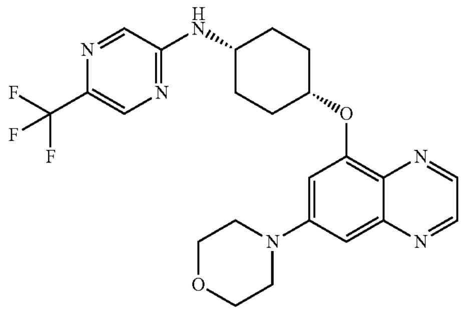 [SMILES: FC(F)(F)c1cnc(N[C@H]2CC[C@@H](Oc3cc(N4CCOCC4)cc4nccnc34)CC2)cn1] | 475.56 | |
| 369 | 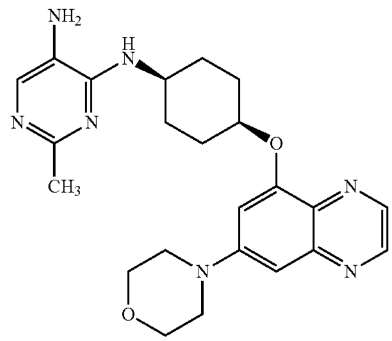 [SMILES: Cc1ncc(N)c(N[C@H]2CC[C@@H](Oc3cc(N4CCOCC4)cc4nccnc34)CC2)n1] | 436.5 | 1H NMR (300 MHz, Chloroform-d) δ 8.71 (d, J = 1.9 Hz, 1H), 8.62 (d, J = 1.9 Hz, 1H), 7.71 (s, 1H), 6.94 (dd, J = 14.6, 2.5 Hz, 2H), 5.09 (d, J = 7.7 Hz, 1H), 4.80 (d, J = 5.4 Hz, 1H), 4.29 (s, 2H), 4.01-3.84 (m, 4H), 3.45-3.28 (m, 4H), 2.49 (s, 3H), 2.21 (q, J = 6.1 Hz, 2H), 1.95 (dt, J = 10.0, 4.1 Hz, 6H). |
| 373 | 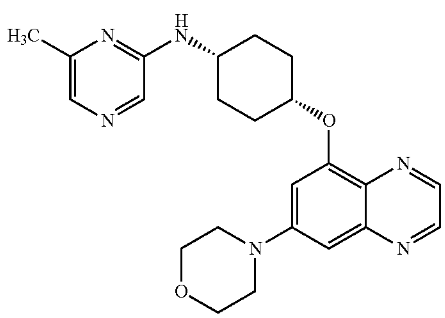 [SMILES: Cc1cncc(N[C@H]2CC[C@@H](Oc3cc(N4CCOCC4)cc4nccnc34)CC2)n1] | 421.51 | 1H NMR (400 MHz, CDCl3) δ 8.71 (d, J = 1.8 Hz, 1H), 8.63 (d, J = 1.8 Hz, 1H), 7.70 (d, J = 5.0 Hz, 2H), 6.97 (d, J = 1.6 Hz, 1H), 6.92 (d, J = 2.1 Hz, 1H), 4.81 (s, 1H), 4.65 (s, 1H), 3.99-3.85 (m, 5H), 3.40-3.30 (m, 4H), 2.37 (s, 3H), 2.28-2.16 (m, 2H), 2.01-1.82 (m, 6H). |
| 374 | 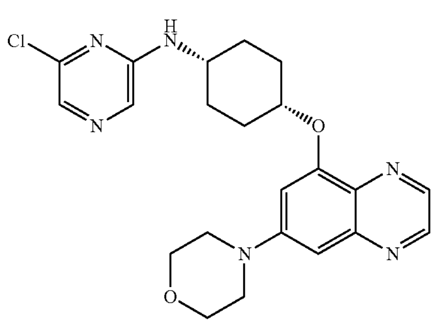 [SMILES: Clc1cncc(N[C@H]2CC[C@@H](Oc3cc(N4CCOCC4)cc4nccnc34)CC2)n1] | 441.45 | |

TABLE 2-continued

| Cmpd. No. | Compound Structure | ESMS (M + H) | ¹H NMR |
|---|---|---|---|
| 375 | 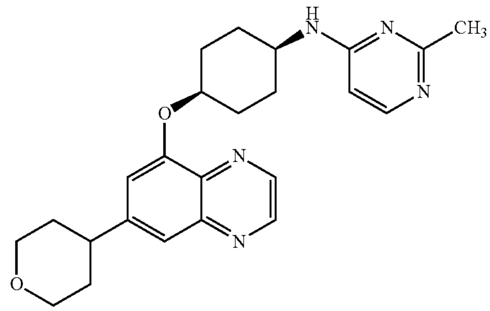 [SMILES: Cc1nccc(N[C@H]2CC[C@@H](Oc3cc(C4CCOCC4)cc4nccnc34)CC2)n1] | 420.57 | 1H NMR (300 MHz, Chloroform-d) δ 8.81-8.67 (m, 2H), 8.01 (d, J = 6.0 Hz, 1H), 7.46 (dd, J = 1.7, 0.7 Hz, 1H), 6.98 (d, J = 1.7 Hz, 1H), 6.06 (d, J = 6.0 Hz, 1H), 4.80 (d, J = 38.5 Hz, 2H), 4.13-3.97 (m, 3H), 3.51 (td, J = 11.3, 3.5 Hz, 2H), 2.99-2.80 (m, 1H), 2.41 (s, 3H), 2.21-2.03 (m, 2H), 1.94-1.70 (m, 7H). |
| 376 | 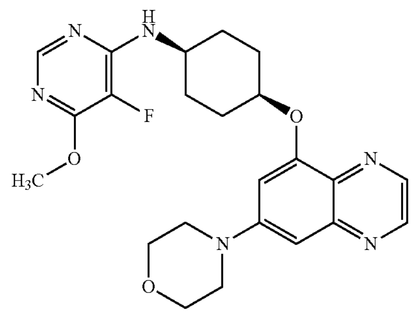 [SMILES: COc1ncnc(N[C@H]2CC[C@@H](Oc3cc(N4CCOCC4)cc4nccnc34)CC2)c1F] | 455.33 | 1H NMR (300 MHz, Chloroform-d) δ 8.69 (d, J = 1.9 Hz, 1H), 8.62 (d, J = 1.9 Hz, 1H), 8.07 (s, 1H), 6.93 (dd, J = 17.0, 2.5 Hz, 2H), 4.98-4.71 (m, 2H), 4.17 (s, 1H), 4.00 (s, 3H), 3.92 (dd, J = 5.8, 3.9 Hz, 4H), 3.42-3.26 (m, 4H), 2.22 (d, J = 9.5 Hz, 2H), 1.93 (dd, J = 6.1, 2.4 Hz, 6H). |
| 377 | 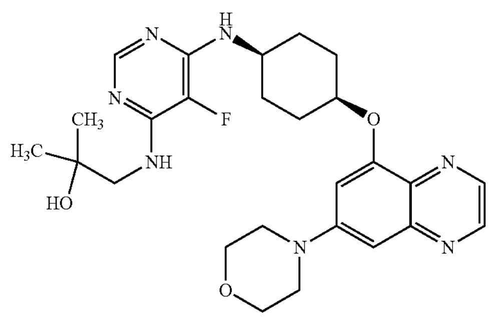 [SMILES: CC(C)(O)CNc1ncnc(N[C@H]2CC[C@@H](Oc3cc(N4CCOCC4)cc4nccnc34)CC2)c1F] | 512.36 | 1H NMR (300 MHz, Chloroform-d) δ 8.69 (d, J = 1.9 Hz, 1H), 8.62 (d, J = 1.9 Hz, 1H), 7.95 (d, J = 1.2 Hz, 1H), 6.92 (dd, J = 16.9, 2.5 Hz, 2H), 4.98 (s, 1H), 4.81-4.66 (m, 2H), 4.16 (s, 1H), 3.97-3.87 (m, 4H), 3.46 (d, J = 6.1 Hz, 2H), 3.39-3.29 (m, 4H), 2.19 (d, J = 12.5 Hz, 2H), 1.91 (d, J = 5.4 Hz, 6H), 1.26 (s, 6H), 0.94-0.83 (m, 1H). |
| 380 | 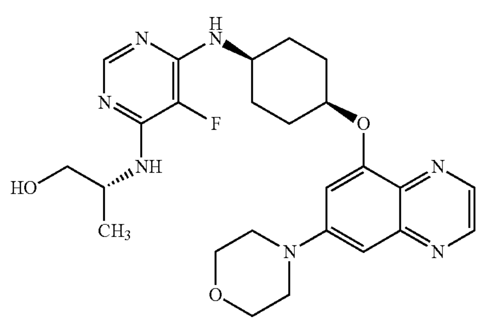 [SMILES: C[C@H](CO)Nc1ncnc(N[C@H]2CC[C@@H](Oc3cc(N4CCOCC4)cc4nccnc34)CC2)c1F] | 498.36 | 1H NMR (300 MHz, Chloroform-d) δ 8.69 (d, J = 2.0 Hz, 1H), 8.62 (d, J = 1.9 Hz, 1H), 8.00-7.91 (m, 1H), 6.92 (dd, J = 17.2, 2.5 Hz, 2H), 4.87-4.64 (m, 2H), 4.59 (d, J = 5.7 Hz, 1H), 4.16 (ddt, J = 9.7, 6.8, 3.7 Hz, 2H), 4.01-3.85 (m, 4H), 3.75 (d, J = 11.2 Hz, 1H), 3.58 (dd, J = 10.9, 7.0 Hz, 1H), 3.48-3.23 (m, 4H), 2.36-2.07 (m, 2H), 1.91 (d, J = 5.5 Hz, 6H), 1.28 (d, J = 6.8 Hz, 3H), 0.97-0.78 (m, 1H). |

TABLE 2-continued

| Cmpd. No. | Compound Structure | ESMS (M + H) | 1H NMR |
|---|---|---|---|
| 382 | 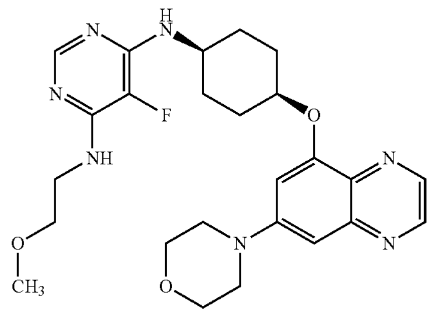 [SMILES: COCCNc1ncnc(N[C@H]2CC[C@@H](Oc3cc(N4CCOCC4)cc4nccnc34)CC2)c1F] | 498.32 | 1H NMR (300 MHz, Chloroform-d) δ 8.69 (d, J = 1.9 Hz, 1H), 8.62 (d, J = 1.9 Hz, 1H), 8.00 (s, 1H), 6.92 (dd, J = 16.5, 2.5 Hz, 2H), 4.92 (s, 1H), 4.77 (s, 1H), 4.64 (d, J = 8.5 Hz, 1H), 4.16 (s, 1H), 4.03-3.82 (m, 4H), 3.65 (q, J = 5.8, 5.4 Hz, 2H), 3.56 (ddd, J = 5.6, 4.7, 1.0 Hz, 2H), 3.48-3.21 (m, 7H), 2.19 (d, J = 10.1 Hz, 2H), 1.91 (d, J = 5.4 Hz, 6H). |
| 386 | 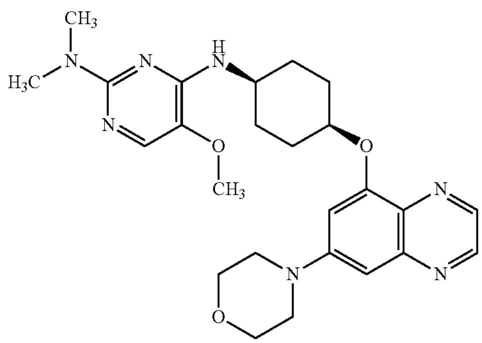 [SMILES: COc1cnc(N(C)C)nc1N[C@H]1CC[C@@H](Oc2cc(N3CCOCC3)cc3nccnc23)CC1] | 480.41 | 1H NMR (400 MHz, CDCl3) δ 8.70 (d, J = 1.9 Hz, 1H), 8.62 (d, J = 1.9 Hz, 1H), 7.49 (s, 1H), 6.95 (d, J = 2.4 Hz, 1H), 6.89 (d, J = 2.4 Hz, 1H), 5.25 (s, 1H), 4.72 (s, 1H), 4.18 (s, 1H), 3.96-3.87 (m, 4H), 3.77 (s, 3H), 3.39-3.30 (m, 4H), 3.10 (s, 6H), 2.21-2.12 (m, 2H), 2.02-1.85 (m, 6H). |
| 387 | 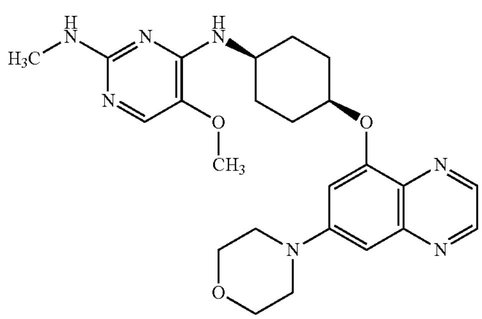 [SMILES: CNc1ncc(OC)c(N[C@H]2CC[C@@H](Oc3cc(N4CCOCC4)cc4nccnc34)CC2)n1] | 466.4 | 1H NMR (400 MHz, CDCl3) δ 8.70 (d, J = 1.9 Hz, 1H), 8.62 (d, J = 1.9 Hz, 1H), 7.49 (s, 1H), 6.95 (d, J = 2.4 Hz, 1H), 6.89 (d, J = 2.4 Hz, 1H), 5.25 (s, 1H), 4.72 (s, 1H), 4.18 (s, 1H), 3.96-3.87 (m, 4H), 3.77 (s, 3H), 3.39-3.30 (m, 4H), 3.10 (s, 6H), 2.21-2.12 (m, 2H), 2.02-1.85 (m, 6H). |
| 388 | 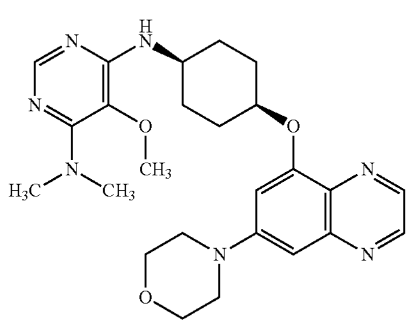 [SMILES: COc1c(N[C@H]2CC[C@@H](Oc3cc(N4CCOCC4)cc4nccnc34)CC2)ncnc1N(C)C] | 480.41 | 1H NMR (400 MHz, CDCl3) δ 8.69 (d, J = 1.9 Hz, 1H), 8.63 (d, J = 1.9 Hz, 1H), 8.04 (s, 1H), 6.94 (d, J = 2.4 Hz, 1H), 6.89 (d, J = 2.4 Hz, 1H), 5.15 (d, J = 8.4 Hz, 1H), 4.75 (s, 1H), 4.14 (s, 1H), 3.97-3.83 (m, 4H), 3.59 (s, 3H), 3.38-3.28 (m, 4H), 3.09 (s, 6H), 2.25-2.13 (m, 2H), 2.00-1.83 (m, 6H). |

TABLE 2-continued

| Cmpd. No. | Compound Structure | ESMS (M + H) | ¹H NMR |
|---|---|---|---|
| 393 | 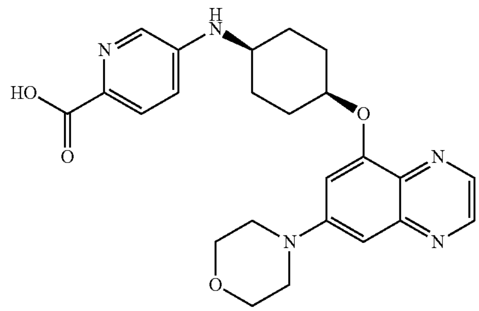 [SMILES: O=C(O)c1ccc(N[C@H]2CC[C@@H](Oc3cc(N4CCOCC4)cc4nccnc34)CC2)cn1] | 450.58 | 1H NMR (300 MHz, DMSO-d6) δ 8.73 (d, J = 1.9 Hz, 1H), 8.58 (d, J = 1.9 Hz, 1H), 8.10 (d, J = 2.7 Hz, 1H), 7.97 (d, J = 8.9 Hz, 1H), 7.38 (dd, J = 9.0, 2.7 Hz, 1H), 7.16 (d, J = 2.4 Hz, 1H), 6.84 (d, J = 2.3 Hz, 1H), 4.96 (m, 1H), 3.79 (m, 4H), 3.66 (m, 1H), 3.3 (m, 4H), 2.14-1.95 (m, 2H), 1.81 (m, 5H). |
| 394 | 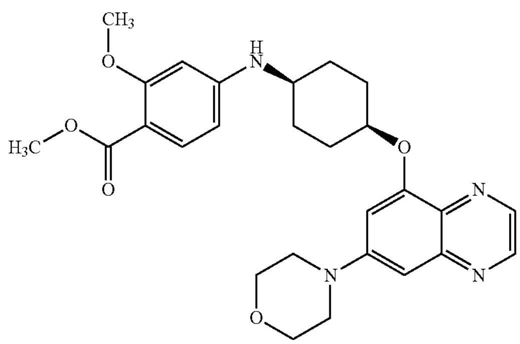 [SMILES: COC(=O)c1ccc(N[C@H]2CC[C@@H](Oc3cc(N4CCOCC4)cc4nccnc34)CC2)cc1OC] | 493.61 | 1H NMR (300 MHz, DMSO-d6) δ 8.72 (d, J = 1.9 Hz, 1H), 8.58 (d, J = 1.9 Hz, 1H), 7.54 (d, J = 8.6 Hz, 1H), 7.14 (d, J = 2.4 Hz, 1H), 6.83 (d, J = 2.3 Hz, 1H), 6.48 (d, J = 7.7 Hz, 1H), 6.30-6.18 (m, 2H), 4.92 (m, 1H), 3.79 (m, 4H), 3.74 (s, 3H), 3.66 (s, 3H), 3.55 (m, 1H), 3.34 (m, 4H), 2.03 (m, 2H), 1.78 (m, 6H). |
| 395 | 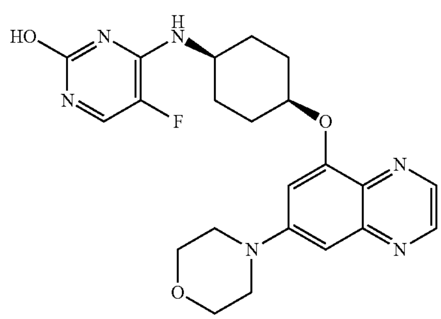 [SMILES: Oc1ncc(F)c(N[C@H]2CC[C@@H](Oc3cc(N4CCOCC4)cc4nccnc34)CC2)n1] | 441.2 | 1H NMR (300 MHz, Chloroform-d) δ 8.61 (d, J = 1.9 Hz, 1H), 8.53 (d, J = 2.0 Hz, 1H), 7.13 (d, J = 5.3 Hz, 1H), 6.84 (dd, J = 20.0, 2.4 Hz, 2H), 6.50 (d, J = 8.2 Hz, 1H), 4.72 (s, 1H), 4.31 (d, J = 7.0 Hz, 1H), 3.83 (dd, J = 5.8, 3.8 Hz, 4H), 3.26 (t, J = 4.9 Hz, 4H), 2.14 (d, J = 12.3 Hz, 2H), 1.95-1.68 (m, 6H). |
| 396 | 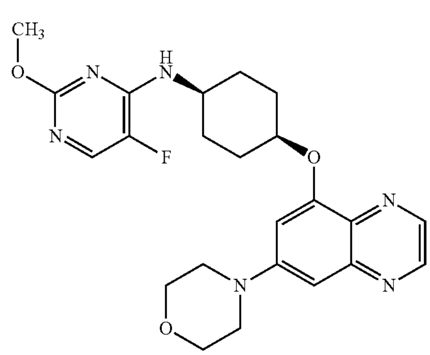 [SMILES: COc1ncc(F)c(N[C@H]2CC[C@@H](Oc3cc(N4CCOCC4)cc4nccnc34)CC2)n1] | 455.2 | 1H NMR (300 MHz, Chloroform-d) δ 8.61 (d, J = 1.9 Hz, 1H), 8.54 (d, J = 1.9 Hz, 1H), 7.72 (d, J = 2.9 Hz, 1H), 6.87 (d, J = 2.5 Hz, 1H), 6.81 (d, J = 2.5 Hz, 1H), 5.03 (d, J = 7.8 Hz, 1H), 4.71 (s, 1H), 4.16 (s, 2H), 3.83 (q, J = 3.9, 3.1 Hz, 7H), 3.32-3.21 (m, 4H), 2.13 (d, J = 11.2 Hz, 2H), 1.83 (t, J = 6.5 Hz, 6H). |

TABLE 2-continued

| Cmpd. No. | Compound Structure | ESMS (M + H) | ¹H NMR |
|---|---|---|---|
| 397 | 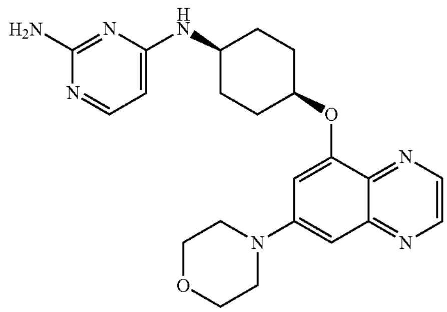 [SMILES: Nc1nccc(N[C@H]2CC[C@@H](Oc3cc(N4CCOCC4)cc4nccnc34)CC2)n1] | 422.5 | 1H NMR (300 MHz, Chloroform-d) δ 8.70 (d, J = 1.9 Hz, 1H), 8.63 (d, J = 1.9 Hz, 1H), 7.89 (d, J = 5.8 Hz, 1H), 7.02-6.88 (m, 2H), 5.79 (d, J = 5.7 Hz, 1H), 4.80 (s, 1H), 4.61 (s, 2H), 4.08-3.88 (m, 5H), 3.35 (dd, J = 5.6, 4.1 Hz, 4H), 2.27-2.09 (m, 2H), 1.91 (d, J = 5.0 Hz, 6H). |
| 399 | 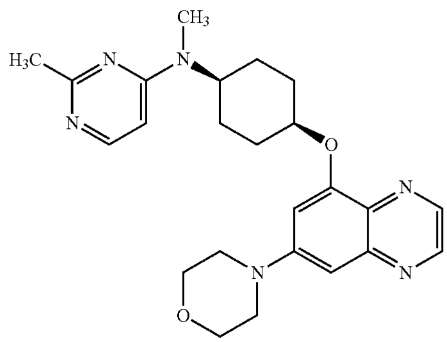 [SMILES: Cc1nccc(N(C)[C@H]2CC[C@@H](Oc3cc(N4CCOCC4)cc4nccnc34)CC2)n1] | 435.35 | 1H NMR (300 MHz, CDCl3) δ 8.69 (d, J = 1.9 Hz, 1H), 8.61 (d, J = 1.9 Hz, 1H), 8.08 (d, J = 6.3 Hz, 1H), 6.96 (d, J = 2.5 Hz, 1H), 6.92 (d, J = 2.4 Hz, 1H), 6.23 (d, J = 6.3 Hz, 1H), 4.87 (s, 1H), 4.69 (s, 1H), 4.00-3.83 (m, 4H), 3.45-3.24 (m, 4H), 2.98 (s, 3H), 2.50 (s, 3H), 2.45-2.30 (m, 2H), 1.92-1.64 (m, 6H). |
| 401 | 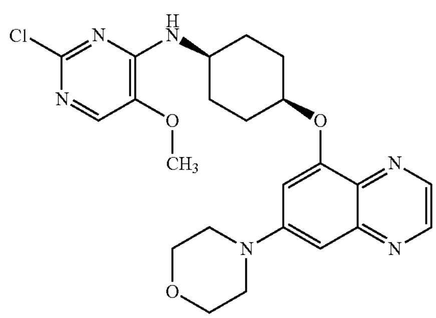 [SMILES: COc1cnc(Cl)nc1N[C@H]1CC[C@@H](Oc2cc(N3CCOCC3)cc3nccnc23)CC1] | 471.32 | 1H NMR (300 MHz, CDCl3) δ 8.69 (d, J = 1.9 Hz, 1H), 8.62 (d, J = 1.9 Hz, 1H), 7.51 (s, 1H), 6.95 (d, J = 2.4 Hz, 1H), 6.89 (d, J = 2.4 Hz, 1H), 5.56 (d, J = 8.0 Hz, 1H), 4.75 (s, 1H), 4.25 (s, 1H), 3.96-3.89 (m, 4H), 3.88 (s, 3H), 3.47-3.23 (m, 4H), 2.29-2.06 (m, 2H), 2.06-1.78 (m, 6H). |
| 402 | 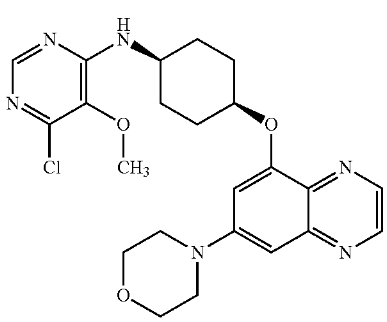 [SMILES: COc1c(Cl)ncnc1N[C@H]1CC[C@@H](Oc2cc(N3CCOCC3)cc3nccnc23)CC1] | 471.36 | 1H NMR (300 MHz, CDCl3) δ 8.70 (d, J = 1.9 Hz, 1H), 8.62 (d, J = 1.9 Hz, 1H), 8.14 (s, 1H), 6.96 (d, J = 2.4 Hz, 1H), 6.90 (d, J = 2.5 Hz, 1H), 5.52 (d, J = 8.6 Hz, 1H), 4.79 (s, 1H), 4.18 (s, 1H), 3.96-3.89 (m, 4H), 3.89 (s, 3H), 3.41-3.27 (m, 4H), 2.31-2.14 (m, 2H), 2.03-1.83 (m, 6H). |

| Cmpd. No. | Compound Structure | ESMS (M + H) | ¹H NMR |
|---|---|---|---|
| 404 | 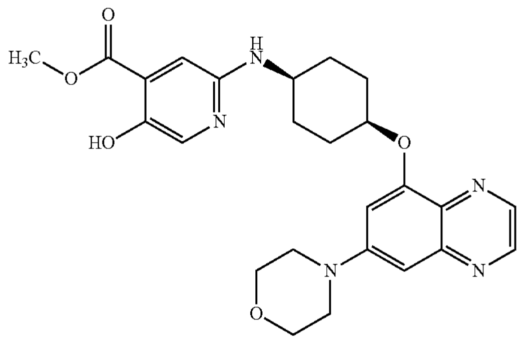 [SMILES: COC(=O)c1cc(N[C@H]2CC[C@@H](Oc3cc(N4CCOCC4)cc4nccnc34)CC2)ncc1O] | 480.56 | 1H NMR (300 MHz, DMSO-d6) δ 8.72 (d, J = 1.9 Hz, 1H), 8.57 (d, J = 1.9 Hz, 1H), 7.69 (s, 1H), 7.15 (d, J = 2.5 Hz, 1H), 7.01 (s, 1H), 6.84 (d, J = 2.3 Hz, 1H), 4.94 (m, 1H), 3.75 (m, 8H), 3.34 (m, 4H), 2.05 (m, 2H), 1.86-1.70 (m, 6H). |
| 405 | 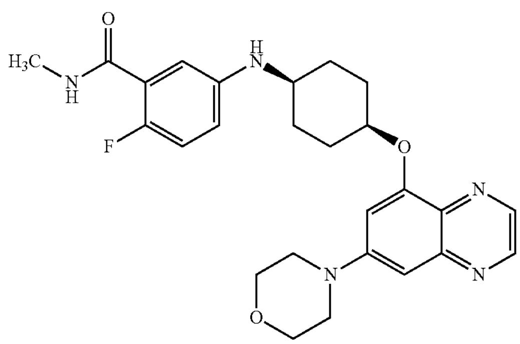 [SMILES: CNC(=O)c1cc(N[C@H]2CC[C@@H](Oc3cc(N4CCOCC4)cc4nccnc34)CC2)ccc1F] | 480.56 | 1H NMR (300 MHz, DMSO-d6) δ 8.72 (d, J = 1.9 Hz, 1H), 8.57 (d, J = 1.9 Hz, 1H), 8.01 (m, 1H), 7.14 (s, 1H), 7.01-6.90 (m, 1H), 6.82 (m, 2H), 6.71 (m, 1H), 5.70 (d, J = 7.9 Hz, 1H), 4.91 (m, 1H), 3.79 (m, 4H), 3.34 (m, 5H), 2.74 (d, J = 4.6 Hz, 3H), 2.02 (m, 2H), 1.76 (m, 6H). |
| 406 | 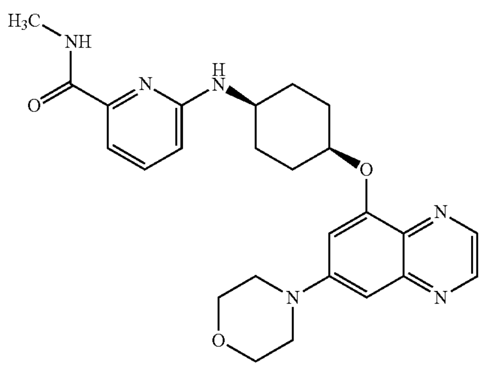 [SMILES: CNC(=O)c1cccc(N[C@H]2CC[C@@H](Oc3cc(N4CCOCC4)cc4nccnc34)CC2)n1] | 463.68 | 1H NMR (300 MHz, DMSO-d6) δ 8.72 (d, J = 1.9 Hz, 1H), 8.58 (d, J = 1.9 Hz, 1H), 8.27 (d, J = 5.2 Hz, 1H), 7.46 (dd, J = 8.4, 7.1 Hz, 1H), 7.15 (d, J = 2.4 Hz, 1H), 7.10 (dd, J = 7.1, 0.9 Hz, 1H), 6.83 (d, J = 2.3 Hz, 1H), 6.75 (d, J = 7.8 Hz, 1H), 6.68 (dd, J = 8.4, 0.9 Hz, 1H), 4.91 (m, 1H), 4.14 (m, 1H), 3.80 (m, 4H), 3.35 (m, 4H), 2.82 (d, J = 4.9 Hz, 3H), 2.03 (m, 2H), 1.93-1.73 (m, 6H). |
| 407 | 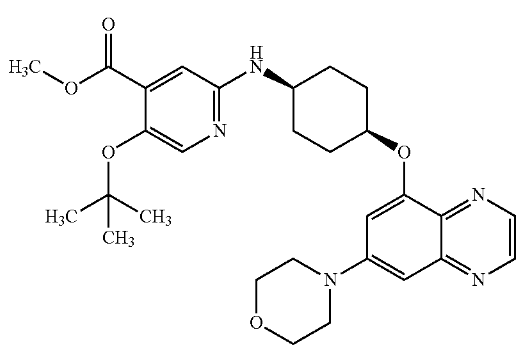 [SMILES: COC(=O)c1cc(N[C@H]2CC[C@@H](Oc3cc(N4CCOCC4)cc4nccnc34)CC2)ncc1OC(C)(C)C] | 536.49 | 1H NMR (300 MHz, Chloroform-d) rotomers, δ 9.07 (m, 1H), 8.89 (m, 1H), 8.75 (m, 1H), 7.47 (m, 1H), 6.96 (s, 1H), 4.95 (m, 1H), 3.97 (m, 4H), 3.82 (m, 4H), 3.38 (s, 3H), 2.24 (m, 8H), 1.60 (s, 9H). |

TABLE 2-continued

| Cmpd. No. | Compound Structure | ESMS (M + H) | ¹H NMR |
|---|---|---|---|
| 408 | 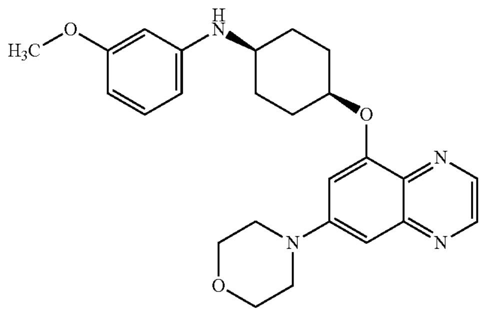 [SMILES: COc1cccc(N[C@H]2CC[C@@H](Oc3cc(N4CCOCC4)cc4nccnc34)CC2)c1] | 435.6 | 1H NMR (300 MHz, DMSO-d6) δ 8.72 (d, J = 1.9 Hz, 1H), 8.57 (d, J = 1.9 Hz, 1H), 7.13 (d, J = 2.4 Hz, 1H), 6.94 (t, J = 8.0 Hz, 1H), 6.83 (d, J = 2.3 Hz, 1H), 6.26-6.14 (m, 2H), 6.10-6.03 (m, 1H), 5.57 (d, J = 7.8 Hz, 1H), 4.90 (m, 1H), 3.79 (m, 4H), 3.66 (s, 3H), 3.33 (m, 4H), 2.03 (m, 2H), 1.77 (m, 6H). |
| 409 | 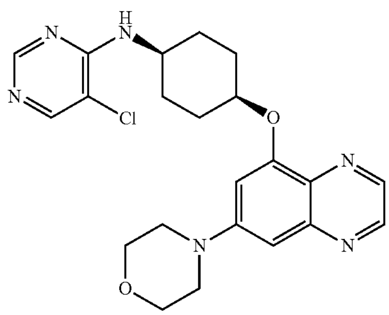 [SMILES: Clc1cncnc1N[C@H]1CC[C@@H](Oc2cc(N3CCOCC3)cc3nccnc23)CC1] | 441.29 | 1H NMR (300 MHz, CDCl3) δ 8.70 (d, J = 1.9 Hz, 1H), 8.63 (d, J = 1.9 Hz, 1H), 8.47 (s, 1H), 8.18 (s, 1H), 6.96 (d, J = 2.4 Hz, 1H), 6.91 (d, J = 2.4 Hz, 1H), 5.47 (d, J = 7.6 Hz, 1H), 4.80 (s, 1H), 4.31-4.19 (m, 1H), 4.02-3.79 (m, 4H), 3.48-3.24 (m, 4H), 2.32-2.17 (m, 2H), 2.09-1.79 (m, 6H). |
| 417 | 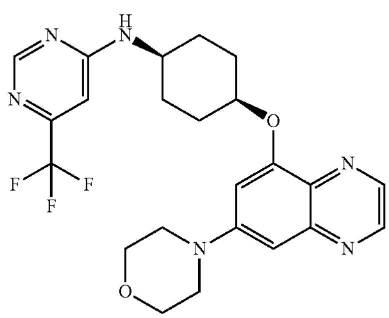 [SMILES: FC(F)(F)c1cc(N[C@H]2CC[C@@H](Oc3cc(N4CCOCC4)cc4nccnc34)CC2)ncn1] | 475.36 | 1H NMR (300 MHz, Chloroform-d) δ 8.81-8.55 (m, 3H), 6.94 (dd, J = 17.2, 2.5 Hz, 2H), 6.65 (d, J = 1.1 Hz, 1H), 4.84 (td, J = 5.1, 2.4 Hz, 1H), 4.01-3.86 (m, 4H), 3.42-3.29 (m, 4H), 2.35-2.11 (m, 2H), 2.05-1.82 (m, 6H). |
| 418 | 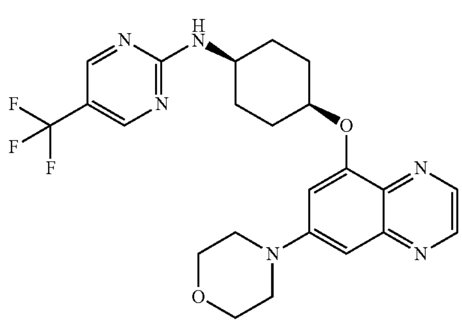 [SMILES: FC(F)(F)c1cnc(N[C@H]2CC[C@@H](Oc3cc(N4CCOCC4)cc4nccnc34)CC2)nc1] | 475.4 | 1H NMR (300 MHz, Chloroform-d) δ 8.71 (d, J = 1.9 Hz, 1H), 8.63 (d, J = 1.9 Hz, 1H), 8.49 (d, J = 4.9 Hz, 1H), 7.04-6.89 (m, 2H), 6.81 (d, J = 4.9 Hz, 1H), 5.54 (d, J = 7.9 Hz, 1H), 4.80 (d, J = 5.2 Hz, 1H), 4.17-3.98 (m, 1H), 3.98-3.87 (m, 4H), 3.42-3.31 (m, 4H), 2.33-2.12 (m, 2H), 2.06-1.72 (m, 6H). |

TABLE 2-continued

| Cmpd. No. | Compound Structure | ESMS (M + H) | ¹H NMR |
|---|---|---|---|
| 419 | 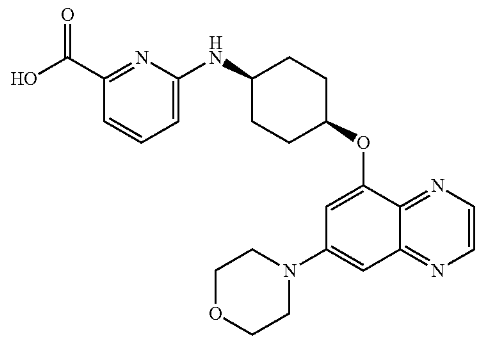 [SMILES: O=C(O)c1cccc(N[C@H]2CC[C@@H](Oc3cc(N4CCOCC4)cc4nccnc34)CC2)n1] | 450.38 | 1H NMR (300 MHz, Chloroform-d) rotomers δ 8.82 (d, J = 2.9 Hz, 1H), 8.74 (m, 1H), 8.00 (m, 1H), 7.55-7.47 (m, 1H), 7.25 (m, 1H), 7.14 (m, 1H), 7.05 (m, 1H), 3.97 (m, 5H), 3.47 (m, 5H), 2.30 (s, 2H), 2.0 (m, 6H).. |
| 420 | 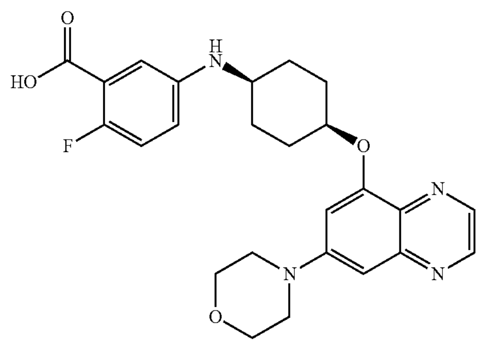 [SMILES: O=C(O)c1cc(N[C@H]2CC[C@@H](Oc3cc(N4CCOCC4)cc4nccnc34)CC2)ccc1F] | 467.48 | 1H NMR (300 MHz, DMSO-d6) δ 8.73 (d, J = 1.9 Hz, 1H), 8.58 (d, J = 2.0 Hz, 1H), 7.27-6.96 (m, 4H), 6.83 (d, J = 2.3 Hz, 1H), 4.92 (m, 1H), 3.85-3.74 (m, 4H), 3.45 (m, 1H), 3.34 (m, 4H), 2.05 (m, 2H), 1.76 (m, 6H). |
| 421 | 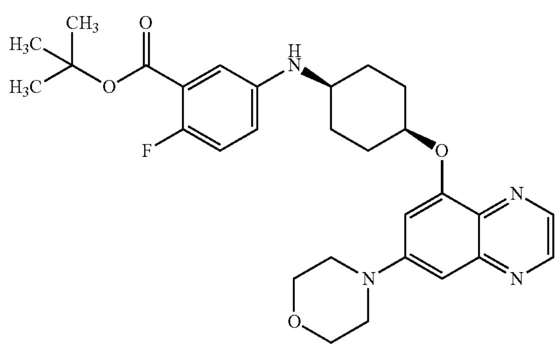 [SMILES: CC(C)(C)OC(=O)c1cc(N[C@H]2CC[C@@H](Oc3cc(N4CCOCC4)cc4nccnc34)CC2)ccc1F] | 523.58 | 1H NMR (300 MHz, DMSO-d6) δ 8.93 (d, J = 1.8 Hz, 1H), 8.80 (d, J = 1.8 Hz, 1H), 7.20 (s, 1H), 7.13-6.85 (m, 4H), 4.92 (m, 1H), 3.86-3.79 (m, 4H), 3.32 (m, 5H), 2.09 (m, 2H), 1.90-1.73 (m, 6H), 1.55 (s, 9H). |
| 422 | 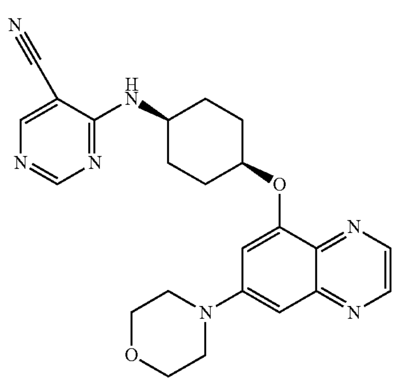 [SMILES: N#Cc1cncnc1N[C@H]1CC[C@@H](Oc2cc(N3CCOCC3)cc3nccnc23)CC1] | 432.5 | 1H NMR (300 MHz, Chloroform-d) δ 8.72-8.52 (m, 3H), 8.38 (s, 1H), 6.87 (dd, J = 15.7, 2.5 Hz, 2H), 5.50 (d, J = 7.9 Hz, 1H), 4.79 (p, J = 3.5 Hz, 1H), 4.20 (dp, J = 14.0, 5.2, 4.7 Hz, 1H), 3.90-3.76 (m, 4H), 3.32-3.22 (m, 4H), 2.29-2.07 (m, 2H), 1.99-1.71 (m, 6H). |

TABLE 2-continued

| Cmpd. No. | Compound Structure | ESMS (M + H) | ¹H NMR |
|---|---|---|---|
| 424 | 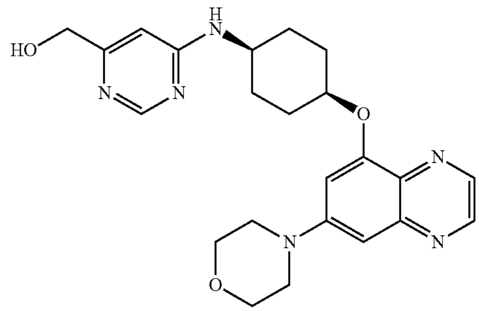 [SMILES: OCc1cc(N[C@H]2CC[C@@H](Oc3cc(N4CCOCC4)cc4nccnc34)CC2)ncn1] | 437.3 | 1H NMR (300 MHz, Chloroform-d) δ 8.62 (d, J = 1.9 Hz, 1H), 8.52 (d, J = 1.9 Hz, 1H), 8.46-8.35 (m, 1H), 6.84 (dd, J = 16.8, 2.5 Hz, 2H), 6.28-6.20 (m, 1H), 5.08 (s, 1H), 4.72 (d, J = 5.2 Hz, 1H), 4.58-4.43 (m, 2H), 3.93-3.77 (m, 4H), 3.34-3.19 (m, 4H), 2.14 (dd, J = 9.6, 5.4 Hz, 2H), 1.93-1.73 (m, 6H). |
| 427 | 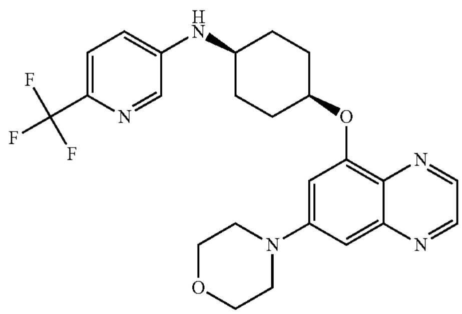 [SMILES: FC(F)(F)c1ccc(N[C@H]2CC[C@@H](Oc3cc(N4CCOCC4)cc4nccnc34)CC2)cn1] | 474.33 | 1H NMR (300 MHz, Choroform-d) δ 8.94-8.63 (m, 2H), 8.07 (d, J = 2.8 Hz, 1H), 7.45 (d, J = 8.7 Hz, 1H), 7.14-6.87 (m, 3H), 4.84 (m, 1H), 3.99-3.87 (m, 4H), 3.62-3.48 (m, 1H), 3.35 (dt, J = 42.8, 4.8 Hz, 4H), 2.32-2.14 (m, 2H), 1.91 (d, J = 17.8 Hz, 6H). |
| 428 | 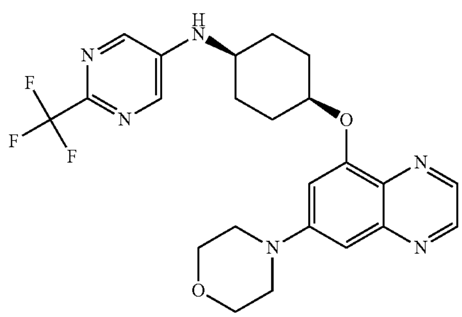 [SMILES: FC(F)(F)c1ncc(N[C@H]2CC[C@@H](Oc3cc(N4CCOCC4)cc4nccnc34)CC2)cn1] | 475.41 | 1H NMR (300 MHz, Chloroform-d) δ 8.81-8.64 (m, 2H), 8.20 (s, 2H), 7.08 (d, J = 2.4 Hz, 1H), 6.94 (d, J = 2.4 Hz, 1H), 4.90-4.82 (m, 1H), 4.42 (m, 1H), 3.98-3.88 (m, 4H), 3.57 (m, 1H), 3.45-3.26 (m, 4H), 2.33-2.18 (m, 2H), 2.04-1.82 (m, 6H). |
| 429 | 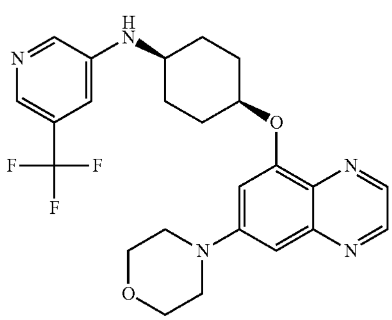 [SMILES: FC(F)(F)c1cncc(N[C@H]2CC[C@@H](Oc3cc(N4CCOCC4)cc4nccnc34)CC2)c1] | 474.37 | 1H NMR (300 MHz, Chloroform-d) δ 8.70 (d, J = 2.0 Hz, 1H), 8.63 (d, J = 2.0 Hz, 1H), 8.42 (m, 1H), 8.16-8.08 (m, 1H), 7.20 (s, 1H), 7.04-6.98 (m, 1H), 6.94 (d, J = 2.4 Hz, 1H), 4.84 (m, 1H), 4.01-3.87 (m, 4H), 3.54 (m, 1H), 3.42-3.26 (m, 4H), 2.33-2.19 (m, 2H), 2.08-1.80 (m, 6H). |
| 430 | 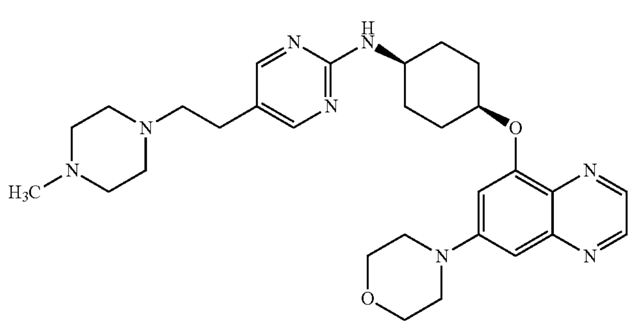 [SMILES: CN1CCN(CCc2cnc(N[C@H]3CC[C@@H](Oc4cc(N5CCOCC5)cc5nccnc45)CC3)nc2)CC1] | 533.47 | 1H NMR (300 MHz, Chloroform-d) δ 8.69 (d, J = 1.9 Hz, 1H), 8.62 (d, J = 1.9 Hz, 1H), 8.15 (s, 2H), 7.03-6.85 (m, 2H), 5.09 (d, J = 8.1 Hz, 1H), 4.78 (s, 1H), 3.92 (dd, J = 5.9, 3.7 Hz, 5H), 3.40-3.24 (m, 4H), 2.71-2.33 (m, 8H), 2.30 (s, 3H), 2.20 (s, 2H), 1.91 (d, J = 5.0 Hz, 6H), 1.26 (d, J = 3.1 Hz, 4H). |

TABLE 2-continued

| Cmpd. No. | Compound Structure | ESMS (M + H) | ¹H NMR |
|---|---|---|---|
| 436 | 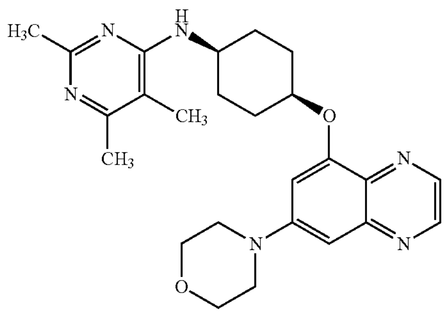 [SMILES: Cc1nc(C)c(C)c(N[C@H]2CC[C@@H](Oc3cc(N4CCOCC4)cc4nccnc34)CC2)n1] | 449.44 | 1H NMR (400 MHz, CDCl3) δ 8.70 (d, J = 1.9 Hz, 1H), 8.61 (d, J = 1.9 Hz, 1H), 6.95 (d, J = 2.4 Hz, 1H), 6.90 (d, J = 2.4 Hz, 1H), 4.88-4.70 (m, 2H), 4.32 (s, 1H), 3.98-3.85 (m, 4H), 3.41-3.27 (m, 4H), 2.53 (s, 3H), 2.40 (s, 3H), 2.26-2.14 (m, 2H), 1.99 (s, 3H), 1.94-1.88 (m, 6H). |
| 438 | 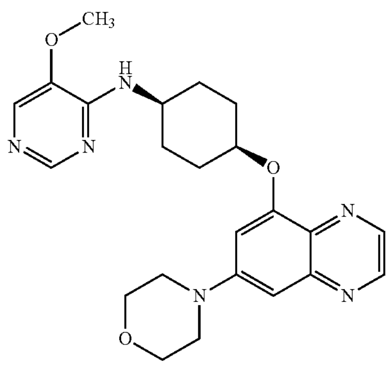 [SMILES: COc1cncnc1N[C@H]1CC[C@@H](Oc2cc(N3CCOCC3)cc3nccnc23)CC1] | 437.3 | 1H NMR (300 MHz, Chloroform-d) δ 8.72 (d, J = 2.0 Hz, 1H), 8.64 (d, J = 1.9 Hz, 1H), 8.28 (s, 1H), 7.72 (s, 1H), 6.94 (dd, J = 16.4, 2.5 Hz, 2H), 5.45 (d, J = 8.2 Hz, 1H), 4.76 (d, J = 6.6 Hz, 1H), 4.26 (s, 1H), 4.01-3.85 (m, 7H), 3.44-3.28 (m, 4H), 2.30-2.11 (m, 2H), 2.08-1.82 (m, 6H). |
| 439 | 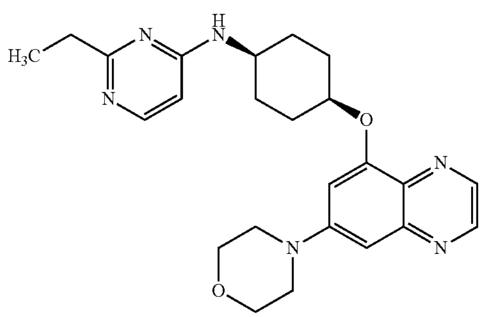 [SMILES: CCc1nccc(N[C@H]2CC[C@@H](Oc3cc(N4CCOCC4)cc4nccnc34)CC2)n1] | 435.44 | 1H NMR (400 MHz, CDCl3) δ 8.71 (d, J = 1.8 Hz, 1H), 8.63 (d, J = 1.8 Hz, 1H), 8.14 (d, J = 5.9 Hz, 1H), 6.98 (d, J = 2.4 Hz, 1H), 6.17 (d, J = 6.0 Hz, 1H), 5.05 (s, 1H), 4.01-3.70 (m, 5H), 3.42-3.25 (m, 4H), 2.77 (q, J = 7.6 Hz, 2H), 2.32-2.16 (m, 2H), 2.04-1.80 (m, 6H), 1.32 (t, J = 7.6 Hz, 3H). |
| 440 | 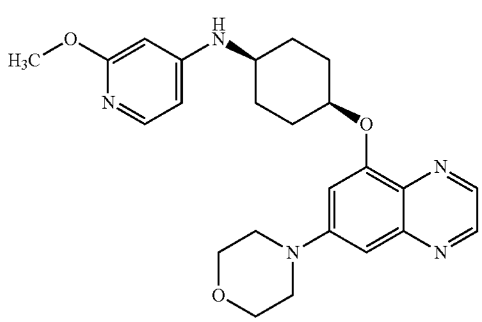 [SMILES: COc1cc(N[C@H]2CC[C@@H](Oc3cc(N4CCOCC4)cc4nccnc34)CC2)ccn1] | 436.22 | 1H NMR (300 MHz, Chloroform-d) δ 8.70 (d, J = 1.9 Hz, 1H), 8.60 (d, J = 1.9 Hz, 1H), 7.81 (d, J = 6.3 Hz, 1H), 6.96 (d, J = 2.4 Hz, 1H), 6.90 (d, J = 2.6 Hz, 1H), 6.24 (d, J = 6.2 Hz, 1H), 5.92 (s, 1H), 4.80 (m, 1H), 3.98 (s, 3H), 3.95-3.87 (m, 4H), 3.54 (m, 1H), 3.38-3.28 (m, 4H), 2.23 (m, 2H), 2.00-1.81 (m, 6H). |

TABLE 2-continued

| Cmpd. No. | Compound Structure | ESMS (M + H) | ¹H NMR |
|---|---|---|---|
| 441 | 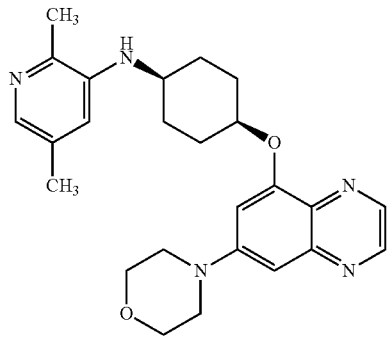 [SMILES: Cc1cnc(C)c(N[C@H]2CC[C@@H](Oc3cc(N4CCOCC4)cc4nccnc34)CC2)c1] | 434.35 | 1H NMR (300 MHz, Chloroform-d) rotomers, δ 8.80 (d, 1H), 8.73 (d, 1H), 7.73 (s, 1H), 7.16-6.99 (m, 3H), 4.91 (m, 1H), 3.95 (m, 4H), 3.55 (m, 1H), 3.37 (m, 4H), 2.73 (s, 3H), 2.41 (s, 3H), 2.29 (m, 2H), 2.13 (m, 6H). |
| 442 | 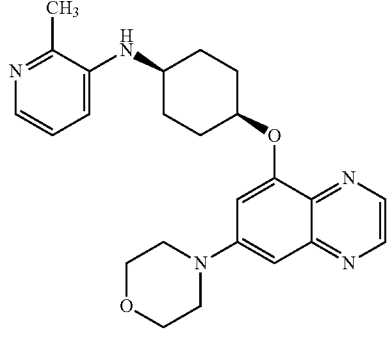 [SMILES: Cc1ncccc1N[C@H]1CC[C@@H](Oc2cc(N3CCOCC3)cc3nccnc23)CC1] | 420.4 | 1H NMR (300 MHz, Chloroform-d) δ 8.70 (d, J = 1.9 Hz, 1H), 8.62 (d, J = 1.9 Hz, 1H), 7.89 (dd, J = 5.0, 1.4 Hz, 1H), 7.19-7.10 (m, 1H), 7.03-6.95 (m, 2H), 6.92 (d, J = 2.6 Hz, 1H), 4.80 (m, 1H), 3.96-3.87 (m, 4H), 3.79 (m, 1H), 3.51 (m, 1H), 3.38-3.29 (m, 4H), 2.51 (m, 3H), 2.25 (m, 2H), 2.00-1.87 (m, 6H). |
| 443 | 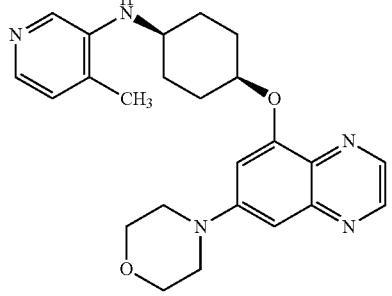 | 420.36 | 1H NMR (300 MHz, Chloroform-d) δ 8.69 (d, J = 1.9 Hz, 1H), 8.61 (d, J = 1.9 Hz, 1H), 8.01 (s, 1H), 7.89 (d, J = 4.8 Hz, 1H), 7.03 (d, J = 4.8 Hz, 1H), 6.96 (d, J = 2.4 Hz, 1H), 6.91 (d, J = 2.5 Hz, 1H), 4.78 (m, 1H), 3.98-3.86 (m, 4H), 3.61 (m, 2H), 3.39-3.28 (m, 4H), 2.30-2.15 (m, 5H), 1.93 (m, 6H). |
| 444 | 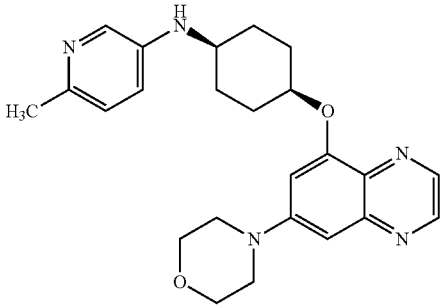 [SMILES: Cc1ccc(N[C@H]2CC[C@@H](Oc3cc(N4CCOCC4)cc4nccnc34)CC2)cn1] | 420.28 | 1H NMR (300 MHz, Chloroform-d) δ 8.69 (d, J = 1.9 Hz, 1H), 8.60 (d, J = 1.9 Hz, 1H), 8.03 (dd, J = 2.7, 0.9 Hz, 1H), 7.12-7.00 (m, 2H), 6.95 (d, J = 2.5 Hz, 1H), 6.90 (d, J = 2.5 Hz, 1H), 4.79 (m, 1H), 4.08-3.87 (m, 5H), 3.49 (m, 1H), 3.38-3.28 (m, 4H), 2.53 (s, 3H), 2.21 (m, 2H), 1.84 (d, J = 6.8 Hz, 6H). |

TABLE 2-continued

| Cmpd. No. | Compound Structure | ESMS (M + H) | ¹H NMR |
|---|---|---|---|
| 445 | 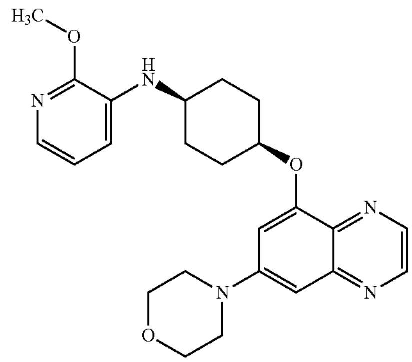 [SMILES: COc1ncccc1N[C@H]1CC[C@@H](Oc2cc(N3CCOCC3)cc3nccnc23)CC1] | 436.43 | 1H NMR (300 MHz, Chloroform-d) δ 8.65 (m, 1H), 8.40 (m, 1H), 7.50 (dd, J = 4.5, 2.2 Hz, 1H), 7.03 (s, 1H), 6.92 (s, 1H), 6.80 (m, 2H), 4.76 (m, 1H), 4.08 (s, 3H), 3.93 (m, 5H), 3.49 (m, 1H), 3.42-3.30 (m, 4H), 2.20 (m, 2H), 1.92 (m, 6H). |
| 446 | 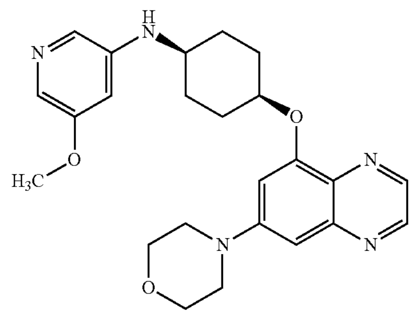 [SMILES: COc1cncc(N[C@H]2CC[C@@H](Oc3cc(N4CCOCC4)cc4nccnc34)CC2)c1] | 436.17 | 1H NMR (300 MHz, Chloroform-d) δ 8.69 (d, J = 1.9 Hz, 1H), 8.60 (d, J = 1.9 Hz, 1H), 7.71 (d, J = 2.4 Hz, 1H), 7.65 (d, J = 2.4 Hz, 1H), 6.96 (d, J = 2.4 Hz, 1H), 6.90 (d, J = 2.4 Hz, 1H), 6.55 (t, J = 2.4 Hz, 1H), 4.79 (m, 1H), 4.13 (m, 1H), 3.92 (m, 4H), 3.85 (s, 3H), 3.48 (m, 1H), 3.38-3.29 (m, 4H), 2.22 (m, 2H), 1.98-1.88 (m, 6H). |
| 447 | 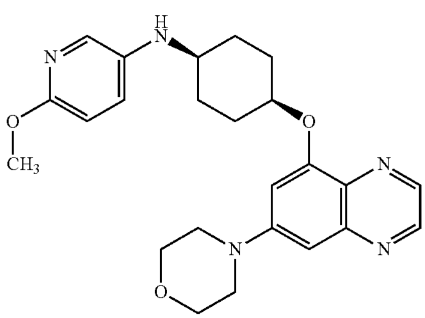 [SMILES: COc1ccc(N[C@H]2CC[C@@H](Oc3cc(N4CCOCC4)cc4nccnc34)CC2)cn1] | 436.34 | 1H NMR (300 MHz, Chloroform-d) δ 8.69 (d, J = 1.9 Hz, 1H), 8.60 (d, J = 2.0 Hz, 1H), 7.70 (s, 1H), 7.15 (m, 1H), 6.96 (d, J = 2.4 Hz, 1H), 6.92 (m, 1H), 6.64 (d, J = 8.8 Hz, 1H), 4.80 (m, 1H), 3.90 (m, 7H), 3.45-3.26 (m, 5H), 2.24-2.12 (m, 2H), 1.98-1.81 (m, 6H). |
| 448 | 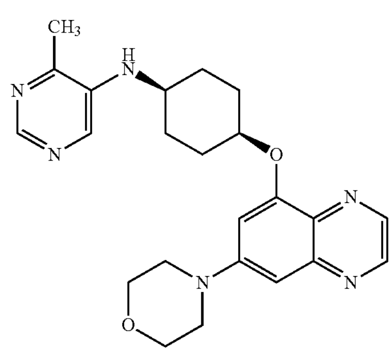 [SMILES: Cc1ncncc1N[C@H]1CC[C@@H](Oc2cc(N3CCOCC3)cc3nccnc23)CC1] | 421.39 | 1H NMR (300 MHz, Chloroform-d) δ 8.78 (dd, J = 4.0, 2.0 Hz, 1H), 8.66 (d, J = 2.1 Hz, 1H), 8.55 (s, 1H), 8.06 (s, 1H), 7.02 (d, J = 2.5 Hz, 1H), 6.96 (d, J = 2.5 Hz, 1H), 4.88 (m, 1H), 3.93 (m, 4H), 3.55 (m, 1H), 3.40 (m, 4H), 3.29 (m, 1H), 2.58 (s, 3H), 2.28 (m, 2H), 2.07 (m, 6H). |

TABLE 2-continued

| Cmpd. No. | Compound Structure | ESMS (M + H) | ¹H NMR |
|---|---|---|---|
| 449 | 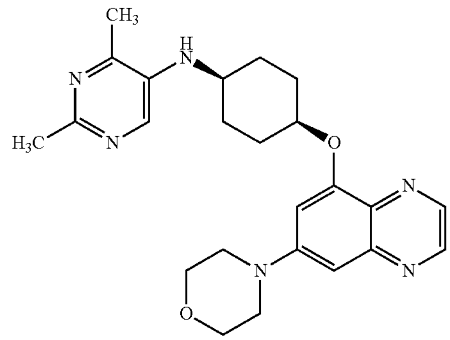 [SMILES: Cc1ncc(N[C@H]2CC[C@@H](Oc3cc(N4CCOCC4)cc4nccnc34)CC2)c(C)n1] | 435.35 | 1H NMR (300 MHz, Chloroform-d) rotomers, δ 8.85 (d, 1H), 8.67 d, 1H), 7.92 (d, 1H), 7.07-6.96 (m, 2H), 4.91 (m, 1H), 4.01-3.88 (m, 4H), 3.53-3.24 (m, 5H), 2.87 (s, 3H), 2.64 (s, 3H), 2.04-1.76 (m, 6H). |
| 450 | 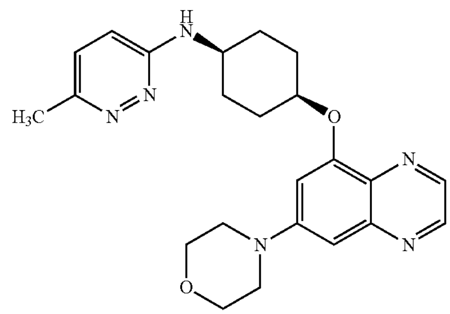 [SMILES: Cc1ccc(N[C@H]2CC[C@@H](Oc3cc(N4CCOCC4)cc4nccnc34)CC2)nn1] | 421.36 | 1H NMR (300 MHz, Chloroform-d) δ 8.69 (d, J = 1.9 Hz, 1H), 8.61 (d, J = 1.9 Hz, 1H), 7.21 (d, J = 9.2 Hz, 1H), 6.99-6.87 (m, 3H), 4.87 (m, 1H), 398-3.82 (m, 5H), 3.39-3.29 (m, 4H), 2.51 (s, 3H), 2.30-2.22 (m, 2H), 2.11-1.84 (m, 6H). |
| 451 | 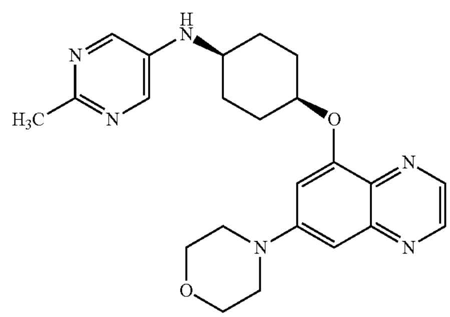 [SMILES: Cc1ncc(N[C@H]2CC[C@@H](Oc3cc(N4CCOCC4)cc4nccnc34)CC2)cn1] | 421.56 | 1H NMR (300 MHz, Chloroform-d) rotomers, δ 8.92 (d, J = 1.8 Hz, 1H), 8.77 (d, J = 1.8 Hz, 1H), 8.30 (m, 2H), 7.02-6.90 (m, 2H), 4.86 (m, 1H), 3.94 (m, 4H), 3.52-3.26 (m, 5H), 2.78 (s, 3H), 2.26 (d, J = 11.8 Hz, 2H), 1.90 (m, 6H). |
| 453 | 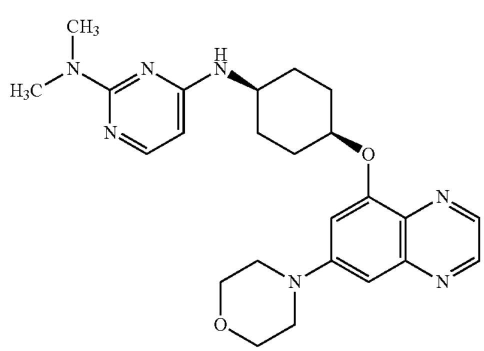 [SMILES: CN(C)c1nccc(N[C@H]2CC[C@@H](Oc3cc(N4CCOCC4)cc4nccnc34)CC2)n1] | 450.43 | 1H NMR (300 MHz, CDCl3) δ 8.69 (s, 1H), 8.62 (s, 1H), 7.89 (d, J = 5.9 Hz, 1H), 6.94 (s, 1H), 6.89 (s, 1H), 5.64 (d, J = 6.0 Hz, 1H), 4.87-4.66 (m, 2H), 3.98-3.83 (m, 4H), 3.44-3.24 (m, 4H), 3.13 (s, 6H), 2.26-2.10 (m, 2H), 2.04-1.75 (m, 6H). |

TABLE 2-continued

| Cmpd. No. | Compound Structure | ESMS (M + H) | ¹H NMR |
|---|---|---|---|
| 454 | 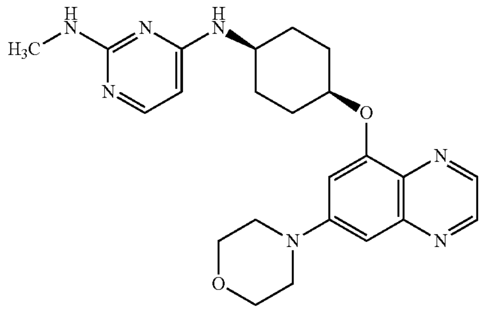 [SMILES: CNc1nccc(N[C@H]2CC[C@@H](Oc3cc(N4CCOCC4)cc4nccnc34)CC2)n1] | 436.34 | 1H NMR (300 MHz, CDCl3) δ 8.61 (d, J = 1.8 Hz, 1H), 8.52 (d, J = 1.9 Hz, 1H), 7.69 (s, 1H), 6.86 (d, J = 2.4 Hz, 1H), 6.80 (d, J = 2.2 Hz, 1H), 5.62 (d, J = 6.0 Hz, 1H), 4.83 (s, 1H), 4.69 (s, 1H), 3.91-3.74 (m, 4H), 3.36-3.10 (m, 4H), 2.86 (d, J = 5.0 Hz, 3H), 2.22-2.03 (m, 2H), 1.91-1.72 (m, 6H). |
| 455 | 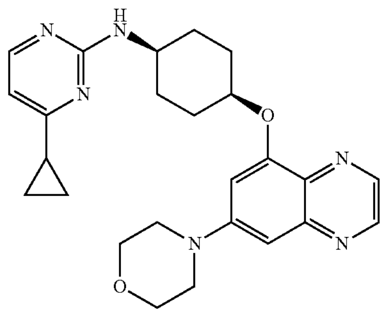 [SMILES: c1cc(C2CC2)nc(N[C@H]2CC[C@@H](Oc3cc(N4CCOCC4)cc4nccnc34)CC2)n1] | 447.41 | 1H NMR (300 MHz, CDCl3) δ 8.69 (d, J = 1.9 Hz, 1H), 8.61 (d, J = 1.9 Hz, 1H), 8.05 (d, J = 5.2 Hz, 1H), 6.94 (d, J = 2.5 Hz, 1H), 6.89 (d, J = 2.5 Hz, 1H), 6.39 (d, J = 5.2 Hz, 1H), 5.13 (bd, 1H), 4.76 (s, 1H), 4.10-3.96 (m, 1H), 3.95-3.83 (m, 4H), 3.40-3.24 (m, 4H), 2.26-2.09 (m, 2H), 1.97-1.76 (m, 7H), 1.10-1.00 (m, 2H), 1.00-0.91 (m, 2H). |
| 456 | 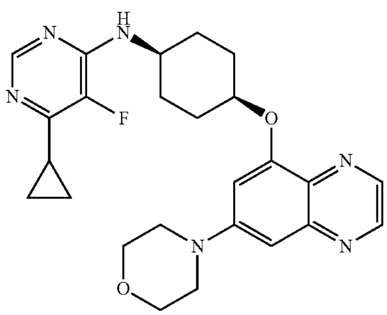 [SMILES: Fc1c(N[C@H]2CC[C@@H](Oc3cc(N4CCOCC4)cc4nccnc34)CC2)ncnc1C1CC1] | 465.29 | 1H NMR (300 MHz, CDCl3) δ 8.72 (d, J = 1.9 Hz, 1H), 8.64 (d, J = 1.9 Hz, 1H), 8.23 (d, J = 1.8 Hz, 1H), 6.97 (d, J = 2.5 Hz, 1H), 6.92 (d, J = 2.4 Hz, 1H), 5.04 (d, J = 7.6 Hz, 1H), 4.81 (s, 1H), 4.21 (s, 1H), 4.02-3.82 (m, 4H), 3.44-3.26 (m, 4H), 2.33-2.10 (m, 3H), 2.06-1.82 (m, 6H), 1.19-1.11 (m, 2H), 1.06-0.97 (m, 2H). |
| 457 | 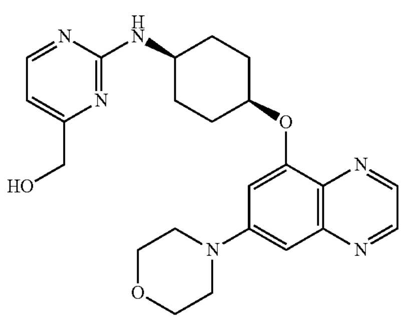 [SMILES: OCc1ccnc(N[C@H]2CC[C@@H](Oc3cc(N4CCOCC4)cc4nccnc34)CC2)n1] | 437.38 | 1H NMR (300 MHz, CDCl3) δ 8.69 (d, J = 1.9 Hz, 1H), 8.62 (d, J = 1.9 Hz, 1H), 8.21 (d, J = 51H NMR (300 MHz, CDCl3) δ 8.69 (d, J = 1.9 Hz, 1H), 8.62 (d, J = 1.9 Hz, 1H), 8.21 (d, J = 5.1 Hz, 1H), 6.95 (d, J = 2.5 Hz, 1H), 6.90 (d, J = 2.5 Hz, 1H), 6.45 (d, J = 5.1 Hz, 1H), 5.33 (d, J = 7.6 Hz, 1H), 4.85-4.74 (m, 1H), 4.56 (s, 2H), 4.12-4.00 (m, 1H), 3.95-3.86 (m, 4H), 3.66 (s, 1H), 3.39-3.27 (m, 4H), 2.18 (dd, J = 14.1, 8.4 Hz, 2H), 2.01-1.83 (m, 6H). |

TABLE 2-continued

| Cmpd. No. | Compound Structure | ESMS (M + H) | ¹H NMR |
|---|---|---|---|
| 463 | 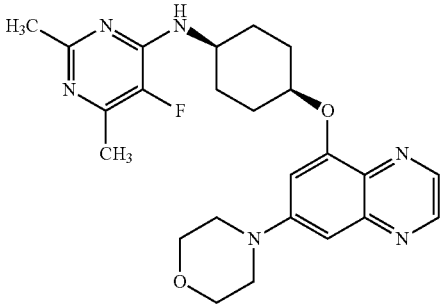 [SMILES: Cc1nc(C)c(F)c(N[C@H]2CC[C@@H](Oc3cc(N4CCOCC4)cc4nccnc34)CC2)n1] | 453.4 | 1H NMR (400 MHz, CDCl3) δ 8.69 (d, J = 1.9 Hz, 1H), 8.62 (d, J = 1.9 Hz, 1H), 6.95 (d, J = 2.4 Hz, 1H), 6.90 (d, J = 2.4 Hz, 1H), 4.95 (d, J = 7.1 Hz, 1H), 4.78 (s, 1H), 4.23 (d, J = 3.8 Hz, 1H), 3.99-3.82 (m, 4H), 3.42-3.25 (m, 4H), 2.45 (d, J = 0.6 Hz, 3H), 2.30 (d, J = 2.8 Hz, 3H), 2.26-2.14 (m, 2H), 1.99-1.86 (m, 6H). |
| 465 | 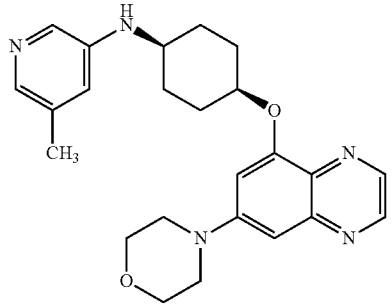 [SMILES: Cc1cncc(N[C@H]2CC[C@@H](Oc3cc(N4CCOCC4)cc4nccnc34)CC2)c1] | 420.19 | 1H NMR (300 MHz, Chloroform-d) δ 8.70 (d, J = 1.9 Hz, 1H), 8.61 (d, J = 1.9 Hz, 1H), 7.86 (d, J = 2.7 Hz, 1H), 7.78 (s, 1H), 6.96 (d, J = 2.4 Hz, 1H), 6.90 (d, J = 2.5 Hz, 1H), 6.78 (t, J = 2.1 Hz, 1H), 4.78 (m, 1H), 4.00-3.86 (m, 4H), 3.50 (s, 1H), 3.38-3.28 (m, 4H), 2.28 (s, 3H), 2.25-2.14 (m, 2H), 1.95-1.85 (m, 6H). |
| 467 | 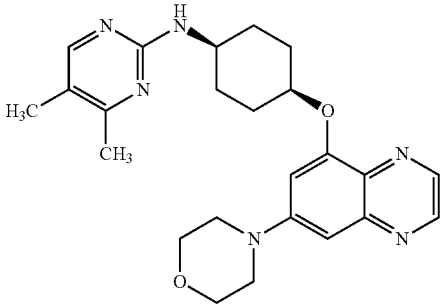 [SMILES: Cc1cnc(N[C@H]2CC[C@@H](Oc3cc(N4CCOCC4)cc4nccnc34)CC2)nc1C] | 435.35 | 1H NMR (400 MHz, CDCl3) δ 8.68 (d, J = 1.9 Hz, 1H), 8.61 (d, J = 1.9 Hz, 1H), 7.95 (s, 1H), 6.94 (d, J = 2.5 Hz, 1H), 6.90 (d, J = 2.5 Hz, 1H), 5.00 (d, J = 7.9 Hz, 1H), 4.83-4.74 (m, 1H), 4.07-3.96 (m, 1H), 3.96-3.87 (m, 4H), 3.38-3.28 (m, 4H), 2.29 (s, 3H), 2.22-2.12 (m, 2H), 2.07 (s, 3H), 1.93-1.85 (m, 6H). |
| 469 | 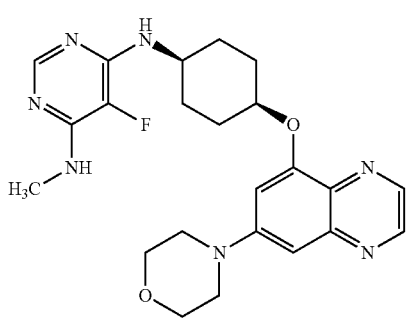 [SMILES: CNc1ncnc(N[C@H]2CC[C@@H](Oc3cc(N4CCOCC4)cc4nccnc34)CC2)c1F] | 454.3 | 1H NMR (400 MHz, CDCl3) δ 8.69 (d, J = 1.9 Hz, 1H), 8.62 (d, J = 1.9 Hz, 1H), 8.03 (s, 1H), 6.95 (d, J = 2.4 Hz, 1H), 6.89 (d, J = 2.4 Hz, 1H), 4.77 (s, 1H), 4.67 (s, 1H), 4.60 (s, 1H), 4.16 (s, 1H), 4.00-3.82 (m, 4H), 3.41-3.25 (m, 4H), 3.04 (d, J = 5.0 Hz, 3H), 2.28-2.11 (m, 2H), 1.99-1.84 (m, 6H). |

TABLE 2-continued

| Cmpd. No. | Compound Structure | ESMS (M + H) | ¹H NMR |
|---|---|---|---|
| 471 | 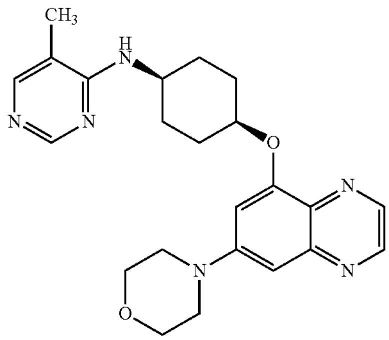 [SMILES: Cc1cncnc1N[C@H]1CC[C@@H](Oc2cc(N3CCOCC3)cc3nccnc23)CC1] | 421.35 | 1H NMR (300 MHz, Chloroform-d) δ 8.62 (d, J = 1.9 Hz, 1H), 8.54 (d, J = 2.0 Hz, 1H), 8.42 (s, 1H), 7.91 (d, J = 13.5 Hz, 1H), 6.93-6.78 (m, 2H), 4.71 (s, 1H), 4.57 (d, J = 7.9 Hz, 1H), 4.22 (s, 1H), 3.91-3.78 (m, 4H), 3.33-3.19 (m, 4H), 2.16 (d, J = 6.6 Hz, 2H), 1.96 (s, 3H), 1.91-1.77 (m, 6H). |
| 472 | 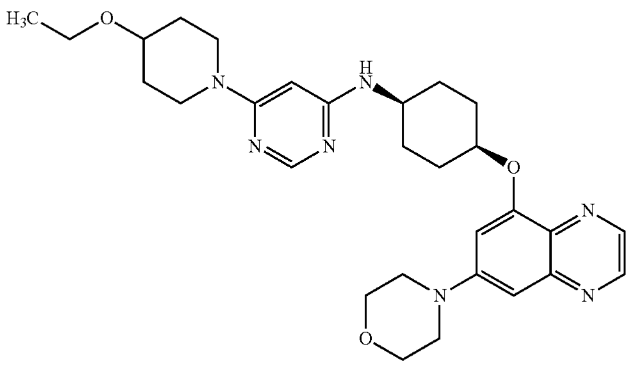 [SMILES: CCOC1CCN(c2cc(N[C@H]3CC[C@@H](Oc4cc(N5CCOCC5)cc5nccnc45)CC3)ncn2)CC1] | 534.2 | 1H NMR (300 MHz, Chloroform-d) δ 8.62 (d, J = 1.9 Hz, 1H), 8.54 (d, J = 1.9 Hz, 1H), 8.10 (d, J = 0.8 Hz, 1H), 6.92-6.77 (m, 2H), 5.36 (dd, J = 7.9, 0.9 Hz, 1H), 4.71 (q, J = 5.2, 4.2 Hz, 2H), 3.97-3.69 (m, 7H), 3.58-3.37 (m, 4H), 3.30-3.03 (m, 6H), 2.22-2.04 (m, 2H), 1.93-1.73 (m, 6H), 1.52 (dtd, J = 12.8, 8.9, 3.8 Hz, 2H), 1.28-1.16 (m, 3H). |
| 474 | 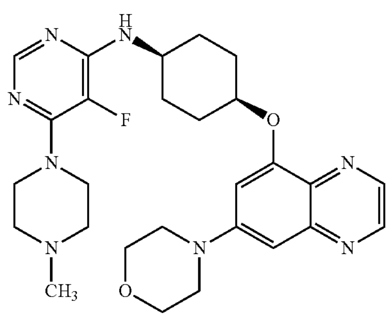 [SMILES: CN1CCN(c2ncnc(N[C@H]3CC[C@@H](Oc4cc(N5CCOCC5)cc5nccnc45)CC3)c2F)CC1] | 523.31 | 1H NMR (400 MHz, CDCl3) δ 8.69 (d, J = 1.9 Hz, 1H), 8.61 (d, J = 1.9 Hz, 1H), 7.99 (d, J = 1.5 Hz, 1H), 6.94 (d, J = 2.4 Hz, 1H), 6.89 (d, J = 2.4 Hz, 1H), 4.82 (d, J = 5.5 Hz, 1H), 4.77 (s, 1H), 4.15 (s, 1H), 3.96-3.85 (m, 4H), 3.76-3.65 (m, 4H), 3.38-3.26 (m, 4H), 2.59-2.45 (m, 4H), 2.34 (s, 3H), 2.27-2.13 (m, 2H), 1.96-1.85 (m, 6H). |
| 476 | 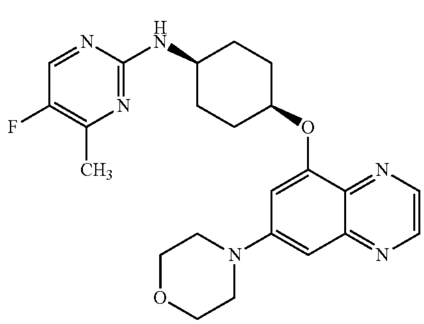 [SMILES: Cc1nc(N[C@H]2CC[C@@H](Oc3cc(N4CCOCC4)cc4nccnc34)CC2)ncc1F] | 439.4 | 1H NMR (400 MHz, CDCl3) δ 8.70 (d, J = 1.9 Hz, 1H), 8.63 (d, J = 1.9 Hz, 1H), 8.03 (d, J = 1.7 Hz, 1H), 6.97 (d, J = 2.5 Hz, 1H), 6.92 (d, J = 2.5 Hz, 1H), 5.18-5.04 (m, 1H), 4.80 (s, 1H), 3.99-3.90 (m, 5H), 3.40-3.32 (m, 4H), 2.36 (d, J = 2.4 Hz, 3H), 2.23-2.15 (m, 2H), 1.95-1.85 (m, 6H). |

| Cmpd. No. | Compound Structure | ESMS (M + H) | 1H NMR |
|---|---|---|---|
| 477 | 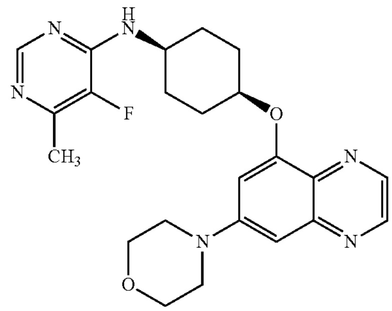 [SMILES: Cc1ncnc(N[C@H]2CC[C@@H](Oc3cc(N4CCOCC4)cc4nccnc34)CC2)c1F] | 439.36 | 1H NMR (400 MHz, CDCl3) δ 8.70 (d, J = 1.9 Hz, 1H), 8.62 (d, J = 1.9 Hz, 1H), 8.26 (d, J = 1.7 Hz, 1H), 6.95 (d, J = 2.4 Hz, 1H), 6.90 (d, J = 2.4 Hz, 1H), 5.07 (d, J = 7.2 Hz, 1H), 4.80 (s, 1H), 4.30-4.13 (m, 1H), 3.98-3.83 (m, 4H), 3.38-3.26 (m, 4H), 2.36 (d, J = 2.8 Hz, 3H), 2.29-2.16 (m, 2H), 1.97-1.85 (m, 6H). |
| 478 | 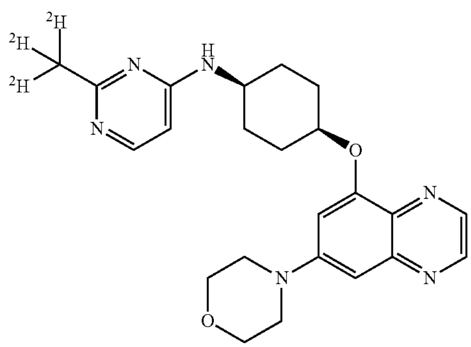 [SMILES: [2H]C([2H])([2H])c1nccc(N[C@H]2CC[C@@H](Oc3cc(N4CCOCC4)cc4nccnc34)CC2)n1] | 424 | 1H NMR (400 MHz, CDCl3) δ 8.64 (t, J = 9.6 Hz, 1H), 8.53 (d, J = 1.9 Hz, 1H), 8.02 (d, J = 5.9 Hz, 1H), 6.89 (d, J = 2.4 Hz, 1H), 6.83 (d, J = 2.4 Hz, 1H), 6.07 (d, J = 6.0 Hz, 1H), 4.91 (s, 1H), 4.73 (s, 1H), 3.83 (dd, J = 17.8, 12.9 Hz, 5H), 3.25 (dd, J = 17.8, 13.0 Hz, 4H), 2.14 (dd, J = 8.9, 5.0 Hz, 2H), 1.91-1.76 (m, 6H). |
| 481 | 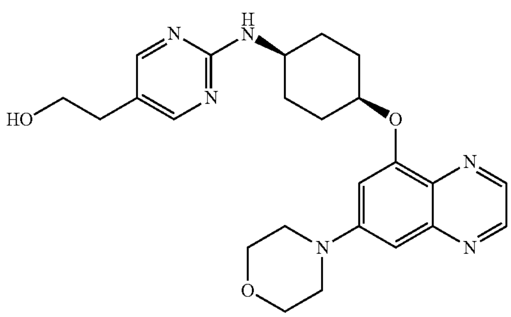 [SMILES: OCCc1cnc(N[C@H]2CC[C@@H](Oc3cc(N4CCOCC4)cc4nccnc34)CC2)nc1] | 451.41 | 1H NMR (300 MHz, Chloroform-d) δ 8.69 (d, J = 1.9 Hz, 1H), 8.62 (d, J = 1.9 Hz, 1H), 8.18 (s, 2H), 6.99-6.87 (m, 2H), 5.16 (d, J = 8.1 Hz, 1H), 4.78 (s, 1H), 4.03-3.87 (m, 5H), 3.80 (t, J = 6.5 Hz, 2H), 3.39-3.29 (m, 4H), 2.67 (t, J = 6.5 Hz, 2H), 2.26-2.14 (m, 2H), 1.90 (t, J = 6.5 Hz, 6H). |
| 482 | 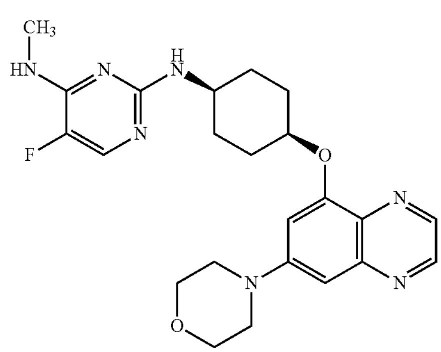 [SMILES: CNc1nc(N[C@H]2CC[C@@H](Oc3cc(N4CCOCC4)cc4nccnc34)CC2)ncc1F] | 454.35 | 1H NMR (400 MHz, CDCl3) δ 8.68 (d, J = 1.9 Hz, 1H), 8.61 (d, J = 1.9 Hz, 1H), 7.65 (d, J = 3.6 Hz, 1H), 6.94 (d, J = 2.4 Hz, 1H), 6.90 (d, J = 2.4 Hz, 1H), 5.14 (s, 1H), 4.90 (s, 1H), 4.76 (s, 1H), 4.01-3.87 (m, 5H), 3.39-3.31 (m, 4H), 3.01 (d, J = 5.0 Hz, 3H), 2.23-2.12 (m, 2H), 1.99-1.81 (m, 6H). |

TABLE 2-continued

| Cmpd. No. | Compound Structure | ESMS (M + H) | ¹H NMR |
|---|---|---|---|
| 485 | 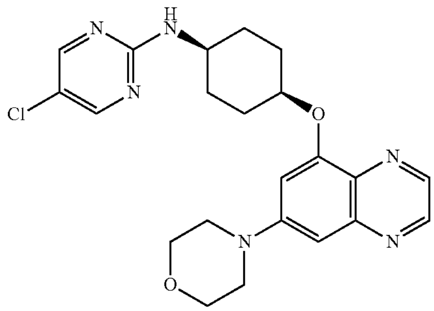 [SMILES: Clc1cnc(N[C@H]2CC[C@@H](Oc3cc(N4CCOCC4)cc4nccnc34)CC2)nc1] | 441.29 | 1H NMR (400 MHz, CDCl3) δ 8.68 (d, J = 1.9 Hz, 1H), 8.62 (d, J = 1.9 Hz, 1H), 8.20 (s, 2H), 6.96 (d, J = 2.3 Hz, 1H), 6.90 (d, J = 2.4 Hz, 1H), 5.27 (d, J = 7.4 Hz, 1H), 4.79 (s, 1H), 4.01-3.84 (m, 5H), 3.40-3.25 (m, 4H), 2.25-2.12 (m, 2H), 1.97-1.82 (m, 6H). |
| 486 | 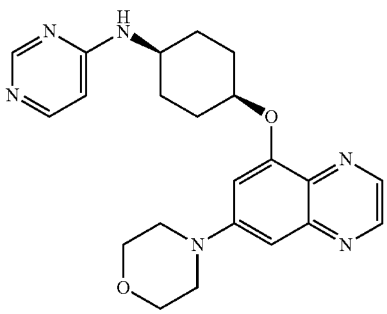 [SMILES: c1cc(N[C@H]2CC[C@@H](Oc3cc(N4CCOCC4)cc4nccnc34)CC2)ncn1] | 407 | 1H NMR (400 MHz, CDCl3) δ 8.62 (d, J = 1.9 Hz, 1H), 8.54 (d, J = 1.9 Hz, 1H), 8.49 (s, 1H), 8.08 (d, J = 6.0 Hz, 1H), 6.89 (d, J = 2.5 Hz, 1H), 6.83 (d, J = 2.5 Hz, 1H), 6.24 (dd, J = 6.0, 1.1 Hz, 1H), 4.88 (s, 1H), 4.78-4.67 (m, 1H), 3.87-3.82 (m, 4H), 3.25 (dd, J = 13.6, 8.8 Hz, 4H), 2.15 (dd, J = 8.8, 5.1 Hz, 2H), 1.90-1.78 (m, 6H). |
| 489 | 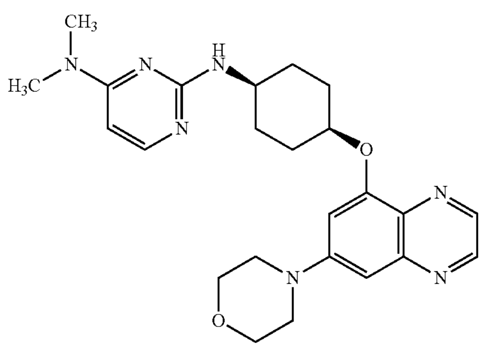 [SMILES: CN(C)c1ccnc(N[C@H]2CC[C@@H](Oc3cc(N4CCOCC4)cc4nccnc34)CC2)n1] | 450.34 | 1H NMR (400 MHz, CDCl3) δ 8.68 (d, J = 1.9 Hz, 1H), 8.61 (d, J = 1.9 Hz, 1H), 7.85 (d, J = 6.1 Hz, 1H), 6.94 (d, J = 2.4 Hz, 1H), 6.90 (d, J = 2.4 Hz, 1H), 5.81 (d, J = 6.1 Hz, 1H), 4.92 (s, 1H), 4.75 (s, 1H), 4.02 (s, 1H), 3.97-3.86 (m, 4H), 3.32 (dd, J = 17.6, 12.8 Hz, 4H), 3.04 (s, 6H), 2.18 (dd, J = 24.2, 17.3 Hz, 2H). |
| 490 | 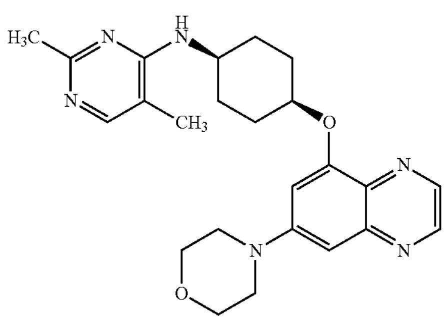 [SMILES: Cc1ncc(C)c(N[C@H]2CC[C@@H](Oc3cc(N4CCOCC4)cc4nccnc34)CC2)n1] | 435.35 | 1H NMR (400 MHz, CDCl3) δ 8.70 (d, J = 1.9 Hz, 1H), 8.62 (d, J = 1.9 Hz, 1H), 7.87 (d, J = 0.7 Hz 1H), 6.95 (d, J = 2.4 Hz, 1H), 6.90 (d, J = 2.4 Hz, 1H), 4.78 (s, 1H), 4.67 (s, 1H), 4.41-4.28 (m, 1H), 3.96-3.88 (m, 4H), 3.38-3.30 (m, 4H), 2.52 (s, 3H), 2.28-2.16 (m, 2H), 2.00 (s, 3H), 1.98-1.90 (m, 6H). |

TABLE 2-continued

| Cmpd. No. | Compound Structure | ESMS (M + H) | ¹H NMR |
|---|---|---|---|
| 491 | 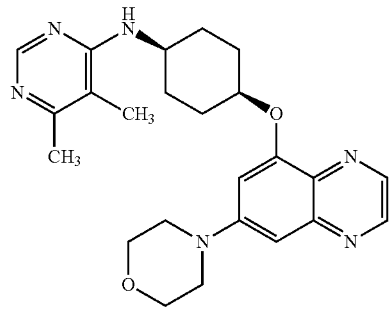 [SMILES: Cc1ncnc(N[C@H]2CC[C@@H](Oc3cc(N4CCOCC4)cc4nccnc34)CC2)c1C] | 435.35 | 1H NMR (400 MHz, CDCl3) δ 8.70 (d, J = 1.7 Hz, 1H), 8.61 (d, J = 1.7 Hz, 1H), 8.42 (s, 1H), 6.95 (s, 1H), 6.90 (s, 1H), 4.79 (s, 2H), 4.28 (s, 1H), 3.98-3.86 (m, 4H), 3.40-3.28 (m, 4H), 2.42 (s, 3H), 2.30-2.16 (m, 2H), 2.02 (s, 3H), 1.99-1.89 (m, 6H). |
| 492 | 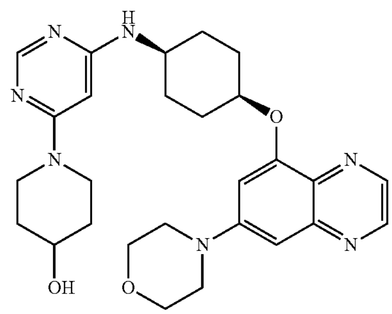 [SMILES: OC1CCN(c2cc(N[C@H]3CC[C@@H](Oc4cc(N5CCOCC5)cc5nccnc45)CC3)ncn2)CC1] | 506.2 | 1H NMR (300 MHz, Chloroform-d) δ 8.71 (d, J = 1.9 Hz, 1H), 8.63 (d, J = 1.9 Hz, 1H), 8.20 (d, J = 0.8 Hz, 1H), 6.97 (d, J = 2.4 Hz, 1H), 6.92 (d, J = 2.5 Hz, 1H), 5.47 (d, J = 1.0 Hz, 1H), 4.76 (d, J = 23.9 Hz, 2H), 4.12-3.75 (m, 7H), 3.41-3.28 (m, 4H), 3.20 (ddd, J = 13.2, 9.6, 3.2 Hz, 2H), 2.20 (d, J = 6.9 Hz, 2H), 1.91 (d, J= 5.2 Hz, 6H). |
| 494 | 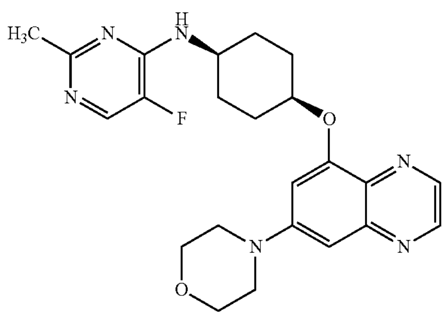 [SMILES: Cc1ncc(F)c(N[C@H]2CC[C@@H](Oc3cc(N4CCOCC4)cc4nccnc34)CC2)n1] | 439.23 | 1H NMR (300 MHz, Chloroform-d) δ 8.62 (d, J = 1.9 Hz, 1H), 8.54 (d, J = 1.9 Hz, 1H), 7.82 (d, J = 3.4 Hz, 1H), 6.88 (d, J = 2.5 Hz, 1H), 6.82 (d, J = 2.5 Hz, 1H), 4.96 (d, J = 8.0 Hz, 1H), 4.72 (d, J = 3.1 Hz, 1H), 4.18 (s, 1H), 3.90-3.78 (m, 4H), 3.35-3.19 (m, 4H), 2.41 (d, J = 0.9 Hz, 3H), 2.13-(q, J = 6.4 Hz, 2H), 1.84 (t, J = 6.3 Hz, 6H). |
| 499 | 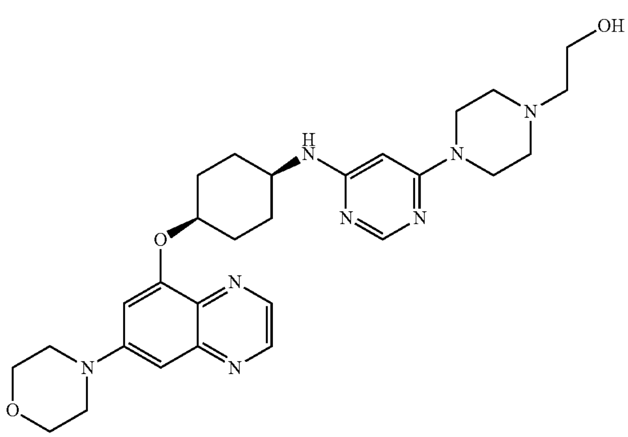 [SMILES: OCCN1CCN(c2cc(N[C@H]3CC[C@@H](Oc4cc(N5CCOCC5)cc5nccnc45)CC3)ncn2)CC1] | 535.24 | 1H NMR (300 MHz, Chloroform-d) δ 8.70 (d, J = 1.9 Hz, 1H), 8.61 (d, J = 1.9 Hz, 1H), 8.19 (d, J = 0.8 Hz, 1H), 6.93 (dd, J = 16.4, 2.5 Hz, 2H), 5.42 (d, J = 1.0 Hz, 1H), 4.87-4.67 (m, 2H), 4.01-3.77 (m, 5H), 3.61 (dt, J = 27.3, 5.1 Hz, 6H), 3.41-3.26 (m, 4H), 2.73 (t, J = 5.3 Hz, 1H), 2.59 (ddd, J = 6.2, 5.0, 3.7 Hz, 6H), 2.19 (d, J = 6.6 Hz, 2H), 1.89 (t, J = 5.2 Hz, 6H). |

TABLE 2-continued

| Cmpd. No. | Compound Structure | ESMS (M + H) | ¹H NMR |
|---|---|---|---|
| 511 | 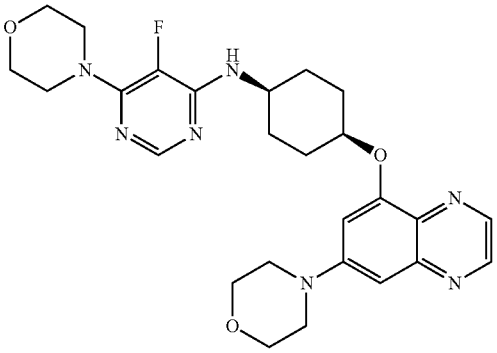 [SMILES: Fc1c(N[C@H]2CC[C@@H](Oc3cc(N4CCOCC4)cc4nccnc34)CC2)ncnc1N1CCOCC1] | 510.2 | 1H NMR (300 MHz, Chloroform-d) δ 8.63 (d, J = 1.9 Hz, 1H), 8.55 (d, J = 1.9 Hz, 1H), 7.93 (d, J = 1.7 Hz, 1H), 6.85 (dd, J = 16.5, 2.5 Hz, 2H), 4.74 (ddd, J = 21.7, 7.5, 3.9 Hz, 2H), 4.09 (p, J = 7.7, 7.2 Hz, 1H), 3.92-3.79 (m, 4H), 3.71 (dd, J = 5.7, 3.7 Hz, 4H), 3.57 (dd, J = 5.7, 3.7 Hz, 4H), 3.34-3.20 (m, 4H), 2.15 (td, J = 11.0, 10.0, 6.2 Hz, 2H), 1.94-1.79 (m, 6H). |
| 512 | 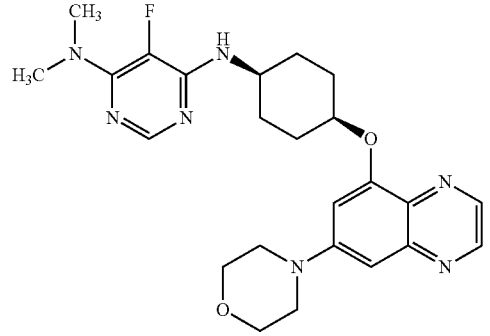 [SMILES: CN(C)c1ncnc(N[C@H]2CC[C@@H](Oc3cc(N4CCOCC4)cc4nccnc34)CC2)c1F] | 468.27 | 1H NMR (300 MHz, Chloroform-d) δ 8.71 (d, J = 1.9 Hz, 1H), 8.64 (d, J = 1.9 Hz, 1H), 7.99 (d, J = 1.8 Hz, 1H), 7.00-6.85 (m, 2H), 4.77 (d, J = 6.6 Hz, 2H), 4.14 (q, J = 7.2 Hz, 1H), 4.03-3.87 (m, 4H), 3.78-3.64 (m, 1H), 3.43-3.28 (m, 4H), 3.15 (d, J = 2.5 Hz, 6H), 2.98-2.84 (m, 1H), 2.20 (d, J = 11.9 Hz, 2H), 1.94 (p, J = 5.8, 5.3 Hz, 6H). |
| 525 | 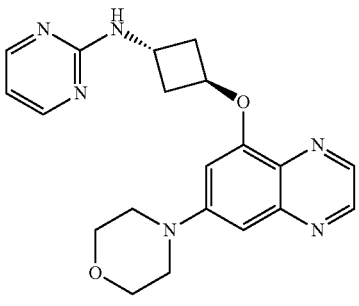 [SMILES: c1cnc(N[C@H]2C[C@H](Oc3cc(N4CCOCC4)cc4nccnc34)C2)nc1] | 379.26 | 1H NMR (400 MHz, CDCl3) δ 8.71 (d, J = 1.9 Hz, 1H), 8.63 (d, J = 1.9 Hz, 1H), 8.31 (s, 1H), 8.30 (s, 1H), 6.93 (d, J = 2.4 Hz, 1H), 6.64-6.54 (m, 2H), 5.38 (d, J = 5.1 Hz, 1H), 5.17-5.07 (m, 1H), 4.68-4.56 (m, 1H), 3.95-3.85 (m, 4H), 3.35-3.27 (m, 4H), 2.94 (ddd, J = 13.4, 8.2, 5.1 Hz, 2H), 2.59 (ddd, J = 13.9, 7.0, 4.5 Hz, 2H). |
| 531 | 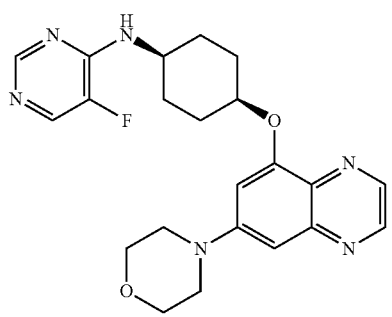 [SMILES: Fc1cncnc1N[C@H]1CC[C@@H](Oc2cc(N3CCOCC3)cc3nccnc23)CC1] | 425.19 | 1H NMR (300 MHz, Chloroform-d) δ 8.71 (d, J = 1.9 Hz, 1H), 8.64 (d, J = 1.9 Hz, 1H), 8.39 (dd, J = 2.7, 0.5 Hz, 1H), 8.04 (d, J = 3.4 Hz, 1H), 6.97 (d, J = 2.5 Hz, 1H), 6.92 (d, J = 2.5 Hz, 1H), 5.15 (d, J = 8.1 Hz, 1H), 4.83 (dq, J = 5.1, 2.6 Hz, 1H), 4.25 (dd, J = 8.1, 4.6 Hz, 1H), 3.98-3.88 (m, 4H), 3.39-3.28 (m, 4H), 2.34-2.17 (m, 2H), 2.03-1.84 (m, 6H). |

TABLE 2-continued

| Cmpd. No. | Compound Structure | ESMS (M + H) | ¹H NMR |
|---|---|---|---|
| 532 | 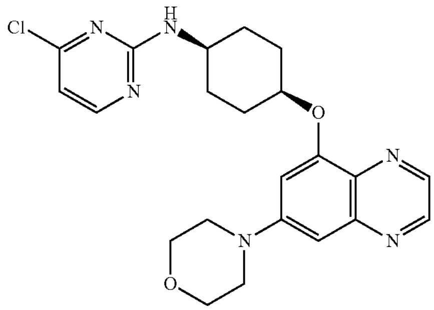 [SMILES: Clc1ccnc(N[C@H]2CC[C@@H](Oc3cc(N4CCOCC4)cc4nccnc34)CC2)n1] | 441.29 | 1H NMR (400 MHz, CDCl3) δ 8.69 (d, J = 1.9 Hz, 1H), 8.61 (d, J = 1.9 Hz, 1H), 8.13 (d, J = 4.8 Hz, 1H), 6.96 (d, J = 2.4 Hz, 1H), 6.90 (d, J = 2.5 Hz, 1H), 6.54 (d, J = 5.2 Hz, 1H), 5.36 (s, 1H), 4.79 (s, 1H), 4.03 (s, 1H), 3.97-3.84 (m, 4H), 3.41-3.23 (m, 4H), 2.26-2.12 (m, 2H), 1.98-1.81 (m, 6H). |
| 533 | 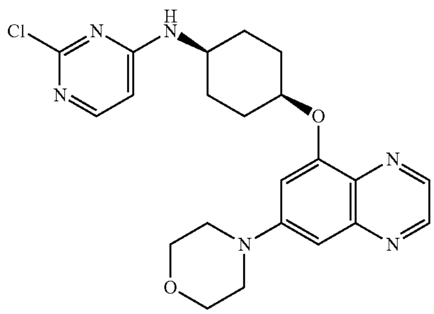 [SMILES: Clc1nccc(N[C@H]2CC[C@@H](Oc3cc(N4CCOCC4)cc4nccnc34)CC2)n1] | 441.25 | 1H NMR (400 MHz, CDCl3) δ 8.69 (d, J = 1.9 Hz, 1H), 8.60 (d, J = 1.9 Hz, 1H), 7.99 (s, 1H), 6.96 (d, J = 2.4 Hz, 1H), 6.90 (d, J = 2.4 Hz, 1H), 6.22 (d, J = 5.9 Hz, 1H), 5.22 (s, 1H), 4.81 (s, 1H), 4.03 (dt, J = 12.1, 6.2 Hz, 1H), 3.94-3.86 (m, 4H), 3.40-3.26 (m, 4H), 2.27-2.13 (m, 2H), 1.90 (t, J = 17.4 Hz, 6H). |
| 534 | 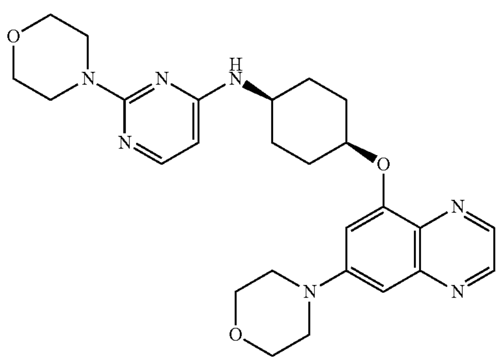 [SMILES: c1cc(N[C@H]2CC[C@@H](Oc3cc(N4CCOCC4)cc4nccnc34)CC2)nc(N2CCOCC2)n1] | 492.39 | 1H NMR (400 MHz, CDCl3) δ 8.69 (s, 1H), 8.61 (s, 1H), 7.89 (d, J = 5.5 Hz, 1H), 6.95 (s, 1H), 6.89 (s, 1H), 5.71 (d, J = 5.8 Hz, 1H), 4.76 (s, 2H), 4.01-3.81 (m, 5H), 3.74 (s, 8H), 3.41-3.26 (m, 4H), 2.26-2.12 (m, 2H), 1.98-1.81 (m, 6H). |
| 535 | 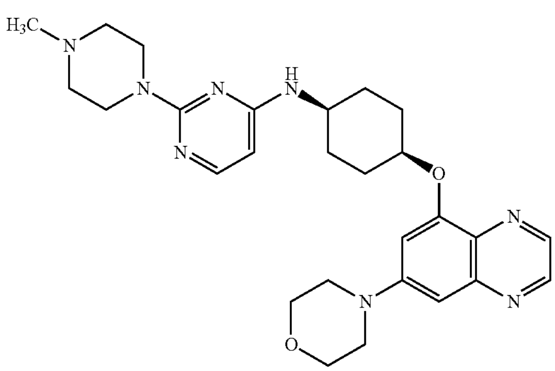 [SMILES: CN1CCN(c2nccc(N[C@H]3CC[C@@H](Oc4cc(N5CCOCC5)cc5nccnc45)CC3)n2)CC1] | 505.35 | 1H NMR (40 0MHz, CDCl3) δ 8.69 (d, J = 1.9 Hz, 1H), 8.61 (d, J = 1.9 Hz, 1H), 7.88 (d, J = 5.7 Hz, 1H), 6.95 (d, J = 2.4 Hz, 1H), 6.89 (d, J = 2.4 Hz, 1H), 5.67 (d, J = 5.8 Hz, 1H), 4.84-4.63 (m, 2H), 3.99-3.83 (m, 5H), 3.82-3.73 (m, 4H), 3.37-3.27 (m, 4H), 2.49-2.40 (m, 4H), 2.33 (s, 3H), 2.23-2.11 (m, 2H), 1.96-1.82 (m, 6H). |

TABLE 2-continued
| Cmpd. No. | Compound Structure | ESMS (M + H) | 1H NMR |
|---|---|---|---|
| 537 | 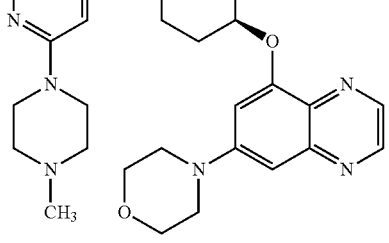 | 505.35 | 1H NMR (400 MHz, CDCl3) δ 8.69 (d, J = 1.7 Hz, 1H), 8.60 (d, J = 1.7 Hz, 1H), 8.18 (s, 1H), 6.95 (d, J = 2.2 Hz, 1H), 6.90 (s, 1H), 5.42 (s, 1H), 4.78 (s, 1H), 4.71 (d, J = 8.3 Hz, 1H), 3.98-3.87 (m, 4H), 3.83 (s, 1H), 3.65-3.48 (m, 4H), 3.41-3.24 (m, 4H), 2.54-2.42 (m, 4H), 2.33 (s, 3H), 2.25-2.11 (m, 2H), 1.97-1.82 (m, 6H). |
| 539 | 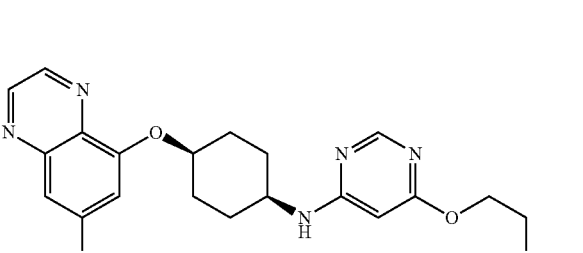 | 481.3 | 1H NMR (300 MHz, CDCl3): ppm 1.76-1.97 (m, 6 H), 2.15-2.26 (m, 2 H), 3.31-3.35 (m, 4 H), 3.43 (s, 3 H), 3.61-3.72 (m, 3 H), 3.90-3.93 (m, 4 H), 4.45-4.48 (m, 2 H), 4.76-4.82 (m, 1 H), 4.94 (d, J = 7.1 Hz, 1 H), 5.73 (s, 1 H), 6.89 (d, J = 2. |
| 547 | 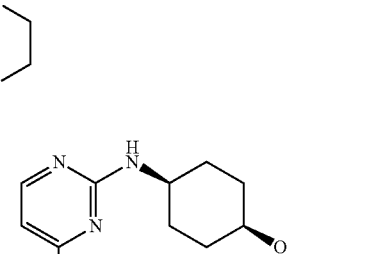 | 505.4 | 1H NMR (400 MHz, CDCl3) δ 8.70 (d, J = 1.9 Hz, 1H), 8.63 (d, J = 1.9 Hz, 1H), 7.90 (d, J = 6.0 Hz, 1H), 6.96 (d, J = 2.4 Hz, 1H), 6.92 (d, J = 2.3 Hz, 1H), 5.89 (d, J = 6.1 Hz, 1H), 4.96 (s, 1H), 4.77 (s, 1H), 4.08-3.98 (m, 1H), 3.96-3.87 (m, 4H), 3.70-3.53 (m, 4H), 3.43-3.27 (m, 4H), 2.53-2.42 (m, 4H), 2.35 (s, 3H), 2.25-2.13 (m, 2H), 2.00-1.85 (m, 6H). |
| 548 | 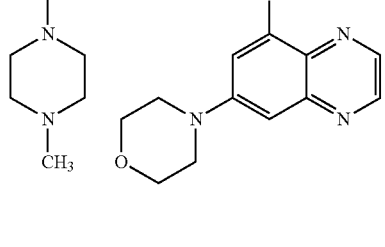 | 492.39 | 1H NMR (400 MHz, CDCl3) δ 8.70 (d, J = 1.8 Hz, 1H), 8.63 (d, J = 1.9 Hz, 1H), 7.93 (d, J = 5.9 Hz, 1H), 6.96 (d, J = 2.3 Hz, 1H), 6.91 (d, J = 2.3 Hz, 1H), 5.87 (d, J = 6.1 Hz, 1H), 4.97 (s, 1H), 4.77 (s, 1H), 4.02 (s, 1H), 3.97-3.88 (m, 4H), 3.83-3.70 (m, 4H), 3.63-3.52 (m, 4H), 3.39-3.27 (m, 4H), 2.25-2.12 (m, 2H), 2.01-1.85 (m, 6H). |

| Cmpd. No. | Compound Structure | ESMS (M + H) | ¹H NMR |
|---|---|---|---|
| 553 | 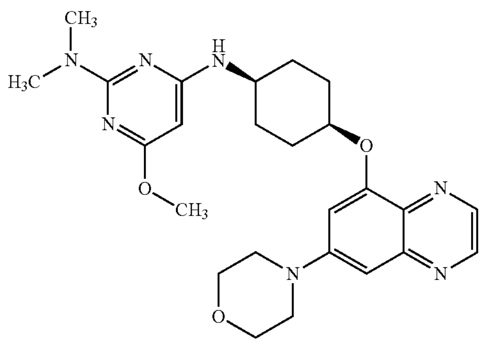 [SMILES: COc1cc(N[C@H]2CC[C@@H](Oc3cc(N4CCOCC4)cc4nccnc34)CC2)nc(N(C)C)n1] | 480.19 | 1H NMR (300 MHz, Chloroform-d) δ 8.71 (d, J = 1.9 Hz, 1H), 8.63 (d, J = 1.9 Hz, 1H), 6.93 (dd, J = 17.8, 2.5 Hz, 2H), 5.07 (s, 1H), 4.78 (d, J = 6.2 Hz, 1H), 4.68 (d, J = 7.9 Hz, 1H), 4.03-3.90 (m, 4H), 3.87 (s, 3H), 3.71 (s, 1H), 3.42-3.28 (m, 4H), 3.13 (s, 6H), 2.27-2.00 (m, 2H), 2.00-1.79 (m, 6H). |
| 558 | 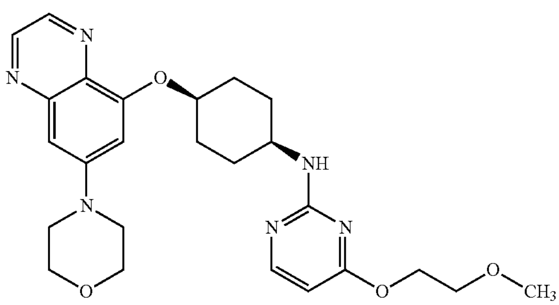 [SMILES: COCCOc1ccnc(N[C@H]2CC[C@@H](Oc3cc(N4CCOCC4)cc4nccnc34)CC2)n1] | 481.3 | 1H NMR (300 MHz, CDCl3): ppm 1.84-1.99 (m, 6H), 2.11-2.25 (m, 2 H), 3.32-3.36 (m, 4 H), 3.43 (s, 3 H), 3.70-3.73 (m, 2 H), 3.90-3.93 (m, 4 H), 3.96-4.07 (m, 1 H), 4.41-4.44 (m, 2 H), 4.72-4.80 (m, 1 H), 5.10 (br. s, 1 H), 6.06 (d, J = 5.6 |
| 565 | 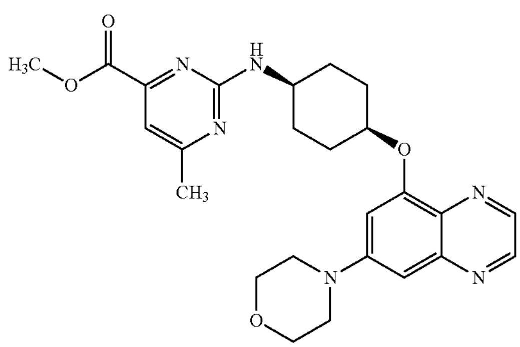 [SMILES: COC(=O)c1cc(C)nc(N[C@H]2CC[C@@H](Oc3cc(N4CCOCC4)cc4nccnc34)CC2)n1] | 479.1 | 1H NMR (300 MHz, Chloroform-d) δ 8.55 (d, J = 1.9 Hz, 1H), 8.47 (d, J = 1.9 Hz, 1H), 6.93 (s, 1H), 6.86-6.72 (m, 2H), 5.25 (s, 1H), 4.66 (s, 1H), 4.05-3.90 (m, 1H), 3.86-3.71 (m, 7H), 3.30-3.09 (m, 4H), 2.27 (d, J = 2.2 Hz, 3H), 2.04 (d, J = 9.2 Hz, 2H), 1.75 (d, J = 4.8 Hz, 6H). |
| 567 | 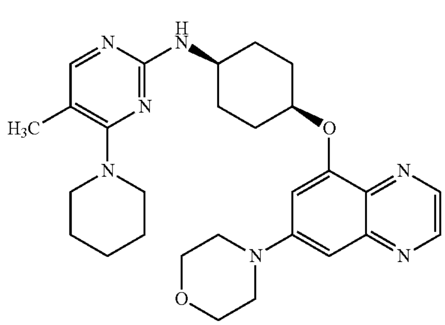 [SMILES: Cc1cnc(N[C@H]2CC[C@@H](Oc3cc(N4CCOCC4)cc4nccnc34)CC2)nc1N1CCCCC1] | 504.1 | 1H NMR (300 MHz, Chloroform-d) δ 8.70 (d, J = 1.9 Hz, 1H), 8.63 (d, J = 1.9 Hz, 1H), 7.74 (s, 1H), 7.00-6.89 (m, 2H), 4.91 (s, 1H), 4.76 (d, J = 6.1 Hz, 1H), 4.04-3.93 (m, 5H), 3.43-3.28 (m, 4H), 2.26-2.14 (m, 2H), 2.08 (d, J = 0.8 Hz, 3H), 2.00-1.92 (m, 6H), 1.69 (d, J = 21.2 Hz, 10H). |

TABLE 2-continued

| Cmpd. No. | Compound Structure | ESMS (M + H) | ¹H NMR |
|---|---|---|---|
| 572 | 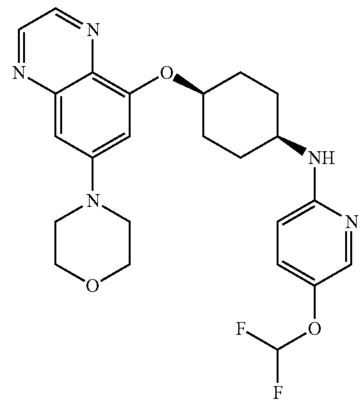 [SMILES: FC(F)Oc1ccc(N[C@H]2CC[C@@H](Oc3cc(N4CCOCC4)cc4nccnc34)CC2)nc1] | 472.2 | 1H NMR (300 MHz, CDCl3): ppm 1.82-1.99 (m, 6 H), 2.14-2.28 (m, 2 H), 3.32-3.35 (m, 4 H), 3.80-3.88 (m, 1 H), 3.90-3.93 (m, 4H), 4.70-4.83 (m, 2 H), 6.37 (d, J = 8.8 Hz, 1 H), 6.38 (t, J = 73.8 Hz, 1 H), 6.90 (d, J = 2.3 Hz, 1 H), 6.95 (d, J = |
| 573 | 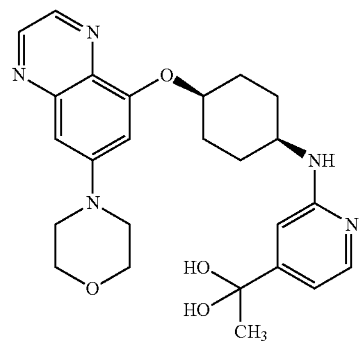 [SMILES: CC(O)(O)c1ccnc(N[C@H]2CC[C@@H](Oc3cc(N4CCOCC4)cc4nccnc34)CC2)c1] | 464.3 | 1H NMR (300 MHz, CDCl3): ppm 1.52 (s, 6 H), 1.73 (br s, 1 H), 1.85-1.96 (m, 6 H), 2.11-2.25 (m, 2 H), 3.30-3.36 (m, 4 H), 3.88-4.00 (m, 5 H), 4.55 (d, J = 8.1 Hz, 1 H), 4.74-4.81 (m, 1 H), 6.52 (s, 1 H), 6.57 (dd, J = 5.4, 1.4 Hz, 1 H), 6.90 (d, |
| 574 | 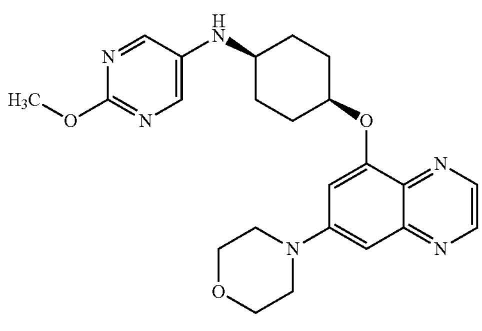 [SMILES: COc1ncc(N[C@H]2CC[C@@H](Oc3cc(N4CCOCC4)cc4nccnc34)CC2)cn1] | 437.42 | 1H NMR (400 MHz, CDCl3) δ 8.69 (d, J = 1.9 Hz, 1H), 8.61 (d, J = 1.9 Hz, 1H), 7.99 (s, 2H), 6.95 (d, J = 2.4 Hz, 1H), 6.89 (d, J = 2.4 Hz, 1H), 4.78 (s, 1H), 4.01-3.84 (m, 7H), 3.41 (s, 2H), 3.37-3.27 (m, 4H), 2.26-2.14 (m, 2H), 1.93-1.81 (m, 6H). |
| 575 | 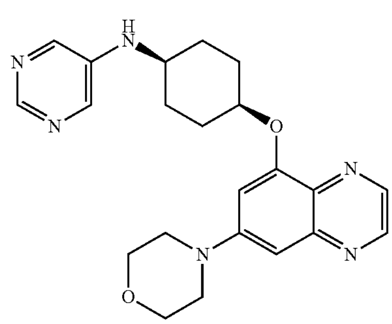 [SMILES: c1ncc(N[C@H]2CC[C@@H](Oc3cc(N4CCOCC4)cc4nccnc34)CC2)cn1] | 407.35 | 1H NMR (400 MHz, CDCl3) δ 8.69 (d, J = 1.9 Hz, 1H), 8.62 (d, J = 1.9 Hz, 1H), 8.57 (s, 1H), 8.13 (s, 2H), 6.98 (d, J = 2.4 Hz, 1H), 6.91 (d, J = 2.5 Hz, 1H), 4.86-4.73 (m, 1H), 3.95-3.88 (m, 4H), 3.56-3.49 (m, 1H), 3.39-3.31 (m, 4H), 2.30-2.18 (m, 2H), 1.97-1.84 (m, 6H). |

| Cmpd. No. | Compound Structure | ESMS (M + H) | ¹H NMR |
|---|---|---|---|
| 576 | 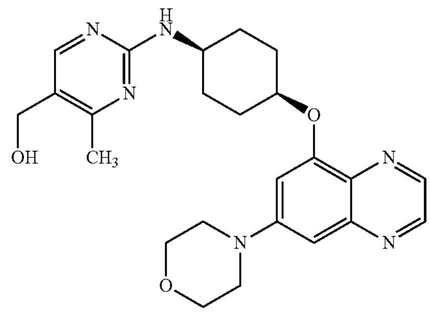 [SMILES: Cc1nc(N[C@H]2CC[C@@H](Oc3cc(N4CCOCC4)cc4nccnc34)CC2)ncc1CO] | 450.13 | 1H NMR (300 MHz, Chloroform-d) δ 8.71 (d, J = 2.0 Hz, 1H), 8.63 (d, J = 1.9 Hz, 1H), 8.13 (s, 1H), 7.01-6.87 (m, 2H), 4.81 (s, 1H), 4.57 (s, 2H), 4.06 (s, 1H), 3.99-3.87 (m, 4H), 3.35 (dd, J = 5.9, 3.8 Hz, 4H), 2.45 (s, 3H), 2.20 (d, J = 8.0 Hz, 2H), 1.93 (d, J = 5.1 Hz, 6H). |
| 577 | 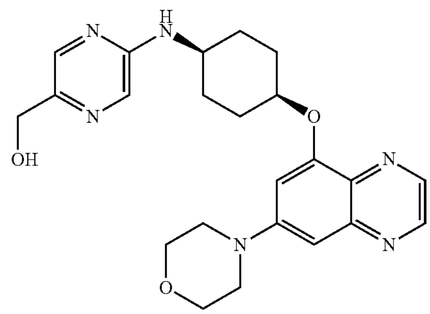 [SMILES: OCc1cnc(N[C@H]2CC[C@@H](Oc3cc(N4CCOCC4)cc4nccnc34)CC2)cn1] | 437.25 | 1H NMR (300 MHz, Chloroform-d) δ 8.71 (d, J = 1.9 Hz, 1H), 8.63 (d, J = 2.0 Hz, 1H), 8.02 (d, J = 1.4 Hz, 1H), 7.87 (d, J = 1.5 Hz, 1H), 6.94 (dd, J = 16.2, 2.5 Hz, 2H), 4.89-4.71 (m, 2H), 4.65 (s, 2H), 4.06-3.85 (m, 4H), 3.40-3.27 (m, 4H), 2.23 (dt, J = 11.5, 5.5 Hz, 2H), 2.04-1.80 (m, 6H). |
| 579 | 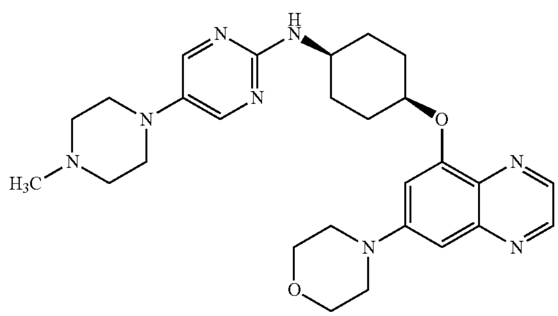 [SMILES: CN1CCN(c2cnc(N[C@H]3CC[C@@H](Oc4cc(N5CCOCC5)cc5nccnc45)CC3)nc2)CC1] | 505.53 | 1H NMR (400 MHz, CDCl3) δ 8.68 (s, 1H), 8.61 (s, 1H), 8.07 (s, 2H), 6.94 (s, 1H), 6.90 (s, 1H), 4.96 (d, J = 8.1 Hz, 1H), 4.78 (s, 1H), 4.02-3.81 (m, 5H), 3.47-3.19 (m, 5H), 3.19-2.83 (m, 4H), 2.76-2.52 (m, 3H), 2.37 (s, 3H), 2.26-2.11 (m, 2H), 2.03-1.82 (m, 6H). |
| 582 | 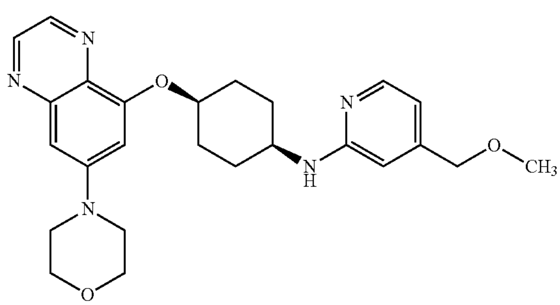 [SMILES: COCc1ccnc(N[C@H]2CC[C@@H](Oc3cc(N4CCOCC4)cc4nccnc34)CC2)c1] | 450.3 | 1H NMR (300 MHz, CDCl3): ppm 1.83 ñ 1.96 (m, 6 H), 2.14-2.26 (m, 2 H), 3.30-3.36 (m, 4 H), 3.41 (s, 3 H), 3.87 ñ 3.95 (m, 5 H), 4.36 (s, 2 H), 4.59-4.89 (m, 2 H), 6.38 (s, 1 H), 6.48 (d, J = 5.2 Hz, 1H), 6.90 (d, J = 2.4 Hz, 1H), 6.95 (d, J = 2.4 |

TABLE 2-continued

| Cmpd. No. | Compound Structure | ESMS (M + H) | ¹H NMR |
|---|---|---|---|
| 583 | 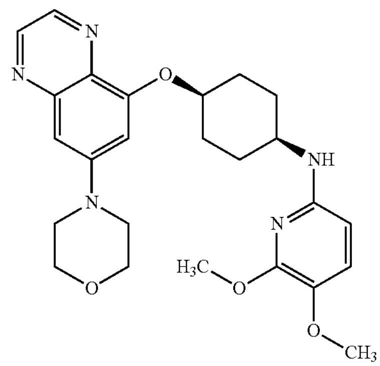 [SMILES: COc1ccc(N[C@H]2CC[C@@H](Oc3cc(N4CCOCC4)cc4nccnc34)CC2)nc1OC] | 466.3 | 1H NMR (300 MHz, CDCl3): ppm 1.84-2.00 (m, 6 H), 2.09-2.24 (m, 2 H), 3.30-3.37 (m, 4 H), 3.64-3.74 (m, 1 H), 3.78 (s, 3H), 3.89-3.95 (m, 7 H), 4.71-4.79 (m, 1 H), 5.88 (d, J = 8.3 Hz, 1H), 6.90 (d, J = 2.4 Hz, 1H), 6.95 (d, J = 2.4 Hz, 1 H) |
| 584 | 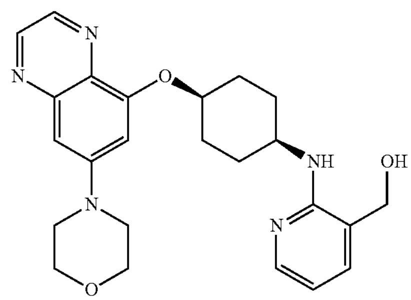 [SMILES: OCc1cccnc1N[C@H]1CC[C@@H](Oc2cc(N3CCOCC3)cc3nccnc23)CC1] | 436.3 | 1H NMR (300 MHz, CDCl3): ppm 1.86-2.04 (m, 6 H), 2.12-2.26 (m, 2 H), 3.28-3.39 (m, 4 H), 3.88-3.96 (m, 4 H), 4.26 (br s, 1 H), 4.62 (s, 2 H), 4.69-4.78 (m, 1 H), 5.56 (br s, 1 H), 6.50 (t, J = 5.3 Hz, 1 H), 6.90 (d, J = 1.9 Hz, 1 H), 6.93 (d, J |
| 586 | 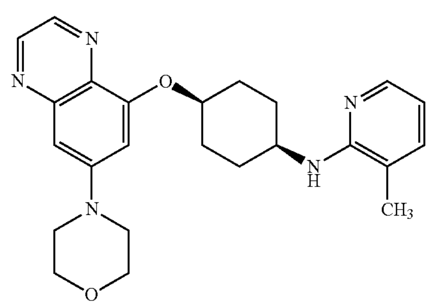 [SMILES: Cc1cccnc1N[C@H]1CC[C@@H](Oc2cc(N3CCOCC3)cc3nccnc23)CC1] | 420.3 | 1H NMR (300 MHz, CDCl3): ppm 1.88 ñ 2.01 (m, 6 H), 2.10 (s, 3 H), 2.15-2.25 (m, 2 H), 3.30-3.37 (m, 4 H), 3.89 ñ 3.95 (m, 4 H), 4.25 (br s, 2 H), 4.71-4.78 (m, 1 H), 6.51 (dd, J = 6.8, 5.4 Hz, 1 H), 6.90 (d, J = 2.3 Hz, 1 H), 6.94 (d, J = 2.3 Hz, 1H |
| 587 | 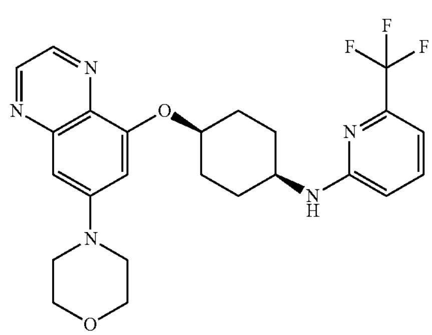 [SMILES: FC(F)(F)c1cccc(N[C@H]2CC[C@@H](Oc3cc(N4CCOCC4)cc4nccnc34)CC2)n1] | 474.2 | 1H NMR (300 MHz, CDCl3): ppm 1.82-1.98 (m, 6 H), 2.12-2.26 (m, 2 H), 3.25-3.43 (m, 4 H), 3.82-3.98 (m, 5 H), 4.80 (br s, 2 H), 6.52 (d, J = 8.4 Hz, 1 H), 6.87-6.93 (m, 2 H), 6.95-7.00 (m, 1 H), 7.50 (t, J = 7.9 Hz, 1 H), 8.63 (d, J = 1.2 Hz, 1H |

| Cmpd. No. | Compound Structure | ESMS (M + H) | 1H NMR |
|---|---|---|---|
| 588 | 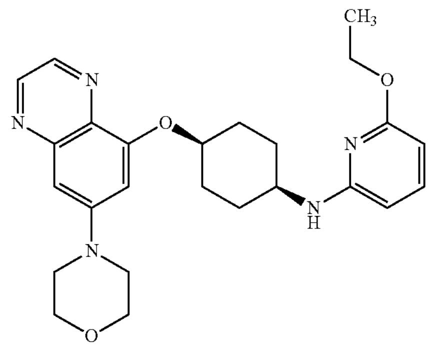 [SMILES: CCOc1cccc(N[C@H]2CC[C@@H](Oc3cc(N4CCOCC4)cc4nccnc34)CC2)n1] | 450.3 | 1H NMR (300 MHz, CDCl3): ppm 1.38 (t, J = 7.0 Hz, 3 H), 1.83-2.00 (m, 6 H), 2.11-2.24 (m, 2 H), 3.30-3.37 (m, 4 H), 3.75-3.85 (m, 1 H), 3.89-3.94 (m, 4 H), 4.25 (q, J = 7.0 Hz, 2 H), 4.42-4.54 (m, 1 H), 4.72-4.79 (m, 1 H), 5.94 (d, J = 7.7 H |
| 589 | 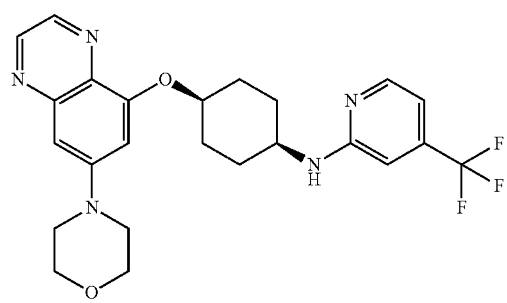 [SMILES: FC(F)(F)c1ccnc(N[C@H]2CC[C@@H](Oc3cc(N4CCOCC4)cc4nccnc34)CC2)c1] | 474.2 | 1H NMR (300 MHz, CDCl3): ppm 1.86-1.99 (m, 6 H), 2.16-2.27 (m, 2 H), 3.31-3.36 (m, 4 H), 3.88-3.95 (m, 5 H), 4.77-4.84 (m, 1 H), 4.90 (br s, 1 H), 6.55 (s, 1 H), 6.72 (d, J = 5.0 Hz, 1 H), 6.91 (d, J = 2.4 Hz, 1 H), 6.95 (d, J = 2.4 Hz, 1 H), 8. |
| 590 | 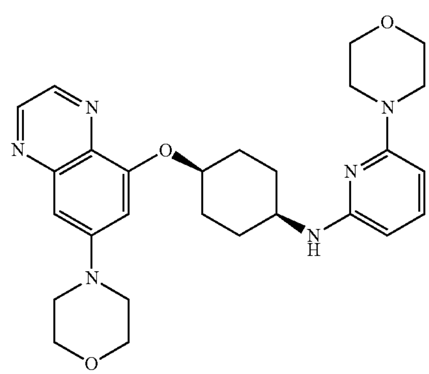 [SMILES: c1cc(N[C@H]2CC[C@@H](Oc3cc(N4CCOCC4)cc4nccnc34)CC2)nc(N2CCOCC2)c1] | 491.3 | 1H NMR (300 MHz, CDCl3): ppm 1.82-1.98 (m, 6 H), 2.10-2.22 (m, 2 H), 3.31-3.35 (m, 4 H), 3.41-3.45 (m, 4 H), 3.69-3.82 (m, H), 3.90-3.93 (m, 4 H), 4.43 (d, J = 7.7 Hz, 1 H), 4.70-4.77 (m, 1 H), 5.81 (d, J = 8.0 Hz, 1 H), 5.90 (d, J = 8.0 H |
| 591 | 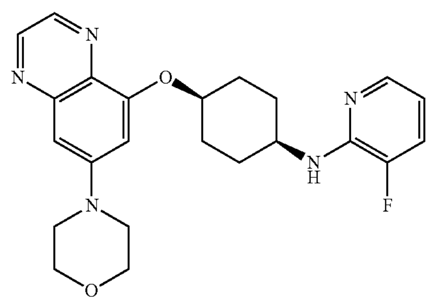 [SMILES: Fc1cccnc1N[C@H]1CC[C@@H](Oc2cc(N3CCOCC3)cc3nccnc23)CC1] | 424.2 | 1H NMR (300 MHz, CDCl3): ppm 1.88-2.00 (m, 6 H), 2.13-2.28 (m, 2 H), 3.29-3.38 (m, 4 H), 3.88-3.95 (m, 4 H), 4.21 (br s, 1 H), 4.62-4.84 (m, 2 H), 6.45-6.54 (m, 1 H), 6.90 (d, J = 2.4 Hz, 1 H), 6.95 (d, J = 2.4 Hz, 1 H), 7.07-7.18 (m, 1 H). |

| Cmpd. No. | Compound Structure | ESMS (M + H) | ¹H NMR |
|---|---|---|---|
| 592 | 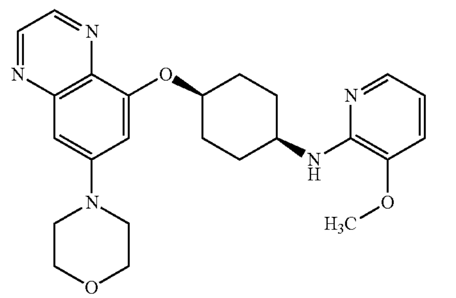 [SMILES: COc1cccnc1N[C@H]1CC[C@@H](Oc2cc(N3CCOCC3)cc3nccnc23)CC1] | 436.3 | 1H NMR (300 MHz, CDCl3): ppm 1.84-2.03 (m, 6 H), 2.11-2.24 (m, 2 H), 3.30-3.37 (m, 4 H), 3.84 (s, 3H), 3.89-3.95 (m, 4 H), 4.17-4.29 (m, 1 H), 4.67-4.76 (m, 1 H), 5.08 (d, J = 7.4 Hz, 1 H), 6.50 (dd, J = 7.3, 5.2 Hz, 1 H), 6.82 (d, J = 7.4 Hz |
| 593 | 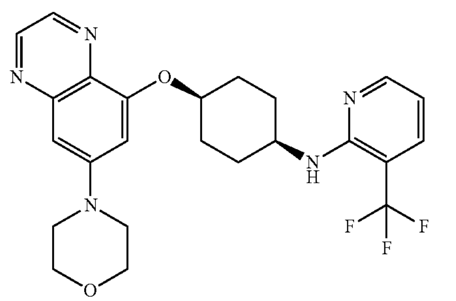 [SMILES: FC(F)(F)c1cccnc1N[C@H]1CC[C@@H](Oc2cc(N3CCOCC3)cc3nccnc23)CC1] | 474.2 | 1H NMR (300 MHz, CDCl3): ppm 1.86-2.00 (m, 6 H), 2.13-2.26 (m, 2 H), 3.30-3.38 (m, 4 H), 3.88-3.97 (m, 4 H), 4.22-4.35 (m, 1 H), 4.73-4.80 (m, 1 H), 4.89-4.99 (m, 1 H), 6.60 (dd, J = 7.1, 5.1 Hz, 1 H), 6.91 (d, J = 2.3 Hz, 1 H), 6.96 (d, J = |
| 594 | 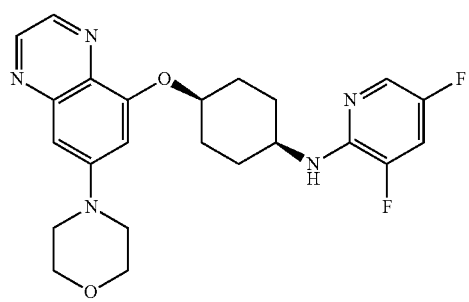 [SMILES: Fc1cnc(N[C@H]2CC[C@@H](Oc3cc(N4CCOCC4)cc4nccnc34)CC2)c(F)c1] | 442.2 | 1H NMR (300 MHz, CDCl3): ppm 1.85-2.00 (m, 6 H), 2.11-2.28 (m, 2 H), 3.29-3.39 (m, 4 H), 3.87-3.97 (m, 4 H), 4.06-4.18 (m, 1 H), 4.56 (d, J = 7.6 Hz, 1H), 4.73-4.81 (m, 1 H), 6.90 (d, J = 2.4 Hz, 1 H), 6.95 (d, J = 2.4 Hz, 1 H), 7.05 (ddd, J = |
| 595 | 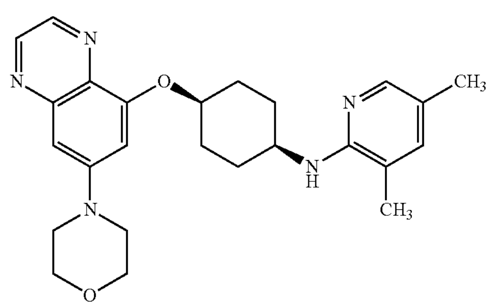 [SMILES: Cc1cnc(N[C@H]2CC[C@@H](Oc3cc(N4CCOCC4)cc4nccnc34)CC2)c(C)c1] | 434.3 | 1H NMR (300 MHz, CDCl3): ppm 1.88-2.02 (m, 6 H), 2.08 (s, 3 H), 2.15 (s, 3 H), 2.14-2.24 (m, 2 H), 3.31-3.36 (m, 4 H), 3.89-3.95 (m, 4 H), 4.03-4.16 (m, 1 H), 4.23 (br s, 1H), 4.69-4.77 (m, 1 H), 6.90 (d, J = 2.4 Hz, 1 H), 6.94 (d, J = 2.4 Hz |
| 597 | 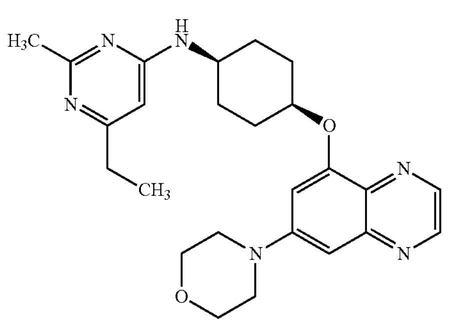 [SMILES: CCc1cc(N[C@H]2CC[C@@H](Oc3cc(N4CCOCC4)cc4nccnc34)CC2)nc(C)n1] | 449.23 | 1H NMR (300 MHz, Chloroform-d) δ 8.71 (d, J = 1.9 Hz, 1H), 8.63 (d, J = 1.9 Hz, 1H), 7.07-6.87 (m, 2H), 6.02 (s, 1H), 4.83 (d, J = 5.5 Hz, 1H), 4.03-3.81 (m, 5H), 3.44-3.25 (m, 4H), 2.72-2.57 (m, 1H), 2.51 (s, 3H), 2.29-2.11 (m, 2H), 2.05-1.72 (m, 6H), 1.27 (t, J = 7.6 Hz, 3H). |

TABLE 2-continued

| Cmpd. No. | Compound Structure | ESMS (M + H) | ¹H NMR |
|---|---|---|---|
| 598 | 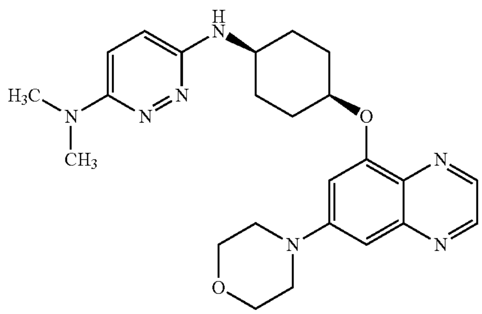 [SMILES: CN(C)c1ccc(N[C@H]2CC[C@@H](Oc3cc(N4CCOCC4)cc4nccnc34)CC2)nn1] | 450.23 | 1H NMR (300 MHz, Chloroform-d) δ 8.61 (d, J = 1.9 Hz, 1H), 8.54 (d, J = 1.9 Hz, 1H), 6.93-6.72 (m, 3H), 6.55 (s, 1H), 4.71 (s, 1H), 4.01 (s, 1H), 3.92-3.76 (m, 4H), 3.34-3.18 (m, 4H), 2.98 (s, 6H), 2.07 (d, J = 24.1 Hz, 2H), 1.87 (d, J = 9.2 Hz, 6H). |
| 600 | 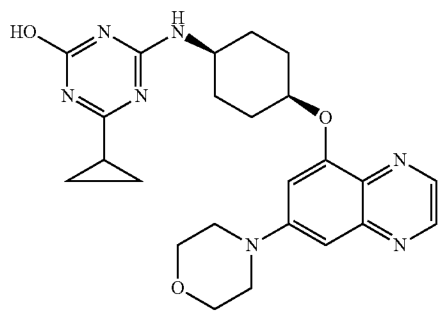 [SMILES: Oc1nc(N[C@H]2CC[C@@H](Oc3cc(N4CCOCC4)cc4nccnc34)CC2)nc(C2CC2)n1] | 464.26 | 1H NMR (300 MHz, Chloroform-d) δ 8.71 (d, J = 2.0 Hz, 1H), 8.62 (d, J = 2.0 Hz, 1H), 7.00-6.85 (m, 2H), 5.44 (d, J = 8.5 Hz, 1H), 4.78 (s, 1H), 3.93 (t, J = 4.8 Hz, 4H), 3.35 (t, J = 4.9 Hz, 4H), 3.06-2.91 (m, 1H), 2.15 (d, J = 26.6 Hz, 2H), 1.89 (s, 6H), 1.30-0.94 (m, 4H). |
| 601 | 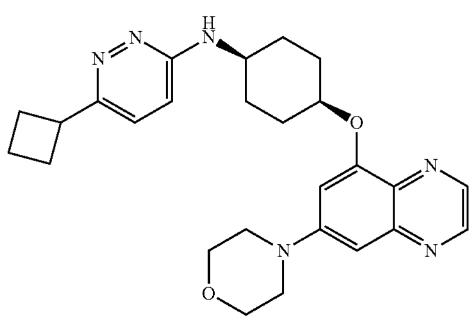 [SMILES: c1cnc2c(O[C@H]3CC[C@@H](Nc4ccc(C5CCC5)nn4)CC3)cc(N3CCOCC3)cc2n1] | 461.32 | 1H NMR (300 MHz, Chloroform-d) δ 8.70 (d, J = 1.9 Hz, 1H), 8.62 (d, J = 1.9 Hz, 1H), 7.06 (d, J = 9.1 Hz, 1H), 6.98-6.86 (m, 2H), 6.58 (d, J = 9.1 Hz, 1H), 4.81 (dq, J = 5.5, 2.7 Hz, 1H), 4.52 (s, 1H), 4.17 (d, J = 5.0 Hz, 1H), 4.01-3.87 (m, 4H), 3.67 (dq, J = 8.9, 8.1 Hz, 1H), 3.43-3.30 (m, 4H), 2.47-2.29 (m, 4H), 2.22 (dt, J = 11.9, 5.5 Hz, 2H), 2.05-1.82 (m, 6H). |
| 602 | 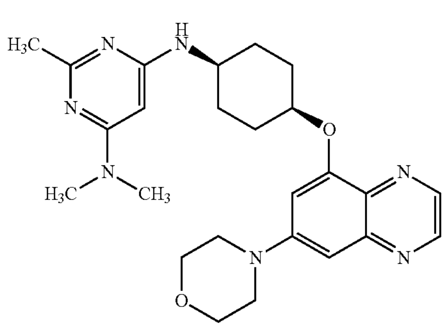 [SMILES: Cc1nc(N[C@H]2CC[C@@H](Oc3cc(N4CCOCC4)cc4nccnc34)CC2)cc(N(C)C)n1] | 464.1 | 1H NMR (300 MHz, Chloroform-d) δ 8.70 (d, J = 1.9 Hz, 1H), 8.62 (d, J = 1.9 Hz, 1H), 7.04-6.92 (m, 2H), 4.82 (d, J = 3.0 Hz, 1H), 3.93 (dd, J = 5.9, 3.8 Hz, 4H), 3.65 (d, J = 8.7 Hz, 1H), 3.44-3.29 (m, 4H), 3.08 (s, 6H), 2.39 (s, 3H), 2.21 (d, J = 14.4 Hz, 2H), 1.92 (dt, J = 17.0, 10.7 Hz, 6H). |

TABLE 2-continued

| Cmpd. No. | Compound Structure | ESMS (M + H) | ¹H NMR |
|---|---|---|---|
| 603 | 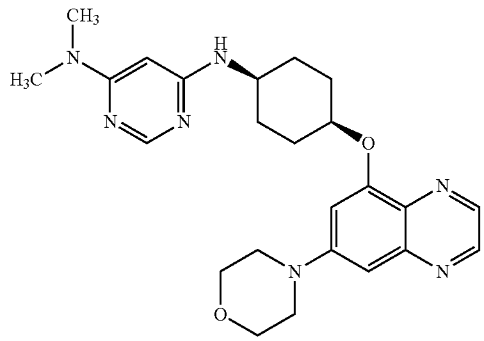 [SMILES: CN(C)c1cc(N[C@H]2CC[C@@H](Oc3cc(N4CCOCC4)cc4nccnc34)CC2)ncn1] | 450.1 | 1H NMR (300 MHz, Chloroform-d) δ 8.70 (d, J = 1.9 Hz, 1H), 8.62 (d, J = 1.9 Hz, 1H), 8.18 (s, 1H), 7.02-6.86 (m, 2H), 4.81 (s, 2H), 4.00-3.76 (m, 5H), 3.42-3.26 (m, 4H), 3.07 (s, 6H), 2.20 (q, J = 6.3, 5.8 Hz, 2H), 2.01-1.79 (m, 6H). |
| 604 | 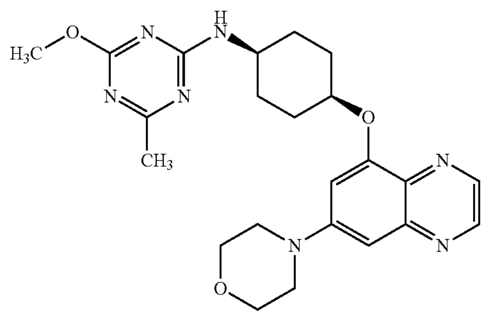 [SMILES: COc1nc(C)nc(N[C@H]2CC[C@@H](Oc3cc(N4CCOCC4)cc4nccnc34)CC2)n1] | 452.1 | 1H NMR (300 MHz, Chloroform-d) δ 8.62 (d, J = 1.9 Hz, 1H), 8.53 (d, J = 1.9 Hz, 1H), 6.87 (d, J = 2.5 Hz, 1H), 6.81 (d, J = 2.6 Hz, 1H), 4.71 (s, 1H), 3.94-3.72 (m, 7H), 3.25 (dd, J = 5.8, 3.8 Hz, 4H), 2.29 (d, J = 10.4 Hz, 3H), 2.21-2.02 (m, 2H), 1.93-1.71 (m, 6H). |
| 605 | 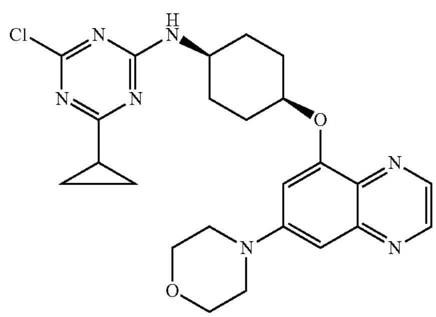 [SMILES: Clc1nc(N[C@H]2CC[C@@H](Oc3cc(N4CCOCC4)cc4nccnc34)CC2)nc(C2CC2)n1] | 482.3 | |
| 607 | 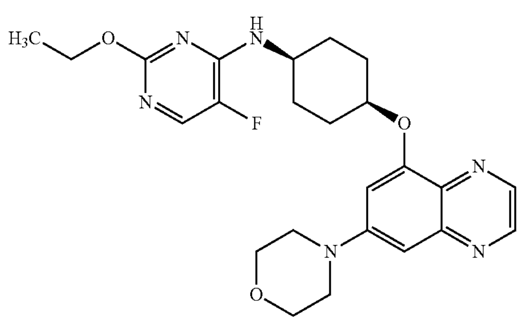 [SMILES: CCOc1ncc(F)c(N[C@H]2CC[C@@H](Oc3cc(N4CCOCC4)cc4nccnc34)CC2)n1] | 469.08 | 1H NMR (300 MHz, Chloroform-d) δ 8.71 (d, J = 1.9 Hz, 1H), 8.63 (d, J = 1.9 Hz, 1H), 7.79 (d, J = 2.9 Hz, 1H), 6.93 (dd, J = 17.8, 2.5 Hz, 2H), 5.19-5.07 (m, 1H), 4.80 (dt, J = 6.7, 3.4 Hz, 1H), 4.32 (q, J = 7.1 Hz, 3H), 3.98-3.87 (m, 4H), 3.41-3.29 (m, 4H), 2.30-2.13 (m, 2H), 2.03-1.84 (m, 6H), 1.41 (t, J = 7.1 Hz, 3H). |

TABLE 2-continued

| Cmpd. No. | Compound Structure | ESMS (M + H) | ¹H NMR |
|---|---|---|---|
| 608 | 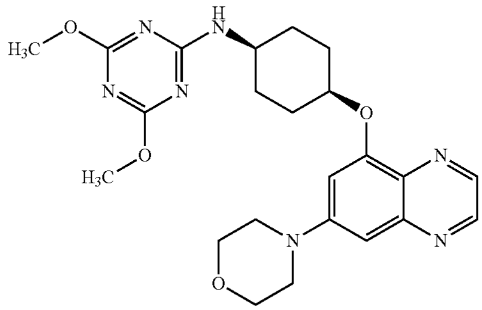 [SMILES: COc1nc(N[C@H]2CC[C@@H](Oc3cc(N4CCOCC4)cc4nccnc34)CC2)nc(OC)n1] | 468.63 | 1H NMR (300 MHz, Chloroform-d) δ 8.71 (d, J = 1.9 Hz, 1H), 8.63 (d, J = 2.0 Hz, 1H), 6.94 (dd, J = 18.9, 2.5 Hz, 2H), 5.42 (d, J = 8.4 Hz, 1H), 4.79 (s, 1H), 4.22-4.06 (m, 1H), 4.03-3.89 (m, 10H), 3.42-3.22 (m, 4H), 2.19 (m, 2H), 2.01-1.79 (m, 6H). |
| 609 | 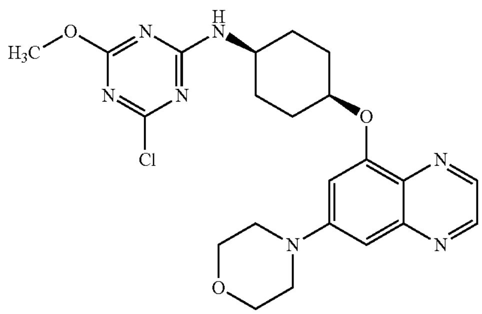 [SMILES: COc1nc(Cl)nc(N[C@H]2CC[C@@H](Oc3cc(N4CCOCC4)cc4nccnc34)CC2)n1] | 471.87 | 1H NMR (300 MHz, Chloroform-d) δ 8.72 (d, J = 1.9 Hz, 1H), 8.63 (d, J = 1.9 Hz, 1H), 7.03-6.84 (m, 2H), 5.66 (d, J = 9.1 Hz, 1H), 4.82 (s, 1H), 4.09-3.84 (m, 7H), 3.35 (dd, J = 5.5, 3.6 Hz, 4H), 2.20 (s, 2H), 1.91 (d, J = 6.4 Hz, 6H). |
| 612 | 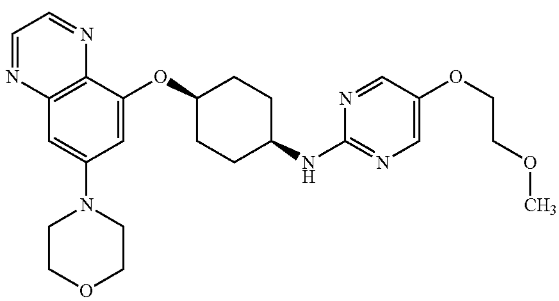 [SMILES: COCCOc1cnc(N[C@H]2CC[C@@H](Oc3cc(N4CCOCC4)cc4nccnc34)CC2)nc1] | 481.3 | 1H NMR (300 MHz, CDCl3): ppm 1.83-1.96 (m, 6 H), 2.14-2.24 (m, 2 H), 3.31-3.35 (m, 4 H), 3.44 (s, 3 H), 3.69-3.72 (m, 2 H), 3.89-3.95 (m, 5 H), 4.06-4.09 (m, 2 H), 4.74-4.83 (m, 1 H), 5.04-5.15 (m, 1 H), 6.90 (d, J = 2.4 Hz, 1 H), 6.94 (d, |
| 614 | 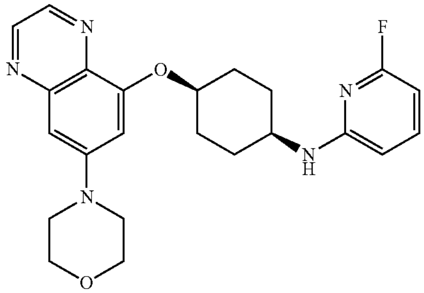 [SMILES: Fc1cccc(N[C@H]2CC[C@@H](Oc3cc(N4CCOCC4)cc4nccnc34)CC2)n1] | 424.2 | 1H NMR (300 MHz, CDCl3): ppm 1.83-1.95 (m, 6 H), 2.12-2.26 (m, 2 H), 3.30-3.40 (m, 4 H), 3.85-3.96 (m, 5 H), 4.55-4.68 (m, 1 H), 4.74-4.82 (m, 1 H), 6.10 (dd, J = 7.7, 1.8 Hz, 1 H), 6.18 (dd, J = 8.0, 1.8 Hz, 1 H), 6.90 (d, J = 1.8 Hz, 1 H), 6 |
| 615 | 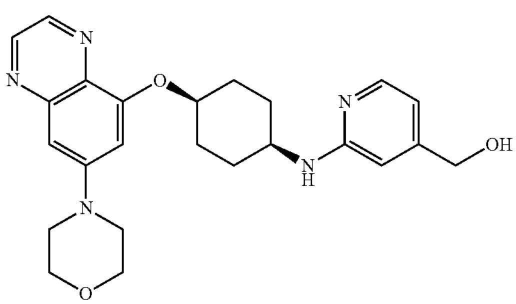 [SMILES: OCc1ccnc(N[C@H]2CC[C@@H](Oc3cc(N4CCOCC4)cc4nccnc34)CC2)c1] | 436.3 | 1H NMR (300 MHz, CDCl3): ppm 1.82-2.10 (m, 7 H), 2.14-2.29 (m, 2 H), 3.26-3.40 (m, 4 H), 3.82-4.05 (m, 5 H), 4.64 (s, 2 H), 4.75-4.84 (m, 1 H), 4.85-5.13 (m, 1 H), 6.46 (s, 1H), 6.51 (d, J = 5.3 Hz, 1 H), 6.90 (d, J = 1.7 Hz, 1 H), 6.94 (d, |

TABLE 2-continued

| Cmpd. No. | Compound Structure | ESMS (M + H) | ¹H NMR |
|---|---|---|---|
| 616 | 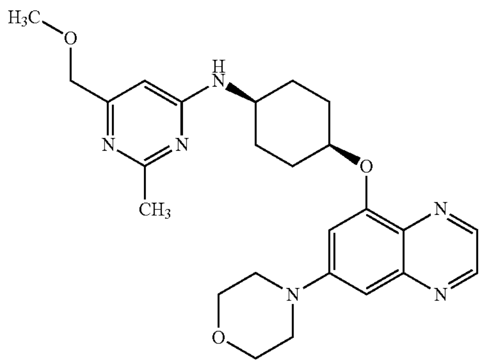 [SMILES: COCc1cc(N[C@H]2CC[C@@H](Oc3cc(N4CCOCC4)cc4nccnc34)CC2)nc(C)n1] | 465.1 | 1H NMR (300 MHz, Chloroform-d) δ 8.71 (d, J = 1.9 Hz, 1H), 8.63 (d, J = 1.9 Hz, 1H), 6.95 (dd, J = 16.6, 2.5 Hz, 2H), 6.30 (s, 1H), 5.02 (s, 1H), 4.82 (s, 1H), 4.38 (d, J = 0.9 Hz, 2H), 3.99-3.83 (m, 5H), 3.39-3.24 (m, 4H), 2.49 (s, 3H), 2.33-2.11 (m, 2H), 1.91 (q, J = 9.0, 6.9 Hz, 6H). |
| 618 | 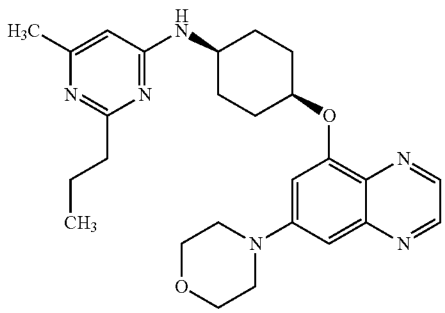 [SMILES: CCCc1nc(C)cc(N[C@H]2CC[C@@H](Oc3cc(N4CCOCC4)cc4nccnc34)CC2)n1] | 463.13 | 1H NMR (300 MHz, Chloroform-d) δ 8.63 (d, J = 1.9 Hz, 1H), 8.55 (d, J = 1.9 Hz, 1H), 6.86 (dd, J = 16.5, 2.5 Hz, 2H), 5.94 (s, 1H), 4.73 (s, 1H), 3.85 (dd, J = 5.9, 3.7 Hz, 4H), 3.35-3.20 (m, 4H), 2.67-2.51 (m, 2H), 2.26 (s, 3H), 2.09 (d, J = 36.8 Hz, 3H), 1.94-1.59 (m, 6H), 0.91 (t, J = 7.4 Hz, 3H). |
| 622 | 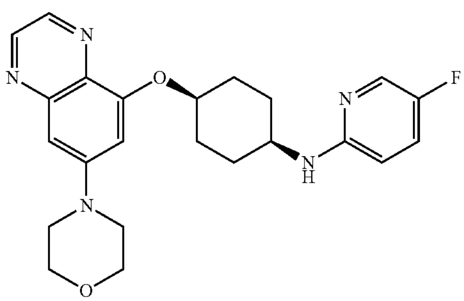 [SMILES: Fc1ccc(N[C@H]2CC[C@@H](Oc3cc(N4CCOCC4)cc4nccnc34)CC2)nc1] | 424.2 | 1H NMR (300 MHz, CDCl3): ppm 1.81-1.98 (m, 6 H), 2.13-2.25 (m, 2 H), 3.29-3.38 (m, 4 H), 3.75-3.85 (m, 1 H), 3.88-3.96 (m, 4 H), 4.56-4.71 (m, 1 H), 4.75-4.83 (m, 1 H), 6.36 (dd, J = 9.1, 3.3 Hz, 1 H), 6.90 (d, J = 1.9 Hz, 1 H), 6.95 (d, J = |
| 623 | 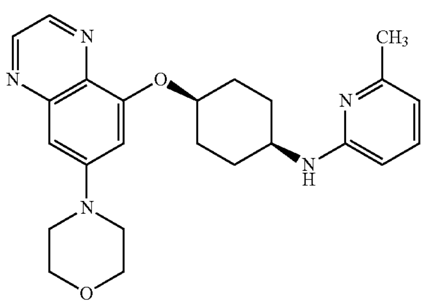 [SMILES: Cc1cccc(N[C@H]2CC[C@@H](Oc3cc(N4CCOCC4)cc4nccnc34)CC2)n1] | 420.3 | 1H NMR (300 MHz, CDCl3): ppm 1.80-1.98 (m, 6 H), 2.13-2.23 (m, 2 H), 2.38 (s, 3 H), 3.25-3.37 (m, 4 H), 3.62-3.77 (m, 1 H), 3.88-3.97 (m, 4 H), 4.76-4.83 (m, 1 H), 6.23 (d, J = 7.9 Hz, 1 H), 6.43 (d, J = 7.3 Hz, 1H), 6.91 (d, J = 2.5 Hz, 1 H) |
| 625 | 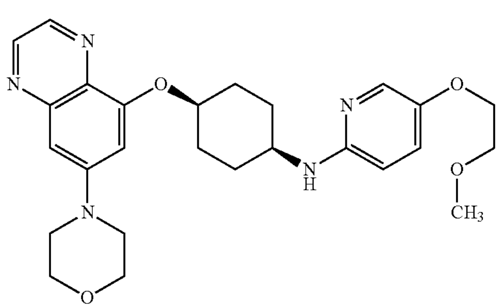 [SMILES: COCCOc1ccc(N[C@H]2CC[C@@H](Oc3cc(N4CCOCC4)cc4nccnc34)CC2)nc1] | 480.3 | 1H NMR (300 MHz, CDCl3): ppm 1.81-1.95 (m, 6 H), 2.11-2.26 (m, 2 H), 3.31-3.35 (m, 4 H), 3.44 (s, 3 H), 3.69-3.73 (m, 2 H), 3.76-3.84 (m, 1 H), 3.89-3.93 (m, 4 H), 4.04-4.08 (m, 2 H), 4.44 (br s, 1 H), 4.74-4.81 (m, 1 H), 6.37 (d, J = 8.9 |

TABLE 2-continued

| Cmpd. No. | Compound Structure | ESMS (M + H) | 1H NMR |
|---|---|---|---|
| 626 | 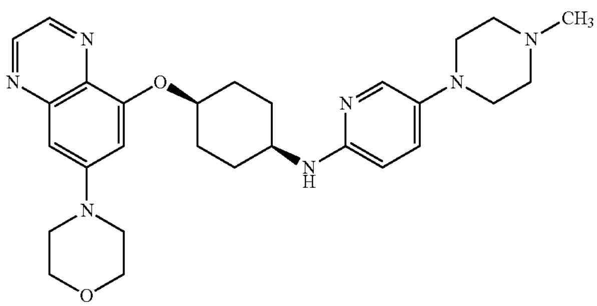 [SMILES: CN1CCN(c2ccc(N[C@H]3CC[C@@H](Oc4cc(N5CCOCC5)cc5nccnc45)CC3)nc2)CC1] | 504.3 | 1H NMR (300 MHz, CDCl3): ppm 1.81-1.98 (m, 6 H), 2.12-2.25 (m, 2 H), 2.37-2.48 (m, 3 H), 2.58-2.77 (m, 4 H), 3.04-3.16 (m, 4 H), 3.28-3.37 (m, 4 H), 3.77-3.85 (m, 1 H), 3.87-3.97 (m, 4 H), 4.32-4.51 (m, 1 H), 4.73-4.83 (m, 1 H), 6.38 ( |
| 627 | 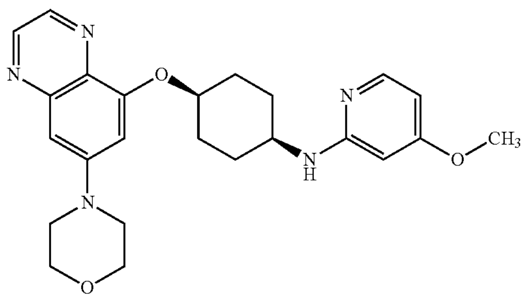 [SMILES: COc1ccnc(N[C@H]2CC[C@@H](Oc3cc(N4CCOCC4)cc4nccnc34)CC2)c1] | 436.3 | 1H NMR (300 MHz, CDCl3): ppm 1.81-2.03 (m, 7 H), 2.12-2.28 (m, 2 H), 3.28-3.39 (m, 4 H), 3.81 (s, 3 H), 3.87-3.98 (m, 5 H), 4.76-4.84 (m, 1 H), 5.87 (d, J = 1.5 Hz, 1 H), 6.21 (dd, J = 5.9, 1.5 Hz, 1 H), 6.91 (d, J = 1.7 Hz, 1 H), 6.95 (d, J = 1 |
| 629 | 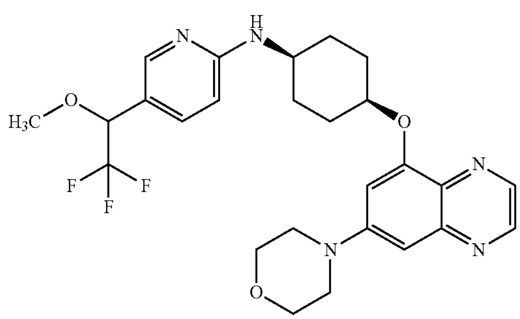 [SMILES: COC(c1ccc(N[C@H]2CC[C@@H](Oc3cc(N4CCOCC4)cc4nccnc34)CC2)nc1)C(F)(F)F] | 518.4 | 1H NMR (300 MHz, CDCl3) δ 8.62 (s, 1H), 8.54 (s, 1H), 8.15-7.93 (m, 1H), 7.40 (d, J = 8.0 Hz, 1H), 6.88 (s, 1H), 6.84 (s, 1H), 6.34 (d, J = 8.6 Hz, 1H), 4.83-4.56 (m, 2H), 4.40-4.22 (m, 1H), 4.00-3.62 (m, 5H), 3.47-3.04 (m, 7H), 2.24-2.02 (m, 2H), 1.96-1.70 (m, 6H). |
| 630 | 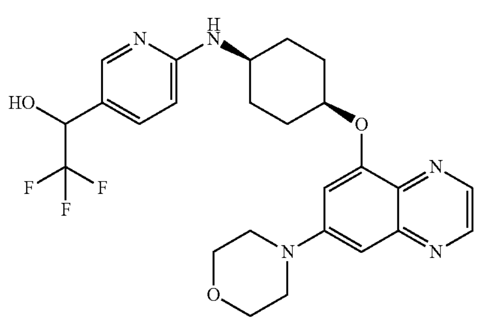 [SMILES: OC(c1ccc(N[C@H]2CC[C@@H](Oc3cc(N4CCOCC4)cc4nccnc34)CC2)nc1)C(F)(F)F] | 504.22 | 1H NMR (400 MHz, CDCl3) δ 8.68 (d, J = 1.8 Hz, 1H), 8.59 (d, J = 1.8 Hz, 1H), 8.06 (s, 1H), 7.55 (d, J = 8.3 Hz, 1H), 6.94 (d, J = 2.3 Hz, 1H), 6.89 (d, J = 2.2 Hz, 1H), 6.41 (d, J = 8.7 Hz, 1H), 4.88 (dd, J = 13.4, 6.7 Hz, 1H), 4.85-4.71 (m, 2H), 3.98-3.85 (m, 5H), 3.39-3.28 (m, 4H), 2.25-2.12 (m, 2H), 1.94-1.82 (m, 6H). |

TABLE 2-continued

| Cmpd. No. | Compound Structure | ESMS (M + H) | ¹H NMR |
|---|---|---|---|
| 633 | 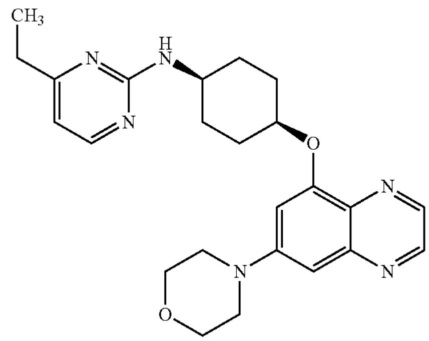 [SMILES: CCc1ccnc(N[C@H]2CC[C@@H](Oc3cc(N4CCOCC4)cc4nccnc34)CC2)n1] | 435.2 | 1H NMR (300 MHz, Chloroform-d) δ 8.70 (d, J = 1.9 Hz, 1H), 8.63 (d, J = 1.9 Hz, 1H), 8.18 (d, J = 5.1 Hz, 1H), 7.01-6.88 (m, 2H), 6.42 (d, J = 5.1 Hz, 1H), 5.15 (d, J = 8.0 Hz, 1H), 4.79 (d, J = 5.7 Hz, 1H), 4.17-4.00 (m, 1H), 3.98-3.83 (m, 4H), 3.67 (td, J = 6.7, 4.0 Hz, 1H), 3.42-3.31 (m, 4H), 2.59 (q, J = 7.6 Hz, 2H), 2.20 (q, J = 6.1 Hz, 2H), 2.03-1.86 (m, 6H), 1.26 (t, J = 7.6 Hz, 3H). |
| 634 | 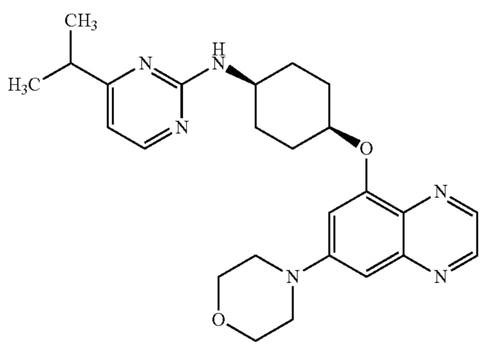 [SMILES: CC(C)c1ccnc(N[C@H]2CC[C@@H](Oc3cc(N4CCOCC4)cc4nccnc34)CC2)n1] | 449.2 | 1H NMR (300 MHz, Chloroform-d) δ 8.71 (d, J = 1.9 Hz, 1H), 8.63 (d, J = 1.9 Hz, 1H), 8.19 (d, J = 5.1 Hz, 1H), 7.01-6.88 (m, 2H), 6.42 (d, J = 5.2 Hz, 1H), 5.14 (d, J = 7.9 Hz, 1H), 4.80 (dt, J = 7.8, 3.8 Hz, 1H), 4.06 (d, J = 4.1 Hz, 0H), 3.99-3.85 (m, 4H), 3.46-3.24 (m, 4H), 2.78 (hept, J = 7.0 Hz, 1H), 2.34-2.11 (m, 2H), 2.04-1.81 (m, 7H), 1.25 (d, J = 7.0 Hz, 6H). |
| 636 | 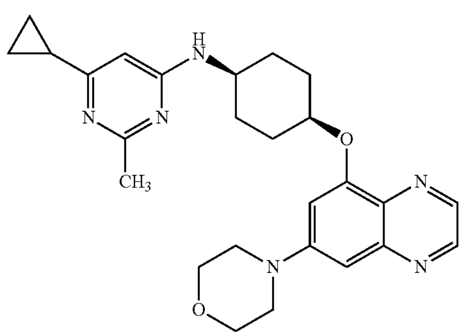 [SMILES: Cc1nc(N[C@H]2CC[C@@H](Oc3cc(N4CCOCC4)cc4nccnc34)CC2)cc(C2CC2)n1] | 461.1 | 1H NMR (300 MHz, Chloroform-d) δ 8.63 (d, J = 1.9 Hz, 1H), 8.54 (d, J = 1.9 Hz, 1H), 6.86 (dd, J = 16.2, 2.5 Hz, 2H), 5.85 (s, 1H), 4.75 (d, J = 5.5 Hz, 1H), 3.96-3.76 (m, 4H), 3.34-3.19 (m, 4H), 2.41 (s, 3H), 2.13 (d, J = 8.5 Hz, 2H), 1.82 (q, J = 10.2, 8.8 Hz, 6H), 1.58-1.33 (m, 3H), 1.03-0.86 (m, 3H). |
| 641 | 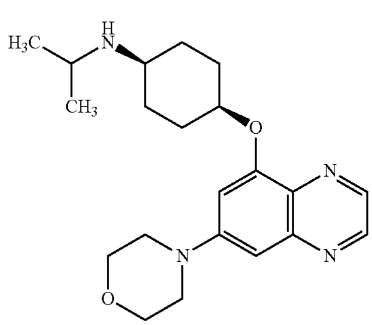 [SMILES: CC(C)N[C@H]1CC[C@@H](Oc2cc(N3CCOCC3)cc3nccnc23)CC1] | 371.56 | 1H NMR (400 MHz, CDCl3) δ 8.73-8.65 (m, 1H), 8.60 (d, J = 1.8 Hz, 1H), 6.93 (d, J = 2.4 Hz, 1H), 6.89 (d, J = 2.3 Hz, 1H), 4.75 (s, 1H), 3.95-3.87 (m, 4H), 3.39-3.28 (m, 4H), 3.05-2.93 (m, 1H), 2.82-2.69 (m, 1H), 2.24-2.08 (m, 2H), 1.80-1.71 (m, 6H), 1.07 (d, J = 6.2 Hz, 6H). |

TABLE 2-continued

| Cmpd. No. | Compound Structure | ESMS (M + H) | ¹H NMR |
|---|---|---|---|
| 642 | 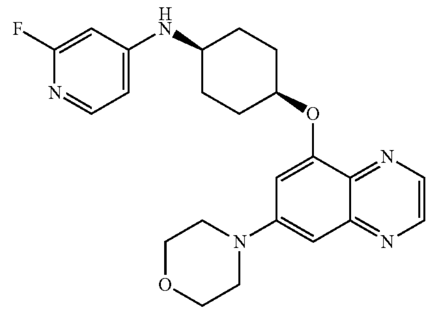 [SMILES: Fc1cc(N[C@H]2CC[C@@H](Oc3cc(N4CCOCC4)cc4nccnc34)CC2)ccn1] | 424.53 | 1H NMR (400 MHz, CDCl3) δ 8.70 (d, J = 1.9 Hz, 1H), 8.61 (d, J = 1.9 Hz, 1H), 7.78 (d, J = 5.8 Hz, 1H), 6.96 (d, J = 2.4 Hz, 1H), 6.90 (d, J = 2.4 Hz, 1H), 6.36-6.26 (m, 1H), 5.99 (d, J = 1.9 Hz, 1H), 4.79 (d, J = 2.4 Hz, 1H), 4.47 (d, J = 7.1 Hz, 1H), 3.99-3.85 (m, 4H), 3.56-3.49 (m, 1H), 3.39-3.26 (m, 4H), 2.28-2.16 (m, 2H), 1.98-1.80 (m, 6H). |
| 643 | 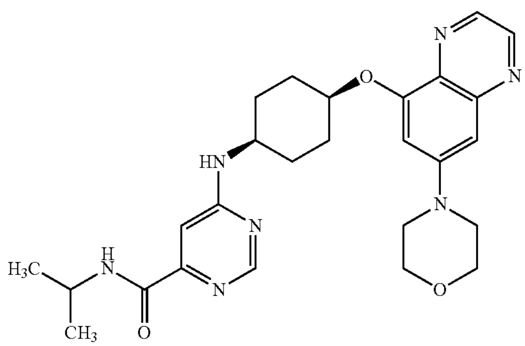 [SMILES: CC(C)NC(=O)c1cc(N[C@H]2CC[C@@H](Oc3cc(N4CCOCC4)cc4nccnc34)CC2)ncn1] | 492.2 | 1H NMR (300 MHz, Chloroform-d) δ 8.70 (d, J = 1.9 Hz, 1H), 8.61 (d, J = 1.9 Hz, 1H), 8.57-8.45 (m, 1H), 7.81 (d, J = 8.4 Hz, 1H), 7.18 (d, J = 1.2 Hz, 1H), 6.93 (dd, J = 16.8, 2.5 Hz, 2H), 5.48 (s, 1H), 4.83 (dp, J = 4.5, 2.4 Hz, 1H), 4.23 (dp, J = 8.3, 6.6 Hz, 1H), 4.00-3.85 (m, 4H), 3.42-3.23 (m, 4H), 2.35-3.15 (m, 2H), 1.97-1.76 (m, 6H), 1.26 (d, J = 6.6 Hz, 6H). |
| 644 | 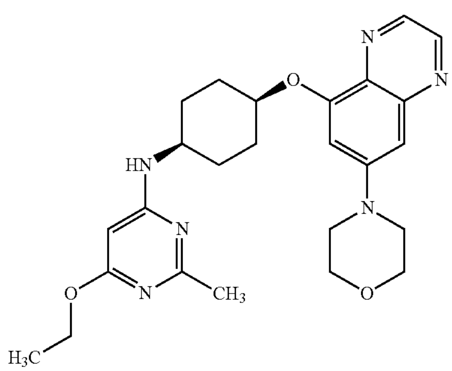 [SMILES: CCOc1cc(N[C@H]2CC[C@@H](Oc3cc(N4CCOCC4)cc4nccnc34)CC2)nc(C)n1] | 465.16 | 1H NMR (300 MHz, Chloroform-d) δ 8.69 (d, J = 1.9 Hz, 1H), 8.61 (d, J = 1.9 Hz, 1H), 6.93 (dd, J = 17.5, 2.5 Hz, 2H), 5.47 (s, 1H), 4.90 (s, 1H), 4.31 (q, J = 7.1 Hz, 2H), 3.92 (dd, J = 5.9, 3.7 Hz, 4H), 3.60 (s, 1H), 3.38-3.28 (m, 4H), 2.40 (s, 3H), 2.19 (d, J = 9.4 Hz, 2H), 1.97-1.80 (m, 6H), 1.36 (t, J = 7.1 Hz, 3H), 4.83-4.76 (m, 1H). |
| 650 | 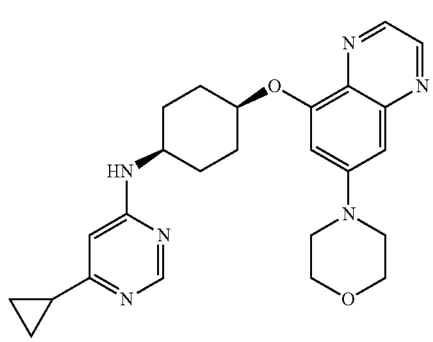 [SMILES: c1nc(N[C@H]2CC[C@@H](Oc3cc(N4CCOCC4)cc4nccnc34)CC2)cc(C2CC2)n1] | 447.2 | 1H NMR (300 MHz, Chloroform-d) δ 8.70 (d, J = 1.9 Hz, 1H), 8.62 (d, J = 1.9 Hz, 1H), 8.47-8.36 (m, 1H), 6.96 (d, J = 2.5 Hz, 1H), 6.90 (d, J = 2.5 Hz, 1H), 6.18 (d, J = 1.2 Hz, 1H), 4.95-4.73 (m, 2H), 4.04-3.78 (m, 5H), 3.44-3.24 (m, 4H), 2.30-2.12 (m, 2H), 2.03-1.70 (m, 7H), 1.17-0.80 (m, 4H). |

| Cmpd. No. | Compound Structure | ESMS (M + H) | ¹H NMR |
|---|---|---|---|
| 651 | 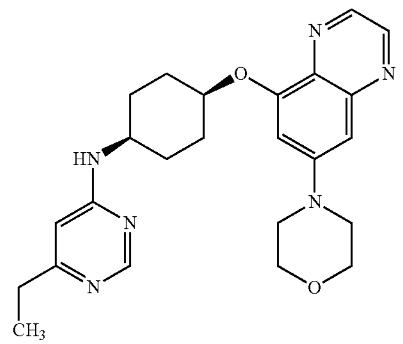 [SMILES: CCc1cc(N[C@H]2CC[C@@H](Oc3cc(N4CCOCC4)cc4nccnc34)CC2)ncn1] | 435.18 | 1H NMR (300 MHz, Chloroform-d) δ 8.70 (d, J = 1.9 Hz, 1H), 8.61 (d, J = 1.9 Hz, 1H), 8.50 (d, J = 1.1 Hz, 1H), 6.93 (dd, J = 15.9, 2.5 Hz, 2H), 6.17 (d, J = 1.1 Hz, 1H), 4.98 (d, J = 8.1 Hz, 1H), 4.86-4.75 (m, 1H), 3.97-3.87 (m, 4H), 3.39-3.29 (m, 4H), 2.61 (q, J = 7.6 Hz, 2H), 2.21 (dt, J = 11.2, 5.0 Hz, 2H), 2.04-1.82 (m, 6H), 1.25 (t, J = 7.6 Hz, 3H). |
| 652 | 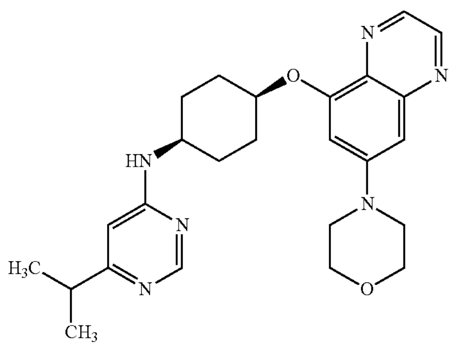 [SMILES: CC(C)c1cc(N[C@H]2CC[C@@H](Oc3cc(N4CCOCC4)cc4nccnc34)CC2)ncn1] | 449.23 | 1H NMR (300 MHz, Chloroform-d) δ 8.70 (d, J = 1.9 Hz, 1H), 8.61 (d, J = 1.9 Hz, 1H), 8.52 (d, J = 1.1 Hz, 1H), 6.93 (dd, J = 16.0, 2.5 Hz, 2H), 6.19-6.12 (m, 1H), 4.91 (d, J = 8.0 Hz, 1H), 4.81 (d, J = 5.4 Hz, 1H), 4.13-3.77 (m, 5H), 3.40-3.29 (m, 4H), 2.80 (hept, J = 6.8 Hz, 1H), 2.27-2.00 (m, 2H), 1.99-1.83 (m, 6H), 1.40-1.12 (m, 6H). |
| 653 | 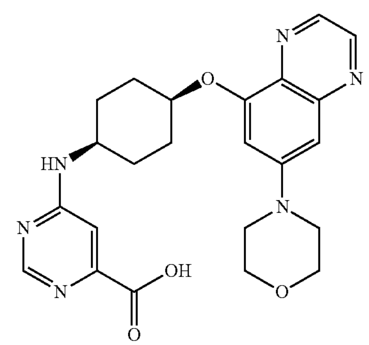 [SMILES: O=C(O)c1cc(N[C@H]2CC[C@@H](Oc3cc(N4CCOCC4)cc4nccnc34)CC2)ncn1] | 451.07 | 1H NMR (300 MHz, Methanol-d4/CDCl3) δ 8.82-8.68 (m, 2H), 8.61 (d, J = 0.8 Hz, 1H), 7.38 (t, J = 0.8 Hz, 1H), 7.18 (s, 1H), 5.11-4.99 (m, 1H), 4.47-4.31 (m, 1H), 3.99-3.88 (m, 4H), 3.74-3.58 (m, 4H), 2.37-2.23 (m, 2H), 2.13-1.80 (m, 6H). |
| 658 | 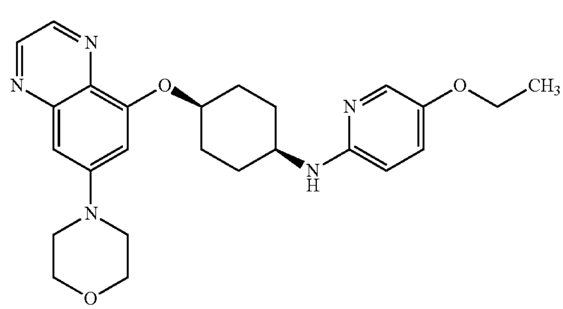 [SMILES: CCOc1ccc(N[C@H]2CC[C@@H](Oc3cc(N4CCOCC4)cc4nccnc34)CC2)nc1] | 450.3 | 1H NMR (300 MHz, CDCl3): ppm 1.37 (t, J = 7.0 HZ, 3 H), 1.84-1.94 (m, 6 H), 2.10-2.25 (m, 2 H), 3.29-3.38 (m, 4 H), 3.75-3.85 (m, 1 H), 3.88-3.95 (m, 4 H), 3.97 (q, J = 7.0 Hz, 2 H), 4.22-4.34 (m, 1 H), 4.73-4.80 (m, 1 H), 6.36 (d, J = 9.0 H |

TABLE 2-continued

| Cmpd. No. | Compound Structure | ESMS (M + H) | ¹H NMR |
|---|---|---|---|
| 659 | 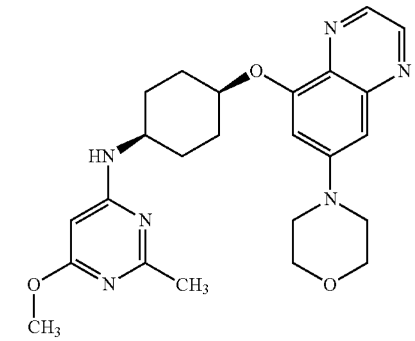 [SMILES: COc1cc(N[C@H]2CC[C@@H](Oc3cc(N4CCOCC4)cc4nccnc34)CC2)nc(C)n1] | 451.34 | 1H NMR (300 MHz, Chloroform-d) δ 8.69 (d, J = 1.9 Hz, 1H), 8.60 (d, J = 1.9 Hz, 1H), 6.92 (dd, J = 19.6, 2.5 Hz, 2H), 5.25 (s, 1H), 4.76 (q, J = 8.3, 7.2 Hz, 2H), 3.97-3.87 (m, 4H), 3.58-3.28 (m, 8H), 2.40 (s, 3H), 2.24-2.13 (m, 2H), 2.07-1.78 (m, 6H). |
| 660 | 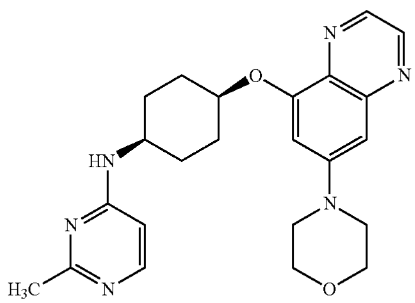 | | |
| 661 | 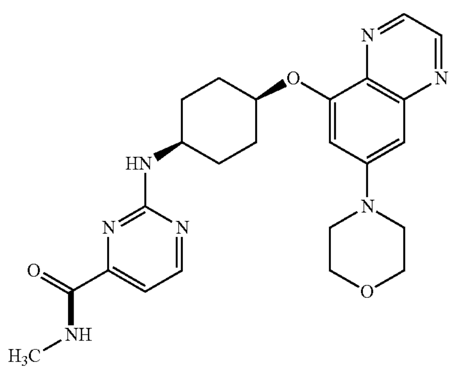 | | |
| 662 | | | |
| 663 | | | |
| 664 | | | |
| 665 | 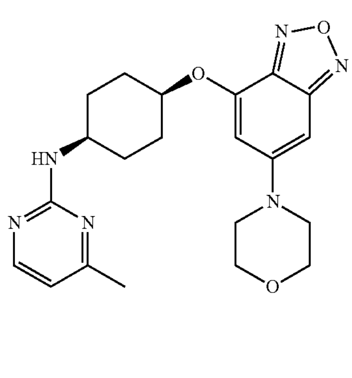 [SMILES: Cc1ccnc(N[C@H]2CC[C@@H](Oc3cc(N4CCOCC4)cc4nonc34)CC2)n1] | | |

TABLE 2-continued

| Cmpd. No. | Compound Structure | ESMS (M + H) | ¹H NMR |
|---|---|---|---|
| 666 | 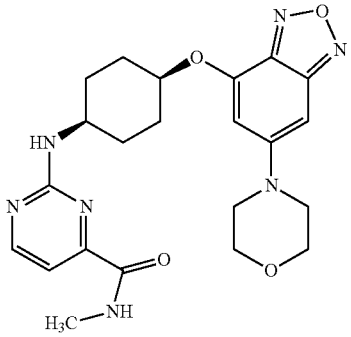 [SMILES: CNC(=O)c1ccnc(N[C@H]2CC[C@@H](Oc3cc(N4CCOCC4)cc4nonc34)CC2)n1] | | |

Biological Assay of Compounds of the Invention

Example 11. DNA-PK Inhibition Assay

Compounds were screened for their ability to inhibit DNA-PK kinase using a standard radiometric assay. Briefly, in this kinase assay the transfer of the terminal $^{33}$P-phosphate in $^{33}$P-ATP to a peptide substrate is interrogated. The assay was carried out in 384-well plates to a final volume of 50 µL per well containing approximately 6 nM DNA-PK, 50 mM HEPES (pH 7.5), 10 mM $MgCl_2$, 25 mM NaCl, 0.01% BSA, 1 mM DTT, 10 µg/mL sheared double-stranded DNA (obtained from Sigma), 0.8 mg/mL DNA-PK peptide (Glu-Pro-Pro-Leu-Ser-Gln-Glu-Ala-Phe-Ala-Asp-Leu-Trp-Lys-Lys-Lys, obtained from American Peptide), and 100 µM ATP.

Accordingly, compounds of the invention were dissolved in DMSO to make 10 mM initial stock solutions. Serial dilutions in DMSO were then made to obtain the final solutions for the assay. A 0.75 µL aliquot of DMSO or inhibitor in DMSO was added to each well, followed by the addition of ATP substrate solution containing $^{33}$P-ATP (obtained from Perkin Elmer). The reaction was started by the addition of DNA-PK, peptide and ds-DNA. After 45 min, the reaction was quenched with 25 µL of 5% phosphoric acid. The reaction mixture was transferred to MultiScreen HTS 384-well PH plates (obtained from Millipore), allowed to bind for one hour, and washed three times with 1% phosphoric acid. Following the addition of 50 µL of Ultima Gold™ high efficiency scintillant (obtained from Perkin Elmer), the samples were counted in a Packard TopCount NXT Microplate Scintillation and Luminescence Counter (Packard BioScience). The $K_i$ values were calculated using Microsoft Excel Solver macros to fit the data to the kinetic model for competitive tight-binding inhibition.

Each of compounds 18, 23, 24, 27-30, 32-34, 36-42, 44-46, 49-55, 59-61, 63-67, 69, 71, 72, 84, 87, 93, 94, 104, 108, 109, 134, 135, 139, 140, 142-146, 152, 155, 158, 160-162, 164, 187, 189-191, 193-210, 215, 219, 223-227, 233-237, 241-243, 245-247, 254, 256, 257, 260, 263-265, 267-269, 272, 273, 275-277, 282, 283, 285, 286, 287, 291, 295, 297, 298, 308, 309, 312, 314, 315-319, 321, 323, 324, 333-336, 340, 341, 351-354, 366, 369, 373-377, 380, 382, 386-388, 393-397, 399, 401, 402, 404-409, 417-422, 424, 427-430, 436, 438-451, 453-457, 463, 465, 467, 469, 471, 472, 474, 476-478, 481, 482, 485, 486, 489-492, 494, 499, 511, 512, 525, 531-535, 537, 539, 547, 548, 553, 558, 565, 567, 572-577, 579, 582-584, 586-595, 597, 598, 600-605, 607-609, 612, 614-616, 618, 622, 623, 625-627, 629, 630, 633, 634, 636, 642-644, 650-653, and 658-666 has a $K_i$ of less than 1.0 micromolar for the inhibition of DNA-PK.

Each of compounds 18, 23, 24, 27-30, 32-34, 36-37, 39-41, 44-46, 49-55, 59-61, 63-67, 69, 71, 72, 84, 87, 93, 94, 104, 108, 109, 134, 135, 139, 140, 142-146, 152, 155, 158, 160-162, 164, 187, 189-191, 193-200, 202-210, 215, 219, 223-227, 233-237, 241-243, 245-247, 254, 256, 257, 260, 263-265, 267-269, 272, 273, 275-277, 282, 283, 285, 286, 287, 291, 295, 297, 298, 308, 309, 312, 314, 315-319, 321, 323, 324, 333-336, 340, 341, 351-354, 366, 369, 373-374, 376-377, 380, 382, 386-388, 393-397, 399, 401, 402, 404-409, 417-422, 424, 427-430, 436, 438-451, 453-457, 463, 465, 467, 469, 471, 472, 474, 476-478, 481, 482, 485, 486, 489-492, 494, 499, 511, 512, 531-535, 537, 539, 547, 548, 553, 558, 565, 567, 572-577, 579, 582-584, 586-595, 597, 598, 600-605, 607-609, 612, 614-616, 618, 622, 623, 625-627, 629, 630, 633, 634, 636, 642-644, 650-653, and 658-666 has a $K_i$ of less than 0.10 micromolar for the inhibition of DNA-PK. For example, Compounds 661, 665, and 666 have a $K_i$ of 0.001 micromolar and Compound 663 has a $K_i$ of 0.008 micromolar for the inhibition of DNA-PK.

Gene Editing Examples

Example 12. Materials and Methods

Methods:
Cells and Culture

Bronchial Epithelial Cells (BECs) were derived from human donors diagnosed with Cystic Fibrosis with a CFTR dF508/dF508 genotype.

Induced Pluripotent Stem Cells (iPSCs) were derived from human dermal fibroblasts after viral transduction with Yamanaka's reprogramming factors, Oct4, Sox2, KLF4 and c-Myc. Derived iPSCs were able to differentiate into 3 germ layers and contained a normal karyotype with 23 pairs of Chromosomes.

Primary human mobilized peripheral blood (mPB) CD34$^+$ hematopoietic stem and progenitor cells (HSPCs) were purchased from Hemacare or AllCells. Cells were thawed, washed and resuspended in complete medium comprised of serum free medium CellGro SCGM (CellGenix) and supplemented with cytokine mix (300 ng/mL SCF, 300 ng/mL Flt3 L, 100 ng/mL TPO, 60 ng/ml IL-3) at a density of 1-3×10$^5$ cells per mL and incubated at 37° C./5% $CO_2$ incubator for 48 hours prior to electroporation.

DNA-PK Inhibitors:

The DNA-PK inhibitor Compounds 661, 663, 665 and 666 were used for the gene editing examples. 10 mM stock solutions were made by using anhydrous DMSO and store at −80° C.

Electroporation:

The synthetic sgRNAs used were purchased HPLC (high-performance liquid chromatography) purified from Synthego and contained chemically modified nucleotides (2'-O-methyl 3'-phosphorothioate) at the three terminal positions at both the 5' and 3' ends. The sequences of the sgRNAs with the modified nucleotides are underlined as follows:

```
AAVS1 sgRNA:
                                    (SEQ ID NO: 3)
5' ACCCCACAGUGGGGCCACUAGUUUUAGAGCUAGAAAUAGCAAGUUAA

AAUAAGGCUAGUCCGUUAUCAACUUGAAAAAGUGGCACCGAGUCGGUG

CUUUU 3'.

NAV 1.7 sgRNA:
                                    (SEQ ID NO: 4)
5' GGCUGAGCGUCCAUCAACCAGUUUUAGAGCUAGAAAUAGCA

AGUUAAAAUAAGGCUAGUCCGUUAUCAACUUGAAAAAGUGGCACCGAG

UCGGUGCUUUU 3'
```

Cas9 mRNA was purchased from TriLink Biotechnologies (L-7206). Cas9 mRNA expresses a version of the *Streptococcus pyogenes* SF370 Cas9 protein (CRISPR Associated Protein 9) with nuclear localization signals. spCas9 mRNA also contains a CAP1 structure, a polyadenylated signal and modified Uridines to obtain optimal expression levels in mammalian cells.

Donor ssODNs were purchase from IDT. ssODNs contain a 10 nucleotide insertion sequence, to measure HDR events by TIDE assay, flanked by 40 nucleotides of homology arms. ssODNs contain 90 nucleotides in total and Phosphorothioate modified nucleotides at the three terminal positions at both 5' and 3' ends. The sequences of donor ssODNs with the underlined Phosphorothioate modified nucleotides are indicated as follows:

```
AAVS1 PAM:
                                    (SEQ ID NO: 5)
5'GGGTACTTTTATCTGTCCCCTCCACCCCACAGTGGGGCCAGAA

TTCTCAGCTAGGGACAGGATTGGTGACAGAAAAGCCCCATCCTTAGG3'

AAVS1 Non-PAM:
                                    (SEQ ID NO: 6)
5'CCTAAGGATGGGGCTTTTCTGTCACCAATCCTGTCCCTAGCTG

AGAATTCTGGCCCCACTGTGGGGTGGAGGGGACAGATAAAAGTACCC3'

NAV1.7 PAM:
                                    (SEQ ID NO: 7)
5'AGCTGTCCATTGGGGAGCATGAGGGCTGAGCGTCCATCAACT

GAGAATTCCCAGGGAGACCACACCGTTGCAGTCCACAGCACTGTGCAT3'

NAV1.7 Non-PAM:
                                    (SEQ ID NO: 8)
5'ATGCACAGTGCTGTGGACTGCAACGGTGTGGTCTCCCTGGGA

ATTCTCAGTTGATGGACGCTCAGCCCTCATGCTCCCAATGGACAGCT3'
```

All electroporations were performed on the Lonza 4D-Nucleofector™ System.

For BECs, the following conditions were used for electroporation: 1.8×E5 Cells, 250 ng of CAS9 mRNA, 500 ng of sgRNA and 0.66 uM of ssODN in 20 ul of P4 Electroporation buffer by using program CM-138. The electroporated cells were transferred to a 96 well plate containing 100 ul of BECs culture media supplemented with DNA-PK inhibitors or left untreated. Cells were incubated at 37° C. in a 5% $CO_2$ incubator.

For iPSCs the following conditions were used: 2.0×E5 Cells, 250 ng of CAS9 mRNA, 500 ng of sgRNA and 0.66 uM of ssODN in 20 ul of P3 Electroporation buffer by using program CA-137. The electroporated cells were transferred to a 96 well plate containing 100 ul of mTEsR1 media (Stem Cell Technologies) supplemented with 10 uM ROCK Inhibitor Y-27632 (Stem Cell Technologies) with or without DNA-PK inhibitors and then incubated at 37° C. in a 5% $CO_2$ incubator.

CD34$^+$ cells were electroporated two days post thaw. The following conditions were used for electroporation: 2.0×E6 cells, 15 µg Cas9 protein (Feldan), 15 µg sgRNA, 1 µM of ssODN in 100 µl of P3 electroporation buffer using program CA-137. Electroporated cells were transferred by equally dividing them into eight wells of a 24-well plate, each well containing various concentrations of DNA-PK inhibitors. Cells were incubated at 37° C. in a 5% $CO_2$ incubator for two days and evaluated for cell viability and gene editing.

Lipid-Mediated Cell Transfection:

One day prior to transfection, BECs were seeded in a 96-well plate at a cell density of 1×E4 cells per well in BECs culture media. First, 0.15 ul of MessengerMax (ThermoFisher, LMRNA 003) was diluted into 5 ul of Opti-MEM and incubated for 10 min at room temperature. Meanwhile, 80 ng of Cas9 mRNA (Trilink, L-7206), 20 ng of sgRNA (Synthego) and 1 picomol of ssODN were added to 5 ul of Opti-MEM and then mixed with MessengerMAx solution. The mixture was incubated for 5 min prior to addition to the cells. The entire solution was added to the cells in a well of 96-well plate with 100 ul of culture media with or without DNA-PK inhibitors. Cells were incubated at 37° C. for in a 5% $CO_2$ incubator.

Measurement of Cell Survival Rates:

Cells were incubated with 5 ug/ml of Hoechst 33342 (Life technologies: H3570) and 0.5 ug/ml of Propidium Iodide (PI; Life technologies: P3566) in culture media for 1 h at 37 degrees. Cells were imaged to measure Hoescht positive events (Live and death cells) and PI positive events (Death cells) by using a High-Content Imaging System (Molecular devices). Relative cell survival rate was calculated as follows: [(Hoescht$^+$ events−PI$^+$ events) of Sample]/(Hoescht$^+$ events−PI$^+$ events) of Control]*100. Control was Mock transfected cells and its cell survival rate was set arbitrarily as 100%.

CD34$^+$ HSPCs cell survival was measured using Cell Titer Glo (CTG) reagent (Promega). 100 µl of cell suspension was mixed with 100 µl complete CTG reagent. The chemiluminescent signal was measure using a luminometer and % of viable cells was calculated as compared to control cells (cells not treated with the DNA-PK inhibitors).

Measurement of Gene Editing Rates:

Genomic DNA was isolated by incubating cells with 50 ul DNA Quickextract solution (Epicentre) per well of 96 well plate for 30 min at 37° C. Cellular extract was mixed and transferred into a PCR plate and then incubated for 6 min at 65° C. and 2 min at 98° C. PCR reactions were carried out with 1 ul of Genomic DNA containing solution by using AccuPrime™ Pfx DNA Polymerase (Thermofisher, 12344024). PCR conditions were 4 min at 94° C. (1×), followed by 15 s at 94° C., 15 s at 60° C. and 1 min at 60° C. (40×). The PCR products were purified and then Sanger sequenced by GENEWIZ. The following primer pairs spanning the target site were used for PCR (FW, forward; RV, reverse). Primers used by Sanger Sequencing are indicated by an asterisk (*):

AAVS1_FW: 5' GGACAACCCCAAAGTACCCC 3' (SEQ ID NO: 9)

AAVS1_RV*: 5' aggatcagtgaaacgcacca 3'. (SEQ ID NO: 10)

NAV1.7_FW*: 5' gccagtgggttcagtggtat 3'. (SEQ ID NO: 11)

NAV1.7_RV: 5' tcagcattatccttgcattttctgt 3'. (SEQ ID NO: 12)

Each sequence chromatogram was analyzed using TIDE (Tracking of Indels by Decomposition) software (http://tide.nki.nl) (See also Brinkman et al., *Nucleic Acids Research*, Volume 42, Issue 22, 16 Dec. 2014, Pages e168). Mock-electroporated samples were used as the reference sequence, and parameters were set to an indel size of 30 nt, and the decomposition window was set to cover the largest possible window with high-quality traces. Total indel (insertion and deletions) rates were obtained directly from TIDE plots. HDR rates were the percentage of events with an insertion of 10 Nucleotides. NHEJ Rates were calculated as Total Indel rate–HDR rate. GraphPad Prism 7 software was used to make Graphs and to calculate the all Statistical information.

Example 13. DNA-PK Inhibitors Improve HDR Gene Editing Rates in BECs

FIG. 1 illustrates the design of the gene editing assays used in the examples below. To investigate the effect of DNA-PK inhibitors on HDR gene editing rates, BECs were electroporated with spCAS9 mRNA, NAV1.7 sgRNA and NAV1.7 Non-PAM ssODN and then incubated with different concentrations Compound 665 or left untreated (Control). Gene editing rates were determined by using TIDE assay 72 hs after electroporation. Gene editing rates were expressed in percentages and classified as HDR and NHEJ. Cell survival rates are shown in percentages where control cells were set as 100%.

Figure 2:
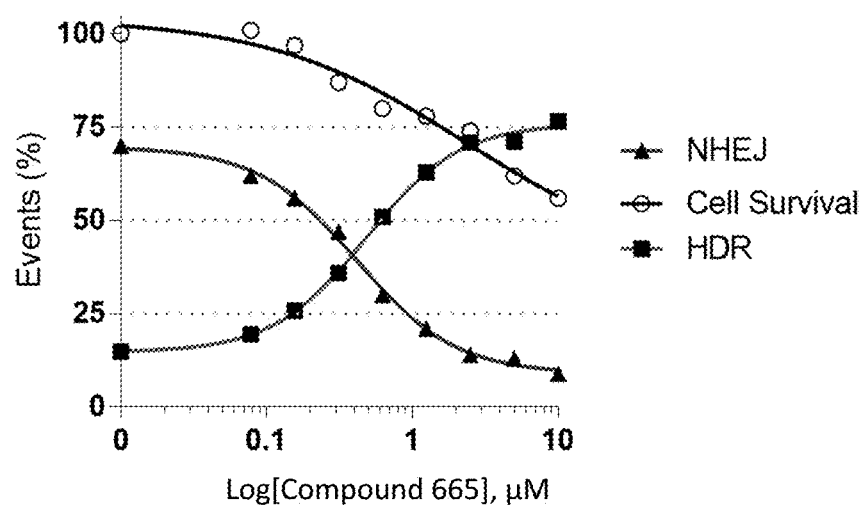
FIG. 2 is a graph showing gene editing rates in BECs treated with a DNA-PK inhibitor.

As shown in FIG. 2, the DNA-PK inhibitor of Compound 665 improves gene editing rates in BECs. For Compound 665, the NHEJ IC50 was 0.4163 µM, the HDR EC50 was 0.4834 µM and the HDR TOP % was 76.03.

Example 14. DNA-PK Inhibitors Improve HDR Gene Editing Rates in CD34+ Cells

Figure 3A:
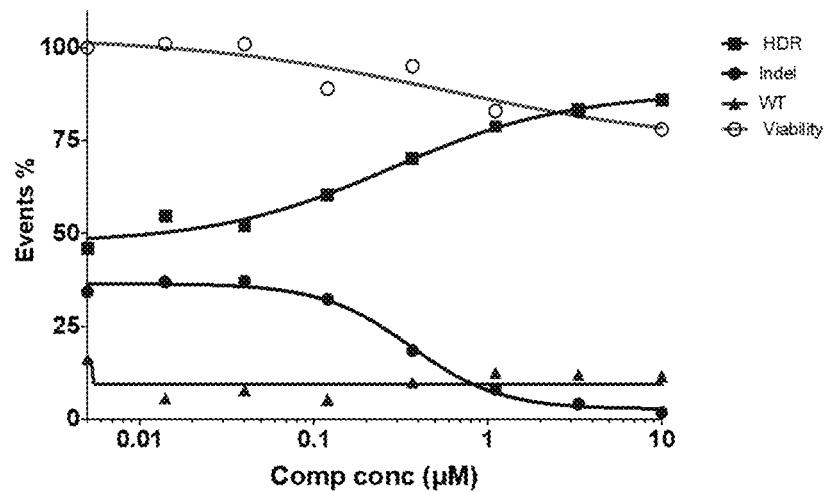
FIGS. 3A and 3B are graphs showing gene editing rates following DNA-PK inhibitor treatment in CD34$^+$ cells from two different donors.

To investigate the effect of DNA-PK inhibitors on HDR gene editing rates, mPB CD34+ cells were electroporated with RNP (spCAS9 protein+NAV1.7 sgRNA) and NAV1.7 Non-PAM ssODN. Cells were then incubated with various concentrations of Compound 665. Gene editing rates were determined by using TIDE assay 48 h after electroporation. Gene editing rates were expressed in percentages and classified as HDR and NHEJ as shown in FIG. 3A (Donor B) and FIG. 3B (Donor C). Cell survival rates are shown in percentages where control cells were set as 100%.

Figure 3B:
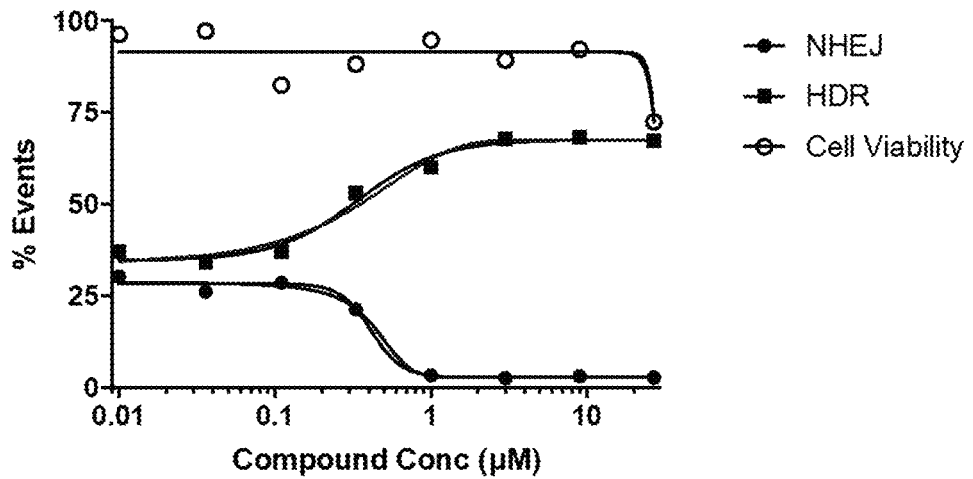

As shown in FIGS. 3A and 3B, the DNA-PK inhibitor of Compound 665 improves gene editing rates in CD34+ cells. EC50 values of HDR and Indel formation for Donor B were 0.28 µM and 0.36 µM, respectively.

Example 15. DNA-PK Inhibitors Improve HDR Gene Editing Rates in iPSCs

To investigate the effect of DNA-PK inhibitors on HDR gene editing rates, iPSCs were electroporated with spCAS9 mRNA, AAVS1 sgRNA and AAVS1 PAM ssODN and then incubated with different concentrations of Compound 665 or left untreated (Control). Gene editing rates were determined by using TIDE assay 72 hs after electroporation. Gene editing rates were expressed in percentages and classified as HDR and NHEJ. Cell survival rates are shown in percentages where control cells were set as 100%.

Figure 4:
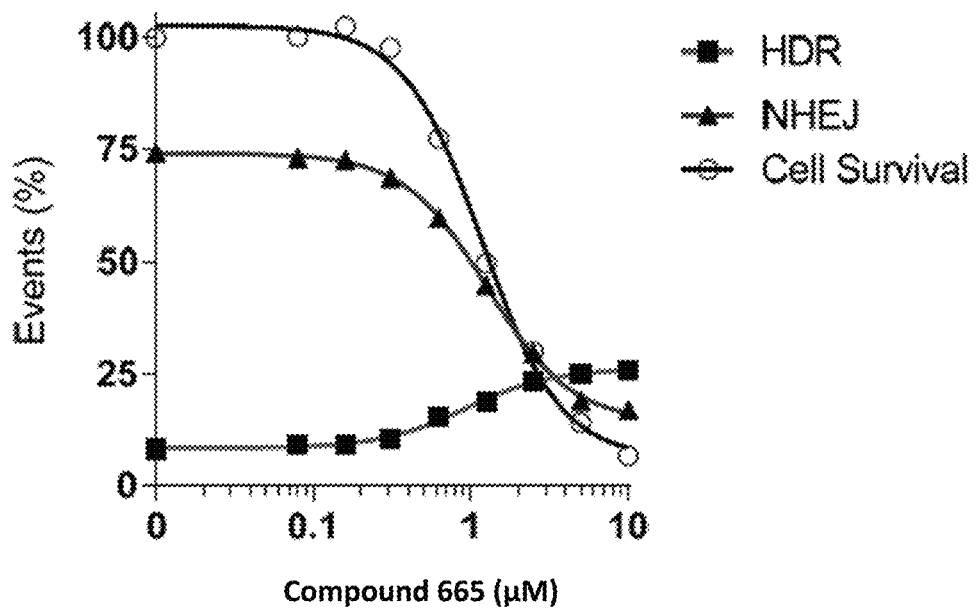
FIG. 4 is a graph showing gene editing rates in iPSCs treated with a DNA-PK inhibitor.

As shown in FIG. 4, the DNA-PK inhibitor of Compound 665 improves gene editing rates in iPSCs. For Compound 665, the NHEJ IC50 was 1.274 µM, the HDR EC50 was 0.9337 µM and the HDR TOP % was 26.27.

Example 16. Determination of Gene Editing Kinetics at ECmax

To investigate the gene editing kinetics at EC max, BECs were electroporated with spCAS9 mRNA, AAVS1 sgRNA and AAVS1 PAM ssODN and then incubated at different times with 10 µM Compound 665 or left untreated (Control). Gene editing rates were determined by using TIDE assay and expressed in percentages of HDR and NHEJ. 10 µM is the Maximum Enhance Concentration (ECmax) of Compound 665.

Figure 5:
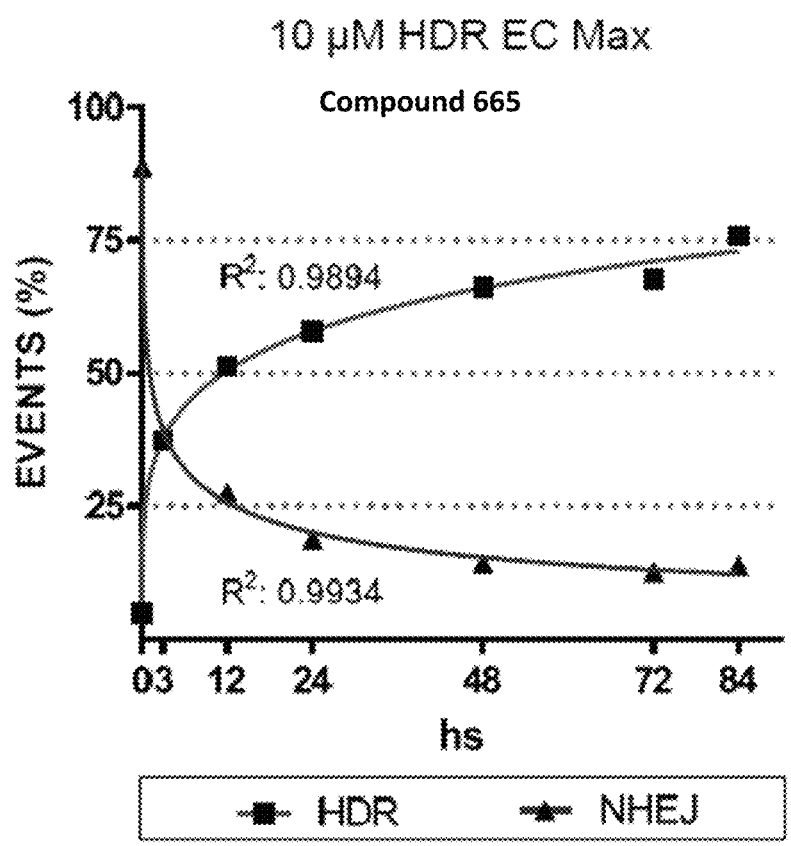
FIG. 5 is a graph showing gene editing kinetics in BECs at the DNA-PK inhibitor ECmax.

FIG. 5 shows that there is a tight inverse correlation between HDR and NHEJ events.

Example 17. Determination of Gene Editing Kinetics at EC50

Figure 6:
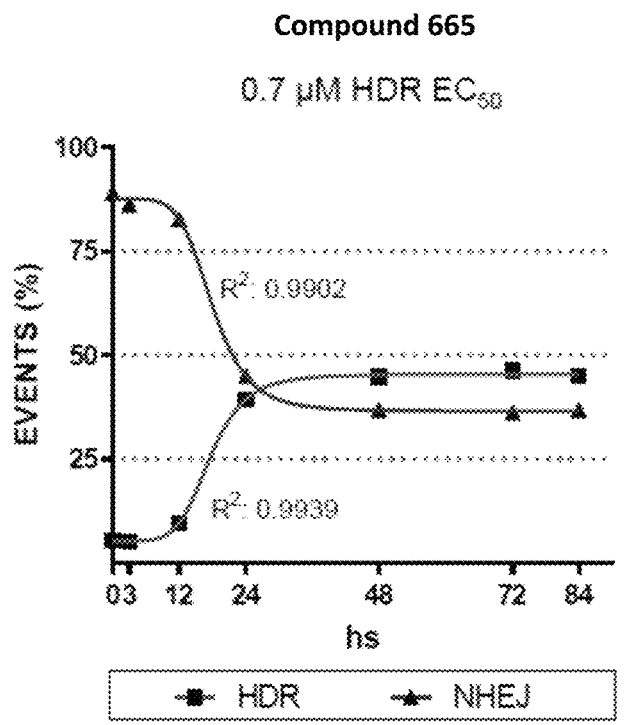
FIG. 6 is a graph showing gene editing kinetics in BECs at the DNA-PK inhibitor EC50.

BECs were electroporated with spCAS9 mRNA, AAVS1 sgRNA and AAVS1 PAM ssODN and then incubated at different times with 0.7 µM Compound 665 or left untreated (Control). Gene editing rates were determined by using TIDE assay and expressed in percentages of HDR and NHEJ. 0.7 µM is the Enhance Concentration 50 (EC50) of Compound 665. FIG. 6 illustrates the time course of DNA-PK inhibition on HDR and NHEJ in BECs.

Figure 7:
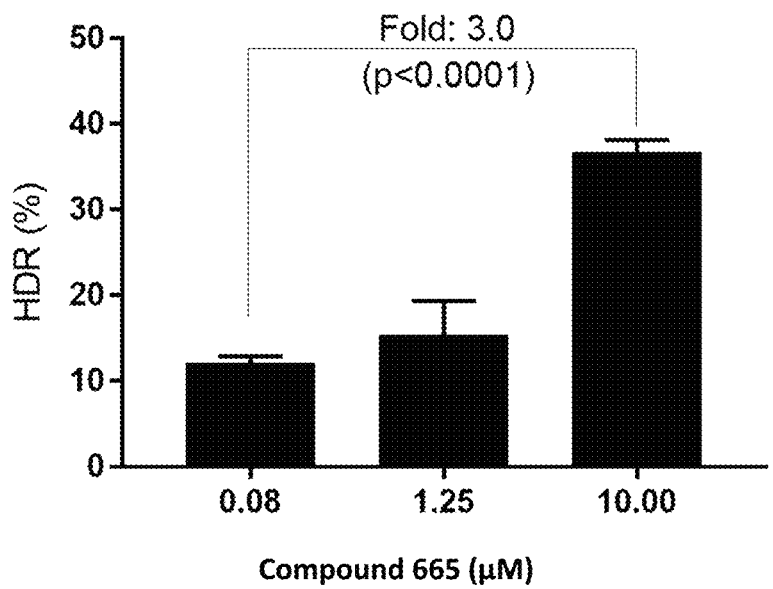
FIG. 7 is a bar graph showing HDR rates for gene editing components delivered by lipid-mediated transfection in BECs.

Example 18. DNA-PK Inhibitors Improve HDR Rates when Gene Editing Components were Delivered by Lipid-Mediated Transfection in BECs To investigate the effects of lipid-mediated transfection, BECs were transfected with spCAS9 mRNA, AAVS1 sgRNA and AAVS1 PAM ssODN and then incubated with different concentration of Compound 665 or left untreated (Control). Gene editing rates were determined by using TIDE assay 72 hs after transfection. FIG. 7 shows increasing HDR efficiency rates with increasing concentrations of Compound 665 delivered by lipid-based transfection.

Summary Table: DNA-PK Inhibitor of Compound 665 Improves HDR Driven Gene Editing

| Cells | Compound 665 | |
|---|---|---|
|  | AAVS1 | NaV1.7 |
|  | HDR EC50 (µM) and Max % | |
| BECs | 0.70 µM | 0.48 µM |
|  | 72% | 76% |
| iPSCs | 0.93 µM | N.D. |
|  | 26% | N.D. |
| CD34+'s |  |  |
| Donor A | 0.38 µM | 0.29 µM |
|  | 84% | 81% |
| Donor B | N.D. | 0.28 µM |
|  | N.D. | 86% |
| Donor C | 0.32 µM | 0.34 µM |
|  | 92% | 68% |

Example 19 mPB CD34+ cells were electroporated with RNP (spCAS9 protein+NAV1.7 sgRNA) and NAV1.7 Non-PAM ssODN. Cells were then incubated with various concentrations of Compounds 661, 663 and 666. Experiments were done as described in the methods above, except lower concentrations of sgRNA (5 µg) and ssODN (0.2 µM) were used. Gene editing rates were determined by using TIDE assay 48 h after electroporation. Gene editing rates were expressed in percentages and classified as HDR and NHEJ. The results for each Compound tested in two separate donors are shown below.

Compound 661

| | Compound 661 | | | | | | | |
|---|---|---|---|---|---|---|---|---|
| Compound | Donor A | | | | Donor D | | | |
| Conc (µM) | % HDR | % Indels | % WT | Viability | % HDR | % Indels | % WT | Viability |
| 10.00 | 28 | 47 | 18.9 | 6 | 13.4 | 64.2 | 11.1 | 11 |
| 3.33 | 32.2 | 57.8 | 5.1 | 47 | 11.5 | 76.7 | 6.4 | 75 |
| 1.11 | 31.7 | 59.4 | 4.2 | 60 | 10.8 | 77.5 | 6 | 62 |
| 0 | 11.9 | 77.4 | 3.3 | 100 | 3.2 | 76.2 | 7.5 | 100 |

Compound 663

| | Compound 663 | | | | | | | |
|---|---|---|---|---|---|---|---|---|
| Compound | Donor A | | | | Donor D | | | |
| Conc (µM) | % HDR | % Indels | % WT | Viability | % HDR | % Indels | % WT | Viability |
| 10.00 | 24.3 | 46.5 | 24.1 | 10 | 13.9 | 76.2 | 1 | 12 |
| 3.33 | | | | 37 | 11.3 | 81.8 | 1.9 | 64 |
| 1.11 | 35.7 | 55.3 | 4.4 | 65 | 8.5 | 81.3 | 5.4 | 83 |
| 0 | 11.9 | 77.4 | 3.3 | 100 | 3.2 | 76.2 | 7.5 | 100 |

Compound 666

| | Compound 666 | | | | | | | |
|---|---|---|---|---|---|---|---|---|
| Compound | Donor A | | | | Donor D | | | |
| Conc (µM) | % HDR | % Indels | % WT | Viability | % HDR | % Indels | % WT | Viability |
| 10.00 | 33.6 | 52 | 9.7 | 36 | 13.7 | 69 | 11.8 | 34 |
| 3.33 | 32.4 | 56.5 | 5.8 | 42 | 14.3 | 73.8 | 5.3 | 69 |
| 1.11 | 31.5 | 58.8 | 3.5 | 65 | 11 | 77.5 | 6.2 | 76 |
| 0 | 11.9 | 77.4 | 3.3 | 100 | 3.2 | 76.2 | 7.5 | 100 |

| Summary Table for Compounds 661, 663, 666 | | | | |
|---|---|---|---|---|
| | Conc. (µM) | Donor A | | Donor D | |
| | | % HDR | % NHEJ | % HDR | % NHEJ |
| Compound 666 | 0 | 11.9 | 77.4 | 3.2 | 76.2 |
| | 0.37 | 23.2 | 67.3 | 5.5 | 79.2 |
| | 1.11 | 31.5 | 58.8 | 11 | 77.5 |
| | 10 | 33.6 | 52 | 13.7 | 69 |
| Compound 661 | 0 | 11.9 | 77.4 | 3.2 | 76.2 |
| | 0.37 | 21.8 | 66.2 | 6.9 | 78.1 |
| | 1.11 | 31.7 | 59.4 | 10.8 | 77.5 |
| | 10 | 28 | 47 | 13.4 | 64.2 |
| Compound 663 | 0 | 11.9 | 77.4 | 3.2 | 76.2 |
| | 0.37 | 24.6 | 64.8 | 8.9 | 79.4 |
| | 1.11 | 35.7 | 55.3 | 8.5 | 81.3 |
| | 10 | 24.3 | 46.5 | 13.9 | 76.2 |

Example 20. DNA-PK Inhibitors Improve HDR Gene Editing Rates in CD34+ Cells

To investigate the effect of DNA-PK inhibitors on HDR gene editing rates, CD34+ cells were electroporated with spCAS9 mRNA, AAVS1 sgRNA and AAVS1 Non-PAM ssODN and then incubated with different concentrations of Compounds 666, 661, 663 or left untreated (Control). Gene editing rates were determined by using TIDE assay 72 hs after electroporation. Gene editing rates were expressed in percentages and classified as HDR and NHEJ. Cell survival rates are shown in percentages where control cells were set as 100%.

Figure 8:
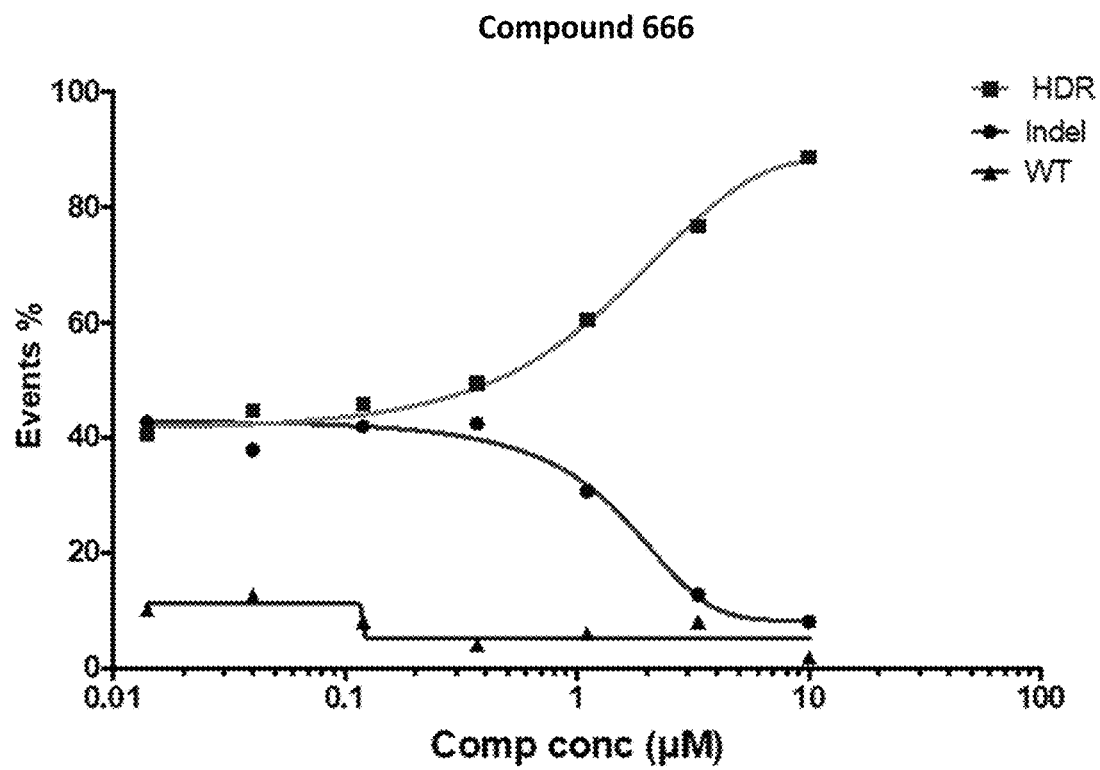
FIG. 8 is a graph showing gene editing rates in CD34⁺ treated with a DNA-PK inhibitor.
Figure 9:
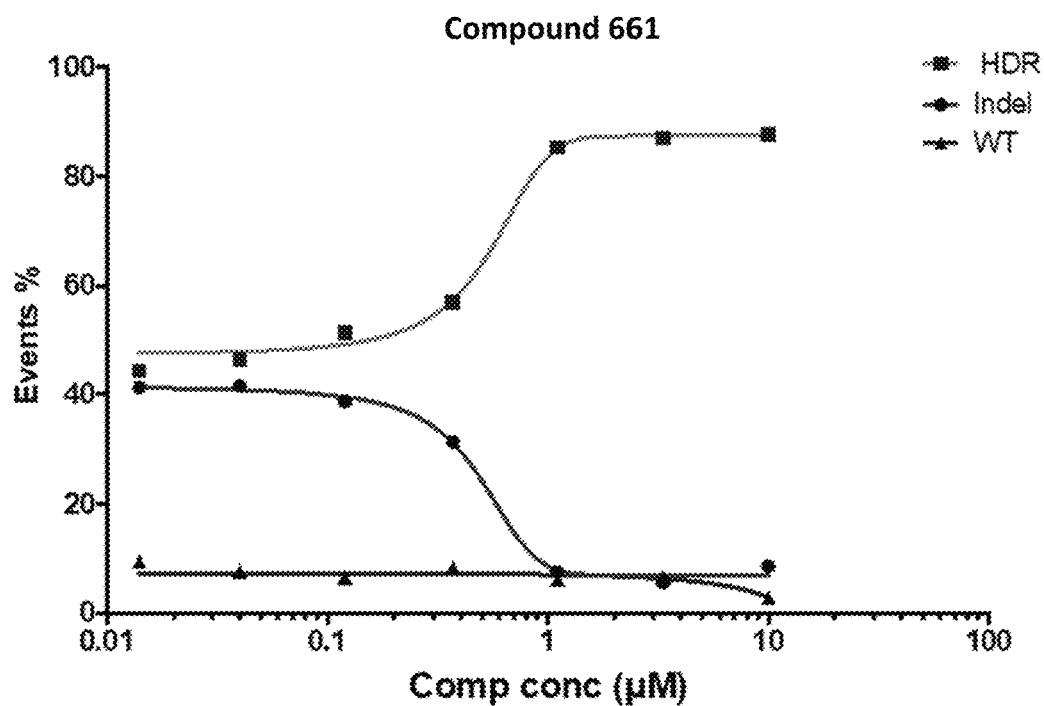
FIG. 9 is a graph showing gene editing rates in CD34⁺ treated with a DNA-PK inhibitor.
Figure 10:
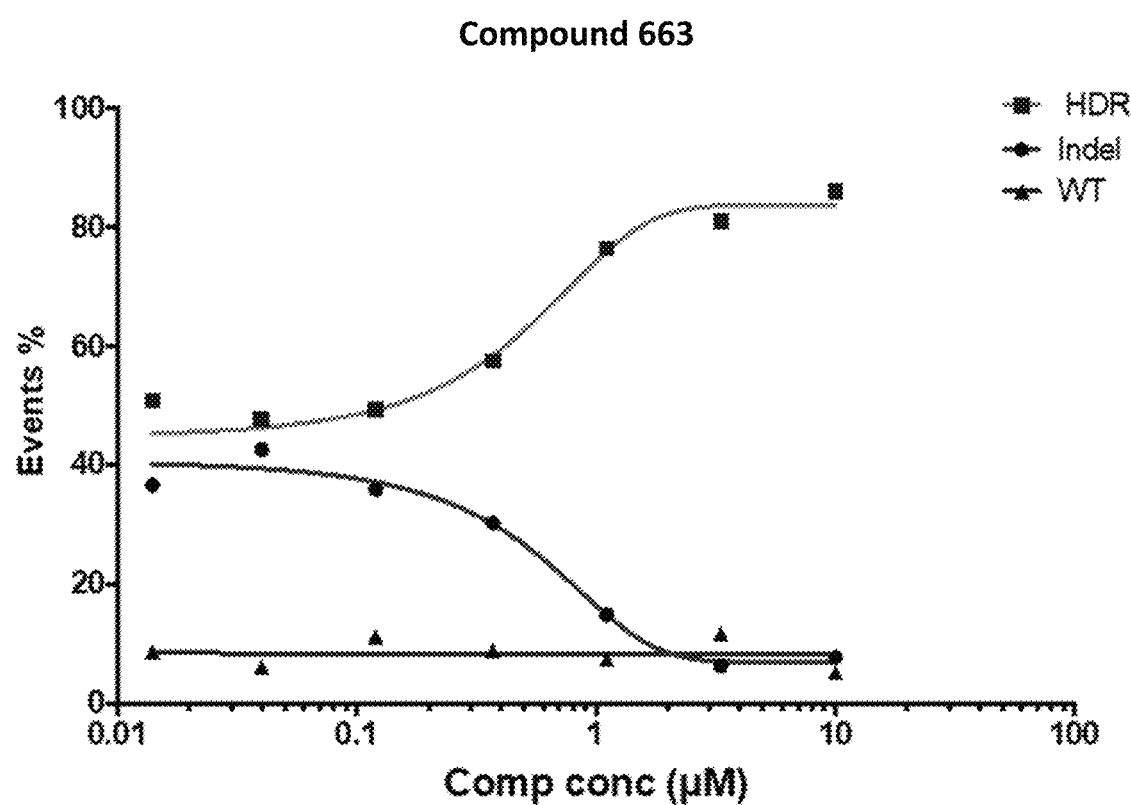
FIG. 10 is a graph showing gene editing rates in CD34⁺ treated with a DNA-PK inhibitor.

As shown, the DNA-PK inhibitors of Compounds 666 (FIG. 8), 661 (FIG. 9) and 663 (FIG. 10) improve HDR rates in CD34+ cells.

Figure 11:
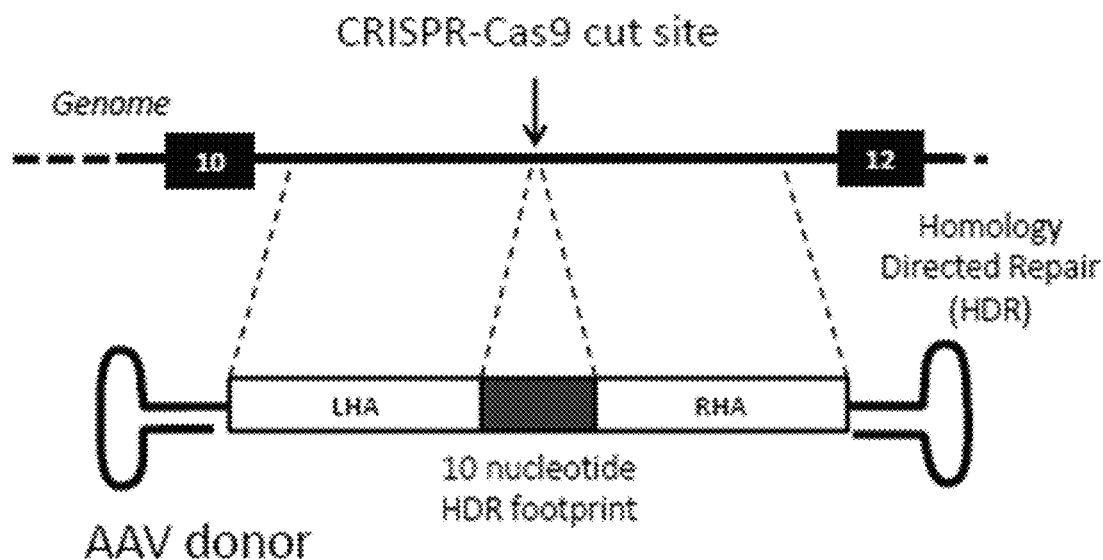
FIG. 11 depicts the design of a gene editing strategy to perform Homology-Driven Repair (HDR) using CRISPR-Cas9 using AAV donors.

Example 21. Precise Gene Editing by HDR Mediated by AAV Donors, CRISPR-Cas9 and Selective DNA-PK Inhibitors FIG. 11 illustrates the design of the gene editing assay used in this example.

Cells

Lung Progenitor Cells (LPCs) were derived from human lung donors diagnosed with Cystic Fibrosis. LPC donor ID 14071 and 14335 contain the CFTR genotypes dF508/dF508 and dF508/G542X, respectively.

CRISPR-Cas9 Gene Editing Reagents

Synthetic sgRNAs were purchased from Synthego. gRNAs were HPLC (high-performance liquid chromatography) purified and contain chemically modified nucleotides (2'-O-methyl 3'-phosphorothioate) at the three terminal positions at both the 5' and 3' ends. gRNAs contain a 22 nucleotides long spacer sequence to promote specific binding to target site and 80 nucleotides long scaffold sequence that allows binding to saCAS9 protein. Complete gRNA sequences are shown in Table 3.

saCas9 mRNA was synthetized by TriLink Biotechnologies. saCas9 mRNA expresses a *Staphylococcus aureus* Cas9 (Uniprot entry code J7RUA5) with SV40 and Nucleo-Plasmine nuclear localization signals. saCas9 mRNA also contains a CAP1 structure and a polyadenylated signal to obtain optimal expression levels in mammalian cells. saCAS9 mRNA was HPLC purified.

AAV Donor Constructs Design and AAV Transductions.

AAV donor constructs contain 500 nucleotide long sequences of left and right homology arms relative to gRNA cut site and a unique HDR footprint insertion of 10 nucleotides. AAV donor preparations were made by using AAV6 serotype, purified and titrated by Vector Biolabs. AAV titration was reported as viral genomes per ml. AAV transduction were done by adding AAV6 vector into cells at specified vector genome copies per cell during 36 h at 37° C.

Electroporation

Electroporations were performed by using the Lonza 4D-Nucleofector™ System coupled to 96-well shuttle system. 1.8×E5 LPC cells were resuspended in 20 ul of P4 Electroporation buffer Lonza (V4SP-4096). 20 ul of cell mixture was combined with 2 ul of CRISPR-Cas9 reagent mix containing 1 ug of saCAS9 mRNA and 1 ug of gRNA. 20 ul of cell and CRISPR-Cas9 mixture was transferred into one well of a 96-well electroporation plate. Cells were electroporated by using program CM-138. A fraction of electroporated LPC cells were transferred into a well of 384-well plate. Cells were transduced with AAV and DNA-PK inhibitor or left untreated (Control) during 36 hs in a 5% $CO_2$ incubator. Genomic DNA was isolated after 72 h.

Genomic DNA Isolation.

Genomic DNA was isolated by incubating cells during 30 min at 37° C. with 50 ul and 15 ul of DNA Quickextract solution (Epicentre) per well of 96-well and 384-well plate, respectively. Cellular extract was mixed and transferred into a 96-well PCR plate and then incubated for 6 min at 65° C. and 2 min at 98° C. Genomic DNA was immediately use in downstream applications or it was store at 4° C.

Measurement of INDEL Rates

Phire Green Hot Start II PCR Master Mix (F126L, Thermo Scientific) was used to amplify DNA fragment corresponding to target genes. PCR reactions were carried out following manufacturer instructions. In brief, 1.25 ul of genomic DNA solution was combined with 23.5 ul of Phire Green Hot Start II PCR Master Mix and the corresponding target genes forward and reverse primers (Table 4). One of the primers binds outside of AAV donor sequence to avoid amplification of AAV donor. PCR reactions were performed with the following thermal cycling protocol: 1) 98° C. 30 s; 2), 98° C. 5 s; 3), 62° C. 5 s; 4) 72° C. 20 s repeat steps 2 to 4 30 times; 5) 72° C. 4 min The PCR products were enzymatically purified. DNA samples were Sanger sequenced by using sequencing primers as shown in Table 4. Each sequencing chromatogram was analyzed using TIDE software against reference sequences (described above). References sequences were obtained from mock-electroporated samples. Tide parameters were set to cover an indel spectrum of +/−30 nucleotides of gRNA cut site and the decomposition window was set to cover the largest possible window with high-quality traces. Total indel (insertion and deletions) rates were obtained directly from TIDE plots. GraphPad Prism 7 software was used to make Graphs and to calculate the all Statistical information.

TABLE 3 sgRNAs sequences

| Target | sgRNA |
|---|---|
| VEGFA | AUUCCCUCUUUAGCCAGAGCGUUUUAGUACUCUGGAAACAGAAU CUACUAAAACAAGGCAAAAUGCCGUGUUUAUCUCGUCAACUUGU UGGCGAGAUUUU (SEQ ID NO: 13) |
| EMX1 | CAACCACAAACCCACGAGGGGUUUUAGUACUCUGGAAACAGAAU CUACUAAAACAAGGCAAAAUGCCGUGUUUAUCUCGUCAACUUGU UGGCGAGAUUUU (SEQ ID NO: 14) |
| FANCF | CAAGGCCCGGCGCACGGUGGGUUUUAGUACUCUGGAAACAGAAU CUACUAAAACAAGGCAAAAUGCCGUGUUUAUCUCGUCAACUUGU UGGCGAGAUUUU (SEQ ID NO: 15) |
| RUNX | AAAGAGAGAUGUAGGGCUAGGUUUUAGUACUCUGGAAACAGAAU CUACUAAAACAAGGCAAAAUGCCGUGUUUAUCUCGUCAACUUGU UGGCGAGAUUUU (SEQ ID NO: 16) |

Note:
Each sgRNA contain a unique 22 nucleotides spacer sequence (Bold) follow by a common 80 nucleotides scaffold sequence.

TABLE 4

PCR and Sequencing primers

| Gene | PCR Forward primer | PCR Reverse Primer | Sequencing primer |
|---|---|---|---|
| VEGFA | AGACGTTCCTT AGTGCTGGC (SEQ ID NO: 17) | AGGAGGGAGCA GGAAAGTGA (SEQ ID NO: 18) | ATTCCCTCTTTAG CCAGAGC (SEQ ID NO: 19) |
| EMX1 | TGGCTGTCCAG GCACTGCTC (SEQ ID NO: 20) | GGCCTGTCCTC CCTCAAG (SEQ ID NO: 21) | CAACCACAAACCC ACGAGGG (SEQ ID NO: 22) |
| FANCF | ACACGGATAAA GACGCTGGG (SEQ ID NO: 23) | ACACGGATAAA GACGCTGGG (SEQ ID NO: 24) | CAAGGCCCGGCGC ACGGTGG (SEQ ID NO: 25) |
| RUNX1 | AACCCAGCATA GTGGTCAGC (SEQ ID NO: 26) | TCTGTGCATGT GCCTGCTAA (SEQ ID NO: 27) | AAAGAGAGATGTA GGGCTAG (SEQ ID NO: 28) |

Figure 12:
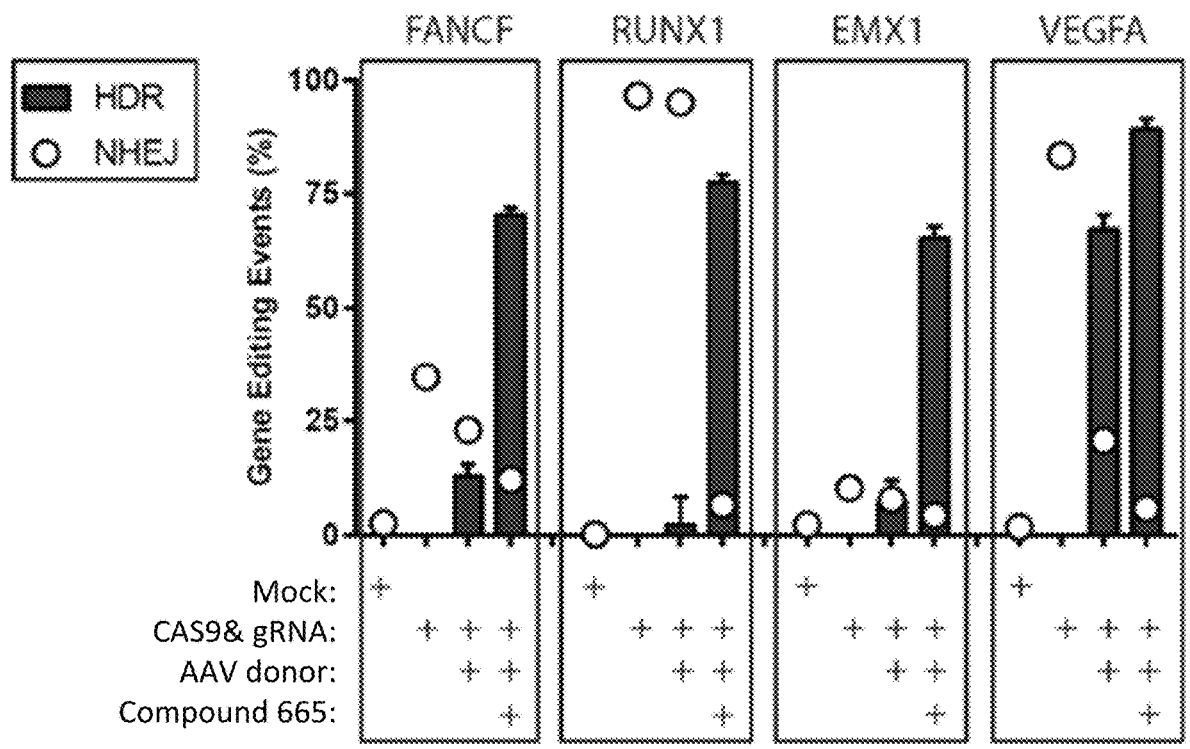
FIG. 12 is a graph showing precise gene editing by HDR mediated by AAV donors, CRISPR-Cas9 and a selective DNA-PK inhibitor.

LPCs were electroporated with saCAS9 mRNA together a set of sgRNA and AAV donors to target Fanconi anemia complementation group F (FANCF), runt-related transcription factor 1 (RUNX1), Empty Spiracles Homeobox 1 (EMX1) and Vascular endothelial growth factor A (VEGFA)

genes. Cells were incubated with DNA-PK inhibitor Compound 665 or left untreated (Control). Total Insertion and Deletions (INDELs) rates were determined by using TIDE assay 72 h after electroporation. Gene editing rates were expressed in percentages and classified as HDR (Bars) and NHEJ (Circles). HDR events were the amount of sequences with 10 nucleotides insertion. NHEJ rates were calculated by using the following formula: NHEJ=Total INDEL events−HDR events. Results are shown in FIG. 12.

Summary:

Results of the addition of DNA-PK inhibitors to different cell types and loci show significant enhancement of HDR across cell types and loci Enhancement of HDR gene editing has been shown in multiple cell types including BECs, iPSCs, CD34+ HPSCs (3 separate donors) Enhancement of HDR gene editing has been shown in multiple loci. Experimental results have also shown that lipid based and electroporation delivery is effective. Electroporation examples include BECs, iPSCs, CD34+ HPSCs and effect delivery using a lipid-based delivery system in BECs. A tight inverse correlation between HDR and NHEJ events has been observed across loci, experimental conditions and cell types.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of repairing a DNA break in one or more target genomic regions via a homology directed repair (HDR) pathway, comprising:
administering to one or more cells that comprise one or more target genomic regions, a genome editing system and a compound of formula

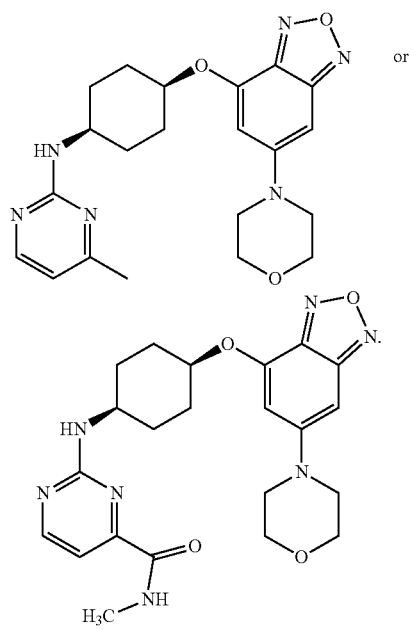

or a pharmaceutically acceptable salt thereof,
wherein the genome editing system interacts with a nucleic acid(s) of the target genomic regions, resulting in a DNA break, and wherein the DNA break is repaired at least in part via a HDR pathway.

2. A method of inhibiting or suppressing repair of a DNA break in one or more target genomic regions via a non-homologous end joining (NHEJ) pathway, comprising:
administering to one or more cells that comprise one or more target genomic regions, a genome editing system and
a compound of formula,

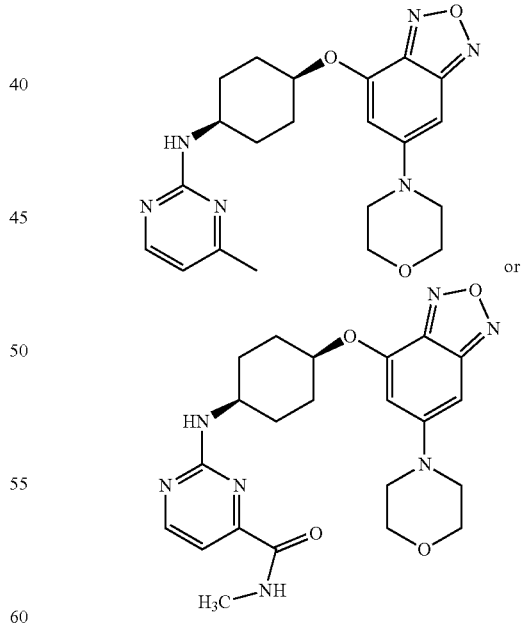

or a pharmaceutically acceptable salt thereof,
wherein the genome editing system interacts with a nucleic acid(s) of the one or more target genomic regions, resulting in a DNA break, and wherein repair of the DNA break via a NHEJ pathway is inhibited or suppressed.

3. A method of modifying expression of one or more genes or proteins comprising:
administering to one or more cells that comprise one or more target genomic regions, a genome editing system and
a compound of formula,

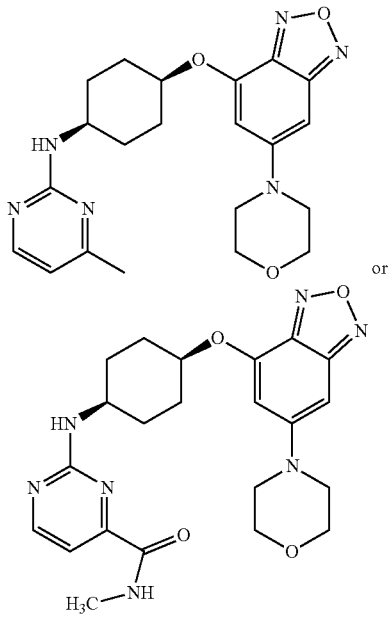

or a pharmaceutically acceptable salt thereof,
wherein the genome editing system interacts with a nucleic acid(s) of the one or more target genomic regions of a target gene(s), resulting in editing the one or more target genomic regions and wherein the edit modifies expression of a downstream gene(s) and/or protein(s) associated with the target gene(s).

4. The method of claim 2, wherein the DNA break comprises a DNA double strand break (DSB).

5. The method of claim 1, wherein the efficiency of editing the target genomic regions in the one or more cells is increased as compared to that in otherwise identical cell or cells but without the compound.

6. The method of claim 1, wherein the efficiency of the repair of the DNA break at the target genomic regions in the one or more cells via a HDR pathway is increased as compared to that in otherwise identical cell or cells but without the compound.

7. The method of claim 2, wherein the efficiency of inhibiting or suppressing the repair of the DNA break at the target genomic regions in the one or more cells via a NHEJ pathway is increased as compared to that in otherwise identical cell or cells but without the compound.

8. The method of claim 5, wherein said efficiency is measured by frequency of targeted polynucleotide integration or targeted mutagenesis.

9. The method of claim 3, wherein the expression of a downstream gene(s) and/or protein(s) associated with the target gene(s) is decreased or increased as compared to the baseline expression level in the one or more cells prior to the administration.

10. The method of claim 3, wherein the expression of a downstream gene(s) and/or protein(s) associated with the target gene(s) is substantially eliminated in the one or more cells.

11. The method of claim 1, wherein the one or more cells that are administered or contacted with said compound have increased survival in comparison to one or more cells that have not been administered or contacted with said compound.

12. The method of claim 1, wherein the genome editing system and the compound are administered into the one or more cells simultaneously or sequentially.

13. The method of claim 1, wherein the genome editing system is administered into the one or more cells prior to or after administration of the compound.

14. The method of claim 1, wherein the one or more cells are in vivo cells within an organism or ex vivo cells from an organism.

15. The method of claim 1, wherein the genome editing system and the compound are administered via same or different route.

16. The method of claim 1, wherein the genome editing system is administered intravenously and the compound is administered orally.

17. The method of claim 1, wherein the genome editing system is selected from a meganuclease based system, a zinc finger nuclease (ZFN) based system, a Transcription Activator-Like Effector-based Nuclease (TALEN) system, a CRISPR-based system, or a NgAgo-based system.

18. The method of claim 17, wherein genome editing system is a CRISPR-based system.

19. The method of claim 18, wherein the CRISPR-based system is a CRISPR-Cas system or a CRISPR-Cpf system.

20. The method of claim 19, wherein the CRISPR-based system is a CRISPR-Cas system and wherein the CRISPR-Cas system comprises: (a) at least one guide RNA element comprising: (i) a targeter RNA comprising a nucleotide sequence substantially complementary to a nucleotide sequence at the one or more target genomic regions or a nucleic acid comprising a nucleotide sequence(s) encoding the targeter RNA; (ii) and an activator RNA comprising a nucleotide sequence that is capable of hybridizing with the targeter RNA or a nucleic acid comprising a nucleotide sequence(s) encoding the activator RNA; and (b) a Cas protein element comprising a Cas protein or a nucleic acid comprising a nucleotide sequence(s) encoding the Cas protein.

21. The method of claim 20, wherein said targeter RNA and activator RNA are fused as a single molecule.

22. The method of claim 20 wherein the Cas protein is a Type-II Cas9 protein.

23. The method of claim 22, wherein the Cas9 protein is a SaCas9, SpCas9, SpCas9n, Cas9-HF, Cas9-H840A, FokI-dCas9, or D10A nickase, or any combinations thereof.

24. The method of claim 19, wherein the CRISPR-based system is a CRISPR-Cpf system and wherein the CRISPR-Cpf system comprises: (a) at least one guide RNA element or a nucleic acid comprising a nucleotide sequence(s) encoding the guide RNA element, the guide RNA comprising a targeter RNA that comprises a nucleotide sequence substantially complementary to a nucleotide sequence at the one or more target genomic regions; and (b) a Cpf protein element comprising a Cpf protein or a nucleic acid comprising a nucleotide sequence encoding the Cpf protein.

25. The method of claim 1, wherein the genome editing system is delivered by one or more vectors, by synthetic RNA or by a nanoformulation.

26. A kit or composition for editing one or more target genomic regions, comprising:
a genome editing system; and
a compound of formula,

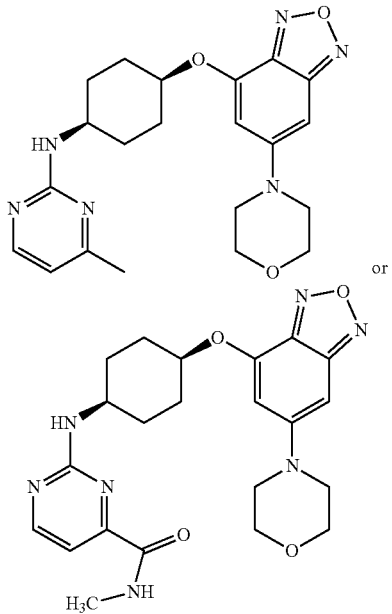

or a pharmaceutically acceptable salt thereof.

27. The kit or composition of claim 26, wherein the genome editing system is a meganuclease based system, a zinc finger nuclease (ZFN) based system, a Transcription Activator-Like Effector-based Nuclease (TALEN) system, a CRISPR-based system, or NgAgo-based system.

28. The kit or composition of claim 27, wherein genome editing system is a CRISPR-based system.

29. The kit or composition of claim 28, wherein the CRISPR-based system is a CRISPR-Cas system or a CRISPR-Cpf system.

30. The kit or composition of claim 29, wherein the CRISPR-based system is a CRISPR-Cas system and wherein the CRISPR-Cas system comprises: (a) at least one guide RNA element comprising: (i) a targeter RNA comprising a nucleotide sequence substantially complementary to a nucleotide sequence at the one or more target genomic regions or a nucleic acid comprising a nucleotide sequence(s) encoding the targeter RNA; (ii) and an activator RNA comprising a nucleotide sequence that is capable of hybridizing with the targeter RNA, or a nucleic acid comprising a nucleotide sequence(s) encoding the activator RNA; and (b) a Cas protein element comprising a Cas protein or a nucleic acid comprising a nucleotide sequence(s) encoding the Cas protein.

31. The kit or composition of claim 30, wherein the Cas protein is a Type-II Cas9 protein.

32. The kit or composition of claim 31, wherein the Cas9 protein is a SaCas9, SpCas9, SpCas9n, Cas9-HF, Cas9-H840A, FokI-dCas9, or D10A nickase, or any combination thereof.

33. The kit or composition of claim 29, wherein the CRISPR-based system is a CRISPR-Cpf system, and wherein the CRISPR-Cpf system comprises: (a) a targeter RNA comprising a nucleotide sequence substantially complementary to a nucleotide sequence at the one or more target genomic regions, or a nucleic acid comprising a nucleotide sequence(s) encoding the targeter RNA; and (b) a Cpf protein element comprising a Cpf protein or a nucleic acid comprising a nucleotide sequence(s) encoding the Cpf protein.

34. The kit or composition of claim 26, wherein the genome editing system is included or packaged in one or more vectors.

35. A compound represented by any one of the following formulae or a pharmaceutically acceptable salt thereof:

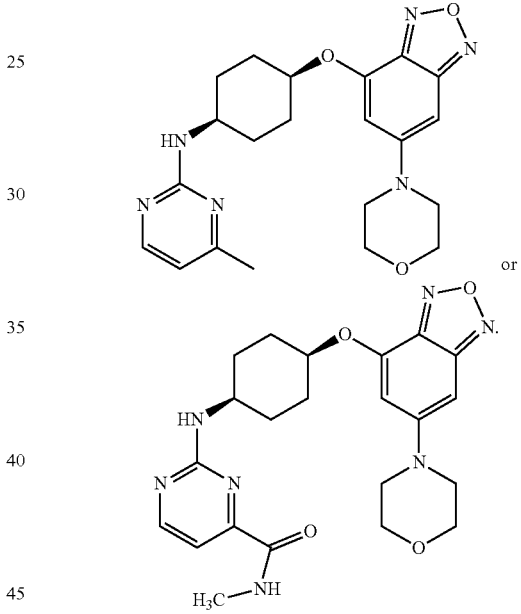

36. A method of repairing, or inhibiting or suppressing repair of, a DNA break in one or more target genomic regions via a homology directed repair (HDR) pathway, or modifying expression of one or more genes or proteins comprising:
administering to one or more cells that comprise one or more target genomic regions, a genome editing system and a compound of claim 35.

* * * * *

UNITED STATES PATENT AND TRADEMARK OFFICE
CERTIFICATE OF CORRECTION

| | |
|---|---|
| PATENT NO. | : 12,121,524 B2 |
| APPLICATION NO. | : 16/962441 |
| DATED | : October 22, 2024 |
| INVENTOR(S) | : Weinberg et al. |

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1131 days.

Signed and Sealed this
Thirteenth Day of May, 2025

Coke Morgan Stewart
*Acting Director of the United States Patent and Trademark Office*